(12) United States Patent
Baxter et al.

(10) Patent No.: US 7,531,545 B2
(45) Date of Patent: May 12, 2009

(54) 2-AMINO-3,4-DIHYDRO-PYRIDO[3,4-D] PYRIMIDINE DERIVATIVES USEFUL AS INHIBITORS OF β-SECRETASE (BACE)

(75) Inventors: Ellen E. Baxter, Glenside, PA (US); Christopher John Creighton, San Diego, CA (US); Yifang Huang, Lansdale, PA (US); Chi Luo, New Hope, PA (US); Michael H. Parker, Chalfont, PA (US); Allen B. Reitz, Lansdale, PA (US); Charles H. Reynolds, Lansdale, PA (US); Tina Morgan Ross, Royersford, PA (US); Eric D. Strobel, Warrington, PA (US); Brett A. Tounge, Blue Bell, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 11/552,792

(22) Filed: Oct. 25, 2006

(65) Prior Publication Data

US 2007/0259898 A1    Nov. 8, 2007

Related U.S. Application Data

(60) Provisional application No. 60/730,165, filed on Oct. 25, 2005.

(51) Int. Cl.
*A61K 31/519* (2006.01)
*C07D 471/04* (2006.01)
*A61P 25/28* (2006.01)

(52) U.S. Cl. .................. 514/264.11; 544/230; 544/279
(58) Field of Classification Search ............ 514/264.11; 544/230, 279
See application file for complete search history.

(56) References Cited

U.S. PATENT DOCUMENTS

| 4,739,056 | A | 4/1988 | Venuti |
| 4,761,416 | A | 8/1988 | Fried et al. |
| 2006/0178383 | A1* | 8/2006 | Bischoff et al. ........ 514/266.23 |

FOREIGN PATENT DOCUMENTS

| EP | 0406958 | 1/1991 |
| EP | 1407774 | 4/2004 |
| JP | 63-196573 | 8/1988 |
| WO | WO 01/38314 | 5/2001 |
| WO | WO 02/100399 | 12/2002 |
| WO | WO 2004/022523 | 3/2004 |
| WO | WO 2004/058686 | 7/2004 |
| WO | WO 2005/049585 | 6/2005 |
| WO | WO 2006/017836 | 2/2006 |
| WO | WO 2006/017844 | 2/2006 |
| WO | WO 2006/024932 | 3/2006 |

OTHER PUBLICATIONS

Cole, et al., Molecular Neurodegeneration 2007, 2:22.*
Hamaguchi, et al., Cell. Mol. Life Sci. 63 (2006) 1538-1552.*
Citron, Trends in Pharm. Sci., vol. 25, Issue 2, Feb. 2004, 92-97.*
Larner, A.J.: "Secretases as Therapeutic Targets in Alzheimer's Disease: Patents 2000-2004". Expert Opinion On Therapeutic Patents, Ashley Publications, GB, vol. 14, No. 10, 2004, pp. 1403-1420, XP002404250.
Database Caplus Online Chronical Abstracts Service Columbus, Ohio, US Ishikawa, Fumyoshi et al.: Quinazolineactic acid derivatives as platlets aggregation inhibitors; XP00236713.
Kienzle, Frank et al., "1,5-Dihydroimidazoquinazolinones as blood platelet aggregation inhibitors", European Journal of Medicinal Chemistry, 17(6), 547-556.
Webb, Thomas Hand Wilcox, Improved Synthesis of Symmetrical and Unsymmetrical 5,11-methandibenzo'b.f.1,5-diazocines. Readily Available Nanoscale Structural Units, Journal of Organic Chemistry, vol. 55, No. 1, 1990, pp. 363-365.
Venuti, M.C. et al., Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl1-Oxybutyramide J. Medicinal Chemistry, American Chemical Society, vol. 30, No. 2, 1987, pp. 303-318.
Patent Abstracts of Japan, vol. 016, No. 160 (P-1340) Apr. 20, 1992, JP 04 011255 (Fuji Photo Film Co Ltd), Jan. 16, 1992, p. 5, compound 20.
U.S. Appl. No. 11/197,669, Baxter et al.
U.S. Appl. No. 11/197,608, Baxter et al.
U.S. Appl. No. 11/197,615, Bischoff et al.
U.S. Appl. No. 11/671,681, Baxter et al.
U.S. Appl. No. 11/671,703, Baxter et al.
U.S. Appl. No. 11/671,732, Baxter et al.
PCT International Search Report, PCT/US2006/041487, Mar. 6, 2007.

* cited by examiner

*Primary Examiner*—Mark L Berch
*Assistant Examiner*—Cecilia M Jaisle
(74) *Attorney, Agent, or Firm*—Hal Woodrow

(57) ABSTRACT

The present invention is directed to novel 2-amino-3,4-dihydro-pyrido[3,4-d]pyrimidine derivatives, pharmaceutical compositions containing them and their use in the treatment of Alzheimer's disease (AD) and related disorders. The compounds of the invention are inhibitors of β-secretase, also known as β-site cleaving enzyme and BACE, BACE1, Asp2 and memapsin2.

14 Claims, No Drawings

2-AMINO-3,4-DIHYDRO-PYRIDO[3,4-D] PYRIMIDINE DERIVATIVES USEFUL AS INHIBITORS OF β-SECRETASE (BACE)

CROSS REFERENCE TO RELATED APPLICATIONS

This application claims the benefit of U.S. Provisional Application 60/730,165, filed on Oct. 25, 2005, which is incorporated by reference herein in its entirety.

FIELD OF THE INVENTION

The present invention is directed to novel 2-amino-3,4-dihydro-pyrido[3,4-d]pyrimidine derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibillary tangles which are generated by hyperphosphorylation of tau protein and amyloid plaques which form by aggregation of β-amyloid$_{1-42}$ (Aβ$_{1-42}$) peptide. Aβ$_{1-42}$ forms oligomers and then fibrils, and ultimately amyloid plaques. The fibrils are believed to be especially neurotoxic and may cause most of the neurological damage associated with AD. Agents that prevent the formation of Aβ$_{1-42}$ have the potential to be disease-modifying agents for the treatment of AD. Aβ$_{1-42}$ is generated from the amyloid precursor protein (APP), comprised of 770 amino acids. The N-terminus of Aβ$_{1-42}$ is cleaved by β-secretase (BACE), and then β-secretase cleaves the C-terminal end. In addition to Aβ$_{1-42}$, β-secretase also liberates Aβ$_{1-40}$ which is the predominant cleavage product as well as Aβ$_{1-38}$ and Aβ$_{1-43}$. Thus, inhibitors of BACE would be expected to prevent the formation of Aβ$_{1-42}$ and would be potential therapeutic agents in the treatment of AD.

SUMMARY OF THE INVENTION

The present invention is directed to a compound of formula (I)

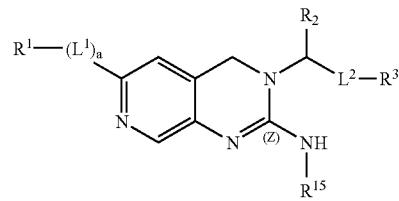

wherein a in an integer from 0 to 1;

$L^1$ is selected from the group consisting of —O—, —S—, —SO—, —SO$_2$— and —NR$^0$—; wherein R$^0$ is selected from the group consisting of hydrogen and C$_{1-4}$alkyl;

$R^1$ is selected from the group consisting of cycloalkyl, aryl, heteroaryl and heterocycloalkyl;

wherein the cycloalkyl, aryl, heteroaryl or heterocycloalkyl is optionally substituted with one or more substituents independently selected from the group consisting of halogen, hydroxy, oxo, carboxy, C$_{1-4}$alkyl, hydroxy substituted C$_{1-4}$alkyl, halogen substituted C$_{1-4}$alkyl, cyano substituted C$_{1-4}$alkyl, C$_{1-4}$alkoxy, halogen substituted C$_{1-4}$alkoxy, nitro and cyano;

$R^2$ is selected from the group consisting of hydrogen, C$_{1-8}$alkyl, C$_{1-8}$alkoxy, hydroxy substituted C$_{1-6}$alkyl, amino substituted C$_{1-6}$alkyl, —C$_{1-4}$alkyl-O—C$_{1-4}$alkyl, —C$_{1-4}$alkyl-O-aralkyl, cycloalkyl, —C$_{1-4}$alkyl-cycloalkyl, aryl, aralkyl, biphenyl, heteroaryl, —C$_{1-4}$alkyl-heteroaryl, heterocycloalkyl and —C$_{1-4}$alkyl-heterocycloalkyl;

wherein the cycloalkyl, aryl, heteroaryl or heterocycloalkyl group, whether alone or as part of a substituent group, is optionally substituted with one or more substituent independently selected from the group consisting of halogen, hydroxy, oxo, carboxy, C$_{1-4}$alkyl, C$_{1-4}$alkoxy, —C(O)—(C$_{1-4}$alkoxy), hydroxy substituted C$_{1-4}$alkyl, fluoro substituted C$_{1-4}$alkyl, fluoro substituted C$_{1-4}$alkoxy, 5-(1,2,3,4-tetrazolyl) and 1-(1,4-dihydro-tetrazol-5-one);

$L^2$ is selected from the group consisting of —(CH$_2$)$_b$—;

b is an integer from 0 to 4;

$R^3$ is selected from the group consisting of

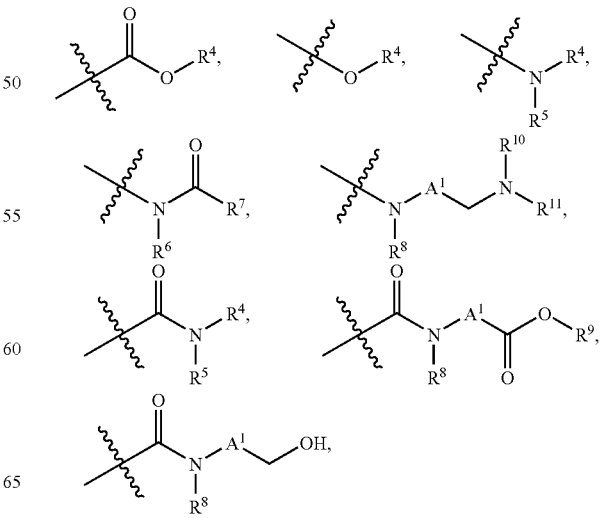

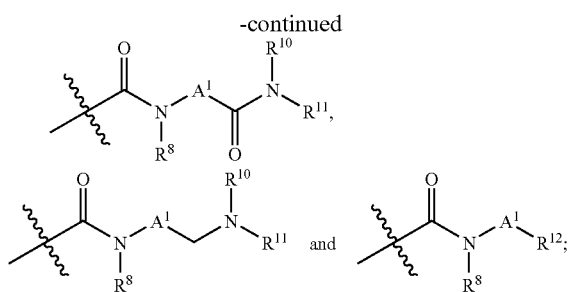

R⁴ and R⁵ are each independently selected from the group consisting of hydrogen, $C_{1-8}$alkyl, —$C_{2-8}$alkenyl, —$C_{2-4}$alkyl-O—$C_{1-4}$alkyl, —$C_{2-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$CH_2CH_2$—O—$CH_2CH_2$—O—$CH_2CH_2$—O—$CH_2CH_2$—OH;

wherein $R^L$, $R^A$ and $R^B$, at each occurrence, are each independently selected from the group consisting of hydrogen, $C_{1-4}$alkyl, t-butoxycarbonyl- and aralkyl;

wherein the alkyl, whether alone or as part of a substituent group, is optionally substituted with one or more substituents independently selected from the group consisting of hydroxy, carboxy $C_{1-4}$alkoxy, —C(O)O—$C_{1-4}$alkyl, $NR^AR^B$, —$NR^L$—C(O)O—$C_{1-4}$alkyl and —$NR^L$—$SO_2$—$NR^AR^B$;

wherein the cycloalkyl, aryl, heteroaryl or heterocycloalkyl, whether alone or as part of a substituent group, is optionally substituted with one or more substituents independently selected from the group consisting of oxo, fluoro, chloro, hydroxy, carboxy, —C(O)O—$C_{1-4}$alkyl, $C_{1-8}$alkyl, $C_{1-4}$alkoxy, trifluoromethyl, cyano, nitro, amino, $C_{1-4}$alkylamino, di($C_{1-4}$alkylamino), cycloalkyl, —$C_{1-4}$alkyl-cycloalkyl, 5-(1,2,3,4-tetrazolyl) and 1-(1,4-dihydro-tetrazol-5-one);

provided that the chloro is not bound to a cycloalkyl or heterocycloalkyl;

alternatively $R^4$ and $R^5$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is saturated, partially unsaturated or aromatic;

wherein the heterocyclyl ring is optionally substituted with one or more substituents independently selected from the group consisting of halogen, hydroxy, carboxy, —C(O)O—$C_{1-4}$alkyl, $C_{1-6}$alkyl, —$C_{1-4}$alkyl-OH, —$C_{1-4}$alkyl-$CO_2H$, $C_{1-4}$alkoxy, trifluoromethyl, cyano, nitro, amino, $C_{1-4}$alkylamino, di($C_{1-4}$alkylamino), $C_{4-8}$cycloalkyl, phenyl, 5 to 6 membered heteroaryl and 1-(1,4-dihydro-tetrazol-5-one);

wherein the phenyl or 5 to 6 membered heteroaryl substituent is further optionally substituted with one or more substituents independently selected from the group consisting of halogen, $C_{1-4}$alkyl and halogenated $C_{1-4}$alkyl;

$R^6$ is selected from the group consisting of hydrogen and $C_{1-4}$alkyl;

$R^7$ is selected from the group consisting of hydrogen, $C_{1-10}$alkyl, $C_{1-8}$alkoxy, cycloalkyl, aryl, biphenyl, partially unsaturated carbocyclyl, heteroaryl, heterocycloalkyl, —$C_{1-4}$alkyl-cycloalkyl, $C_{1-4}$aralkyl, —$C_{1-4}$alkyl-partially unsaturated carbocyclyl, —$C_{1-4}$alkyl-heteroaryl, —$C_{1-4}$alkyl-heterocycloalkyl and spiro-heterocyclyl;

wherein the alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^CR^D)_2$, —$C_{1-4}$alkyl-C(O)—N($R^CR^D)_2$, —$NR^C$—C(O)—$C_{1-4}$alkyl, —$SO_2$—N($R^CR^D$), —$C_{1-4}$alkyl-$SO_2$—N($R^CR^D)_2$, phenyl, 5-(1,2,3,4-tetrazolyl) and 1-(1,4-dihydro-tetrazol-5-one);

provided that the halogen is not bound to an alkyl, cycloalkyl or heterocycloalkyl;

wherein $R^C$ and $R^D$ at each occurrence are independently selected from the group consisting of hydrogen and $C_{1-4}$alkyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

alternatively, $R^6$ and $R^7$ are taken together with the atoms to which they are bound to form a 5 to 10 membered, saturated heterocycloalkyl; wherein the 5 to 10 membered, saturated heterocycloalkyl is optionally substituted with one to two oxo groups;

$R^8$ is selected from the group consisting of hydrogen, $C_{1-4}$alkyl and cycloalkyl;

$A^1$ is —$C_{1-6}$alkyl-; wherein the alkyl is optionally substituted with one or more substituents independently selected from the group consisting of $C_{2-8}$alkyl, hydroxy substituted $C_{1-6}$alkyl, $C_{1-4}$alkoxy substituted $C_{1-4}$alkyl, aralkyloxy substituted $C_{1-4}$alkyl, $C_{3-6}$alkenyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, —$C_{1-4}$alkyl-$NR^ER^F$, —S—$C_{1-4}$alkyl, —$C_{1-3}$alkyl-O—$C_{1-3}$alkyl, —$C_{1-3}$alkyl-S—$C_{1-3}$alkyl, —$C_{1-3}$alkyl-O-aralkyl, —$C_{1-4}$alkyl-guanidino, —$C_{1-4}$alkyl-$CO_2R^E$ and —$C_{1-4}$alkyl-C(O)O—$C_{1-4}$alkyl;

wherein $R^E$ and $R^F$, at each occurrence, are independently selected from the group consisting of hydrogen and $C_{1-4}$alkyl;

wherein the cycloalkyl, aryl, heteroaryl or heterocycloalkyl, whether alone or as part of a substituent group, is optionally substituted with one or more substituents independently selected from the group consisting of fluoro, chloro, hydroxy, oxo, carboxy, $C_{1-4}$alkyl, $C_{1-4}$alkoxy, hydroxy substituted $C_{1-4}$alkyl, halogen substituted $C_{1-4}$alkyl, halogen substituted $C_{1-4}$alkyl, —C(O)O—$C_{1-4}$alkyl, 5-(1,2,3,4-tetrazolyl) and 1-(1,4-dihydro-tetrazol-5-one);

provided that the chloro is not bound to a cycloalkyl or heterocycloalkyl;

$R^9$ is selected from the group consisting of hydrogen, $C_{1-12}$alkyl, hydroxy substituted $C_{1-6}$alkyl, amino substituted $C_{1-6}$alkyl, allyl, $C_{1-8}$alkoxy, cycloalkyl, —$C_{1-4}$alkyl-cycloalkyl, aryl, aralkyl, biphenyl, heteroaryl, —$C_{1-4}$alkyl-heteroaryl, heterocycloalkyl, —$C_{1-4}$alkyl-heterocycloalkyl, —$C_{1-4}$alkyl-O—$C_{1-8}$alkyl, —$C_{1-4}$alkyl-O-aryl, —$C_{1-4}$alkyl-O-aralkyl, $C_{1-4}$alkyl-O—C(O)—$C_{1-6}$alkyl, —$C_{1-4}$alkyl-O—C(O)—O—$C_{1-6}$alkyl, —$C_{1-4}$alkyl-O—C(O)—O—$C_{1-8}$cycloalkyl, —$C_{1-4}$alkyl-O—C(O)—C(NHCO($C_{1-6}$alkyl))=CH—$C_{1-6}$alkyl, 5-methyl-2-oxo-[1,3]dioxol-4-ylmethyl-, —$CH_2$—N($C_{1-4}$alkyl)-C(O)-aryl, —$CH_2$—C(O)—$NR^GR^H$, $CH_2$—O—$CH_2$—O—C(O)-2-(N-alkyl-1,4-dihydropyridyl), α-cyclodextrinyl, β-cyclodextrinyl and γ-cyclodextrinyl;

wherein $R^G$ and $R^H$ are each independently selected from the group consisting of hydrogen and $C_{1-4}$alkyl;

wherein the $C_{3-8}$cycloalkyl, aryl, heteroaryl or heterocycloalkyl, whether alone or as part of a substituent group, is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{10}$ and $R^{11}$ are each independently selected from the group consisting of hydrogen, $C_{1-8}$alkyl, hydroxy substituted $C_{1-4}$alkyl, —$C_{2-4}$alkyl-O—$C_{1-4}$alkyl, aralkyloxy substituted $C_{1-4}$alkyl, —$C_{1-4}$alkyl-NR$^J$R$^K$, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, $C_{2-6}$-dialkanoic acid and —$C_{1-4}$alkyl-C(O)O—R$^J$;

wherein R$^J$ and R$^K$, at each occurrence, are each independently selected from the group consisting of hydrogen and $C_{1-4}$alkyl;

wherein the cycloalkyl, aryl, heteroaryl or heterocycloalkyl, whether alone or as part of a substituent group is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^{10}$ and $R^{11}$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{12}$ is selected from the group consisting of $C_{1-4}$alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), aralkyl, 5-(1,2,3,4-tetrazolyl) and 1-(1,4-dihydro-tetrazol-5-one);

$R^{15}$ is selected from the group consisting of hydrogen, hydroxy, amino, —C(O)—$C_{1-6}$alkyl and —C(O)—$C_{1-4}$alkyl-O—$C_{1-4}$alkyl;

or a pharmaceutically acceptable salt thereof.

The present invention is further directed to compounds of formula (CI)

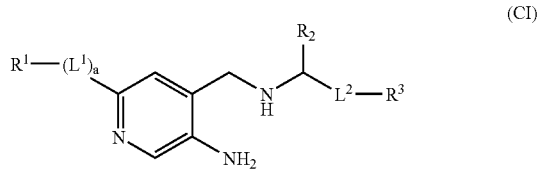

wherein $R^1$, a, $L^1$, $R^2$, $L^2$ and $R^3$ are as herein defined, useful as intermediates in the synthesis of the compounds of formula (I).

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme in a subject in need thereof, comprising administering to the subject a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with stroke, dementia associated with Parkinson's disease and dementia associated with beta-amyloid, preferably Alzheimer's disease, in a subject in need thereof comprising administering to the subject an effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I)

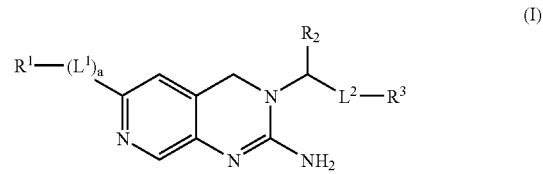

wherein $R^1$, a, $L^1$, $R^2$, $L^2$ and $R^3$ are as herein defined. The compounds of formula (I) are inhibitors of the β-secretase enzyme (also known as β-site cleaving enzyme, BACE, BACE1, Asp2 or memapsin2), and are useful in the treatment of Alzheimer's disease (AD), mild cognitive impairment (MCI), senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment, the present invention is directed to compounds of formula (I-O)

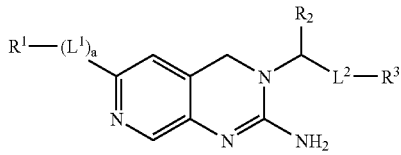

(I-O)

wherein a in an integer from 0 to 1;

L¹ is selected from the group consisting of —O—, —S—, —SO—, —SO₂— and —NR⁰—; wherein R⁰ is selected from the group consisting of hydrogen and $C_{1-4}$alkyl;

R¹ is selected from the group consisting of cycloalkyl, aryl, heteroaryl and heterocycloalkyl;

wherein the cycloalkyl, aryl, heteroaryl or heterocycloalkyl is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{1-4}$alkoxy, halogen substituted $C_{1-4}$alkoxy, nitro and cyano;

R² is selected from the group consisting of hydrogen, $C_{1-8}$alkyl, $C_{1-8}$alkoxy, hydroxy substituted $C_{1-6}$alkyl, amino substituted $C_{1-6}$alkyl, —$C_{1-4}$alkyl-O—$C_{1-4}$alkyl, —$C_{1-4}$alkyl-O-aralkyl, cycloalkyl, —$C_{1-4}$alkyl-cycloalkyl, aryl, aralkyl, biphenyl, heteroaryl, —$C_{1-4}$alkyl-heteroaryl, heterocycloalkyl and —$C_{1-4}$alkyl-heterocycloalkyl;

wherein the cycloalkyl, aryl, heteroaryl or heterocycloalkyl group, whether alone or as part of a substituent group, is optionally substituted with one or more substituent independently selected from the group consisting of halogen, hydroxy, oxo, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one);

L² is selected from the group consisting of —(CH₂)$_b$—;

b is an integer from 0 to 4;

R³ is selected from the group consisting of

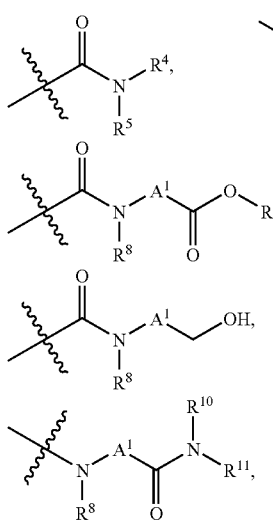

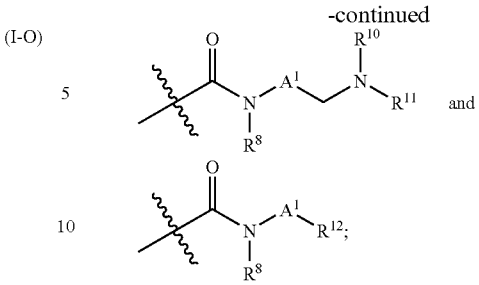

-continued $R^4$ and $R^5$ are each independently selected from the group consisting of hydrogen, $C_{1-8}$alkyl, hydroxy substituted $C_{1-4}$alkyl, —$C_{2-4}$alkyl-O—$C_{1-4}$alkyl, —$C_{2-4}$alkyl-O-aralkyl, —$C_{1-4}$alkyl-NR$^A$R$^B$, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl;

wherein R$^A$ and R$^B$, at each occurrence, are each independently selected from the group consisting of hydrogen, $C_{1-4}$alkyl and aralkyl;

wherein the $C_{1-8}$alkyl is optionally substituted with one or more substituents independently selected from the group consisting of hydroxy and carboxy;

wherein the cycloalkyl, aryl, heteroaryl or heterocycloalkyl, whether alone or as part of a substituent group, is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^4$ and $R^5$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^6$ is selected from the group consisting of hydrogen and $C_{1-4}$alkyl;

$R^7$ is selected from the group consisting of hydrogen, $C_{1-10}$alkyl, cycloalkyl, aryl, biphenyl, partially unsaturated carbocyclyl, heteroaryl, heterocycloalkyl, —$C_{1-4}$alkyl-cycloalkyl, $C_{1-4}$aralkyl, —$C_{1-4}$alkyl-partially unsaturated carbocyclyl, —$C_{1-4}$alkyl-heteroaryl, —$C_{1-4}$alkyl-heterocycloalkyl and spiro-heterocyclyl;

wherein the $C_{1-10}$alkyl, cycloalkyl, aryl, heteroaryl, heterocycloalkyl or spiro-heterocyclyl, whether alone or as part of a substituent group is optionally substituted with one or more substituents independently selected from the group consisting of halogen, hydroxy, oxo, carboxy, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N(R$^C$R$^D$)₂, —$C_{1-4}$alkyl-C(O)—N(R$^C$R$^D$)₂, —NR$^C$—C(O)—$C_{1-4}$alkyl, —SO₂—N(R$^C$R$^D$), —$C_{1-4}$alkyl-SO₂—N(R$^C$R$^D$)₂, phenyl, 5-(1,2,3,4-tetrazolyl) and 1-(1,4-dihydro-tetrazol-5-one);

provided that the halogen is not bound to a $C_{1-10}$alkyl, cycloalkyl or heterocycloalkyl;

wherein $R^C$ and $R^D$ at each occurrence are independently selected from the group consisting of hydrogen and $C_{1-4}$alkyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

$R^8$ is selected from the group consisting of hydrogen, $C_{1-4}$alkyl and cycloalkyl;

$A^1$ is —$C_{1-6}$alkyl-; wherein the alkyl is optionally substituted with one or more substituents independently selected from the group consisting of $C_{2-8}$alkyl, hydroxy substituted $C_{1-6}$alkyl, $C_{1-4}$alkoxy substituted $C_{1-4}$alkyl, aralkyloxy substituted $C_{1-4}$alkyl, $C_{3-6}$alkenyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, —$C_{1-4}$alkyl-NR$^E$R$^F$, —S—$C_{1-4}$alkyl, —$C_{1-3}$alkyl-O—$C_{1-3}$alkyl, —$C_{1-3}$alkyl-S—$C_{1-3}$alkyl, —$C_{1-3}$alkyl-O-aralkyl, —$C_{1-4}$alkyl-guanidino, —$C_{1-4}$alkyl-CO$_2$R$^E$ and —$C_{1-4}$alkyl-C(O)O—$C_{1-4}$alkyl;

wherein $R^E$ and $R^F$, at each occurrence, are independently selected from the group consisting of hydrogen and $C_{1-4}$alkyl;

wherein the cycloalkyl, aryl, heteroaryl or heterocycloalkyl, whether alone or as part of a substituent group, is optionally substituted with one or more substituents independently selected from the group consisting of fluoro, chloro, hydroxy, oxo, carboxy, $C_{1-4}$alkyl, $C_{1-4}$alkoxy, hydroxy substituted $C_{1-4}$alkyl, halogen substituted $C_{1-4}$alkyl, halogen substituted $C_{1-4}$alkyl, —C(O)O—$C_{1-4}$alkyl, 5-(1,2,3,4-tetrazolyl) and 1-(1,4-dihydro-tetrazol-5-one);

provided that the chloro is not bound to a cycloalkyl or heterocycloalkyl;

$R^9$ is selected from the group consisting of hydrogen, $C_{1-12}$alkyl, hydroxy substituted $C_{1-6}$alkyl, amino substituted $C_{1-6}$alkyl, allyl, $C_{1-8}$alkoxy, cycloalkyl, —$C_{1-4}$alkyl-cycloalkyl, aryl, aralkyl, biphenyl, heteroaryl, —$C_{1-4}$alkyl-heteroaryl, heterocycloalkyl, —$C_{1-4}$alkyl-heterocycloalkyl, —$C_{1-4}$alkyl-O—$C_{1-8}$alkyl, —$C_{1-4}$alkyl-O-aryl, —$C_{1-4}$alkyl-O-aralkyl, $C_{1-4}$alkyl-O—C(O)—$C_{1-6}$alkyl, —$C_{1-4}$alkyl-O—C(O)—O—$C_{1-6}$alkyl, —$C_{1-4}$alkyl-O—C(O)—O—$C_{1-8}$cycloalkyl, —$C_{1-4}$alkyl-O—C(O)—C(NHCO($C_{1-6}$alkyl))=CH—$C_{1-6}$alkyl, 5-methyl-2-oxo-[1,3]dioxol-4-ylmethyl-, —CH$_2$—N($C_{1-4}$alkyl)-C(O)-aryl, —CH$_2$—C(O)—NR$^G$R$^H$, CH$_2$—O—CH$_2$—O—C(O)-2-(N-alkyl-1,4-dihydropyridyl), α-cyclodextrinyl, β-cyclodextrinyl and γ-cyclodextrinyl;

wherein $R^G$ and $R^H$ are each independently selected from the group consisting of hydrogen and $C_{1-4}$alkyl;

wherein the cycloalkyl, aryl, heteroaryl or heterocycloalkyl, whether alone or as part of a substituent group, is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{10}$ and $R^{11}$ are each independently selected from the group consisting of hydrogen, $C_{1-8}$alkyl, hydroxy substituted $C_{1-4}$alkyl, —$C_{2-4}$alkyl-O—$C_{1-4}$alkyl, benzyloxy substituted $C_{1-4}$alkyl, —$C_{1-4}$alkyl-NR$^J$R$^K$, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$C_{1-4}$alkyl-C(O)O—R$^J$;

wherein $R^J$ and $R^K$, at each occurrence, are each independently selected from the group consisting of hydrogen and $C_{1-4}$alkyl;

wherein the cycloalkyl, aryl, heteroaryl or heterocycloalkyl, whether alone or as part of a substituent group is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^{10}$ and $R^{11}$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{12}$ is selected from the group consisting of $C_{1-4}$alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), aralkyl, 5-(1,2,3,4-tetrazolyl) and 1-(1,4-dihydro-tetrazol-5-one);

or a pharmaceutically acceptable salt thereof.

In an embodiment of the present invention a is 0. In another embodiment of the present invention a is 1.

In an embodiment of the present invention $L^1$ is —O—. In another embodiment of the present invention $L^1$ is selected from the group consisting of —O—, —S—, —SO— and —SO$_2$. In another embodiment of the present invention, $L^1$ is —NR$^0$—; wherein $R^0$ is selected from the group consisting of hydrogen and methyl.

In an embodiment of the present invention $R^1$ is aryl. In another embodiment of the present invention $R^1$ is selected from the group consisting of cycloalkyl and aryl. In another embodiment of the present invention $R^1$ is selected from the group consisting of aryl and heteroaryl. In another embodiment of the present invention $R^1$ is selected from the group consisting of heteroaryl and heterocycloalkyl.

In an embodiment of the present invention, $R^1$ is selected from the group consisting of aryl and heteroaryl; wherein the aryl or heteroaryl is optionally substituted with one to two substituents independently selected from the group consisting of hydroxy, carboxy, $C_{1-4}$alkyl, hydroxy substituted $C_{1-4}$alkyl, halogen substituted $C_{1-4}$alkyl, $C_{1-4}$alkoxy and halogen substituted $C_{1-4}$alkoxy.

In another embodiment of the present invention, $R^1$ is selected from the group consisting of aryl and heteroaryl; wherein the aryl or heteroaryl is optionally substituted with one to two substituents independently selected from the group consisting of halogen, hydroxy, carboxy, $C_{1-4}$alkyl, hydroxy substituted $C_{1-4}$alkyl, halogen substituted $C_{1-4}$alkyl, $C_{1-4}$alkoxy and halogen substituted $C_{1-4}$alkoxy.

In another embodiment of the present invention, $R^1$ is selected from the group consisting of aryl; wherein the aryl is optionally substituted with a substituent selected from the group consisting of halogen and $C_{1-4}$alkoxy. In another embodiment of the present invention, $R^1$ is selected from the group consisting of phenyl, 2-fluorophenyl and 2-methoxyphenyl. In another embodiment of the present invention, $R^1$ is phenyl.

In an embodiment of the present invention, $R^2$ is selected from the group consisting of hydrogen, $C_{1-6}$alkyl, hydroxy substituted $C_{1-4}$alkyl, —$C_{1-4}$alkyl-O—$C_{1-4}$alkyl, —$C_{1-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group, whether alone or as part of a substituent group, is optionally substituted with one to two substituent independently selected from the group consisting of hydroxy, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one).

In another embodiment of the present invention, $R^2$ is selected from the group consisting of hydrogen, $C_{1-4}$alkyl, hydroxy substituted $C_{1-4}$alkyl, —$C_{1-4}$alkyl-O—$C_{1-4}$alkyl, —$C_{1-4}$alkyl-O-aralkyl, cycloalkyl and heterocycloalkyl.

In another embodiment of the present invention, $R^2$ is selected from the group consisting of hydrogen, cyclohexyl, (S)-cyclohexyl, isopropyl, (S)-isopropyl, 1-(2-hydroxy-ethyl), 1-(2-methoxy-ethyl), 1-(2-isopropyloxy-ethyl), 1-((S)-(2-benzyloxy)-ethyl), 4-tetrahydropyranyl and (S)-4-tetrahydropyranyl. In another embodiment of the present invention, $R^2$ is selected from the group consisting of hydrogen (S), (S)-cyclohexyl, isopropyl, (S)-isopropyl, and (S)-4-tetrahydropyranyl. In another embodiment of the present invention, $R^2$ is selected from the group consisting of (S)-cyclohexyl, (S)-isopropyl, and (S)-4-tetrahydropyranyl. In another embodiment of the present invention, $R^2$ is selected from the group consisting of (S)-isopropyl and (S)-4-tetrahydropyranyl.

In an embodiment of the present invention, $R^2$ is selected from the group consisting of hydrogen, $C_{1-6}$alkyl, hydroxy substituted $C_{1-4}$alkyl, —$C_{1-4}$alkyl-O—$C_{1-4}$alkyl, —$C_{1-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group, whether alone or as part of a substituent group, is optionally substituted with one to two substituent independently selected from the group consisting of hydroxy, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one).

In another embodiment of the present invention, $R^2$ is selected from the group consisting of hydrogen, $C_{1-4}$alkyl, hydroxy substituted $C_{1-4}$alkyl, —$C_{1-4}$alkyl-O—$C_{1-4}$alkyl, —$C_{1-4}$alkyl-O-aralkyl, cycloalkyl, heterocycloalkyl and —$C_{1-4}$alkyl-heterocycloalkyl.

In another embodiment of the present invention, $R^2$ is selected from the group consisting of hydrogen, cyclohexyl, (S)-cyclohexyl, (R)-cyclohexyl, isopropyl, (S)-isopropyl, (R)-isopropyl, (S)-isobutyl, 1-(2-hydroxy-ethyl), 1-(S)-(1-(R)-hydroxy-ethyl), 1-(2-methoxy-ethyl), 1-(2-isopropyloxy-ethyl), 1-(S)-(1-(R)-benzyloxy-ethyl), (S)-(2-benzyloxy-ethyl), 4-tetrahydropyranyl, (S)-4-tetrahydropyranyl and (S)-4-tetrahydropyranyl-methyl.

In another embodiment of the present invention, $R^2$ is selected from the group consisting of (S)-cyclohexyl, (R)-cyclohexyl, (S)-isopropyl, (R)-isopropyl, 1-(S)-(1-(R)-hydroxy-ethyl), 1-(S)-(1-(R)-benzyloxy-ethyl) and (S)-4-tetrahydropyranyl. In another embodiment of the present invention, $R^2$ is selected from the group consisting of (S)-cyclohexyl, (R)-cyclohexyl, (S)-isopropyl, (R)-isopropyl, (S)-4-tetrahydropyranyl and 1-(S)-(1-(R)-hydroxy-ethyl). In another embodiment of the present invention, $R^2$ is selected from the group consisting of (S)-cyclohexyl, (R)-cyclohexyl, (S)-isopropyl and (S)-4-tetrahydropyranyl.

In an embodiment of the present invention b is an integer from 0 to 3. In another embodiment of the present invention b is an integer from 1 to 2. In another embodiment of the present invention b is 2.

In an embodiment of the present invention, $L^2$ is selected from the group consisting of —$(CH_2)_b$—; b is an integer from 0 to 3. In another embodiment of the present invention, $L^2$ is selected from the group consisting of —$CH_2$—, —$CH_2$—$CH_2$— and —$CH_2CH_2CH_2$—.

In an embodiment of the present invention, $R^3$ is selected from the group consisting of

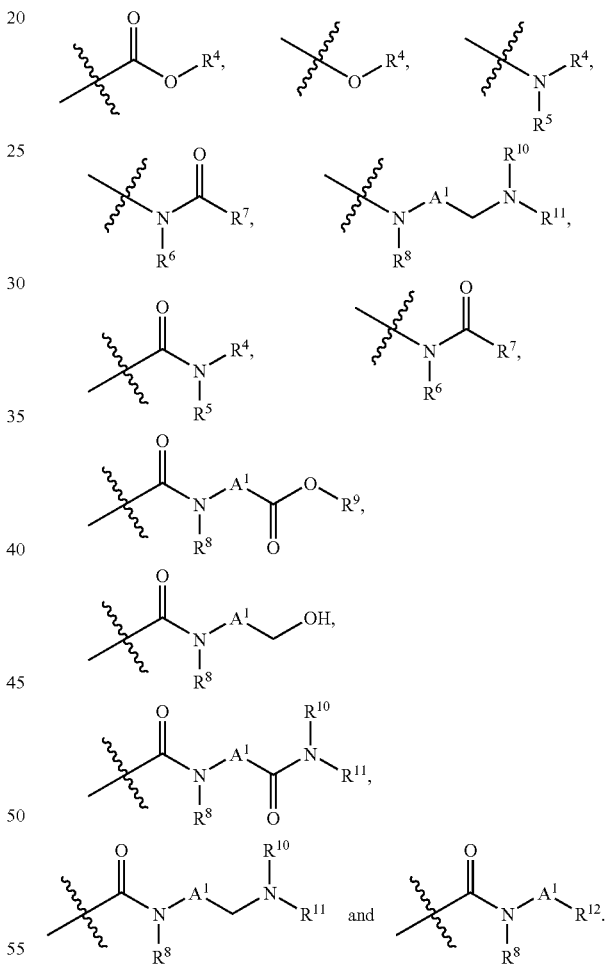

In another embodiment of the present invention, $R^3$ is selected from the group consisting of

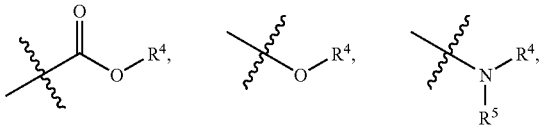

-continued
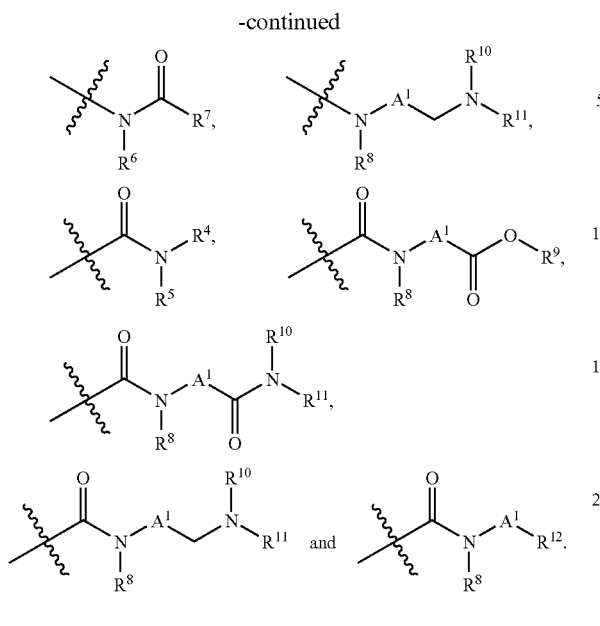
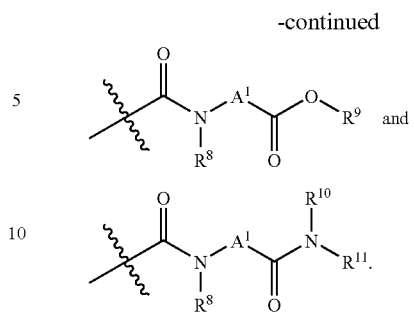
In another embodiment of the present invention, $R^3$ is selected from the group consisting of
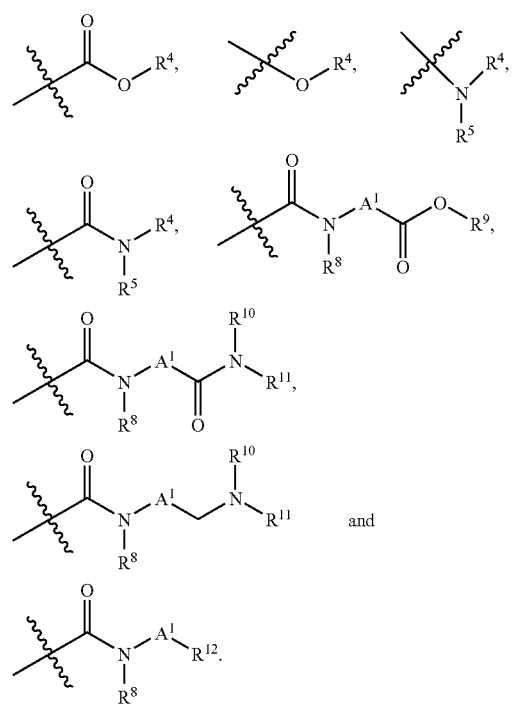
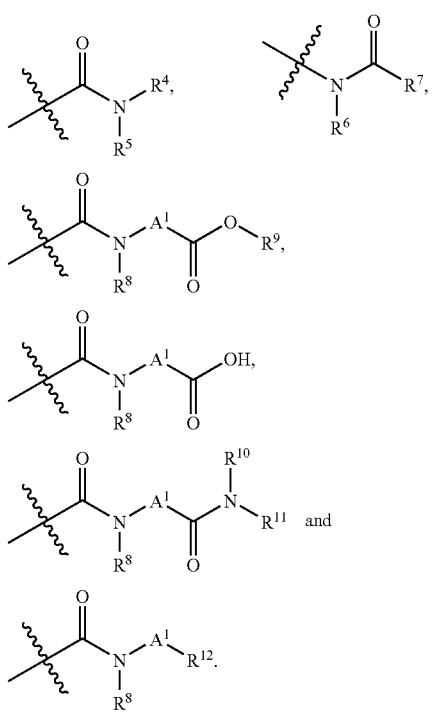
In another embodiment of the present invention, $R^3$ is selected from the group consisting of
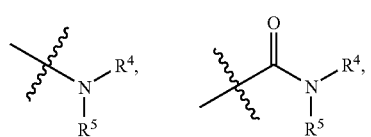
In another embodiment of the present invention, $R^3$ is selected from the group consisting of
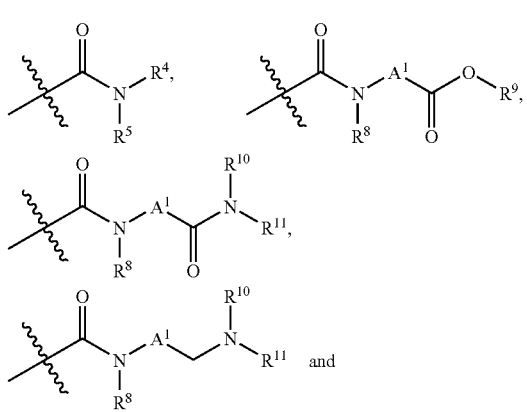

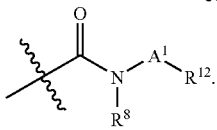

In another embodiment of the present invention, $R^3$ is selected from the group consisting of

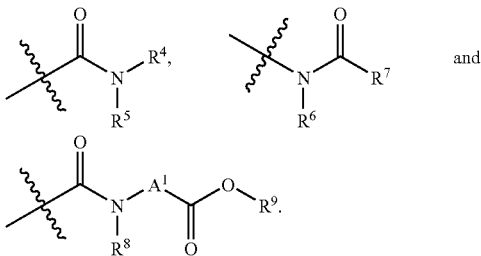

In another embodiment of the present invention, $R^3$ is selected from the group consisting of

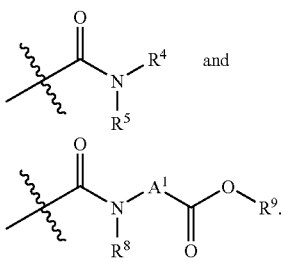

In another embodiment of the present invention, $R^3$ is selected from the group consisting of

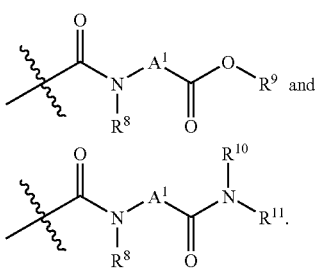

In an embodiment of the present invention, $R^4$ and $R^5$ are each independently selected from the group consisting of hydrogen, $C_{1-8}$alkyl, hydroxy substituted $C_{1-4}$alkyl, —$C_{2-4}$alkyl-O—$C_{1-4}$alkyl, —$C_{2-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the $C_{1-8}$alkyl is optionally substituted with one to two substituents independently selected from the group consisting of hydroxy and carboxy; and wherein the cycloalkyl, aryl, heteroaryl or heterocycloalkyl, whether alone or as part of a substituent group, is optionally substituted with one to three substituents independently selected from the group consisting of hydroxy, carboxy, —C(O)O— $C_{1-4}$alkyl, $C_{1-4}$alkyl, $C_{1-4}$alkoxy, cyano, 5-(1,2,3,4-tetrazolyl) and 1-(1,4-dihydro-tetrazol-5-one).

In another embodiment of the present invention, $R^4$ and $R^5$ are each independently selected from the group consisting of hydrogen, $C_{1-6}$alkyl, hydroxy substituted $C_{1-4}$alkyl, —$C_{1-4}$alkyl-O—$C_{1-4}$alkyl, —$C_{2-4}$alkyl-O-aralkyl and cycloalkyl. In another embodiment of the present invention, $R^4$ and $R^5$ are each independently selected from the group consisting of $C_{1-6}$alkyl, cycloalkyl, —$C_{1-4}$alkyl-cycloalkyl, aralkyl, heteroaryl, —$C_{1-4}$alkyl-heteroaryl and —$C_{1-4}$alkyl-heterocycloalkyl; wherein the alkyl, cycloalkyl, heteroaryl or heterocycloalkyl, whether alone or as part of a substituent group, is optionally substituted with one to two substituents independently selected from the group consisting of hydroxy, carboxy, cyano, $C_{1-4}$alkyl, $C_{1-4}$alkoxy, —C(O)O—$C_{1-4}$alkyl and 5-(1,2,3,4-tetrazolyl).

In another embodiment of the present invention, $R^4$ and $R^5$ are each independently selected from the group consisting of hydrogen, methyl, 1-(2-hydroxy-ethyl), 1-(2-benzyloxy-ethyl), 1-(3-hydroxy-n-propyl), 1-(2-t-butoxy-ethyl), 1-(3,3-dimethyl-n-butyl) and cyclohexyl. In another embodiment of the present invention, $R^4$ and $R^5$ are each independently selected from the group consisting of ethoxy-carbonyl-ethyl, 1-(2-carboxy-ethyl), cyclohexyl, isopropyl, 2-(1,3-dihydroxy-n-propyl), 1-(4-carboxy-n-butyl), 3-n-pentyl, t-butyl, 1-(3,3-dimethyl-n-butyl), 4-carboxy-cyclohexyl, 4-cyano-cyclohexyl, 4-(5-(1,2,3,4-tetrazolyl))-cyclohexyl, 4-ethoxy-carbonyl-cyclohexyl, cis-(4-methoxy-carbonyl-cyclohexyl), cis-(4-carboxy-cyclohexyl), trans-(4-methoxy-carbonyl-cyclohexyl), trans-(4-carboxy-cyclohexyl), phenyl-ethyl, cyclopentyl-methyl, 2-adamantyl, 5-(1,2,3,4-tetrazolyl)-methyl, 2-imidazolyl-methyl, 2-pyridyl-methyl, 3-pyridyl-methyl, 4-pyridyl-methyl, 4-pyridyl-ethyl, 3-(1,2,4-triazolyl)-methyl, 1-pyrrolidinyl-ethyl, 4-imidazolyl-methyl, 2-(1-methyl-imidazolyl), 2-(1-methyl-imidazolyl)-methyl, 2-furyl-methyl, 1-(2-(4-morpholinyl)-ethyl), 1-(3-(4-morpholinyl)-n-propyl), 5-(2,2-dimethyl-1,3-dioxanyl), —CH((R)-isopropyl)-CH$_2$OH, 2-(S)-(1-hydroxy-3-t-butoxy-n-propyl), 1-(R)-(1-(3-(5-methyl-1,2,4-oxadiazolyl))-2-t-butoxy)-ethyl and 1-(1-(5-(R)-1,2,3,4-tetrazolyl)-2-t-butoxy)-ethyl.

In another embodiment of the present invention, $R^4$ and $R^5$ are each independently selected from the group consisting of hydrogen, methyl, 1-(2-hydroxy-ethyl), 1-(2-benzyloxy-ethyl) and 1-(3-hydroxy-n-propyl). In another embodiment of the present invention, $R^4$ and $R^5$ are each independently selected from the group consisting of cyclohexyl, isopropyl, 3-n-pentyl, 4-carboxy-cyclohexyl, cis-(4-methoxy-carbonyl-cyclohexyl), cis-(4-carboxy-cyclohexyl), trans-(4-methoxy-carbonyl-cyclohexyl), 2-adamantyl and —CH((R)-isopropyl)-CH$_2$—OH.

In another embodiment of the present invention, $R^4$ and $R^5$ are each independently selected from the group consisting of hydrogen, methyl, 1-(2-hydroxy-ethyl) and 1-(2-benzyloxy-ethyl). In another embodiment of the present invention, $R^4$ and $R^5$ are each independently selected from the group consisting of cyclohexyl, 3-n-pentyl, 4-carboxy-cyclohexyl, cis-(4-methoxy-carbonyl-cyclohexyl), cis-(4-carboxy-cyclohexyl), trans-(4-methoxy-carbonyl-cyclohexyl), 2-adamantyl and —CH((R)-isopropyl)-CH$_2$—OH.

In another embodiment of the present invention, $R^4$ and $R^5$ are each independently selected from the group consisting of methyl, 1-(2-hydroxy-ethyl) and 1-(2-benzyloxy-ethyl). In another embodiment of the present invention, $R^4$ and $R^5$ are each independently selected from the group consisting of cyclohexyl, 4-carboxy-cyclohexyl, cis-(4-methoxy-carbonyl-cyclohexyl) and cis-(4-carboxy-cyclohexyl).

In another embodiment of the present invention, $R^4$ and $R^5$ are each independently selected from the group consisting of hydrogen, 1-(2-hydroxy-ethyl), and cyclohexyl. In another embodiment of the present invention, $R^4$ and $R^5$ are each independently selected from the group consisting of cyclohexyl, t-butyl, 5-(1,2,3,4-tetrazlyl)-methyl, 2-imidazolyl-methyl, 4-pyridyl-methyl, 3-(1,2,4-triazolyl)-methyl, 2-(1-methyl-imidazolyl)-methyl and 1-(R)-(1-(3-(5-methyl-1,2,4-oxadiazolyl))-2-t-butoxy)-ethyl.

In another embodiment of the present invention, $R^4$ and $R^5$ are each independently selected from the group consisting of hydrogen, 1-(2-hydroxy-ethyl) and cyclohexyl. In another embodiment of the present invention, $R^4$ and $R^5$ are each independently is selected from the group consisting of cyclohexyl, 2-imidazolyl-methyl, 4-pyridyl-methyl, 3-(1,2,4-triazolyl)-methyl, 2-(1-methyl-imidazolyl)-methyl and 1-(R)-(1-(3-(5-methyl-1,2,4-oxadiazolyl))-2-t-butoxy)-ethyl.

In an embodiment of the present invention, $R^4$ is selected from the group consisting of 1-(2-hydroxy-ethyl) and cyclohexyl. In an embodiment of the present invention, $R^5$ is 2-(1-methyl-imidazolyl)-methyl.

In an embodiment of the present invention, $R^4$ and $R^5$ are each independently selected from the group consisting of hydrogen, $C_{1-8}$alkyl, $C_{2-8}$alkenyl, —$C_{2-4}$alkyl-O—$C_{1-4}$alkyl, —$C_{2-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$CH_2CH_2$—O—$CH_2CH_2$—O—$CH_2CH_2$—O—$CH_2CH_2$—OH; wherein the alkyl, whether alone or as part of a substituent group, is optionally substituted with one to two substituents independently selected from the group consisting of hydroxy, carboxy, $C_{1-4}$alkoxy, —C(O)O—$C_{1-4}$alkyl, $NR^AR^B$, —$NR^L$—C(O)O—$C_{1-4}$alkyl and —$NR^L$—$SO_2$—$NR^AR^B$; wherein the cycloalkyl, aryl, heteroaryl or heterocycloalkyl, whether alone or as part of a substituent group, is optionally substituted with one or more substituents independently selected from the group consisting of fluoro, chloro, hydroxy, carboxy, oxo, —C(O)O—$C_{1-4}$alkyl, $C_{1-6}$alkyl, $C_{1-4}$alkoxy, cycloalkyl, —$C_{1-4}$alkyl-cycloalkyl, cyano, 5-(1,2,3,4-tetrazolyl) and 1-(1,4-dihydro-tetrazol-5-one); wherein $R^L$, $R^A$ and $R^B$, at each occurrence, are each independently selected from the group consisting of hydrogen, $C_{1-2}$alkyl and t-butoxy-carbonyl-; provided that the chloro is not bound to a cycloalkyl or heterocycloalkyl.

In another embodiment of the present invention, $R^4$ and $R^5$ are each independently selected from the group consisting of hydrogen, $C_{1-6}$alkyl, $C_{2-8}$alkenyl, hydroxy substituted $C_{1-4}$alkyl, —$C_{2-4}$alkyl-O—$C_{1-4}$alkyl, —$C_{2-4}$alkyl-O-aralkyl, cycloalkyl, —$C_{1-4}$alkyl-cycloalkyl, aralkyl, —$C_{1-4}$alkyl-heteroaryl and —$C_{1-4}$alkyl-heterocycloalkyl; wherein the —$C_{1-4}$alkyl-heteroaryl or —$C_{1-4}$alkyl-heterocycloalkyl is optionally substituted on the heteroaryl or heterocycloalkyl portion with a substituent selected from the group consisting of $C_{1-6}$alkyl, $C_{3-8}$cycloalkyl and —$C_{1-4}$alkyl-$C_{3-8}$cycloalkyl.

In another embodiment of the present invention, $R^4$ and $R^5$ are each independently selected from the group consisting of hydrogen, methyl, n-propyl, isobutyl, t-butyl, 1-(2-hydroxy-ethyl), 1-(2-benzyloxy-ethyl), 1-(3-hydroxy-n-propyl), 1-(2-methoxy-ethyl), 1-(2-t-butoxy-ethyl), 1-(3,3-dimethyl-n-butyl), 1-(3-methyl-buten-2-yl), 1-(2-propen-2-yl), cyclohexyl, cyclohexyl-methyl, cyclohexyl-ethyl, benzyl, 5-(3-t-butyl-isoxazolyl)-methyl, 5-(3-cyclohexyl-4,5-dihydro-isoxazolyl)-methyl, 5-(3-t-butyl-4,5-dihydro-isoxazolyl)-methyl, 5-(3-(2,2-dimethyl-n-propyl)-4,5-dihydro-isoxazolyl)-methyl and 4-(1-cyclohexylmethyl-1,2,3-triazolyl)-methyl.

In another embodiment of the present invention, $R^4$ and $R^5$ are each independently selected from the group consisting of hydrogen, methyl, isobutyl, 1-(2-hydroxy-ethyl), 1-(3,3-dimethyl-n-butyl), 1-(2-methoxy-ethyl), 1-(2-t-butoxy-ethyl), cyclohexyl, cyclohexyl-methyl, cyclohexyl-ethyl, benzyl, 5-(3-t-butyl-isoxazolyl)-methyl and 5-(3-t-butyl-4,5-dihydro-isoxazolyl)-methyl.

In another embodiment of the present invention, $R^4$ and $R^5$ are each independently selected from the group consisting of hydrogen, methyl, isobutyl, 1-(2-hydroxy-ethyl), 1-(3,3-dimethyl-n-butyl), 1-(2-t-butoxy-ethyl), cyclohexyl, cyclohexyl-methyl, cyclohexyl-ethyl, benzyl and 5-(3-t-butyl-4,5-dihydro-isoxazolyl)-methyl.

In another embodiment of the present invention, $R^4$ and $R^5$ are each independently selected from the group consisting of hydrogen, methyl, isobutyl, 1-(2-hydroxy-ethyl), 1-(2-t-butoxy-ethyl), 1-(3,3-dimethyl-n-butyl) and cyclohexyl.

In another embodiment of the present invention, $R^4$ and $R^5$ are each independently selected from the group consisting of $C_{1-6}$alkyl, —$C_{2-4}$alkyl-O—$C_{1-4}$alkyl, cycloalkyl, —$C_{1-4}$alkyl-cycloalkyl, aralkyl, heteroaryl, —$C_{1-4}$alkyl-heteroaryl, —$C_{1-4}$alkyl-heterocycloalkyl and —$CH_2CH_2$—O—$CH_2CH_2$—O—$CH_2CH_2$—O—$CH_2CH_2$—OH; wherein the alkyl, whether alone or as part of a substituent group, is optionally substituted with one to two substituent independently selected from the group consisting of hydroxy, carboxy, $C_{1-4}$alkoxy, —C(O)O—$C_{1-4}$alkyl, $NR^AR^B$, —$NR^L$—C(O)—O—$C_{1-4}$alkyl, and —$NR^L$—$SO_2$—$NR^AR^B$; wherein the cycloalkyl, aryl, heteroaryl or heterocycloalkyl, whether alone or as part of a substituent group, is optionally substituted with one to three substituents independently selected from the group consisting of fluoro, chloro, hydroxy, carboxy, oxo, cyano, $C_{1-4}$alkyl, $C_{1-4}$alkoxy, —C(O)O—$C_{1-4}$alkyl and 5-(1,2,3,4-tetrazolyl); wherein $R^L$, $R^A$ and $R^B$, at each occurrence, are each independently selected from the group consisting of hydrogen, $C_{1-2}$alkyl and t-butoxy-carbonyl-; provided that the chloro is not bound to a cycloalkyl or heterocycloalkyl.

In another embodiment of the present invention, $R^4$ and $R^5$ are each independently selected from the group consisting of 1-(2-ethoxycarbonyl-ethyl), 1-(2-methoxy-ethyl), 1-(2-carboxy-ethyl), 1-(2-hydroxy-ethyl), 1-(2-t-butoxycarbonylamino-ethyl), 1-(1,1-dimethyl-2-hydroxy-ethyl), 1-(2-t-butoxy-ethyl), 1-(2-amino-ethyl), 1-(2-dimethylamino-ethyl), 1-(2-aminosulfonylamino-ethyl), 1-(1-(R)-methyl-2-hydroxy-ethyl), 1-(1-(S)-methyl-2-hydroxy-ethyl), 1-(1-(R)-isopropyl-2-hydroxy-ethyl), isopropyl, 1-(3-ethoxy-n-propyl), 2-(1,3-dihydroxy-n-propyl), 1-(2,2-dimethyl-n-propyl), 1-(2,2-dimethyl-3-hydroxy-n-propyl), isobutyl, 1-(4-carboxy-n-butyl), 3-n-pentyl, isobutyl, t-butyl, 1-(3,3-dimethyl-n-butyl), cyclohexyl, 4-carboxy-cyclohexyl, 4-cyano-cyclohexyl, 4-(5-(1,2,3,4-tetrazolyl))-cyclohexyl, 4-ethoxy-carbonyl-cyclohexyl, cis-(4-methoxy-carbonyl-cyclohexyl), cis-(4-carboxy-cyclohexyl), trans-(4-methoxy-carbonyl-cyclohexyl), trans-(4-carboxy-cyclohexyl), 4-fluorobenzyl, phenyl-ethyl, 1-(3-phenyl-n-propyl), cyclopropyl-methyl, cyclopentyl-methyl, 2-adamantyl, 5-(1,2,3,4-tetrazolyl)-methyl, 2-imidazolyl-methyl, 2-(1-methyl-4,5-dichloro-imidazolyl)-methyl, 2-pyridyl-methyl, 3-pyridyl-methyl, 4-pyridyl-methyl, 4-pyridyl-ethyl, 3-(1,2,4-triazolyl)-methyl, 1-(2-(1-pyrrolidinyl)-ethyl), 4-imidazolyl-methyl, 2-(1-methyl-imidazolyl), 2-(1-methyl-imidazolyl)-methyl, 2-furyl-methyl, 2-(R)-tetrahydrofuryl-methyl, 2-thienyl-methyl, 3-thienyl-methyl, 3-(1,1-dioxo-tetrahydro-thienyl), 2-thiazolyl-methyl, 5-thiazolyl-methyl, 1-(2-(4-morpholinyl)-ethyl), 1-(3-(4-morpholinyl)-n-propyl), 4-(1-t-butoxycarbonyl-piperidinyl), 5-(2,2-dimethyl-1,3-dioxanyl), —CH((R)-isopropyl)-$CH_2$OH, 2-(S)-(1-hydroxy-3-t-butoxy-n-propyl), 1-(R)-(1-(3-(5-methyl-1,2,4-oxadiazolyl))-

2-t-butoxy)-ethyl, 1-(1-(5-(R)-1,2,3,4-tetrazolyl)-2-t-butoxy)-ethyl and —CH$_2$CH$_2$—O—CH$_2$CH$_2$—O—CH$_2$CH$_2$—O—CH$_2$CH$_2$—OH.

In another embodiment of the present invention, R$^4$ and R$^5$ are each independently selected from the group consisting of cyclohexyl, isobutyl, t-butyl, 1-(2-methoxy-ethyl), 1-(2-hydroxy-ethyl), 1-(2-t-butoxy-ethyl), 1-(3-ethoxy-n-propyl), 1-(2,2-dimethyl-3-hydroxy-n-propyl), 1-(1,1-dimethyl-2-hydroxy-ethyl), 1-(2,2-dimethyl-n-propyl), 1-(3,3-dimethyl-n-butyl), 4-fluorobenzyl, cyclopropyl-methyl, 5-(1,2,3,4-tetrazolyl)-methyl, 2-imidazolyl-methyl, 5-thiazolyl-methyl, 2-pyridyl-methyl, 4-pyridyl-methyl, 2-thienyl-methyl, 3-thienyl-methyl, 3-(1,2,4-triazolyl)-methyl, 2-(1-methylimidazolyl)-methyl, 2-(1-methyl-4,5-dichloro-imidazolyl)-methyl, 1-(2-(4-morpholinyl)-ethyl), 2-(R)-tetrahydrofuryl-methyl, 1-(R)-(1-(3-(5-methyl-1,2,4-oxadiazolyl))-2-t-butoxy)-ethyl, 1-(1-(R)-methyl-2-hydroxy-ethyl), 1-(1-(S)-methyl-2-hydroxy-ethyl), 1-(2-t-butoxycarbonyl-amino-ethyl), 1-(2-aminosulfonylamino-ethyl), 1-(4-t-butoxycarbonyl-piperidinyl) and —CH$_2$CH$_2$—O—CH$_2$CH$_2$—O—CH$_2$CH$_2$—O—CH$_2$CH$_2$—OH.

In another embodiment of the present invention, R$^4$ and R$^5$ are each independently selected from the group consisting of isobutyl, 1-(2,2-dimethyl-n-propyl), 1-(3,3-dimethyl-n-butyl), 1-(3-ethoxy-n-propyl), 1-(2-t-butoxy-ethyl), 1-(2,2-dimethyl-3-hydroxy-n-propyl), 1-(1,1-dimethyl-2-hydroxy-ethyl), 1-(1-(R)-methyl-2-hydroxy-ethyl), cyclohexyl, cyclopropyl-methyl, 4-fluorobenzyl, 1-(2-(4-morpholinyl)-ethyl), 2-imidazolyl-methyl, 2-pyridyl-methyl, 4-pyridyl-methyl, 2-thienyl-methyl, 3-thienyl-methyl, 3-(1,2,4-triazolyl)-methyl, 5-thiazolyl-methyl, 2-(1-methyl-imidazolyl)-methyl, 2-(1-methyl-4,5-dichloro-imidazolyl)-methyl, 1-(R)-(1-(3-(5-methyl-1,2,4-oxadiazolyl))-2-t-butoxy)-ethyl, 4-(1-t-butoxycarbonyl-piperidinyl), 2-(R)-tetrahydrofuryl-methyl, 1-(2-t-butoxycarbonylamino-ethyl) and 1-(2-aminosulfonylamino-ethyl) and —CH$_2$CH$_2$—O—CH$_2$CH$_2$—O—CH$_2$CH$_2$—O—CH$_2$CH$_2$—OH.

In another embodiment of the present invention, R$^4$ and R$^5$ are each independently selected from the group consisting of 1-(1-(R)-methyl-2-hydroxy-ethyl), 1-(1,1-dimethyl-2-hydroxy-ethyl), 1-(2-t-butoxy-ethyl), 1-(2-t-butoxycarbonylamino-ethyl), 1-(2-aminosulfonylamino-ethyl), 1-(2,2-dimethyl-n-propyl), 1-(2,2-dimethyl-3-hydroxy-n-propyl), 1-(3,3-dimethyl-n-butyl), cyclopropyl-methyl, 2-(1-methyl-imidazolyl)-methyl, 2-pyridyl-methyl and 1-(2-(4-morpholinyl)-ethyl).

In an embodiment of the present invention, R$^4$ and R$^5$ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one).

In another embodiment of the present invention, R$^4$ and R$^5$ are taken together with the nitrogen atom to which they are bound to form a heterocyclyl ring containing at least one nitrogen atom; wherein the heterocyclyl ring is optionally substituted with carboxy.

In another embodiment of the present invention, R$^4$ and R$^5$ are taken together with the nitrogen atom to which they are bound to form a heterocyclyl ring selected form the group consisting of 1-(2-(S)-carboxy-pyrrolidinyl), 1-(2-(S)-carboxy-octahydroindolyl) and 1-(2-(S)-carboxy-piperidinyl).

In another embodiment of the present invention, R$^4$ and R$^5$ are taken together with the nitrogen atom to which they are bound to form a heterocyclyl ring selected form the group consisting of 1-(2-(S)-carboxy-octahydroindolyl) and 1-(2-(S)-carboxy-piperidinyl).

In an embodiment of the present invention, R$^4$ and R$^5$ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—C$_{1-4}$alkyl, C$_{1-6}$alkyl, —C$_{1-4}$alkyl-OH, C$_{1-4}$alkyl-CO$_2$H, C$_{1-4}$alkoxy, cyano, C$_{4-8}$cycloalkyl, phenyl, trifluoromethylphenyl, a 5 to 6 membered heteroaryl group and 1-(1,4-dihydro-tetrazol-5-one).

In another embodiment of the present invention, R$^4$ and R$^5$ are taken together with the nitrogen atom to which they are bound to form a heterocyclyl ring containing at least one nitrogen atom; wherein the heterocyclyl ring is optionally substituted with a substituent selected from the group consisting of hydroxy, carboxy, C$_{1-6}$alkyl, —C$_{1-4}$alkyl-OH, —C$_{1-4}$alkyl-CO$_2$H, C$_{4-8}$cycloalkyl, phenyl, trifluoromethylphenyl and a 5 to 6 membered heteroaryl group.

In another embodiment of the present invention, R$^4$ and R$^5$ are taken together with the nitrogen atom to which they are bound to form a heterocyclyl ring selected form the group consisting of 4-morpholinyl, 1-(2-(S)-hydroxymethyl-pyrrolidinyl), 1-(2-(R)-hydroxymethyl-pyrrolidinyl), 1-(2-(S)-carboxy-pyrrolidinyl), 1-(2-(S)-carboxy-octahydroindolyl), 1-(4-t-butyl-1,2,3-triazolyl), 1-(4-(3,3-dimethyl-n-propyl)-1,2,3-triazolyl), 1-(4-cyclohexyl-1,2,3-triazolyl), 1-(4-hydroxymethyl-1,2,3-triazolyl), 1-(4-(2-pyridyl)-1,2,3-triazolyl), 1-(4-methyl-piperazinyl), 1-(4-phenyl-piperidinyl), 1-(4-hydroxyethyl-piperidinyl), 1-(4-hydroxy-4-(3-trifluoromethylphenyl)-piperidinyl), 1-(2-(S)-carboxymethyl-piperidinyl) and 1-(2-(S)-carboxy-piperidinyl).

In another embodiment of the present invention, R$^4$ and R$^5$ are taken together with the nitrogen atom to which they are bound to form a heterocyclyl ring selected form the group consisting of 1-(2-(S)-carboxy-octahydroindolyl), 1-(2-(S)-carboxy-piperidinyl), 1-(2-hydroxyethyl-piperidinyl), 4-morpholinyl, 1-(4-t-butyl-1,2,3-triazolyl) and 1-(4-cyclohexyl-1,2,3-triazolyl).

In another embodiment of the present invention, R$^4$ and R$^5$ are taken together with the nitrogen atom to which they are bound to form a heterocyclyl ring selected form the group consisting of 1-(2-(S)-carboxy-octahydroindolyl), 1-(2-(S)-carboxy-piperidinyl), 1-(4-t-butyl-1,2,3-triazolyl) and 1-(4-cylohexyl-1,2,3-triazolyl).

In another embodiment of the present invention, R$^4$ and R$^5$ are taken together with the nitrogen atom to which they are bound to form 1-(4-t-butyl-1,2,3-triazolyl).

In an embodiment of the present invention, R$^6$ is selected from the group consisting of hydrogen and C$_{1-2}$alkyl. In another embodiment of the present invention, R$^6$ is hydrogen.

In an embodiment of the present invention, R$^7$ is selected from the group consisting of hydrogen, C$_{1-6}$alkyl, cycloalkyl, aryl, heteroaryl, heterocycloalkyl, —C$_{1-4}$alkyl-cycloalkyl, C$_{1-4}$aralkyl, —C$_{1-4}$alkyl-heteroaryl and —C$_{1-4}$alkyl-heterocycloalkyl; wherein the C$_{1-5}$alkyl, cycloalkyl, aryl, heteroaryl or heterocycloalkyl, whether alone or as part of a substituent group is optionally substituted with one to two substituents independently selected from the group consisting of hydroxy, carboxy, C$_{1-6}$alkyl, hydroxy substituted C$_{1-4}$alkyl, carboxy substituted C$_{1-4}$alkyl, C$_{1-4}$alkoxy, cyano, —C(O)—C$_{1-4}$alkyl, —C(O)—C$_{1-4}$aralkyl, —C(O)O—C$_{1-4}$alkyl, —C(O)

O—C$_{1-4}$aralkyl, —C$_{1-4}$alkyl-C(O)O—C$_{1-4}$alkyl, phenyl, 5-(1,2,3,4-tetrazolyl) and 1-(1,4-dihydro-tetrazol-5-one); and wherein the phenyl is optionally substituted with one to two substituent independently selected from the group consisting of hydroxy, carboxy, —C(O)O—C$_{1-4}$alkyl, —C(O)—C$_{1-4}$alkyl, C$_{1-4}$alkyl and C$_{1-4}$alkoxy.

In another embodiment of the present invention, R$^7$ is selected from the group consisting of C$_{1-4}$alkyl and cycloalkyl. In another embodiment of the present invention, R$^7$ is selected from the group consisting of cyclohexyl and t-butoxy. In another embodiment of the present invention, R$^7$ is selected from the group consisting of C$_{1-4}$alkoxy and cycloalkyl. In another embodiment of the present invention, R$^7$ is t-butoxy.

In another embodiment of the present invention, R$^7$ is selected from the group consisting of hydrogen, C$_{1-6}$alkyl, C$_{1-6}$alkoxy, cycloalkyl, aryl, heteroaryl, heterocycloalkyl, —C$_{1-4}$alkyl-cycloalkyl, C$_{1-4}$aralkyl, —C$_{1-4}$alkyl-heteroaryl and —C$_{1-4}$alkyl-heterocycloalkyl-; wherein the alkyl, cycloalkyl, aryl, heteroaryl or heterocycloalkyl, whether alone or as part of a substituent group is optionally substituted with one to two substituents independently selected from the group consisting of hydroxy, carboxy, C$_{1-6}$alkyl, hydroxy substituted C$_{1-4}$alkyl, carboxy substituted C$_{1-4}$alkyl, C$_{1-4}$alkoxy, cyano, —C(O)—C$_{1-4}$alkyl, —C(O)—C$_{1-4}$aralkyl, —C(O)O—C$_{1-4}$alkyl, —C(O)O—C$_{1-4}$aralkyl, —C$_{1-4}$alkyl-C(O)O—C$_{1-4}$alkyl, phenyl, 5-(1,2,3,4-tetrazolyl) and 1-(1,4-dihydro-tetrazol-5-one); wherein the phenyl is optionally substituted with one to two substituent independently selected from the group consisting of hydroxy, carboxy, —C(O)O—C$_{1-4}$alkyl, —C(O)—C$_{1-4}$alkyl, C$_{1-4}$alkyl and C$_{1-4}$alkoxy.

In another embodiment of the present invention, R$^6$ and R$^7$ are taken together with the atoms to which they are bound to form a 5 to 10 membered, saturated nitrogen containing heterocyclyl; wherein the 5 to 10 membered, saturated nitrogen containing heterocyclyl is substituted with one to two oxo groups.

In another embodiment of the present invention, R$^6$ and R$^7$ are taken together with the atoms to which they are bound to form a 5 to 10 membered, saturated heterocycloalkyl selected from the group consisting of 3-(1,3-diaza-spiro[4.5]decan-2-one) and 1-(1,3-diaza-spiro[4.5]decane-2,4-dione).

In an embodiment of the present invention, R$^8$ is selected from the group consisting of hydrogen, C$_{1-4}$alkyl and C$_{3-8}$cycloalkyl. In another embodiment of the present invention, R$^8$ is selected from the group consisting of hydrogen, C$_{1-4}$alkyl and C$_{5-6}$cycloalkyl. In another embodiment of the present invention, R$^8$ is selected from the group consisting of hydrogen, methyl and cyclohexyl. In another embodiment of the present invention, R$^8$ is selected from the group consisting of hydrogen and methyl. In another embodiment of the present invention, R$^8$ is hydrogen.

In an embodiment of the present invention, A$^1$ is —C$_{1-4}$alkyl-; wherein the alkyl is optionally substituted with one to two substituents independently selected from the group consisting of C$_{2-8}$alkyl, hydroxy substituted C$_{1-4}$alkyl, C$_{1-4}$alkoxy substituted C$_{1-4}$alkyl, aralkyloxy substituted C$_{1-4}$alkyl, cycloalkyl, —C$_{1-4}$alkyl-cycloalkyl, aryl, aralkyl, heteroaryl, —C$_{1-4}$alkyl-heteroaryl, heterocycloalkyl and —C$_{1-4}$alkyl-heterocycloalkyl; wherein the cycloalkyl, aryl, heteroaryl or heterocycloalkyl, whether alone or as part of a substituent group, is optionally substituted with one to two substituents independently selected from the group consisting of hydroxy, carboxy, C$_{1-4}$alkyl, C$_{1-4}$alkoxy, hydroxy substituted C$_{1-4}$alkyl, —C(O)O—C$_{1-4}$alkyl, 5-(1,2,3,4-tetrazolyl) and 1-(1,4-dihydro-tetrazol-5-one).

In another embodiment of the present invention, A$^1$ is —C$_{1-2}$alkyl-; wherein the alkyl is optionally substituted with a substituent selected from the group consisting of hydroxy-C$_{1-2}$alkyl, C$_{1-4}$alkoxy substituted C$_{1-2}$alkyl, benzyloxy substituted C$_{1-2}$alkyl and aralkyl.

In another embodiment of the present invention, A$^1$ is selected from the group consisting of —CH$_2$—, —CH(CH$_2$—OH)—, —CH—((R)—CH$_2$—OH)—, —CH—((S)—CH$_2$—OH)—, —CH(CH$_2$—O-t-butyl)-,—CH((R)—CH$_2$—O-t-butyl)-, —CH((S)—CH$_2$—O-t-butyl)-, —CH(CH$_2$—O-benzyl)-, —CH((S)—CH$_2$—O-benzyl)-, —CH((R)—CH$_2$—O-benzyl)-, —CH(benzyl)-, —CH((R)-benzyl)- and —CH((S)-benzyl)-.

In another embodiment of the present invention, A$^1$ is selected from the group consisting of —CH—((R)—CH$_2$—OH)—, —CH—((S)—CH$_2$—OH)—, —CH((S)—CH$_2$—O-benzyl)- and —CH((R)—CH$_2$—O-benzyl)-. In another embodiment of the present invention, A$^1$ is selected from the group consisting of —CH—((R)—CH$_2$—OH)—, —CH((S)—CH$_2$—O-benzyl)- and —CH((R)—CH$_2$—O-benzyl)-. In another embodiment of the present invention, A$^1$ is selected from the group consisting of —CH—((R)—CH$_2$—OH)— and —CH((S)—CH$_2$—O-benzyl)-.

In another embodiment of the present invention, A$^1$ is selected from the group consisting of —CH$_2$—, —CH((R)—CH$_2$—O-t-butyl)-, —CH((S)—CH$_2$—O-t-butyl)-, —CH((S)—CH$_2$—O-benzyl)- and —CH((R)—CH$_2$—O-benzyl)-. In another embodiment of the present invention, A$^1$ is selected from the group consisting of —CH((R)—CH$_2$—O-t-butyl)- and —CH((S)—CH$_2$—O-benzyl)-.

In another embodiment of the present invention, A$^1$ is selected from the group consisting of —CH$_2$—, —CH(CH$_2$—OH)—, —CH—((R)—CH$_2$—OH)—, —CH—((S)—CH$_2$—OH)—, —CH(CH$_2$—O-t-butyl)-, —CH((R)—CH$_2$—O-t-butyl)-, —CH((S)—CH$_2$—)-t-butyl)-, —CH(CH$_2$—O-benzyl)-, —CH((S)—CH$_2$—O-benzyl)-, —CH((R)—CH$_2$—O-benzyl)-, —CH(benzyl)-, —CH((R)-benzyl)- and —CH((S)-benzyl)-.

In another embodiment of the present invention, A$^1$ is selected from the group consisting of —CH$_2$—, —CH((R)—CH$_2$—O-t-butyl)-, —CH((S)—CH$_2$—O-t-butyl)-, —CH((S)—CH$_2$—O-benzyl)- and —CH((R)—CH$_2$—O-benzyl)-.

In an embodiment of the present invention, R$^9$ is selected from the group consisting of hydrogen, C$_{1-6}$alkyl, hydroxy substituted C$_{1-6}$alkyl, C$_{1-6}$alkoxy, C$_{3-8}$cycloalkyl, —C$_{1-4}$alkyl-C$_{3-8}$cycloalkyl, aryl, aralkyl, heteroaryl, —C$_{1-4}$alkyl-heteroaryl, heterocycloalkyl and —C$_{1-4}$alkyl-heterocycloalkyl; wherein the C$_{3-8}$cycloalkyl, aryl, heteroaryl or heterocycloalkyl, whether alone or as part of a substituent group, is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one).

In another embodiment of the present invention, R$^9$ is selected from the group consisting of hydrogen, C$_{1-4}$alkyl and aralkyl. In another embodiment of the present invention, R$^9$ is selected from the group consisting of hydrogen, methyl and benzyl. In another embodiment of the present invention, R$^9$ is selected from the group consisting of hydrogen and methyl. In another embodiment of the present invention, R$^9$ is methyl.

In an embodiment of the present invention, R$^9$ is selected from the group consisting of hydrogen, C$_{1-6}$alkyl, hydroxy substituted C$_{1-6}$alkyl, C$_{1-6}$alkoxy, C$_{3-8}$cycloalkyl, —C$_{1-4}$alkyl-C$_{3-8}$cycloalkyl, aryl, aralkyl, heteroaryl, —C$_{1-4}$alkyl-heteroaryl, heterocycloalkyl and —C$_{1-4}$alkyl-heterocycloalkyl; wherein the C$_{3-8}$cycloalkyl, aryl, heteroaryl or heterocycloalkyl, whether alone or as part of a substituent group, is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one).

In another embodiment of the present invention, $R^9$ is selected from the group consisting of hydrogen, $C_{1-4}$alkyl and aralkyl. In another embodiment of the present invention, $R^9$ is selected from the group consisting of hydrogen, methyl, ethyl, isopropyl and benzyl. In another embodiment of the present invention, $R^9$ is selected from the group consisting of hydrogen, methyl and isopropyl. In another embodiment of the present invention, $R^9$ is methyl.

In an embodiment of the present invention, $R^{10}$ and $R^{11}$ are each independently selected from the group consisting of hydrogen, $C_{1-6}$alkyl, hydroxy substituted $C_{1-4}$alkyl, —$C_{2-4}$alkyl-O—$C_{1-4}$alkyl, benzyloxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl, whether alone or as part of a substituent group is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, 5-(1,2,3,4-tetrazolyl) and 1-(1,4-dihydro-tetrazol-5-one).

In another embodiment of the present invention, $R^{10}$ and $R^{11}$ are each independently selected from the group consisting of hydrogen and hydroxy substituted $C_{1-4}$alkyl. In another embodiment of the present invention, $R^{10}$ is hydrogen.

In another embodiment of the present invention, $R^{10}$ and $R^{11}$ are each independently selected from the group consisting of hydrogen, —CH—(CH$_3$)—CH$_2$OH, —CH—((R)—CH$_3$)—CH$_2$OH and —CH—((S)—CH$_3$)—CH$_2$OH. In another embodiment of the present invention, $R^{10}$ and $R^{11}$ are each independently selected from the group consisting of hydrogen, —CH—((R)—CH$_3$)—CH$_2$OH and —CH—((S)—CH$_3$)—CH$_2$OH.

In an embodiment of the present invention, $R^{10}$ and $R^{11}$ are each independently selected from the group consisting of hydrogen, $C_{1-6}$alkyl, hydroxy substituted $C_{1-4}$alkyl, —$C_{2-4}$alkyl-O—$C_{1-4}$alkyl, benzyloxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and $C_{2-6}$dialkanoic acid; wherein the cycloalkyl, aryl, heteroaryl or heterocycloalkyl, whether alone or as part of a substituent group is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, 5-(1,2,3,4-tetrazolyl) and 1-(1,4-dihydro-tetrazol-5-one).

In another embodiment of the present invention, $R^{10}$ and $R^{11}$ are each independently selected from the group consisting of hydrogen, hydroxy substituted $C_{1-4}$alkyl and $C_{2-6}$dialkanoic acid. In another embodiment of the present invention, $R^{10}$ and $R^{11}$ are each independently selected from the group consisting of hydrogen, —CH—(CH$_3$)—CH$_2$OH, —CH—((R)—CH$_3$)—CH$_2$OH, —CH—((S)—CH$_3$)—CH$_2$OH, 2-(S)-pentadoic acid and 2-(R)-pentadoic acid. In another embodiment of the present invention, $R^{10}$ and $R^{11}$ are each independently selected from the group consisting of hydrogen, —CH—((R)—CH$_3$)—CH$_2$OH, —CH—((S)—CH$_3$)—CH$_2$OH, 2-(S)-pentadioic acid and 2-(R)-pentadioic acid.

In another embodiment of the present invention, $R^{10}$ is hydrogen. In another embodiment of the present invention, $R^{11}$ is 2-(S)-pentadioic acid.

In an embodiment of the present invention, $R^{10}$ and $R^{11}$ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, 5-(1,2,3,4-tetrazolyl) and 1-(1,4-dihydro-tetrazol-5-one).

In another embodiment of the present invention, $R^{10}$ and $R^{11}$ are taken together with the nitrogen atom to which they are bound to form a heterocyclyl ring containing at least one nitrogen atom and further containing 0 to 1 heteroatoms independently selected from O or N.

In another embodiment of the present invention, $R^{10}$ and $R^{11}$ are taken together with the nitrogen atom to which they are bound to form a heterocyclyl ring selected from the group consisting of 1-piperidinyl and 4-morpholinyl. In another embodiment of the present invention, $R^{10}$ and $R^{11}$ are taken together with the nitrogen atom to which they are bound to form 4-morpholinyl.

In an embodiment of the present invention, $R^{10}$ and $R^{11}$ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, 5-(1,2,3,4-tetrazolyl) and 1-(1,4-dihydro-tetrazol-5-one).

In another embodiment of the present invention, $R^{10}$ and $R^{11}$ are taken together with the nitrogen atom to which they are bound to form a 5 to 6 membered heterocyclyl ring containing at least one nitrogen atom. In another embodiment of the present invention, $R^{10}$ and $R^{11}$ are taken together with the nitrogen atom to which they are bound to form a heterocyclyl ring selected from the group consisting of 1-piperidinyl and 4-morpholinyl. In another embodiment of the present invention, $R^{10}$ and $R^{11}$ are taken together with the nitrogen atom to which they are bound to form 4-morpholinyl.

In an embodiment of the present invention, $R^{12}$ is selected from the group consisting of $C_{1-4}$alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, benzyl, 5-(1,2,3,4-tetrazolyl) and 1-(1,4-dihydro-tetrazol-5-one).

In another embodiment of the present invention, $R^{12}$ is selected from the group consisting of hydroxy substituted $C_{1-4}$alkyl, 5-(1,2,3,4-tetrazolyl), benzyl substituted 5-(1,2,3,4-tetrazolyl) and —$C_{1-4}$alkyl-heterocyclyoalkyl. In another embodiment of the present invention, $R^{12}$ is selected from the group consisting of hydroxy-methyl, 5-(1-benzyl-1,2,3,4-tetrazolyl), 5-(1,2,3,4-tetrazolyl), 1-piperidinyl-methyl and 4-morpholinyl-methyl. In another embodiment of the present invention, $R^{12}$ is 5-(1,2,3,4-tetrazolyl).

In an embodiment of the present invention, $R^{12}$ is selected from the group consisting of $C_{1-4}$alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group is optionally substituted with one to two substituents independently selected from the group consisting of hydroxy, carboxy, —C(O)O—$C_{1-4}$alkyl, $C_{1-4}$alkyl, $C_{1-4}$alkoxy, cyano, benzyl, 5-(1,2,3,4-tetrazolyl) and 1-(1,4-dihydro-tetrazol-5-one).

In another embodiment of the present invention, $R^{12}$ is selected from the group consisting of hydroxy substituted $C_{1-4}$alkyl, 5-(1,2,3,4-tetrazolyl), 4-(1,2,3,5-tetrazolyl), benzyl substituted 5-(1,2,3,4-tetrazolyl), benzyl substituted 4-(1,2,3,5-tetrazolyl) and —$C_{1-4}$alkyl-(5 to 6 membered heterocyclyoalkyl).

In another embodiment of the present invention, $R^{12}$ is selected from the group consisting of hydroxy-methyl, 5-(1-benzyl-1,2,3,4-tetrazolyl), 4-(1-benzyl-1,2,3,5-(1,2,3,4-tetrazolyl)) 5-(1,2,3,4-tetrazolyl), 1-piperidinyl-methyl and 4-morpholinyl-methyl. In another embodiment of the present invention, $R^{12}$ is selected from the group consisting of hydroxy-methyl, 5-(1-benzyl-1,2,3,4-tetrazolyl), 4-(1-benzyl-1,2,35-(1,2,3,4-tetrazolyl)), 5-(1,2,3,4-tetrazolyl), 1-piperidinyl-methyl and 4-morpholinyl-methyl. In another embodiment of the present invention, $R^{12}$ is selected from the group consisting of 5-(1,2,3,4-tetrazolyl) and 4-(1-benzyl-1,2,3,5-(1,2,3,4-tetrazolyl)).

In another embodiment of the present invention, $R^{15}$ is selected from the group consisting of hydrogen, hydroxy, amino, —C(O)—$C_{1-4}$alkyl, and —C(O)—$C_{1-4}$alkyl-O—$C_{1-4}$alkyl. In another embodiment of the present invention, $R^{15}$ is selected from the group consisting of hydrogen and hydroxy. In another embodiment of the present invention, $R^{15}$ is selected from the group consisting of —C(O)—$C_{1-4}$alkyl, and —C(O)—$C_{1-4}$alkyl-O—$C_{1-4}$alkyl.

In another embodiment of the present invention, $R^{15}$ is selected from the group consisting of hydrogen, hydroxy, amino, isopropyl-carbonyl-, n-butyl-carbonyl- and methoxy-methyl-carbonyl-. In another embodiment of the present invention, $R^{15}$ is hydrogen.

In additional embodiments, the present invention is directed to any single or subset of compounds of formula (I) selected from the group consisting of the compounds listed in Tables 1-9 below.

In an embodiment of the present invention are compounds of formula (I) whose $IC_{50}$, as measured according to the procedure described in Example 61 is less than or equal to about 1.0 μM, preferably, less than or equal to about 0.5 μM, more preferably, less than or equal to about 0.2 μM, more preferably, less than or equal to about 0.1 μM.

Additional embodiments of the present invention, include those wherein the substituents selected for one or more of the variables defined herein (e.g. $R^1$, $R^2$, $R^3$, $L^1$ $L^2$, a, etc.) are independently selected to be any individual substituent or any subset of substituents selected from the complete list as defined herein.

Representative compounds of the present invention are as listed in Tables 1 through 9, below. Unless otherwise noted, all compounds were prepared as mixtures of stereo-isomers. For substituent groups bound through two points within the structures in the Tables below, for example $L^1$, the substituent group is identified as it would be incorporated into the structure heading the table.

TABLE 1

Representative compounds of formula (I)

| ID No | $R^7$ |
|---|---|
| 1 | cylcohexyl |
| 2 | t-butoxy |

TABLE 2

Representative compounds of formula (I)

| ID No | $R^1$ | $R^2$ | $R^5$ |
|---|---|---|---|
| 3 | 2-methoxy-phenyl | (S)-cyclohexyl | cyclohexyl |
| 4 | 2-fluoro-phenyl | (S)-cyclohexyl | cyclohexyl |

TABLE 3

Representative compounds of formula (I)

| ID No. | $R^2$ | $R^4$ | $R^5$ |
|---|---|---|---|
| 5 | (S)-cyclohexyl | methyl | cyclohexyl |
| 6 | H | H | 2-adamantyl |
| 7 | (S)-cyclohexyl | 1-(2-hydroxy-ethyl) | cyclohexyl |
| 8 | (S)-isopropyl | methyl | 4-carboxy-cyclohexyl |
| 10 | (S)-isopropyl | 1-(2-hydroxy-ethyl) | 4-cyano-cyclohexyl |
| 11 | (S)-isopropyl | methyl | 4-cyano-cyclohexyl |
| 12 | (S)-isopropyl | 1-(2-hydroxy-ethyl) | 4-(5-(1,2,3,4-tetrazolyl))-cyclohexyl |
| 13 | (S)-isopropyl | methyl | 4-(5-(1,2,3,4-tetrazolyl))-cyclohexyl |
| 14 | (S)-isopropyl | 1-(2-hydroxy-ethyl) | 4-ethoxy-carbonyl-cyclohexyl |
| 15 | (S)-isopropyl | methyl | 1-(2-(ethoxycarbonyl-ethyl) |
| 16 | (S)-isopropyl | methyl | 1-(2-carboxy-ethyl) |
| 17 | (S)-cyclohexyl | methyl | 4-ethoxy-carbonyl-cyclohexyl |
| 18 | (S)-cyclohexyl | methyl | 4-carboxy-cyclohexyl |
| 19 | (S)-isopropyl | 1-(3-hydroxy-n-propyl) | cyclohexyl |
| 20 | (S)-isopropyl | 1-(2-hydroxy-ethyl) | 4-carboxy-cyclohexyl |
| 21 | (S)-isopropyl | 1-(2-hydroxy-ethyl) | isopropyl |
| 22 | 1-(2-hydroxy-ethyl) | methyl | cyclohexyl |
| 23 | 1-(2-methoxy-ethyl) | methyl | cyclohexyl |
| 24 | 2-isopropyloxy-ethyl | methyl | cyclohexyl |
| 25 | (S)-(2-benzyloxy-ethyl) | methyl | cyclohexyl |

TABLE 3-continued

Representative compounds of formula (I)

| ID No. | R² | R⁴ | R⁵ |
|---|---|---|---|
| 26 | (S)-4-tetrahydro-pyranyl | methyl | 4-carboxy-cyclohexyl |
| 27 | (S)-4-tetrahydro-pyranyl | methyl | 4-ethoxy-carbonyl-cyclohexyl |
| 29 | (S)-isopropyl | H | —CH((R)-isopropyl)-CH₂OH |
| 31 | (S)-isopropyl | 1-(2-hydroxy-ethyl) | cyclohexyl |
| 32 | (S)-4-tetrahydro-pyranyl | methyl | cis-(4-methoxy-carbonyl)-cyclohexyl |
| 33 | (S)-4-tetrahydro-pyranyl | methyl | cis-(4-carboxy)-cyclohexyl |
| 34 | (S)-4-tetrahydro-pyranyl | methyl | trans-(4-methoxy-carbonyl)-cyclohexyl |
| 35 | (S)-4-tetrahydro-pyranyl | methyl | trans-(4-carboxy)-cyclohexyl |
| 36 | (S)-isopropyl | H | —CH((R)-isopropyl)-CH₂OH |
| 37 | (S)-cyclohexyl | 1-(2-hydroxy-ethyl) | cis-(4-carboxy)-cyclohexyl |
| 38 | (S)-4-tetrahydro-pyranyl | 1-(2-hydroxy-ethyl) | cis-(4-carboxy)-cyclohexyl |
| 39 | (S)-4-tetrahydro-pyranyl | 1-(2-benzyloxy-ethyl) | cis-(4-carboxy)-cyclohexyl |
| 41 | (S)-isopropyl | H | 2-(1,3-dihydroxy-n-propyl) |
| 42 | (S)-isopropyl | methyl | cis-(4-methoxy-carbonyl)-cyclohexyl |
| 43 | (S)-isopropyl | methyl | cis-(4-carboxy)-cyclohexyl |
| 44 | (S)-cyclohexyl | methyl | 1-(4-carboxy-n-butyl) |
| 49 | (S)-cyclohexyl | 1-(2-benzyloxy-ethyl) | 3-n-pentyl |
| 50 | (S)-cyclohexyl | 1-(2-hydroxy-ethyl) | 3-n-pentyl |
| 77 | (S)-cyclohexyl | cyclohexyl | 5-(1,2,3,4-tetrazolyl)-methyl- |
| 78 | (S)-cyclohexyl | cyclohexyl | 2-imidazolyl-methyl- |
| 79 | (S)-cyclohexyl | cyclohexyl | 4-pyridyl-methyl- |
| 80 | (S)-cyclohexyl | cyclohexyl | 3-(1,2,4-triazolyl)-methyl- |
| 81 | (S)-cyclohexyl | cyclohexyl | 1-(2-(1-pyrrolidinyl)-ethyl) |
| 82 | (S)-cyclohexyl | cyclohexyl | 4-imidazolyl-methyl- |
| 83 | (S)-cyclohexyl | cyclohexyl | 2-(1-methyl-imidazolyl)-methyl- |
| 104 | (S)-cyclohexyl | cyclohexyl | 2-pyridyl-methyl- |
| 105 | (S)-cyclohexyl | cyclohexyl | 3-pyridyl-methyl- |
| 106 | (S)-cyclohexyl | cyclohexyl | 4-pyridyl-ethyl- |
| 107 | (S)-cyclohexyl | H | 2-(S)-(1-hydroxy-3-t-butoxy-n-propyl) |
| 110 | (S)-cyclohexyl | H | 1-(R)-(1-(3-(5-methyl-1,2,4-oxadiazolyl))-2-t-butoxy)-ethyl- |
| 112 | (S)-cyclohexyl | H | 1-(1-(5-(R)-1,2,3,4-tetrazolyl)-2-t-butoxy)-ethyl- |
| 113 | (S)-cyclohexyl | 1-(2-t-butoxy-ethyl) | 4-pyridyl-methyl- |
| 114 | (S)-cyclohexyl | 1-(2-t-butoxy-ethyl) | 2-furyl-methyl- |
| 115 | (S)-cyclohexyl | 1-(2-hydroxy-ethyl)- | t-butyl |
| 116 | (S)-cyclohexyl | H | 1-(2-(4-morpholinyl)-ethyl) |
| 117 | (S)-cyclohexyl | H | t-butyl |
| 118 | (S)-cyclohexyl | H | 1-(3,3-dimehyl-n-butyl) |
| 119 | (S)-cyclohexyl | H | 1-pyrrolidinyl-ethyl- |
| 120 | (S)-cyclohexyl | methyl | 2-(1,3-dihydroxy-n-propyl) |
| 121 | (S)-cyclohexyl | 1-(2-hydroxy-ethyl)- | 3-pyridyl-methyl- |
| 122 | (S)-cyclohexyl | methyl | phenyl-ethyl- |
| 130 | (S)-cyclohexyl | methyl | 5-(2,2,-dimethyl-1,3-dioxanyl) |
| 131 | (S)-cyclohexyl | 1-(2-hydroxy-ethyl)- | cyclopentyl-methyl- |
| 132 | (S)-cyclohexyl | H | 1-(3-(4-morpholinyl))-n-propyl) |
| 133 | (S)-cyclohexyl | 1-(3,3,-dimethyl-n-butyl)- | 2-(1-methyl-imidazolyl) |
| 137 | (S)-cyclohexyl | 1-(3,3,-dimethyl-n-butyl) | 4-pyridyl-methyl- |
| 138 | (S)-cyclohexyl | 1-(3,3,-dimethyl-n-butyl) | 1-(1-(R)-methyl-2-hydroxy-ethyl) |
| 139 | (S)-cyclohexyl | 1-(3,3,-dimethyl-n-butyl) | 1-(1-(S)-methyl-2-hydroxy-ethyl) |
| 141 | (S)-cyclohexyl | 1-(2-hydroxy-ethyl) | 2-thienyl-methyl- |
| 142 | (S)-cyclohexyl | 1-(2-methoxy-ethyl) | 1-(2-methoxy-ethyl) |
| 145 | (S)-cyclohexyl | 1-(3,3-dimethyl-n-butyl) | 1-(2-t-butoxycarbonyl-amino-ethyl) |
| 146 | (S)-cyclohexyl | 1-(3,3,-dimethyl-n-butyl) | 1-(2-amino-ethyl)- |
| 147 | (S)-cyclohexyl | 1-(3,3-dimethyl-n-butyl) | 1-(2-amino-sulfonyl-amino-ethyl)- |
| 150 | (S)-cyclohexyl | H | 4-(1-t-butoxycarbonyl-piperidinyl) |
| 154 | (S)-cyclohexyl | 1-(2-t-butoxy-ethyl) | 2-thienyl-methyl- |
| 155 | (S)-cyclohexyl | 1-(2-t-butoxy-ethyl)- | 2-pyridyl-methyl- |
| 156 | (S)-cyclohexyl | 1-(2-t-butoxy-ethyl) | 3-thienyl-methyl- |
| 157 | (S)-cyclohexyl | 1-(2-t-butoxy-ethyl) | 2-thiazolyl-methyl |
| 158 | (S)-cyclohexyl | 1-(2-t-butoxy-ethyl) | 4-fluoro-benzyl |
| 159 | (S)-cyclohexyl | 1-(2-t-butoxy-ethyl) | 5-thiazolyl-methyl- |
| 160 | (S)-cyclohexyl | H | 1-(2,2-dimethyl-n-propyl) |
| 162 | (S)-cyclohexyl | 1-(2-t-butoxy-ethyl) | 2-pyridyl-methyl- |
| 165 | (S)-cyclohexyl | methyl | 1-(2-dimethylamino-ethyl) |
| 170 | (S)-cyclohexyl | methyl | 3-(1,1-dioxo-tetrahydro-thienyl) |
| 171 | (S)-cyclohexyl | methyl | 1-(2-hydroxy-ethyl) |
| 172 | (S)-cyclohexyl | 1-(3,3-dimethyl-n-butyl) | 2-(1-methyl-4,5-dichloro-imidazolyl)-methyl |

TABLE 3-continued

Representative compounds of formula (I)

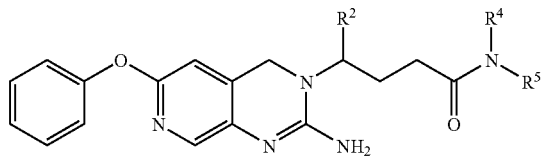

| ID No. | R² | R⁴ | R⁵ |
|---|---|---|---|
| 173 | (S)-cyclohexyl | H | 1-(3-ethoxy-n-propyl) |
| 174 | (S)-cyclohexyl | 1-(3,3-dimethyl-n-butyl) | 1-(2-(4-morpholinyl)-ethyl)- |
| 175 | (S)-isopropyl | H | 1-(1-(R)-methyl-2-hydroxy-ethyl) |
| 176 | (S)-cyclohexyl | cyclohexyl | —CH₂CH₂—O—CH₂CH₂—O—CH₂CH₂—O—CH₂CH₂—OH— |
| 177 | 1-(S)-(1-(R)-hydroxy-ethyl) | methyl | cyclohexyl |
| 178 | 1-(S)-(1-(R)-hydroxy-ethyl) | methyl | 1-(1-(R)-methyl-2-hydroxy-ethyl) |
| 179 | (S)-cyclohexyl | H | 1-(2,2-dimethyl-3-hydroxy-n-propyl) |
| 180 | (S)-cyclohexyl | H | 1-(1,1-dimethyl-2-hydroxy-ethyl) |
| 181 | (S)-cyclohexyl | H | 1-(2-t-butoxy-ethyl) |
| 183 | (S)-cyclohexyl | methyl | 1-(1-(R)-methyl-2-hydroxy-ethyl) |
| 185 | 1-(S)-(1-(R)-benzyloxy-ethyl) | 1-(3,3-dimethyl-n-butyl) | 4-pyridyl-methyl- |
| 186 | 1-(S)-(1-(R)-hydroxy-ethyl) | H | 1-(2,2-dimethyl-n-propyl) |
| 189 | (S)-cyclohexyl | isobutyl | 1-(2-(4-morpholinyl)-ethyl)- |
| 190 | (S)-isopropyl | isobutyl | 1-(2-(4-morpholinyl)-ethyl)- |
| 204 | (S)-cyclohexyl | H | 1-(2,2-dimethyl-n-propyl) |
| 208 | (S)-cyclohexyl | H | isobutyl |
| 210 | (S)-cyclohexyl | H | 2-(R)-tetrahydrofuryl-methyl |
| 212 | (S)-cyclohexyl | H | cyclopropyl-methyl- |
| 219 | (S)-4-tetrahydro-pyranyl-methyl | H | 1-(2,2-dimethyl-n-propyl) |
| 223 | (S)-cyclohexyl | H | 1-(2,2-dimethyl-n-propyl) |

TABLE 4

Representative compounds of formual (I)

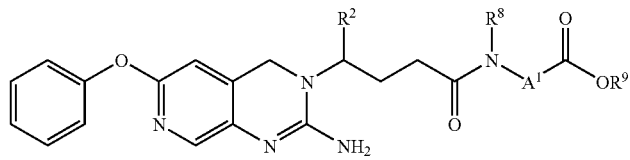

| ID No | R² | A¹ | R⁸ | R⁹ |
|---|---|---|---|---|
| 28 | (S)-isopropyl | —CH((R)—CH₂—OH)— | H | methyl |
| 30 | (S)-isopropyl | —CH((R)—CH₂—OH)— | H | H |
| 40 | (S)-isopropyl | —CH((S)—CH₂—OH)— | H | methyl |
| 45 | (S)-isopropyl | —CH((S)—CH₂—O-benzyl)- | H | methyl |
| 46 | (S)-isopropyl | —CH((S)—CH₂—OH)— | H | H |
| 47 | (S)-isopropyl | —CH((S)—CH₂—O-benzyl)- | H | H |
| 48 | (S)-isopropyl | —CH((R)—CH₂—O-benzyl)- | H | benzyl |
| 51 | (S)-isopropyl | —CH((S)—CH₂—O-benzyl)- | methyl | methyl |
| 52 | (S)-isopropyl | —CH((S)—CH₂—O-benzyl)- | methyl | H |
| 53 | (S)-isopropyl | —CH((R)—CH₂—O-benzyl)- | H | methyl |
| 54 | (S)-isopropyl | —CH((R)—CH₂—O-benzyl)- | H | H |
| 55 | (S)-4-tetrahydro-pyranyl | —CH((S)—CH₂—O-benzyl)- | H | methyl |
| 56 | (S)-4-tetrahydro-pyranyl | —CH((S)—CH₂—O-benzyl)- | methyl | methyl |
| 57 | (S)-4-tetrahydro-pyranyl | —CH((S)—CH₂—O-benzyl)- | H | H |
| 58 | (S)-4-tetrahydro-pyranyl | —CH((S)—CH₂—O-benzyl)- | methyl | methyl |
| 60 | (S)-4-tetrahydro-pyranyl | —CH((R)—CH₂—O-t-butyl)- | methyl | H |
| 61 | (S)-cyclohexyl | —CH((S)—CH₂—O-t-butyl)- | H | methyl |
| 62 | (S)-cyclohexyl | —CH((S)—CH₂—O-t-butyl)- | H | H |
| 63 | (S)-cyclohexyl | —CH((R)—CH₂—O-t-butyl)- | H | methyl |
| 64 | (S)-cyclohexyl | —CH((R)—CH₂—O-t-butyl)- | H | H |
| 65 | (S)-cyclohexyl | —CH((S)—CH₂—O-t-butyl)- | methyl | methyl |

TABLE 4-continued

Representative compounds of formual (I)

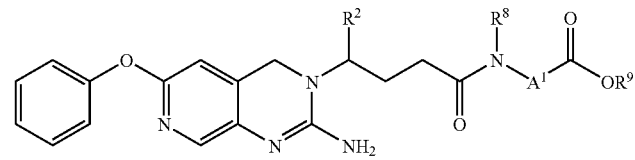

| ID No | R² | A¹ | R⁸ | R⁹ |
|---|---|---|---|---|
| 66 | (S)-cyclohexyl | —CH((S)—CH₂—O-t-butyl)- | methyl | H |
| 69 | (S)-isopropyl | —CH((S)—CH₂—O-t-butyl)- | H | methyl |
| 70 | (S)-isopropyl | —CH((S)—CH₂—O-t-butyl)- | H | H |
| 71 | (S)-isopropyl | —CH((R)—CH₂—O-benzyl)- | methyl | methyl |
| 84 | (S)-cyclohexyl | —CH₂— | cyclohexyl | H |
| 85 | (S)-isopropyl | —CH((R)—CH₂—O-benzyl)- | methyl | H |
| 86 | (S)-isopropyl | —CH₂— | cyclohexyl | H |
| 87 | (S)-isopropyl | —CH((R)—CH₂—O-t-butyl)- | H | methyl |
| 88 | (S)-isopropyl | —CH((R)—CH₂—O-t-butyl)- | H | H |
| 136 | (S)-cyclohexyl | —CH((S)—CH₂—O-t-butyl)- | H | isopropyl |
| 140 | (S)-cyclohexyl | —CH((R)—CH₂—O-t-butyl)- | H | isopropyl |
| 227 | (S)-isopropyl | —CH((R)—CH₂—O-benzyl) | H | isopropyl |
| 228 | (S)-isopropyl | —CH((R)—CH₂—O-benzyl) | H | ethyl |

TABLE 5

Representative compounds of formula (I)

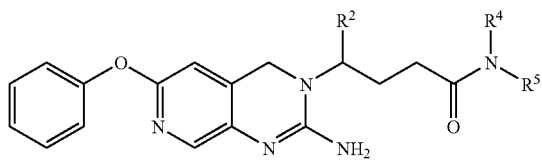

| ID No. | R² | R⁴ + R⁵ together with N atom |
|---|---|---|
| 89 | (S)-cyclohexyl | 2-(S)-carboxy-pyrrolidin-l-yl |
| 90 | (S)-cyclohexyl | 1-(2-(S)-carboxy-octahydro-indolyl) |
| 91 | (S)-cyclohexyl | 1-(2-(S)-carboxy-piperidinyl) |
| 92 | (S)-cyclohexyl | 1-(2-(S)-carboxy-octahydro-indolyl) |
| 93 | (S)-cyclohexyl | 1-(2-(S)-carboxymethyl-piperidinyl) |
| 143 | (S)-cyclohexyl | 1-(2-(S)-hydroxymethyl-pyrrolidinyl) |
| 144 | (S)-cyclohexyl | 1-(2-(R)-hydroxymethyl-pyrrolidinyl) |

TABLE 5-continued

Representative compounds of formula (I)

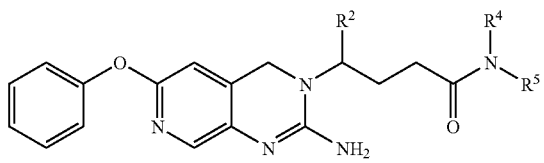

| ID No. | R² | R⁴ + R⁵ together with N atom |
|---|---|---|
| 148 | (S)-cyclohexyl | 1-(4-hydroxy-4-(3-trifluoromethylphenyl)-piperidinyl) |
| 149 | (S)-cyclohexyl | 1-(4-phenyl-piperidinyl) |
| 164 | (S)-cyclohexyl | 1-(4-hydroxyethyl-piperidnyl) |
| 166 | (S)-cyclohexyl | 4-morpholinyl |
| 169 | (S)-cyclohexyl | 1-(4-methyl-piperazinyl) |

TABLE 6

Representative compounds of formula (I)

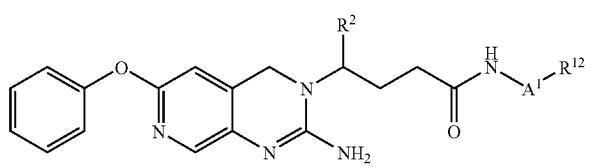

| ID No. | R² | A¹ | R¹² |
|---|---|---|---|
| 94 | (S)-tetrahydro-pyranyl | —CH((R)—CH₂—O-benzyl)- | hydroxy-methyl- |
| 95 | (S)-isopropyl | —CH((R)—CH₂—O-t-butyl-) | 5-(1-benzyl-1,2,3,4-tetrazolyl) |
| 96 | (S)-isopropyl | —CH((R)—CH₂—O-t-butyl-) | 4-(1-benzyl-1,2,3,5-(1,2,3,4-tetrazolyl)) |
| 97 | (S)-isopropyl | —CH((R)—CH₂—O-t-butyl-) | 5-(1,2,3,4-tetrazolyl) |
| 99 | (S)-cyclohexyl | —CH((R)—CH₂—O-t-butyl-) | 1-piperidinyl-methyl- |

TABLE 6-continued

Representative compounds of formula (I)

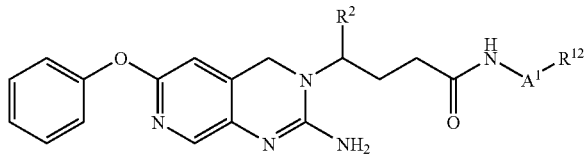

| ID No. | R² | A¹ | R¹² |
|---|---|---|---|
| 101 | (S)-isopropyl | —CH((R)—CH₂—O-t-butyl-) | 1-piperidinyl-methyl- |
| 102 | (S)-cyclohexyl | —CH((R)—CH₂—O-t-butyl-) | 4-morpholinyl-methyl- |

TABLE 7

Representative compounds of formula (I)

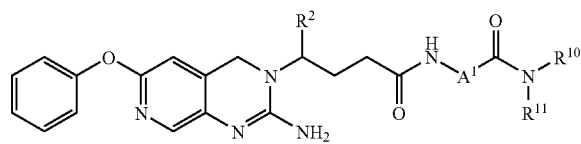

| ID No. | R² | A¹ | R¹⁰ + R¹¹ with N atom² |
|---|---|---|---|
| 98 | (S)-isopropyl | —CH((R)—CH₂—O-t-butyl-) | 1-piperidinyl |
| 100 | (S)-cyclohexyl | —CH((R)—CH₂—O-t-butyl-) | 1-piperidinyl |
| 103 | (S)-cyclohexyl | —CH((R)—CH₂—O-t-butyl-) | 4-morpholinyl |

TABLE 8

Representative compounds of formula (I)

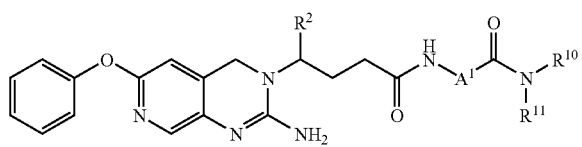

| ID No. | R² | A¹ | R¹⁰ | R¹¹ |
|---|---|---|---|---|
| 108 | (S)-cyclohexyl | —CH((R)—CH₂—O-t-butyl)- | H | —CH((S)—CH₃)—CH₂OH |
| 109 | (S)-cyclohexyl | —CH((R)—CH₂—O-t-butyl)- | H | —CH((R)—CH₃)—CH₂OH |
| 111 | (S)-cyclohexyl | —CH((R)—CH₂—O-t-butyl)- | H | H |
| 224 | (S)-cyclohexyl | —CH((R)—CH₂—O-t-butyl)- | H | 2-(S)-pentadioic acid |
| 225 | (S)-cyclohexyl | —CH((R)—CH₂—O-t-butyl)- | H | 2-(S)-pentadioic acid |

TABLE 9

Representative compounds of formula (I)

| ID No. | R² | A¹ | Stereo "*" |
|---|---|---|---|
| 126 | (S)-cyclohexyl | —CH(benzyl)- | (S) |
| 127 | (S)-cyclohexyl | —CH(benzyl)- | (R) |

TABLE 10

Representative compounds of formula (I)

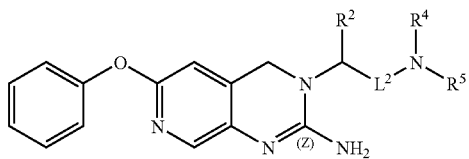

| ID No. | R² | L² | R⁴ + R⁵ taken together |
|---|---|---|---|
| 151 | (R)-cyclohexyl | —CH₂— | 1-(4-cyclohexyl-1,2,3-triazolyl) |
| 152 | (R)-cyclohexyl | —CH₂— | 1-(4-t-butyl-1,2,3-triazolyl) |

TABLE 10-continued

Representative compounds of formula (I)

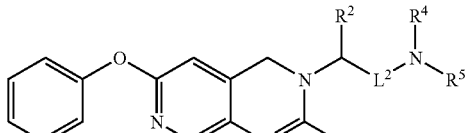

| ID No. | R² | L² | R⁴ + R⁵ taken together |
|---|---|---|---|
| 153 | (R)-cyclohexyl | —CH₂— | 1-(4-(2-pyridyl)-1,2,3-triazolyl) |

TABLE 10-continued

Representative compounds of formula (I)

| ID No. | R² | L² | R⁴ + R⁵ taken together |
|---|---|---|---|
| 163 | (R)-cyclohexyl | —CH₂— | 1-(4-hydroxymethyl-1,2,3-triazolyl) |
| 198 | (S)-cyclohexyl | —CH₂CH₂— | 1-(4-cyclohexyl-1,2,3-triazolyl) |
| 199 | (S)-cyclohexyl | —CH₂CH₂— | 1-(4-t-butyl-1,2,3-triazolyl) |

TABLE 11

Representative compounds of formula (I)

| ID No. | R² | L² | R⁴ | R⁵ |
|---|---|---|---|---|
| 161 | (S)-cyclohexyl | —CH₂CH₂CH₂— | H | 1-(2,2-dimethyl-n-propyl) |
| 182 | (S)-cyclohexyl | —CH₂CH₂CH₂— | 1-(3,3-dimethyl-n-butyl) | 1-(2-(4-morpholinyl)-ethyl)- |
| 184 | (S)-cyclohexyl | —CH₂CH₂CH₂— | methyl | 1-(1-(R)-methyl-2-hydroxy-ethyl) |
| 187 | (S)-cyclohexyl | —CH₂CH₂CH₂— | methyl | cyclohexyl |
| 188 | (S)-ispropyl | —CH₂CH₂CH₂— | H | 1-(1-(R)-isopropyl-2-hydroxy-ethyl) |
| 191 | (S)-isopropyl | —CH₂CH₂CH₂— | H | 1-(1-(R)-methyl-2-hydroxy-ethyl) |
| 192 | (S)-cyclohexyl | —CH₂CH₂CH₂— | isobutyl | 1-(2-(4-morpholinyl)-ethyl)- |
| 193 | (S)-isopropyl | —CH₂CH₂CH₂— | isobutyl | 1-(2-(4-morpholinyl)-ethyl)- |
| 194 | (S)-cyclohexyl | —CH₂CH₂CH₂— | H | 1-(2,2-dimethyl-3-hydroxy-n-propyl) |
| 195 | (S)-cyclohexyl | —CH₂CH₂CH₂— | H | 1-(2-t-butoxy-ethyl) |
| 197 | (S)-cyclohexyl | —CH₂CH₂CH₂— | methyl | 1-(2-dimethylamino-ethyl) |
| 206 | (S)-cyclohexyl | —CH₂CH₂— | methyl | cyclohexyl |
| 209 | (S)-cyclohexyl | —CH₂CH₂CH₂— | methyl | isobutyl |
| 211 | (S)-cyclohexyl | —CH₂CH₂CH₂— | H | 2-(R)-tetrahydrofuryl-methyl |
| 213 | (S)-cyclohexyl | —CH₂CH₂CH₂— | H | cyclopropyl-methyl- |
| 214 | (S)-cyclohexyl | —CH₂CH₂— | H | 1-(2,2-dimethyl-n-propyl) |
| 216 | (S)-cyclohexyl | —CH₂CH₂— | H | 1-(3,3-dimethyl-n-butyl) |

TABLE 12

Representative compounds of formula (I)

| ID No. | R² | L² | R⁴ | R⁵ |
|---|---|---|---|---|
| 196 | H | —CH₂CH₂CH₂— | methyl | cyclohexyl |
| 200 | (S)-cyclohexyl | —CH₂— | H | 1-(2,2-dimethyl-n-propyl) |
| 202 | (S)-cyclohexyl | —CH₂— | H | 1-(3,3-dimethyl-n-butyl) |
| 205 | (S)-cyclohexyl | —CH₂— | methyl | cyclohexyl |
| 218 | (S)-cyclohexyl | —CH₂— | H | 1-(2,2-dimethyl-n-propyl) |
| 220 | (S)-isobutyl | absent | H | phenylethyl- |

TABLE 12-continued

Representative compounds of formula (I)

| ID No. | R² | L² | R⁴ | R⁵ |
|---|---|---|---|---|
| 221 | (S)-isobutyl | absent | methyl | phenylethyl- |
| 222 | (S)-isobutyl | absent | H | 1-(3-phenyl-n-propyl) |

TABLE 13

Representative compounds of formula (I)

| ID No. | R² | L² | A¹ | R¹⁰ | R¹¹ |
|---|---|---|---|---|---|
| 167 | (S)-cyclohexyl | —CH₂CH₂CH₂— | —CH((R))—CH₂—O-t-butyl)- | H | H |

TABLE 14

Representative compounds of formula (I)

| ID No. | R² | A¹ | R¹⁰ | R¹¹ |
|---|---|---|---|---|
| 168 | (S)-cyclohexyl | —CH((R))—CH₂—O-t-butyl)- | H | H |

TABLE 15

Representative compounds of formula (I)

| ID No. | R² | R⁶ + R⁷ together |
|---|---|---|
| 135 | (R)-cyclohexyl | 3-(1,3-diaza-spiro[4.5]decan-2-one) |
| 229 | (R)-cyclohexyl | 3-(1,3-diaza-spiro[4.5]decane-2,4-dione) |

TABLE 16

Representative compounds of formula (I)

| ID No. | R² | L² | R⁴ |
|---|---|---|---|
| 74 | (S)-isopropyl | —CH₂CH₂— | H |
| 75 | (S)-cyclohexyl | —CH₂CH₂— | t-butyl |
| 125 | (S)-cyclohexyl | —CH₂CH₂— | H |
| 231 | (S)-isopropyl | —CH₂CH₂— | benzyl |

TABLE 17

Representative compounds of formula (I)

| ID No. | R² | L² | R⁴ |
|---|---|---|---|
| 232 | (R)-isopropyl | —CH₂— | cyclohexyl-ethyl- |
| 233 | (R)-isopropyl | —CH₂— | 1-(3-methyl-buten-2-yl) |
| 234 | (R)-isopropyl | —CH₂— | cyclohexyl-methyl- |
| 235 | (R)-isopropyl | —CH₂— | 5-(3-cyclohexyl-4,5-dihydro-isoxazolyl)-methyl- |
| 236 | (R)-isopropyl | —CH₂— | 5-(3-t-butyl-4,5-dihydro-isoxazolyl)-methyl- |
| 237 | (R)-isopropyl | —CH₂— | 5-(3-t-butyl-isoxazolyl)-methyl- |
| 238 | (R)-isopropyl | —CH₂— | 5-(3-(2,2-dimethyl-n-propyl)-4,5-dihydro-isoxazolyl)-methyl- |
| 239 | (R)-isopropyl | —CH₂— | 4-(1-(cyclohexyl-methyl)-1,2,3-triazolyl)-methyl- |
| 240 | (R)-isopropyl | —CH₂— | n-propyl |
| 241 | (R)-isopropyl | —CH₂— | 1-(propen-2-yl) |

TABLE 18

Representative Compounds of Formula (I)

| ID No. | R² | L² | R³ | R¹⁵ |
|---|---|---|---|---|
| 245 | (R)-cyclohexyl | —CH₂— | 1-(4-t-butyl-1,2,3-triazolyl) | amino |
| 246 | (R)-cyclohexyl | —CH₂— | 1-(4-t-butyl-1,2,3-triazolyl) | hydroxy |
| 247 | (R)-cyclohexyl | —CH₂— | 1-(4-t-butyl-1,2,3-triazolyl) | methoxy-methylcarbonyl- |
| 248 | (R)-cyclohexyl | —CH₂— | 1-(4-t-butyl-1,2,3-triazolyl) | isobutyl-carbonyl- |
| 249 | (R)-cyclohexyl | —CH₂— | 1-(4-t-butyl-1,2,3-triazolyl) | n-butyl-carbonyl |

TABLE 18-continued

Representative Compounds of Formula (I)

| ID No. | R² | L² | R³ | R¹⁵ |
|---|---|---|---|---|
| 250 | (R)-cyclohexyl | —CH₂CH₂CH₂— | 1-(4-(1-3,3-dimethyl-n-propyl)-1,2,3-triazolyl) | hydroxy |

The present invention is further directed to intermediates in the synthesis of the compound of formula (I). In an embodiment, the present invention is directed to compounds of formula (CI)

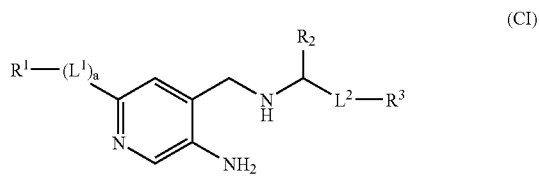

(CI)

wherein $R^1$, a, $L^1$, $R^2$, b and $R^3$ are as herein defined. The compounds of formula (CI) are useful as intermediates in the preparation of the compounds of formula (I) of the present invention.

As used herein, unless otherwise noted, the term "halogen" shall mean chlorine, bromine, fluorine and iodine. Preferably, the halogen is fluoro or chloro. More preferably, the halogen is fluoro.

As used herein, unless otherwise noted, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{X-Y}$alkyl" wherein X and Y are integers, shall include straight and branched chains comprising between X and Y carbon atoms. Preferably, the alkyl group contains one to ten carbon atoms, more preferably one to eight carbon atoms, more preferably one to six carbon atoms, more preferably one to four carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{1-4}$alkoxy" shall include straight and branched chains comprising one to four carbon atoms.

As used herein, unless otherwise noted, the terms "halogen substituted $C_{1-4}$alkyl" and "halogenated $C_{1-4}$alkyl", shall mean a straight or branched chain alkyl group comprising one to four carbon atoms, wherein the alkyl is substituted with one or more, preferably one to five, more preferably one to three halogen atoms. Preferably, the halogen is selected from chloro or fluoro.

Similarly, the terms "halogen substituted $C_{1-4}$alkoxy" and "halogenated $C_{1-4}$alkoxy" shall mean a straight or branched chain alkoxy group comprising one to four carbon atoms, wherein the alkoxy is substituted with one or more, preferably one to five, more preferably one to three halogen atoms. Preferably, the halogen is selected from chloro or fluoro.

As used herein, unless otherwise noted, the term "hydroxy substituted $C_{1-4}$alkyl" shall mean a straight or branched chain $C_{1-4}$alkyl, wherein the $C_{1-4}$alkyl is substituted with one or more, preferably one to three hydroxy groups, more preferably one to two hydroxy groups. Most preferably, the $C_{1-4}$alkyl group is substituted with one hydroxy group. Preferably, wherein the $C_{1-4}$alkyl group has a terminal carbon atom, the hydroxy group is bound at said terminal carbon atom. As used herein, unless otherwise noted, the term "carboxy substituted $C_{1-4}$alkyl" shall mean a straight or branched chain $C_{1-4}$alkyl, wherein the $C_{1-4}$alkyl is substituted with one or more, preferably one to three carboxy groups, more preferably one to two carboxy groups. Most preferably, the $C_{1-4}$alkyl group is substituted with one carboxy group. Preferably, wherein the $C_{1-4}$alkyl group has a terminal carbon atom, the carboxy group is bound at said terminal carbon atom.

As used herein, unless otherwise noted, the term "amino substituted $C_{1-4}$alkyl" shall mean a straight or branched chain $C_{1-4}$alkyl, wherein the $C_{1-4}$alkyl is substituted with one to two, preferably one amino, $C_{1-4}$alkylamino or di($C_{1-4}$alkylamino) groups. More preferably, the $C_{1-4}$alkyl group is substituted with one amino, $C_{1-4}$alkylamino or di($C_{1-4}$alkylamino) group. Preferably, wherein the $C_{1-4}$alkyl group has a terminal carbon atom, the amino, $C_{1-4}$alkylamino or di($C_{1-4}$ alkylamino) group is bound at said terminal carbon atom.

As used herein, unless otherwise noted, "aryl" shall refer to fully conjugated aromatic ring structures such as phenyl, naphthyl, and the like.

As used herein, unless otherwise noted, "$C_{1-4}$aralkyl" or "aralkyl" shall mean any $C_{1-4}$alkyl group substituted with an aryl group such as phenyl, naphthyl and the like. For example, benzyl, phenylethyl, phenylpropyl, naphthylmethyl, and the like. Unless otherwise noted, the "$C_{1-4}$aralkyl" group is bound through the alkyl portion. For example, phenylethyl- is bound through the terminal carbon atom of the ethyl group (i.e. phenyl-CH₂—CH₂—).

As used herein, unless otherwise noted, "$C_{1-4}$aralkoxy" or "aralkoxy" shall denote an oxygen ether radical of the above described straight or branched chain $C_{1-4}$alkyl group substituted with an aryl group. Unless otherwise noted, the "$C_{1-4}$ aralkoxy" group is bound through the oxygen atom. For example, benzyloxy and the like.

As used herein, unless otherwise noted, the term "cycloalkyl" shall mean any three to sixteen member stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norboranyl, adamantyl, spiropentane, 2,2,2-bicyclooctyl, and the like. Unless otherwise noted, "cycloalkyl" groups do not contain N, O or S heteroatoms.

As used herein, unless otherwise noted, the term "partially unsaturated carbocyclyl" shall mean any three to sixteen member stable monocyclic, bicyclic, polycyclic, bridge or spiro-bound ring system containing at least one carbon atom which is not part of an unsaturated bond (i.e. a double or triple bond) or any bicyclic, polycyclic, bridged or spiro-bound, partially aromatic (e.g. benzo-fused) rings system. Suitable examples include, but are not limited to 1,2,3,4-tetrahydronaphthyl, fluorenyl, 9,10-dihydroanthracenyl, indanyl, and the like. Unless otherwise noted, "partially unsaturated carbocyclyl" groups do not contain N, O or S heteroatoms.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, 5-(1,2,3,4-tetrazolyl), and the like. Preferred heteroaryl groups include furyl, thienyl, imidazolyl, pyridyl, triazolyl, benzimidazolyl and 5-(1,2,3,4-tetrazolyl).

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, and the like. Preferred heterocycloalkyl groups include piperidinyl, morpholinyl, tetrahydropyranyl and azepinyl.

As used herein, unless otherwise noted, the term "heterocyclyl" shall include any heteroaryl or heterocycloalkyl group as herein defined. In an embodiment, the heterocyclyl group is a 5 to 6 or 9 to 10 membered heteroaryl group. In another embodiment, the heterocyclyl group is a 5 to 6 or 9 to 10 membered heterocycloalkyl group.

As used herein, the notation "*" shall denote the presence of a stereogenic center.

When a particular group is "substituted" (e.g., cycloalkyl, aryl, heterocycloalkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, 2,2-dichloroethyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetyl, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)-" substituent refers to a group of the formula

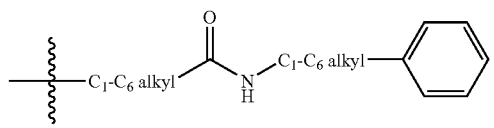

Unless otherwise noted, the position at which substituent groups on the compounds of formula (I) are bound to the 2-amino-3,4-dihydro-pyrido[3,4-d]pyrimidine core shall be denoted as follows:

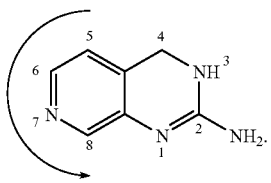

Abbreviations used in the specification, particularly the Schemes and Examples, are as follows:

| | |
|---|---|
| Ac = | Acetyl (i.e. —C(O)—CH$_3$) |
| AD = | Alzheimer's Disease |
| APP = | AmyloiD Precursor Protein |
| BACE = | β Amyloid Site Cleaving Enzyme |
| BPE-Rh = | (1,2-Bis(phospholano)ethane)-Rh catalyst |
| Cbz = | Carbobenzyloxy |
| DCC = | N,N-Dicyclohexylcarbodiimide |
| DCM = | Dichloromethane |
| DIAD = | Diidopropyl azodicarboxylate |
| DIPEA or DIEA = | Diisopropylethylamine |
| DMA = | N,N-Dimethylacetamide |
| DMAP = | 4-N,N-Dimethylaminopyridine |
| DME = | Dimethoxyethane |
| DMF = | N,N-Dimethylformamide |
| DMSO = | Dimethylsulfoxide |
| EDC or EDCl = | 1-(3-Dimethylaminoproyl)-3-ethylcarbodiimide hydrochoride |
| EtOAc = | Ethyl acetate |
| EtOH = | Ethanol |
| HBTU = | O-Benzotriazol-1-yl-N,N,N',N'-tetramethyluronium hexafluorophosphate |
| HEPES = | 4-(2-Hydroxyethyl)-1-Piperazine Ethane Sulfonic Acid |
| HOBT or HOBt = | 1-Hydroxybenzotriazole |
| HPLC = | High Pressure Liquid Chromatography |
| LAH = | Lithium Aluminum Hydride |
| LC/MS = | Liquid Chromatography/Mass Spectrometry |
| mCPBA or MCPBA = | m-Chloro-peroxybenzoic acid |
| MeOH = | Methanol |
| NaBH(OAc)$_3$ = | Sodium triacetoxyborohydride |
| NCS = | N-Chloro-succinimide |
| NMR = | Nuclear Magnetic Resonance |
| OM99-2 = | 4-amino-4-{1-[2-carbamoyl-1-(4-{1-[3-carboxy-1-(1-carboxy-2-phenyl-ethylcarbamoyl)-propylcarbamoyl]-ethylcarbamoyl}-2-hydroxy-1-isobutyl-pentylcarbamoyl)-ethylcarbamoyl]-2-methyl-propylcarbamoyl}-butyric acid |
| Pd—C or Pd/C = | Palladium on Carbon Catalyst |
| Pd$_2$(dba)$_3$ = | Tris(dibenzylidene acetone)dipalladium(0) |
| Pd(dppf)Cl$_2$ = | Dichloro[1,1'-bis(diphenylphosphino)-ferrocene]palladium |
| t-BOC or Boc or BOC = | Tert-Butoxycarbonyl |
| t-Bu = | tert-butyl (—C(CH$_3$)$_3$) |
| TEA = | Triethylamine |
| TFA = | Trifluoroacetic Acid |
| THF = | Tetrahydrofuran |
| TLC = | Thin Layer Chromatography |

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley &

Sons, 1999. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the general process outlined in Scheme 1.

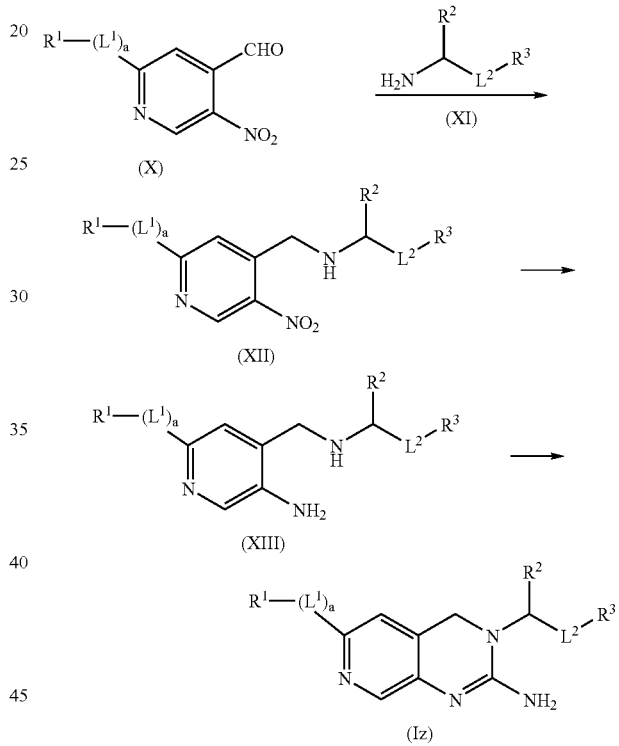

Accordingly, a suitably substituted compound of formula (X), a known compound or compound prepared by known methods, is reacted with a suitably substituted compound of formula (XI), a known compound or compound prepared by known methods, in the presence of a reducing agent such as NaBH(OAc)$_3$, and the like, in an organic solvent such as dichloromethane, 1,2-dichloroethane, THF, acetonitrile, and the like, or in the presence of a reducing agent such as NaBH$_3$CN, NaBH$_4$, and the like, in an organic solvent such as methanol, acetonitrile, and the like, to yield the corresponding compound of formula (XII).

The compound of formula (XII) is reacted with hydrogen gas, in the presence of a catalyst such as Pd on carbon (Pd/C), and the like, in a protic solvent such as methanol, ethanol, and the like, to yield the corresponding compound of formula (XIII). Alternatively, the compound of formula (XII) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (XIII).

The compound of formula (XIII) is reacted with cyanogen bromide, and the like, in an organic solvent such as methanol, ethanol, toluene, and the like, to yield the corresponding compound of formula (Ia). Alternatively, the compound of formula (XIII) is reacted with 2-methyl-2-thiopseudourea, in the presence of an acid such as hydrochloric acid, sulfuric acid, and the like, in an organic solvent such as butanol, and the like, to yield the corresponding compound of formula (Iz).

Compounds of formula (I) wherein $R^3$ is

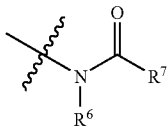

may alternatively be prepared according to the process outlined in Scheme 2.

$A^1$-NHPg$^1$ and then reducing the nitro group to the corresponding amine), is reacted with cyanogen bromide, in an organic solvent such as methanol, ethanol, toluene, and the like, to yield the corresponding compound of formula (XV).

Alternatively, the compound of formula (XIV) is reacted with 2-methyl-2-thiopsuedourea, in the presence of an acid such as hydrochloric acid, sulfuric acid, and the like, in an organic solvent such as ethanol, butanol, xylene, or dioxane, or in an aqueous solvent such as water to yield the corresponding compound of formula (XV).

The compound of formula (XV) is deprotected according to known methods, to yield the corresponding compound of formula (XVI). For example, wherein $Pg^1$ is BOC, the compound of formula (XV) is deprotected by reacting with an acid such as TFA, HCl, and the like; wherein $Pg^1$ is Cbz, the compound of formula (XV) is deprotected by reacting with a hydrogen source such as $H_2$ (g) in the presence of a catalyst, such as palladium on carbon or palladium black. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999)

The compound of formula (XVI) is reacted with a suitably substituted acid chloride, a compound of formula (XVII), a known compound or compound prepared by known methods, in the presence of a base such as TEA, DIPEA, pyridine, and the like, in an organic solvent such as dioxane, DCM, chloroform, and the like; to yield the corresponding compound of formula (Ia).

Compounds of formula (I) wherein $R^3$ is

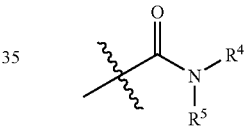

may alternatively be prepared according to the process outlined in Scheme 3.

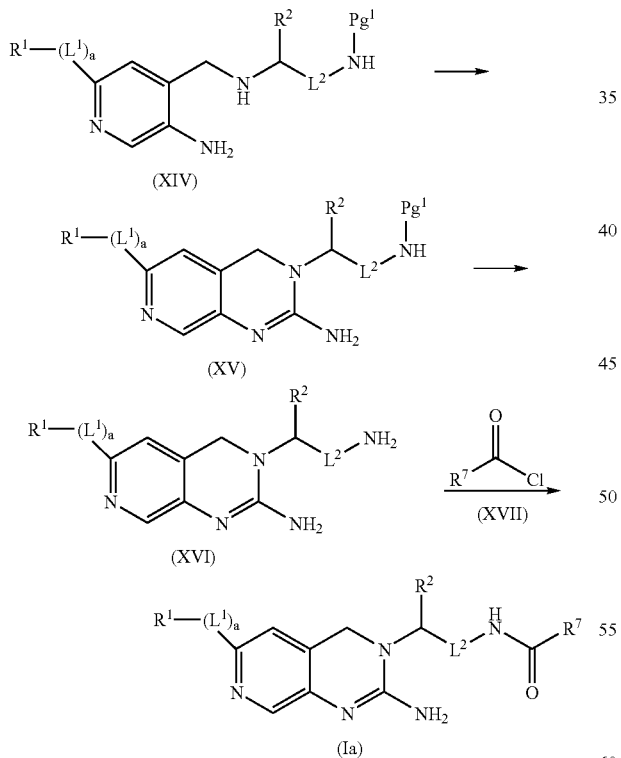

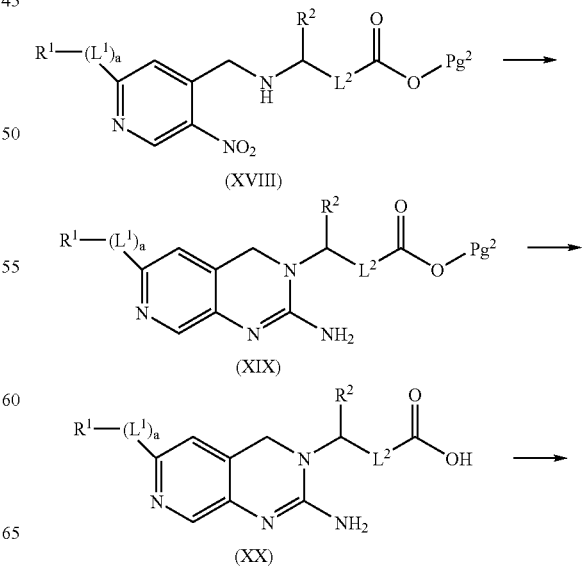

Accordingly, a suitably substituted compound of formula (XIV), wherein $Pg^1$ is a suitable nitrogen protecting group such as Cbz, BOC, and the like, preferably BOC, a known compound or compound prepared by known methods, (for example by reacting the compound of formula (X), as defined in Scheme 1 above, with a compound of the formula NH$_2$-

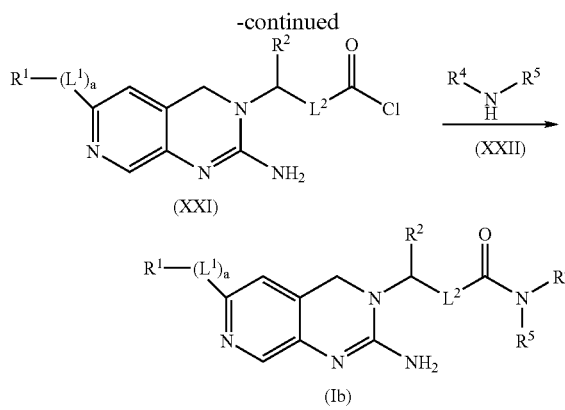

(XXI)

(Ib)

Accordingly, a suitably substituted compound of formula (XVIII), wherein $Pg^2$ is a suitable carboxylic acid protecting group such as t-butyl, methyl, and the like, preferably t-butyl, a known compound or compound prepared by known methods, (for example by reacting a compound of formula (X), as defined in Scheme 1 above, with a compound of the formula $NH_2$-$L^2$-$CO_2Pg^2$ and then reducing the nitro group to the corresponding amine), is reacted with cyanogen bromide, in an organic solvent such as methanol, ethanol, toluene, and the like, to yield the corresponding compound of formula (XIX).

Alternatively, the compound of formula (XVIII) is reacted with 2-methyl-2-thiopseudourea, in the presence of an acid such as hydrochloric acid, sulfuric acid, and the like, in an organic solvent such as ethanol, butanol, xylene, dioxane, and the like, or in an aqueous solvent such as water, to yield the corresponding compound of formula (XIX).

The compound of formula (XIX) is deprotected according to known methods, to yield the corresponding compound of formula (XX). For example, wherein $Pg^2$ is t-butyl, the compound of formula (XIX) is deprotected by reacting with an acid such as TFA, HCl, and the like; wherein $Pg^1$ is methyl, the compound of formula (XIX) is deprotected by reacting with a base such as lithium hydroxide or sodium hydroxide in a solvent such as water or DMSO. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999).

The compound of formula (XX) is reacted with a chlorinating agent, such as neat thionyl chloride or oxalyl chloride or phosphorus pentachloride in a solvent such as dichloromethane, benzene, THF, DMF, or carbon tetrachloride, at a temperature of 0° C. to room temperature to reflux to yield the corresponding compound of formula (XXI).

The compound of formula (XXI) is reacted with a suitably substituted amine, a compound of formula (XXII), a known compound or compound prepared by known methods, in the presence of an organic base, such as triethylamine, diisopropylethylamine, pyridine, and the like, in an organic solvent such as dichloromethane, chloroform, THF, and the like, at a temperature in the range of from about 0° C. to about room temperature, to yield the corresponding compound of formula (Ib).

Compounds of formula (XVIII) and (XIX) may be prepared, for example, as outlined in Scheme 4.

Scheme 4

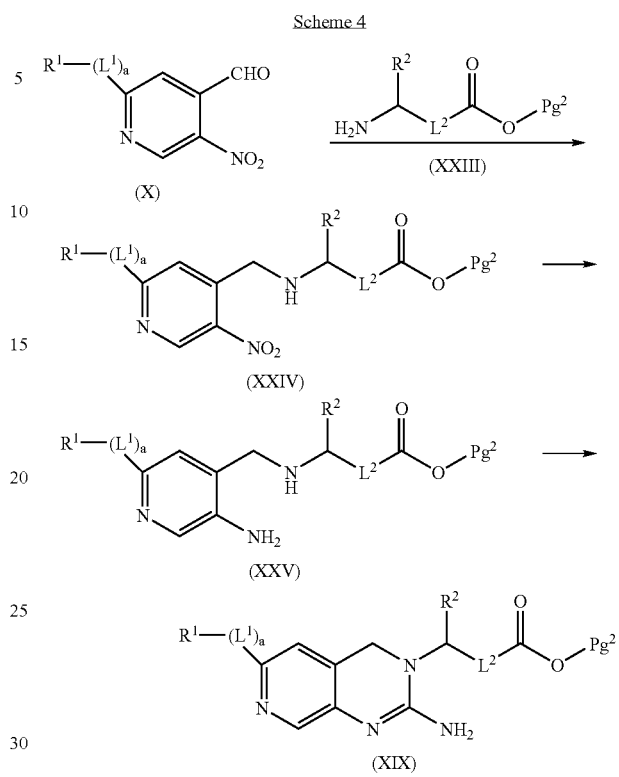

Accordingly, a suitably substituted compound of formula (X), a known compound or compound prepared by known methods, is reacted with a suitably substituted compound of formula (XXIII), wherein $Pg^2$ is a suitable carboxylic acid protecting group such as t-butyl, methyl, and the like, preferably t-butyl, a known compound or compound prepared by known methods, in the presence of a reducing agent such as $NaBH(OAc)_3$, and the like, in an organic solvent such as dichloromethane, 1,2-dichloroethane, THF, acetonitrile, and the like, or in the presence of a reducing agent such as $NaBH_3CN$, $NaBH_4$, and the like, in an organic solvent such as methanol, acetonitrile, and the like, to yield the corresponding compound of formula (XXIV).

The compound of formula (XXIV) is reacted with hydrogen gas, in the presence of a catalyst such as Pd on carbon (Pd/C), and the like, in a protic solvent such as methanol, ethanol, and the like, to yield the corresponding compound of formula (XXV). Alternatively, the compound of formula (XXIV) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (XXV).

The compound of formula (XXV) is reacted with cyanogen bromide, and the like, in an organic solvent such as methanol, ethanol, toluene, and the like, to yield the corresponding compound of formula (Ic). Alternatively, the compound of formula (XXV) is reacted with 2-methyl-2-thiopseudourea, in the presence of an acid such as hydrochloric acid, sulfuric acid, and the like, in an organic solvents such as butanol, and the like, to yield the corresponding compound of formula (XIX).

One skilled in the art will recognize that compounds of formula (I) wherein $R^3$ is

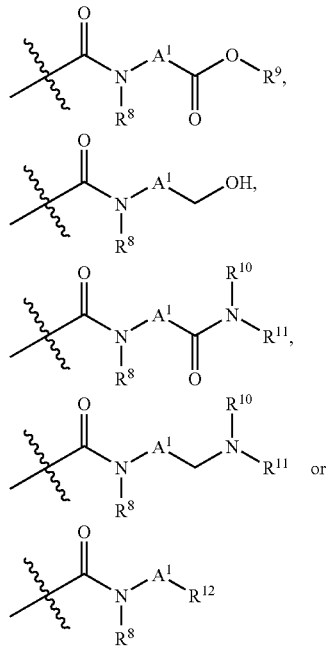

may be similarly prepared according to the processes described above, and as further described in detail for representative examples in Examples 10, 20, 28, 29 and 27, which follow herein.

Compounds of formula (X) wherein $(L^1)_a$ is —O— and $R^1$ is for example, aryl or heteroaryl, may be prepared according to the process outlined in Scheme 5.

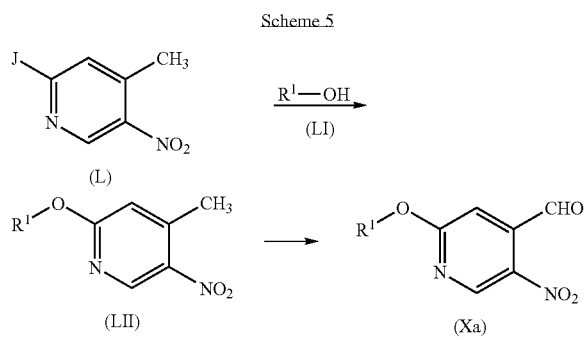

Accordingly, a suitably substituted compound of formula (L) wherein J is chloro, a known compound or compound prepared by known methods, is reacted with a suitably substituted compound of formula (LI), a known compound or compound prepared by known methods, in the presence of a base such as $K_2CO_3$, $Cs_2CO_3$, and the like, in an organic solvent such as DMF, DMA, and the like, preferably DMF, at a temperature in the range of from about 25° C. to about 150° C., preferably, at an elevated temperature in the range of from about 100° C. to about 120° C., optionally in the presence of microwave irradiation, to yield the corresponding compound of formula (LII).

The compound of formula (LII) is reacted with an electrophilic formyl source such as DMF dimethyl acetal, DMF diethyl acetal, and the like, in an organic solvent such as DMF, DMA, and the like, preferably DMF; or with neat tripiperidinomethane, preferably under vacuum; or with neat tert-butoxy-bis(dimethyl)aminomethane, at an elevated temperature in the range of from about 100° C. to about 150° C., preferably, at an elevated temperature in the range of from about 130° C. to about 140° C., followed by reaction with an oxidizing agent such as $NaIO_4$, $KMnO_4$, and the like, in an organic solvent such as THF, DME, and the like, in the presence of water as a co-solvent, to yield the corresponding compound of formula (Xa).

Compounds of formula (X) wherein $(L^1)_b$ is —S— may be similarly prepared according to the process described above by reacting a compound of formula (L) wherein J is F or Cl, with a substituting a suitably substituted compound of the formula $R^1$—SH (i.e. substituting the compound of formula $R^3$—SH for the compound of formula (LI)). The resulting compound may then be optionally, selectively oxidized to yield the corresponding compound of formula (X) wherein the —S— is oxidized to —SO— and/or —$SO_2$—.

Compounds of formula (X) wherein $(L^1)_a$ is —$NR^0$—, may be similarly prepared according to the process outlined in Scheme 5 above, by reacting a compound of formula (L) wherein J is Br with a suitably substituted compound of the formula $R^1$—$NHR^0$, in the presence of a catalyst or mixture thereof, such as a 1:3 mixture of $Pd_2(dba)_3$ and dppf, and the like, in an organic solvent such as DMF, DME, toluene, and the like; or a catalyst such as $Pd_2(dba)_3$ or $Pd(dppf)Cl_2$ in the presence or a base such as $Cs_2CO_3$, $NaOC(CH_3)_3$, and the like, in an organic solvent such as toluene, and the like, to yield the corresponding compound of formula (X) wherein $(L^1)_a$ is —$NR^0$—.

Compounds of formula (X) wherein $(L^1)_a$ is absent (i.e. a=0) may be prepared according to the process outlined in Scheme 6.

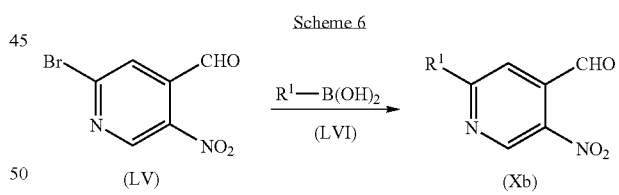

Accordingly, a suitably substituted compound of formula (LV), a known compound or compound prepared by known methods is reacted with a suitably substituted compound of formula (LVI), wherein $R^1$ is aryl or heteroaryl, a known compound or compound prepared by known methods, in the presence of a catalyst such $Pd(PPh_3)_4$, $Pd(dppf)Cl_2$, and the like, in the presence of a base such as $Na_2CO_3$, $K_2CO_3$, $NaHCO_3$, and the like, in a mixture of an organic solvent such as toluene, DME, THF, MeOH, and the like, and a protic solvent such as water, and the like, at an elevated temperature in the range of from about 60° C. to about 150° C., preferably, at an elevated temperature in the range of from about 100° C. to about 120° C., optionally in the presence of microwave irradiation, to yield the corresponding compound of formula (Xb).

Compounds of formula (I) wherein $R^3$ is

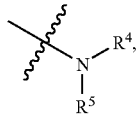

may be prepared according to the process outlined in Scheme 7.

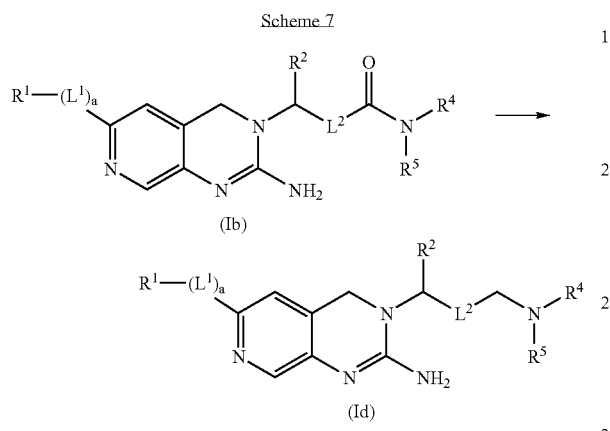

Accordingly, a suitably substituted compound of formula (Ib) is reacted with a suitably selected reducing agent, such as lithium aluminum hydride, diisobutyl aluminum hydride, borane, and the like; in an organic solvent, such as THF, diethyl ether, glyme, diglyme, and the like; at a temperature in the range of from about 25° C. to about 150° C., optionally in the presence of microwave irradiation, to yield the corresponding compound of formula (Id).

Compounds of formula (I) wherein $L^2$ is —(CH$_2$)— may be prepared according to the process outlined in Scheme 8.

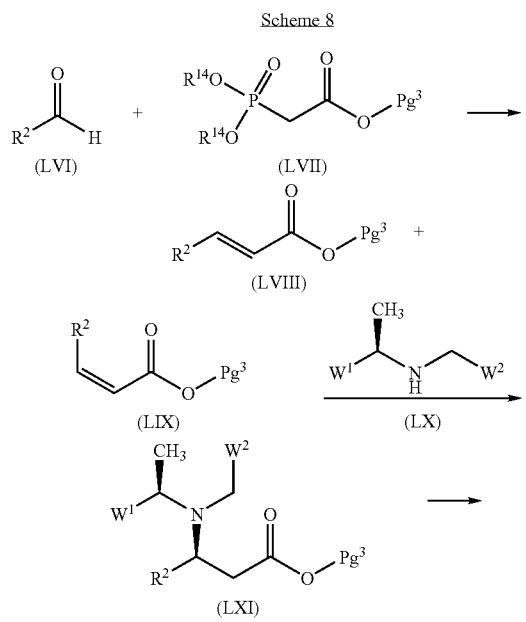

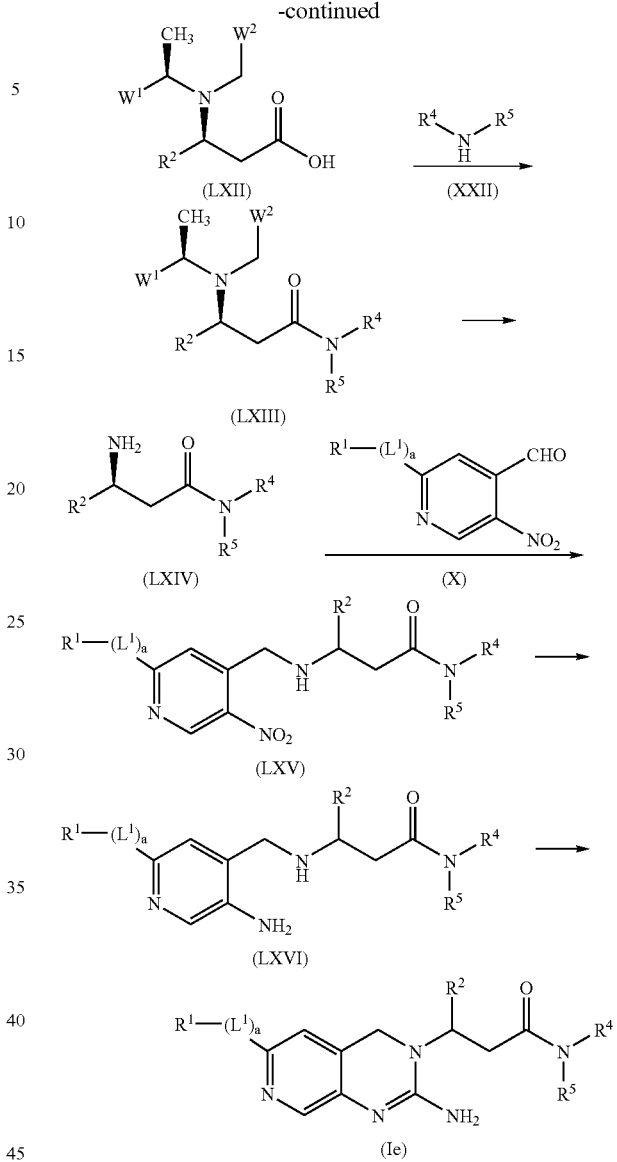

Accordingly, a suitably substituted compound of formula (LVI), a known compound or compound prepared by known methods, is reacted with a suitably substituted alkyl (dialkylphosphono)acetate (LVII), wherein each $R^{14}$ is independently selected from $C_{1-4}$alkyl, preferably both $R^{14}$ groups are the same and are selected from C1-4alkyl, preferably methyl or ethyl, a known compound or compound prepared by known methods, in the presence of a base, such as sodium hydride, lithium hexamethyldisilazide, lithium diisopropylamide, and the like, in an organic solvent, such as THF, diethyl ether, glyme, and the like, at a temperature in the range of from about −78° C. to about 25° C., to yield a mixture of the corresponding compound of formula (LVIII) and the corresponding compound of formula (LIX).

Preferably, the compound of formula (LVIII) is isolated and separated from the mixture, according to known methods, for example by column chromatography.

A chiral amine, a compound of formula (LX), is reacted with a base, such as n-butyllithium, and the like, in an organic solvent such as THF, diethyl ether, and the like, at a temperature in the range of from about −100° C. to about 25° C., preferably at a temperature in the range of from about −100° C. to about −78° C., and then reacted with the compound of formula (LVIII), to yield the corresponding compound of formula (LXI).

The compound of formula (LXI) is deprotected according to known methods, to yield the corresponding compound of formula (LXII). For example, wherein Pg³ is t-butyl, the compound of formula (XIX) is deprotected by reacting with an acid such as TFA, HCl, and the like; wherein Pg³ is methyl, the compound of formula (LXI) is deprotected by reacting with a base such as lithium hydroxide or sodium hydroxide in a solvent such as water or DMSO. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999).

The compound of formula (LXII) is reacted with a suitably substituted compound of formula (XXII), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield a the corresponding compound of formula (LXIII).

The compound of formula (LXIII) is deprotected according to known methods, to yield the corresponding compound of formula (LXIV). For example, the compound of formula (LXIII) may be deprotected by reacting with hydrogen gas in the presence of a catalyst such as palladium on carbon or palladium hydroxide in an organic solvent, such as methanol, ethanol, and the like, optionally in the presence of an acid, such as hydrochloric acid or acetic acid, (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999). One skilled in the art will recognize that the chiral substituents on the substituted amine portion of the compound of formula (LXIII) control the stereochemistry of the compound, which stereochemistry is preserved in the deprotection step.

The compound of formula (LXIV), is reacted with a suitably substituted compound of formula (X), a known compound or compound prepared by known methods, in the presence of a reducing agent such as NaBH(OAc)₃, and the like, in an organic solvent such as dichloromethane, 1,2-dichloroethane, THF, acetonitrile, and the like, or in the presence of a reducing agent such as NaBH₃CN, NaBH₄, and the like, in an organic solvent such as methanol, acetonitrile, and the like, to yield the corresponding compound of formula (LXV).

The compound of formula (LXV) is reacted with hydrogen gas, in the presence of a catalyst such as Pd on carbon (Pd/C), and the like, in a protic solvent such as methanol, ethanol, and the like, to yield the corresponding compound of formula (LXVI). Alternatively, the compound of formula (LXV) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (LXVI).

The compound of formula (LXVI) is reacted with cyanogen bromide, and the like, in an organic solvent such as methanol, ethanol, toluene, and the like, to yield the corresponding compound of formula (Id). Alternatively, the compound of formula (LXVI) is reacted with 2-methyl-2-thiopseudourea, in the presence of an acid such as hydrochloric acid, sulfuric acid, and the like, in an organic solvents such as butanol, and the like, to yield the corresponding compound of formula (Ie).

Compounds of formula (I) wherein R³ is

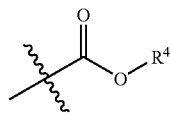

may be prepared according to the process outlined in Scheme 9.

Scheme 9

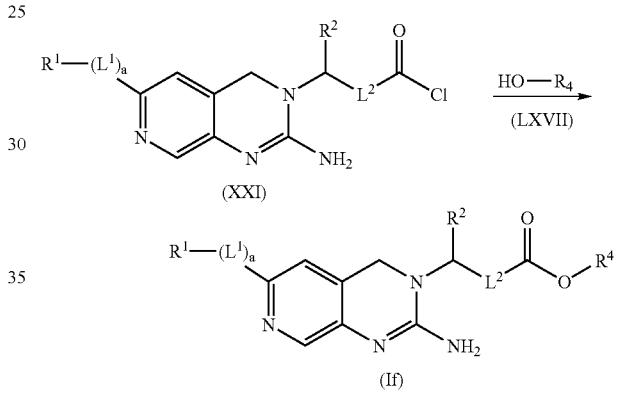

Accordingly, a suitably substituted compound of formula (XXI) is reacted with a suitably substituted alcohol (LXVII), a known compound or compound prepared by known methods, in an organic solvent, such as DCM, THF, and the like, at a temperature in the range of from about −0° C. to about 25° C., to yield the corresponding compound of formula (If).

Compounds of Formula (I) wherein R³ is

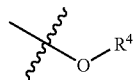

may be prepared according to the process outlined in Scheme 10.

Scheme 10

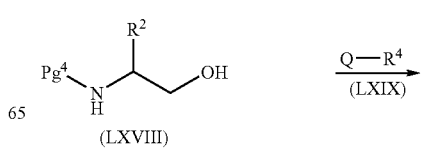

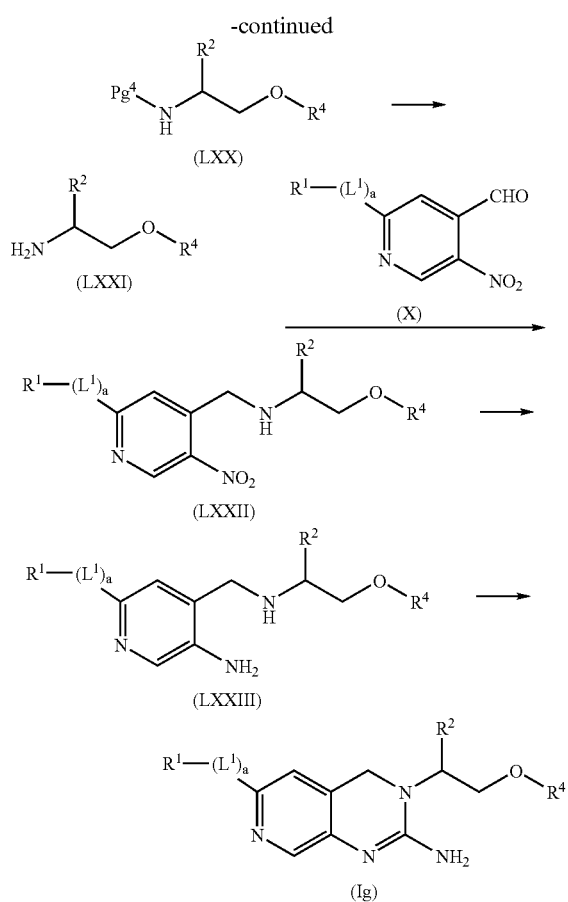

Accordingly, a suitably substituted compound of formula (LXVIII), a known compound or compound prepared by known methods, is reacted with a suitably substituted alkyl halide, a compound of formula (LXIX), wherein Q is iodo, bromo, or chloro, a known compound or compound prepared by known methods, in the presence of a base, such as potassium hydroxide, sodium hydride, potassium hydride, potassium tert-butoxide, and the like, in an organic solvent, such as DMF, THF, diethyl ether, glyme, and the like, at a temperature in the range of from about 0° C. to about 25° C., to yield the corresponding compound of formula (LXX).

The compound of formula (LXX) is deprotected according to known methods, to yield the corresponding compound of formula (LXXI). For example, wherein $Pg^4$ is BOC, the compound of formula (LXX) is deprotected by reacting with an acid such as TFA, HCl, and the like; wherein $Pg^4$ is Cbz, the compound of formula (LXX) is deprotected by reacting with a hydrogen source such as $H_2$ (g) in the presence of a catalyst, such as palladium on carbon or palladium black. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999)

The compound of formula (LXXI) is reacted with a suitably substituted compound of formula (X), a known compound or compound prepared by known methods, in the presence of a reducing agent such as $NaBH(OAc)_3$, and the like, in an organic solvent such as dichloromethane, 1,2-dichloroethane, THF, acetonitrile, and the like, or in the presence of a reducing agent such as $NaBH_3CN$, $NaBH_4$, and the like, in an organic solvent such as methanol, acetonitrile, and the like, to yield the corresponding compound of formula (LXXII).

The compound of formula (LXXII) is reacted with hydrogen gas, in the presence of a catalyst such as Pd on carbon (Pd/C), and the like, in a protic solvent such as methanol, ethanol, and the like, to yield the corresponding compound of formula (LXXIII). Alternatively, the compound of formula (LXXII) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (LXXIII).

The compound of formula (LXXIII) is reacted with cyanogen bromide, and the like, in an organic solvent such as methanol, ethanol, toluene, and the like, to yield the corresponding compound of formula (Ig). Alternatively, the compound of formula (LXVI) is reacted with 2-methyl-2-thiopseudourea, in the presence of an acid such as hydrochloric acid, sulfuric acid, and the like, in an organic solvents such as butanol, and the like, to yield the corresponding compound of formula (Ig).

Compounds of Formula (I) wherein $R^3$ is

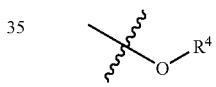

and wherein $R^4$ is —$CH_2$-(5-(3-substituted-4,5-dihydroisoxazolyl) may alternatively be prepared according to the process outlined in Scheme 11.

Scheme 11

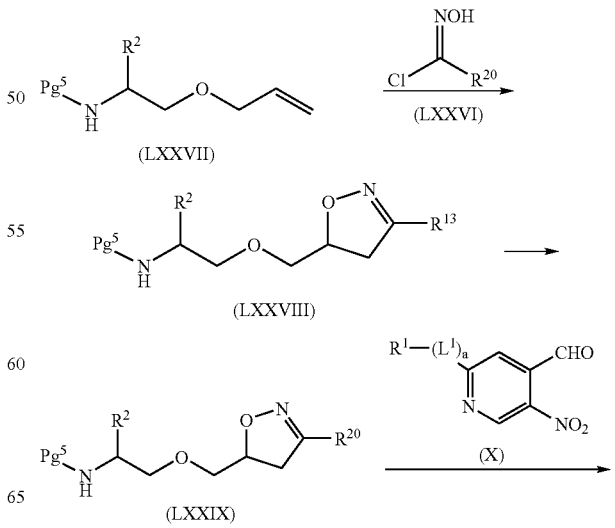

-continued

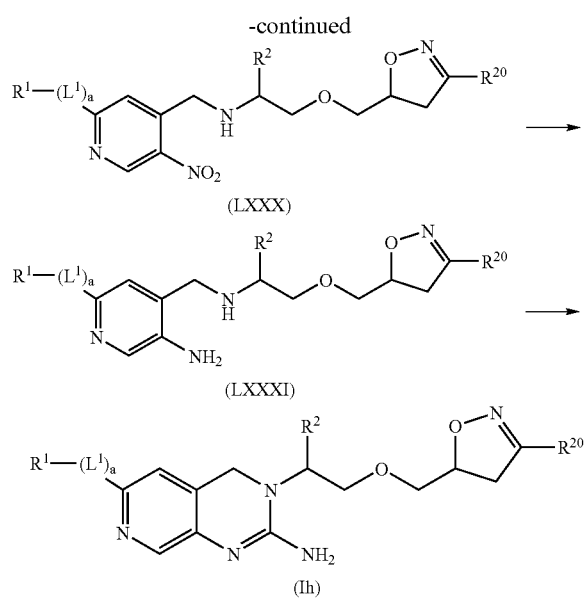

Accordingly, a suitably substituted compound of formula (LXXVII), a known compound or compound prepared by known methods, is reacted with a suitably substituted compound of formula (LXXVI), wherein $R^{20}$ is substituent as herein defined, for example a cycloalkyl such as cyclohexyl or an alkyl such as t-butyl or 2,2-dimethyl-n-propyl, a known compound or compound prepared by known methods, for example as outlined in Scheme 12 below, in the presence of a base, such as triethylamine, diisopropylethylamine, pyridine, and the like, in an organic solvent, such as toluene, diethyl ether, chloroform, benzene, and the like, to yield the corresponding compound of formula (LXXVIII).

The compound of formula (LXXVIII) is deprotected according to known methods, to yield the corresponding compound of formula (LXXIX). For example, wherein $Pg^5$ is BOC, the compound of formula (LXXVIII) is deprotected by reacting with an acid such as TFA, HCl, and the like; wherein $Pg^5$ is Cbz, the compound of formula (LXXVIII) is deprotected by reacting with a hydrogen source such as $H_2$ (g) in the presence of a catalyst, such as palladium on carbon or palladium black. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999).

The compound of formula (LXXIX) is reacted with a suitably substituted compound of formula (X), a known compound or compound prepared by known methods, in the presence of a reducing agent such as $NaBH(OAc)_3$, and the like, in an organic solvent such as dichloromethane, 1,2-dichloroethane, THF, acetonitrile, and the like; or in the presence of a reducing agent such as $NaBH_3CN$, $NaBH_4$, and the like, in an organic solvent such as methanol, acetonitrile, and the like; to yield the corresponding compound of formula (LXXX).

The compound of formula (LXXX) is reacted with hydrogen gas, in the presence of a catalyst such as Pd on carbon (Pd/C), and the like, in a protic solvent such as methanol, ethanol, and the like, to yield the corresponding compound of formula (LXXXI). Alternatively, the compound of formula (LXXX) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like; or in a mixture of an organic solvent and water as a co-solvent, or in aqueous acid such as acetic acid, and the like, optionally in the presence of microwave irradiation, to yield the corresponding compound of formula (LXXXI).

The compound of formula (LXXXI) is reacted with cyanogen bromide, and the like, in an organic solvent such as methanol, ethanol, toluene, and the like, to yield the corresponding compound of formula (Ih). Alternatively, the compound of formula (LXXXI) is reacted with 2-methyl-2-thiopseudourea, in the presence of an acid such as hydrochloric acid, sulfuric acid, and the like, in an organic solvents such as butanol, and the like, to yield the corresponding compound of formula (Ih).

The compound of formula (LXXVI) may be prepared according to the process outlined in Scheme 12 below.

Scheme 12

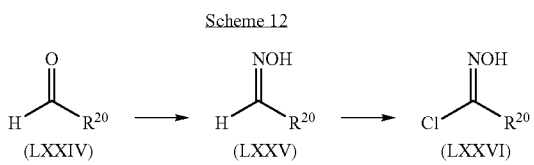

Accordingly, a suitably substituted compound of formula (LXXIV), a known compound or compound prepared by known methods, is reacted with N-hydroxylamine hydrochloride, in the presence of a base, such as sodium hydroxide, sodium carbonate, potassium carbonate, and the like, in a protic solvent, such as methanol, ethanol, and water, and the like, at a temperature in the range of from about 0° C. to about 25° C., to yield the corresponding compound of formula (LXXV).

The compound of formula (LXXV) is reacted with a chlorinating agent, such as N-chlorosuccinimide, and the like, in an organic solvent, such as DMF, N-methylpyrrolidinone, chloroform, and the like, optionally in the presence of a base, such as pyridine, triethylamine, and the like, at a temperature in the range of from about 0° C. to about 60° C., preferably, at a temperature in the range of from about 0° C. to about 25° C., to yield the corresponding compound of formula (LXXVI). Alternatively, the compound of formula (LXXV) is reacted with a chlorinating agent, such as tert-butylhypochlorite, in an organic solvent, such as methylene chloride, toluene, and the like, in a temperature in the range of from about −78° C. to about 25° C.; or with chlorine gas in an organic solvent, such as diethyl ether, chloroform, and the like; or in an aqueous solvent, optionally in the presence of an acid, such as HCl, and the like; to yield the corresponding compound of formula (LXXVI).

Compounds of Formula (I) wherein $R^3$ is

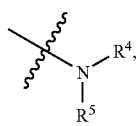

and wherein $R^4$ and $R^5$ are taken together with the nitrogen atom to which they are bound to form 1-(4-substituted-1,2,3-triazolyl), may be prepared according to the process outlined in Scheme 13.

Scheme 13

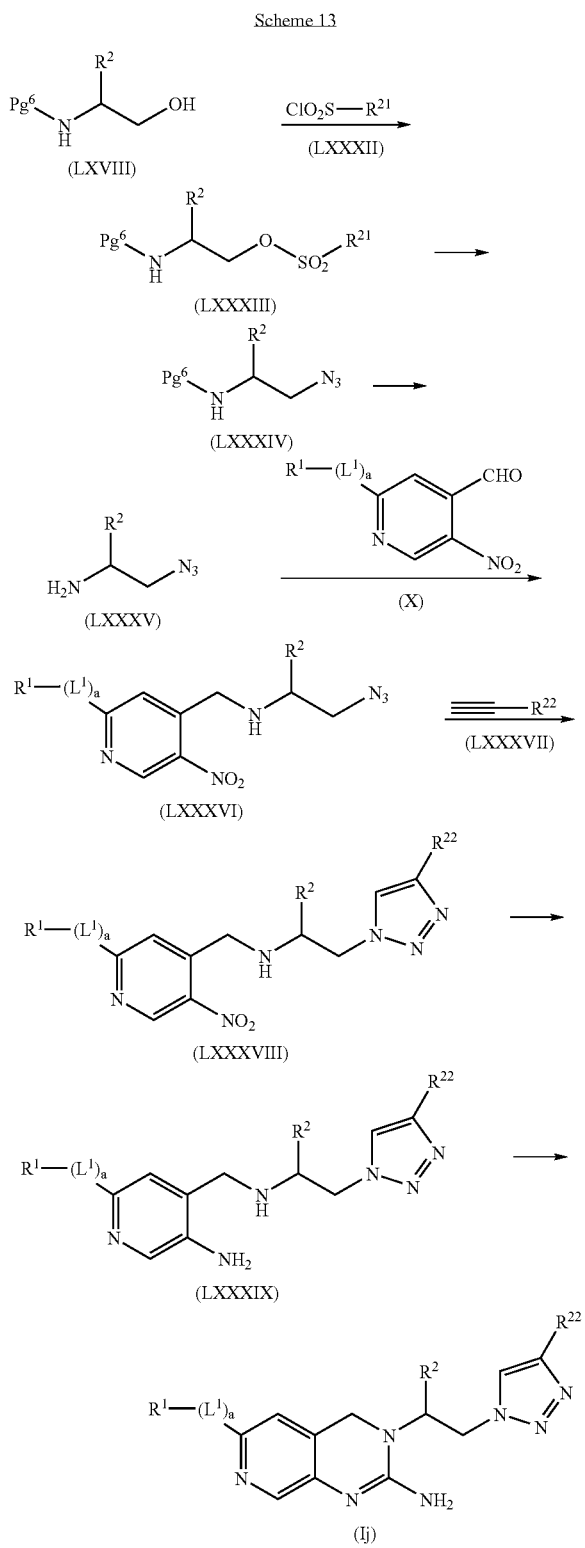

the —SO$_2$—R$^{21}$ portion is a suitable leaving group), a known compound or compound prepared by known methods, in the presence of a base, such as triethylamine, diisopropylethylamine, pyridine, and the like, in an organic solvent, such as DCM, chloroform and the like, to yield the corresponding compound of formula (LXXXIII).

The compound of formula (LXXXIII) is reacted with sodium azide, in an aprotic solvent, such as DMF, N-methylpyrrolidone, and the like, at a temperature in the range of from about 25° C. to about 150° C., preferably at a temperature in the range of from about 70° C. to about 100° C., to yield the corresponding compound of formula (LXXXIV).

The compound of formula (LXXXIV) is deprotected according to known methods, to yield the corresponding compound of formula (LXXXV). For example, wherein Pg$^6$ is BOC, the compound of formula (LXXXIV) is deprotected by reacting with an acid such as TFA, HCl, and the like; wherein Pg$^6$ is Cbz, the compound of formula (LXXXIV) is deprotected by reacting with a hydrogen source such as H$_2$ (g) in the presence of a catalyst, such as palladium on carbon or palladium black. (See for example, *Protective Groups in Organic Chemistry*, ed. J. F. W. McOmie, Plenum Press, 1973; or T. W. Greene & P. G. M. Wuts, *Protective Groups in Organic Synthesis*, John Wiley & Sons, 1999).

The compound of formula (LXXXV) is reacted with a suitably substituted compound of formula (X), a known compound or compound prepared by known methods, in the presence of a reducing agent such as NaBH(OAc)$_3$, and the like, in an organic solvent such as dichloromethane, 1,2-dichloroethane, THF, acetonitrile, and the like; or in the presence of a reducing agent such as NaBH$_3$CN, NaBH$_4$, and the like, in an organic solvent such as methanol, acetonitrile, and the like; to yield the corresponding compound of formula (LXXXVI).

The compound of formula (LXXXVI) is reacted with a suitably substituted acetylene, a compound of formula (LXXXVII), wherein R$^{22}$ is a substitutent as herein defined, for example wherein R$^{22}$ is cycloalkyl-alkyl- such as cyclohexyl-methyl-, a known compound or compound prepared by known methods; in the presence of a copper catalyst, such as copper, copper iodide, copper sulfate, and the like, in an organic solvent, such as THF, CH$_3$CN, and toluene, and the like, or in a protic solvent, such as water, ethanol, t-butanol, and the like; optionally in the presence of water; optionally in the presence of a base such as sodium ascorbate, diisopropylethylamine, and the like; at a temperature in the range of from about 25° C. to about 100° C., preferably, at a temperature in the range of from about 25° C. to about 50° C., to yield the corresponding compound of formula (LXXXVIII).

The compound of formula (LXXXVIII) is reacted with hydrogen gas, in the presence of a catalyst such as Pd on carbon (Pd/C), and the like, in a protic solvent such as methanol, ethanol, and the like, to yield the corresponding compound of formula (LXXXIX). Alternatively, the compound of formula (LXXXVIII) is reacted with a reducing agent such as stannous chloride, and the like, in an organic solvent such as methanol, ethanol, ethyl acetate, THF and the like; or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like; or in a mixture of an organic solvent and water as a co-solvent; or in aqueous acid such as acetic acid, and the like, optionally in the presence of microwave irradiation, to yield the corresponding compound of formula (LXXXIX).

The compound of formula (LXXXIX) is reacted with cyanogen bromide, and the like, in an organic solvent such as methanol, ethanol, toluene, and the like, to yield the corre- Accordingly, a suitably substituted compound of formula (LXVI), a known compound or compound prepared by known methods, is reacted with a substituted sulfonyl chloride, a compound of formula (LXXXII) wherein R$^{21}$ is methyl, 4-methyl-phenyl, or other suitable group (such that sponding compound of formula (Ii). Alternatively, the compound of formula (LXXXIX) is reacted with 2-methyl-2-thiopseudourea, in the presence of an acid such as hydrochloric acid, sulfuric acid, and the like, in an organic solvents such as butanol, and the like, to yield the corresponding compound of formula (Ij).

Compounds of Formula (I) wherein $R^{15}$ is hydroxy may be prepared according to the process outlined in Scheme 14.

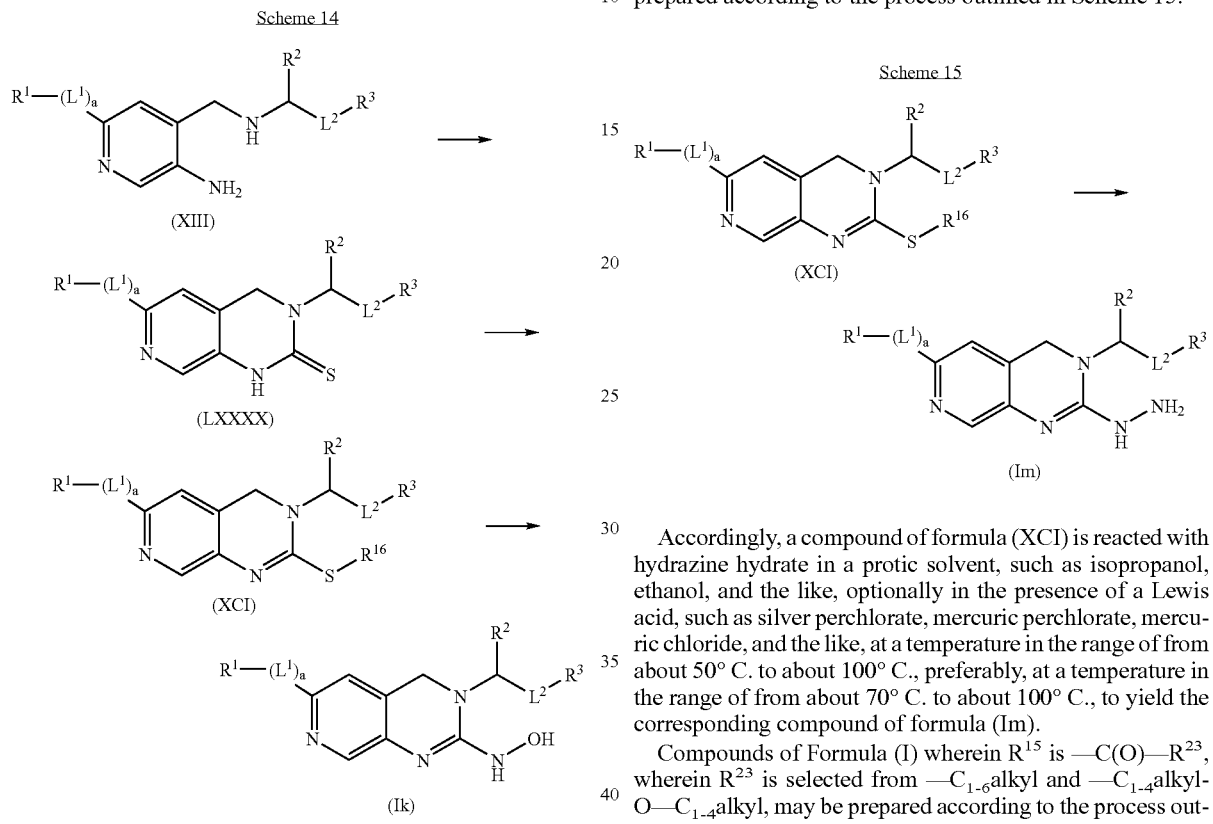

Accordingly, a suitably substituted compound of formula (XIII) is reacted with a thiocarbonylation agent, such as thiocarbonyldiimidazole, in an organic solvent, such as chloroform, DCM, or acetonitrile, and the like, to yield the corresponding compound of formula (LXXXX). Alternatively, the compound of formula (XIII) is reacted with carbon disulfide, in the presence of a base, such as potassium hydroxide, ammonium hydroxide, and the like, in a protic solvent, such as ethanol, methanol, and the like, optionally with heating, to yield the corresponding compound of formula (LXXXX). Alternatively, the compound of formula (XIII) is reacted with thiophosgene in the presence of a base, such as DIPEA, triethylamine, and the like, in an organic solvent, such as ether, acetonitrile, and the like, to yield the corresponding compound of formula (LXXXX).

The compound of formula (LXXXX) is reacted with a suitably selected alkylating agent, such as methyl iodide, dimethyl sulfate, and the like, in the presence of a base, such as potassium hydroxide, sodium hydroxide, and the like, in a protic solvent such as methanol, water, and the like, to yield the corresponding compound of formula (XCI).

The compound of formula (XCI) is reacted with an oxidizing agent, such as mCPBA, in an organic solvent, such as dichloromethane, chloroform, and the like; or with an oxidizing agent, such as oxone, in a protic solvent, such as methanol, ethanol, and the like, optionally in the presence of water, followed by the addition of hydroxylamine hydrochloride in a protic solvent, such as isopropanol, ethanol, and the like, in the presence of a base, such as potassium carbonate, DIPEA, and the like, at a temperature in the range of from about 25° C. to about 100° C., preferably at a temperature in the range of from about 50° C. to about 80° C., to yield the corresponding compound of formula (Ik).

Compounds of Formula (I) wherein $R^{15}$ is amino may be prepared according to the process outlined in Scheme 15.

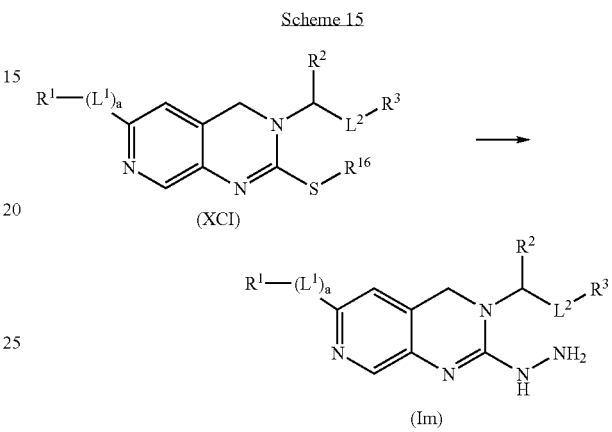

Accordingly, a compound of formula (XCI) is reacted with hydrazine hydrate in a protic solvent, such as isopropanol, ethanol, and the like, optionally in the presence of a Lewis acid, such as silver perchlorate, mercuric perchlorate, mercuric chloride, and the like, at a temperature in the range of from about 50° C. to about 100° C., preferably, at a temperature in the range of from about 70° C. to about 100° C., to yield the corresponding compound of formula (Im).

Compounds of Formula (I) wherein $R^{15}$ is —C(O)—$R^{23}$, wherein $R^{23}$ is selected from —$C_{1-6}$alkyl and —$C_{1-4}$alkyl-O—$C_{1-4}$alkyl, may be prepared according to the process outlined in Scheme 16.

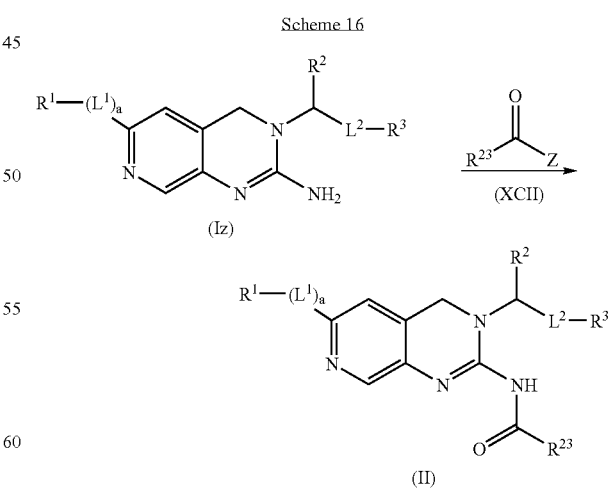

Accordingly, a suitably substituted compound of formula (Iz) is reacted with an acid chloride, a compound of formula (XCII), wherein Z is chloro or bromo, a known compound or compound prepared by known methods, in the presence of a base, such as triethylamine, DIPEA, pyridine, DMAP, and the like, in an organic solvent, such as DCM, chloroform, and the like, at a temperature in the range of from about −20° C. to about 25° C., preferably at a temperature in the range of from about 0° C. to about 25° C., to yield the corresponding compound of formula (In).

Alternatively, a suitably substituted compound of formula (Iz) is reacted with a carboxylic acid, a compound of formula (XCII) wherein Z is hydroxyl, a known compound or compound prepared by known methods, in the presence of a coupling agent such as HBTU, EDCl, HOBT, and the like, in the presence of a base such as DIPEA, triethylamine, pyridine, and the like, in an organic solvent such as DMF, DCM, and the like, to yield the corresponding compound of formula (In).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-1000 mg/kg/day, preferably, at a dosage of from about 0.5 to about 500 mg/kg/day, more preferably, at a dosage of from about 1.0 to about 250 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by BACE described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by BACE is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 1000 mg/kg of body weight per day. Preferably, the range is from about 0.5 to about 500 mg/kg of body weight per day, most preferably, from about 1.0 to about 250 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

2-(2-Fluoro-phenyl)-5-nitro-pyridine-4-carbaldehyde

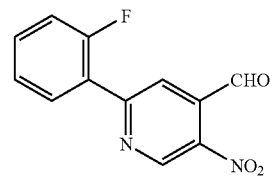

A solution of 2-chloro-4-methyl-5-nitropyridine (5 g, 28 mmol) in dimethoxyethane (40 mL) was treated with 2-fluorophenylboronic acid (5.3 g, 35 mmol) and 2M $K_2CO_3$ (40 mL). The reaction mixture was stirred for 5 minutes and then degassed (argon), treated with tetrakis(triphenylphosphine)palladium (1.7 g, 1.4 mmol) and stirred at 110° C. under argon for 2.4 h. The reaction mixture was cooled, poured into water and extracted into EtOAc. The organic phase washed with brine, dried ($Na_2SO_4$), and concentrated in vacuo to yield crude 2-(2-fluoro-phenyl)-4-methyl-5-nitro-pyridine as a hygroscopic solid. The solid was purified by column chromatography (4:2:0.5 $CHCl_3$:hexanes:EtOAc) to yield 2-(2-fluoro-phenyl)-4-methyl-5-nitro-pyridine as a light yellow solid.

A mixture of 2-(2-fluoro-phenyl)-4-methyl-5-nitro-pyridine (5.4 g, 23 mmol) in DMF (30 mL) was treated with N,N-dimethylformamide dimethyl acetal (3.6 g, 30 mmol), and the mixture was stirred at 115° C. for 1 h, cooled, and concentrated in vacuo to yield crude {2-[2-(2-fluoro-phenyl)-5-nitro-pyridin-4-yl]-vinyl}-dimethyl-amine as a brown solid. The solid was dissolved in THF (100 mL), and water (100 mL), and then sodium periodate (14.06 g, 66 mmol) was added. The suspension was stirred at room temperature for 24 h. The reaction mixture was filtered, and the filtrate was concentrated, and then diluted with EtOAc. The organic extract washed with saturated aqueous $NaHCO_3$ solution, dried ($Na_2SO_4$), and concentrated in vacuo to yield crude title compound as a solid. The crude solid was purified by column chromatography (4:2:0.5; $CHCl_3$:hexanes:EtOAc) to yield 2-(2-fluoro-phenyl)-5-nitro-pyridine-4-carbaldehyde, the title compound as a yellow solid.

EXAMPLE 2

5-Nitro-2-phenoxy-pyridine-4-carbaldehyde

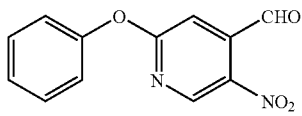

A solution of 2-chloro-4-methyl-5-nitropyridine (10 g, 0.058 mol), in DMF (100 mL) was treated with phenol (6.6 g, 0.07 mol) and potassium carbonate (9.6 g, 0.07 mol) and the reaction mixture was stirred at 110° C. for 4 hr and then cooled. To the reaction mixture was then added water. The reaction mixture was extracted into EtOAc, dried and concentrated to a syrup, which was purified via column chromatography (4:2:0.5; CHCl$_3$:hexanes:EtOAc, v/v) to yield 4-methyl-5-nitro-2-phenoxy-pyridine as a light yellow solid.
MS, m/z 231 (M+H).

A mixture of 4-methyl-5-nitro-2-phenoxy-pyridine (0.2 g, 0.86 mmol) and N,N-dimethylformamide dimethyl acetal (0.13 g, 1.1 mmol) in DMF (1 mL) was stirred at 130° C. for 1 hr, then cooled and concentrated to yield crude dimethyl-[2-(5-nitro-2-phenoxy-pyridin-4-yl)-vinyl]-amine as a syrup.
MS, m/z 286 (M+H).

To a solution of dimethyl-[2-(5-nitro-2-phenoxy-pyridin-4-yl)-vinyl]-amine (0.2 g, 0.7 mmol) in THF (2 mL) and water (2 mL) was added sodium periodate (0.46 g, 2.1 mmol). The reaction mixture was stirred for 30 min, treated with EtOAc and the solids filtered. The filtrate was washed with sat NaHCO$_3$, dried (Na$_2$SO$_4$), and concentrated to yield 5-nitro-2-phenoxy-pyridine-4-carbaldehyde, the title compound, as a bright yellow solid.
MS, m/z 245 (M+H).

EXAMPLE 3

4-Methyl-5-nitro-2-phenoxy-pyridine

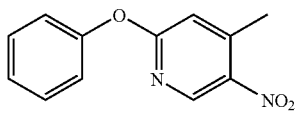

A solution of phenol (0.30 g, 3.1 mmol) in DMF (10 mL) was treated with cesium carbonate (1.41 g, 4.3 mmol) and stirred for 15 min. 2-Chloro-5-nitro pyridine (0.5 g, 2.9 mmol) was added, and the reaction mixture was stirred and monitored via TLC. After the reaction was complete, the reaction mixture was treated with water, extracted into EtOAc, and the organic extract washed with 1N NaOH and brine, dried (Na$_2$SO$_4$) and concentrated to yield 4-methyl-5-nitro-2-phenoxypyridine as a solid.

EXAMPLE 4

4-Amino-4S,N-dicyclohexyl-N-(2-hydroxy-ethyl)-butyramide

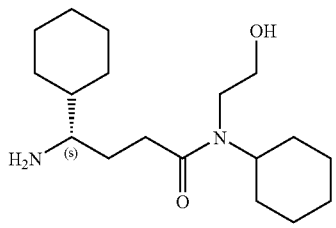

To an ice cooled solution of Boc-D-cyclohexylglycine (10 g, 39 mmol) in DCM (200 mL), N,O-dimethylhydroxyamine HCl salt (4.6 g, 46 mmol), HOBT (7 g, 51 mmol), and TEA (11 mL) were added followed by addition of 1,3-dimethylamino propyl-3-ethylcarbodiimide (EDC, 10 g, 51 mmol). The reaction mixture was allowed to warm to room temperature and then stirred overnight. EtOAc (300 mL) was added. The resulting solution washed with aqueous citric acid solution, aqueous NaHCO$_3$ solution, and aqueous NaCl solution. The organic layer was separated, dried with MgSO$_4$, and then evaporated to yield [cyclohexyl-(methoxy-methyl-carbamoyl)-methyl]-carbamic acid tert-butyl ester as a colorless oil, which was used in the next step without further purification.
MH$^+$ 301.2

To an ice cooled solution of [cyclohexyl-(methoxy-methyl-carbamoyl)-methyl]-carbamic acid tert-butyl ester (12.3 g, 40 mmol) in THF (100 mL) was slowly added LAH (1M in THF; 45 mL), with the reaction mixture temperature maintained below 5° C. The ice bath was removed, and the reaction mixture was stirred at room temperature for 20 min. A solution of NaHSO$_4$ (7.3 g) in water (10 mL) was then slowly added to the reaction mixture to quench the reaction. The reaction mixture was then filtered through Celite. EtOAc (300 mL) was added to the filtrate, and the organic layer washed with aqueous NaCl solution, dried with MgSO$_4$ and evaporated to yield (1-cyclohexyl-2-oxo-ethyl)-carbamic acid tert-butyl ester as an oil, which was used in the next step without further purification.
MH$^+$ 242.2

To an ice cooled solution of trimethyl phosphonoacetate (19 mL, 0.11 mol) in THF (200 mL) was added 60% NaH (3.1 g, 0.08 mol) in portions. The ice bath was removed and the reaction mixture was stirred at room temperature for 30 min. The reaction mixture was then cooled to 0° C. before a solution of (1-cyclohexyl-2-oxo-ethyl)-carbamic acid tert-butyl ester (9 g, 37 mmol) in THF (200 mL) was added. The reaction mixture was stirred at room temperature for another 20 min. Water (100 mL) was added, and then most of the THF was evaporated. The product was extracted with EtOAc (400 mL), and the organic layer was washed with aqueous NaCl solution and then dried with MgSO$_4$. Evaporation yielded a residue which was purified by column chromatography (1:1 heptane:EtOAc) to yield 4-tert-butoxycarbonylamino-4-cyclohexyl-but-2-enoic acid methyl ester as a white solid.
$^1$H NMR (300 MHz, CDCl$_3$): δ1.1-1.3 (m, 7H), 1.44 (s, 9H), 1.6-1.8 (m, 5H), 3.73 (s, 3H), δ4.17 (m, 0.6×1H), 4.58 (m, 0.4×1H), 5.9 (dd, J=1.4 Hz, J=15.6 Hz, 1H), 6.88 (dd, J=5.6 Hz, J=15.6 Hz, 1H).

To a solution of 4-tert-butoxycarbonylamino-4-cyclohexyl-but-2-enoic acid methyl ester (9 g, 30 mmol) in MeOH (100 mL) was added Pd—C (10% on activated carbon) (1 g) under N$_2$, and the reaction mixture was subjected to hydrogenation under 20 psi for 4 hours. The catalyst was filtered out, and the MeOH was evaporated to yield 4-tert-butoxycarbonylamino-4-cyclohexyl-butyric acid methyl ester as a white solid.
$^1$H NMR (300 MHz, CDCl$_3$): δ0.9-1.3 (m, 7H), 1.43 (s, 9H), 1.5-1.8 (m, 6H), 2.37 (t, J=7.52 Hz, 2H), 3.4 (m, 1H), 3.67 (s, 3H), 4.29 (m, 1H).

To a solution of 4-tert-butoxycarbonylamino-4-cyclohexyl-butyric acid methyl ester (9 g) in MeOH (100 mL) was added 1N NaOH (31 mL) and the reaction mixture was stirred at room temperature overnight. Citric acid (7 g) was then added, and the MeOH was removed under vacuum. The product was extracted with EtOAc (300 mL). The organic layer was washed with aqueous NaCl solution, dried with MgSO$_4$, and evaporated to yield 4-tert-butoxycarbonylamino-4-cyclohexyl-butyric acid as an off white solid.
MH$^-$ 284.1

To an ice cooled solution of N-cyclohexylethanolamine (0.55 g, 3.9 mmol) and 4-tert-butoxycarbonylamino-4-cyclohexyl-butyric acid (1.0 g, 3.5 mol), in DCM (200 mL), HOBT (0.62 g, 4.5 mmol) and TEA (1.0 mL) were added followed by addition of 1,3-dimethylamino propyl-3-ethylcarbodiimide (EDC, 0.87 g, 4.5 mmol). The reaction mixture was allowed to warm to room temperature and then stirred overnight. EtOAc (300 mL) was added to the reaction mixture. The reaction mixture was then washed with aqueous citric acid solution, saturated NaHCO$_3$ solution, and NaCl solution. The organic layer was collected, dried with MgSO$_4$, and then evaporated to yield {1-cyclohexyl-3-[cyclohexyl-(2-hydroxy-ethyl)-carbamoyl]-propyl}-carbamic acid tert-butyl ester as an oil, which was used in the next step without further purification.

MH$^+$ 411.4

A solution of {1-cyclohexyl-3-[cyclohexyl-(2-hydroxyethyl)-carbamoyl]-propyl}-carbamic acid 1-butyl ester (1.5 g, 3.6 mmol) in 20% TFA:CH$_2$Cl$_2$ (60 mL) was stirred at room temperature for 1 hour. The solvent was evaporated, including most of the TFA. EtOAc (200 mL) was added to the residue, and the resulting solution was then washed with aqueous NaHCO$_3$ and aqueous NaCl solution. The organic layer was dried with MgSO$_4$ and then evaporated to yield 4-amino-4-(S)—N-dicyclohexyl-N-(2-hydroxy-ethyl)-butyramide, the title compound as a light brown oil.

MH$^+$ 311.0

EXAMPLE 5

4-(2-Amino-6-phenoxy-4H-pyrido[3,4-d]pyrimidin-3-yl)-4S,N-dicyclohexyl-N-(2-hydroxy-ethyl)-butyramide (Compound #7)

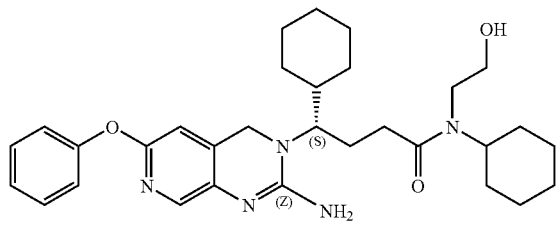

To a solution of 4-amino-4,N-dicyclohexyl-N-(2-hydroxy-ethyl)-butyramide (2.0 g, 6.5 mmol) and 5-nitro-2-phenoxy-pyridine-4-carbaldehyde (1.6 g, 6.5 mmol) in 1,2 dichloroethane (50 mL), NaBH(OAc)$_3$ (2.0 g, 9.4 mmol) was added, and the reaction mixture was stirred at room temperature overnight. After the addition of 1N NaOH solution, the reaction mixture was then extracted with EtOAc (200 mL×2). The organic layer was dried with Mg$_2$SO$_4$ and then evaporated to a residue which was purified by column chromatography to yield 4,N-dicyclohexyl-N-(2-hydroxy-ethyl)-4-[(5-nitro-2-phenoxy-pyridin-4-ylmethyl)-amino]-butyramide as an oil.

To a solution of 4,N-dicyclohexyl-N-(2-hydroxy-ethyl)-4-[(5-nitro-2-phenoxy-pyridin-4-ylmethyl)-amino]-butyramide (0.1 g, 0.18 mmol) in MeOH (10 mL) was added a catalytic amount of Pd—C (10% on activated carbon) under N$_2$, and the reaction mixture was subjected to hydrogenation under 5 psi for one hour. The catalyst was filtered out, and the MeOH was evaporated to yield a residue which was purified by preparative TLC (100% EtOAc) to yield 4-[(5-amino-2-phenoxy-pyridin-4-ylmethyl)-amino]-4,N-dicyclohexyl-N-(2-hydroxy-ethyl)-butyramide as an oil.

MH$^+$ 509.1

A solution of 4-[(5-amino-2-phenoxy-pyridin-4-ylmethyl)-amino]-4,N-dicyclohexyl-N-(2-hydroxy-ethyl)-butyramide (0.06 g, 0.11 mmol) and BrCN (3M in CH$_2$Cl$_2$, 0.04 mL) in EtOH (5 mL) was stirred at room temperature overnight. The EtOH was then evaporated to yield an oil. The oil was stirred in diethyl ether (50 mL) for 30 min, resulting in the formation of a solid, 4-(2-amino-6-phenoxy-4H-pyrido[3,4-d]pyrimidin-3-yl)-4S,N-dicyclohexyl-N-(2-hydroxy-ethyl)-butyramide, as its corresponding HBr salt, which was collected by filtration.

MH$^+$ 534.2

$^1$H NMR (300 MHz, CDCl$_3$): δ0.9-2.1 (m, 24H), 2.4-2.6 (m, 2H), 3.3-3.7 (m, 4H), 4.0-4.3 (m, 2H), 4.45 (dd, J=5.5 Hz, J=11 Hz, 1H), 6.65 (s, 1H), 7.1 (d, J=7.92 Hz, 2H), 7.20 (t, J=7.36 Hz, 1H), 7.36 (t, J=7.64 Hz, 2H), 7.88 (s, 1H).

EXAMPLE 6

3-(S)-Benzyloxy-2-(4-tert-butoxycarbonylamino-5-methyl-(S)-hexanoylamino)-propionic acid methyl ester

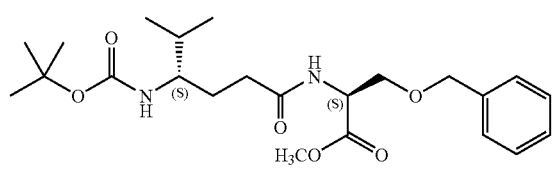

A mixture of 2-amino-3-benzyloxy-propionic acid methyl ester (0.48 g, 1.9 mmol), 4-tert-butoxycarbonylamino-5-methyl-hexanoic acid (0.48 g, 1.9 mmol), HBTU (1.1 g, 2.9 mmol), DIPEA (0.7 mL, 4.18 mmol) and DMF (50 mL) was stirred at room temperature for 14 hours. To the reaction mixture was added sodium bicarbonate (200 mL), and the product was extracted into ethyl acetate (200 mL×2). The combined organic layers were washed with water, dried over MgSO$_4$, and concentrated to yield an oil which was purified by column chromatography (50% EtOAc/Heptane) to yield the title compound as an oil.

EXAMPLE 7

1-[2-(2-(S)-Benzyloxy-1-methoxycarbonyl-ethylcarbamoyl)-ethyl]-2-methyl-prolyl-amine hydrochloride salt

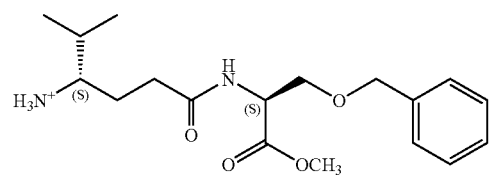

3-Benzyloxy-2-(4-tert-butoxycarbonylamino-5-methyl-hexanoylamino)-propionic acid methyl ester (0.98 g, 1.9 mmol) was added slowly into hydrochloric acid in isopropyl alcohol ([5M], 10 mL) and toluene (0.2 mL). The reaction mixture was then stirred for 1.5 hours at room temperature. The reaction solvent was evaporated, and the residue was dried under high vacuum overnight to yield the title compound as an oil.

EXAMPLE 8

3-(S)-Benzyloxy-2-{5-methyl-4-[(5-nitro-2-phenoxy-pyridin-4-ylmethyl)-amino]-(S)-hexanoylamino}-propionic acid methyl ester

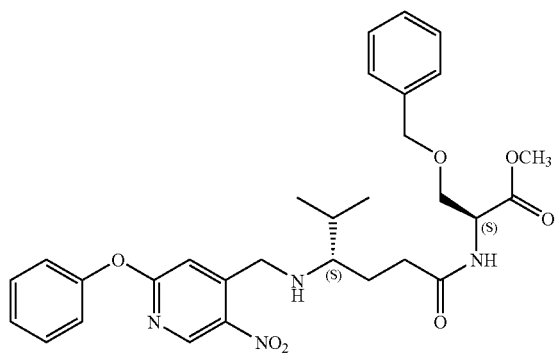

A mixture of 1-[2-(2-benzyloxy-1-methoxycarbonyl-ethylcarbamoyl)-ethyl]-2-methyl-propyl-amine hydrochloride salt (0.74 g, 2.2 mmol), 5-nitro-2-phenoxy-pyridine-4-carbaldehyde (0.73, 3 mmol), dichloroethane (100 mL), triethylamine (0.6 mL, 4.4 mmol), and sodium triacetoxyborohydride was stirred overnight for 16 hrs. Sodium hydroxide solution ([0.1N], 100 mL) was then added to the reaction mixture. The organic layer was separated, treated with $MgSO_4$, filtered, and the solvent was evaporated to yield a crude oil. The crude oil was purified by column chromatography (40% ethyl acetate:heptane) to yield the title compound as a residue.

EXAMPLE 9

2-{4-[(5-Amino-2-phenoxy-pyridin-4-ylmethyl)-amino]-5-methyl-(S)-hexanoylamino}-3-(S)-benzyloxy-propionic acid methyl ester

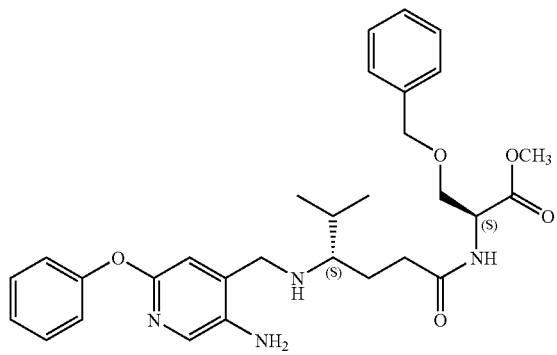

A solution of 3-benzyloxy-2-{5-methyl-4-[(5-nitro-2-phenoxy-pyridin-4-ylmethyl)-amino]-hexanoylamino}-propionic acid methyl ester (0.8 g, 1.38 mmol), 10% Pd on carbon (0.8 g) and methanol (25 mL) were shaken under a hydrogen atmosphere (50 psi). After 3.5 hours, the reaction mixture was filtered through Celite, and the Celite was then washed with MeOH (200 mL). Low boiling materials were removed under low pressure to yield an oil. The oil was dissolved in $CH_2Cl_2$ (200 mL) and then extracted with $NaHCO_3$ solution. The organic layer was separated, dried over $MgSO_4$, filtered, and concentrated to yield the title compound as a residue.

EXAMPLE 10

2-[4-(2-Amino-6-phenoxy-4H-pyrido[3,4-d]pyrimidin-3-yl)-5-methyl-(S)-hexanoylamino]-3-(S)-benzyloxy-propionic acid methyl ester hydrobromide salt (Compound #45)

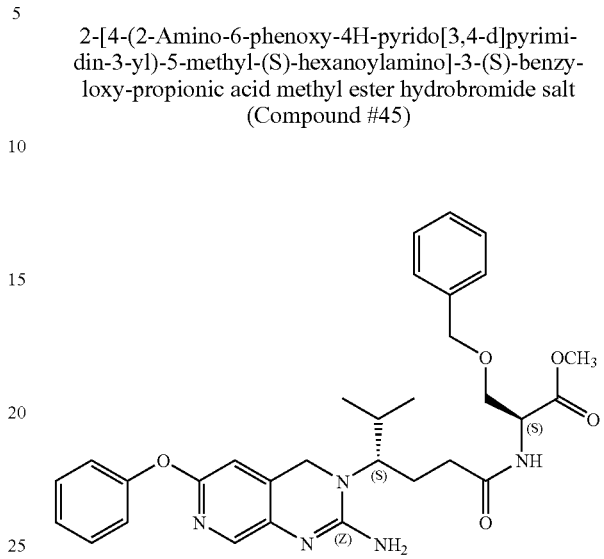

To a solution of 2-{4-[(5-amino-2-phenoxy-pyridin-4-ylmethyl)-amino]-5-methyl-hexanoylamino}-3-benzyloxy-propionic acid methyl ester (0.35 g, 0.648 mmol) in ethanol was added cyanogen bromide in dichloromethane (0.22 mL, [3M]) and the reaction mixture was stirred at room temperature for three hours. The solvent was evaporated to yield the title compound as a brown solid which was taken directly to the next step without further purification.

EXAMPLE 11

2-[4-(2-Amino-6-phenoxy-4H-pyrido[3,4-d]pyrimidin-3-yl)-5-methyl-(S)-hexanoylamino]-3-(S)-benzyloxy-propionic acid (Compound #47)

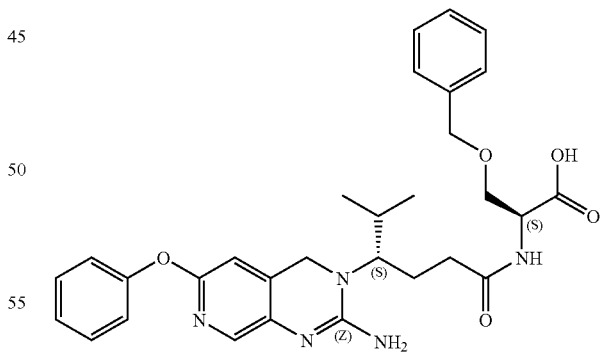

2-[4-(2-Amino-6-phenoxy-4H-pyrido[3,4-d]pyrimidin-3-yl)-5-methyl-hexanoylamino]-3-benzyloxy-propionic acid methyl ester hydrobromide salt (0.13 g, 0.23 mmol) was dissolved in THF. Aqueous LiOH solution ([2.5 N] 0.5 mL) was then added and the reaction mixture was stirred 2 hours. The solvent was evaporated with high vacuum, and then 1N HCl (1 mL) was added and, the reaction mixture was stirred 5 min. The solvent was evaporated on high vacuum overnight to yield crude product which was purified by reverse phase chromatography to yield the title compound, benzoic acid 2-[4-(2-amino-6-phenoxy-4H-pyrido[3,4-d]pyrimidin-3-yl)-5-methyl-hexanoylamino]-2-carboxy-ethyl ester trifluoroacetic acid salt, as a solid.

$^1$H NMR (400 MHz, MeOD.) δ 0.8 (d, 3H), 1.0 (d, 3H), 2.0 (m, 2H), 2.2 (m, 2H), 2.4 (m, 1H), 3.25 (m, 3H), 3.65-3.85 (m, 3H), 4.5 (m, 5H), 6.85 (s, 1H), 7.1 (d, 2H), 7.15-7.4 (m, 9H), 7.8 (s, 1H)

LC-MS (ES) MH+=546.9, 545.8, 455.9.

EXAMPLE 12

3-(S)-Benzyloxy-2-(tert-butoxycarbonyl-methyl-amino)-propionic acid methyl ester

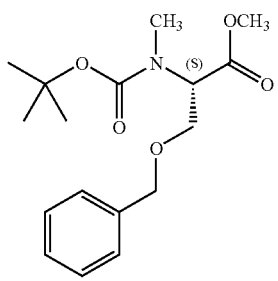

A mixture of 3-benzyloxy-2-(tert-butoxycarbonyl-methyl-amino)-propionic acid (0.67 g, 2.17 mmol), trimethylsilyl diazomethane ([2M], 4.3 mL, 6.3 mmol) in diethyl ether, methanol (20 mL, and diethyl ether (20 mL) was stirred at room temperature for 16 hours. To this reaction mixture was added acetic acid (2 mL) to quench excess trimethylsilyldiazomethane. The solvent was then evaporated. The residue was dissolved in ethyl acetate and washed with saturated ammonium chloride solution and then with saturated sodium bicarbonate solution. The organic layer was dried over MgSO$_4$, filtered and concentrated to yield the title compound as an oil.

EXAMPLE 13

3-Benzyloxy-2-methylamino-propionic acid methyl ester hydrochloride salt

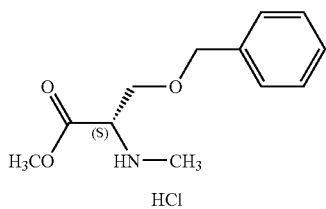

3-Benzyloxy-2-(tert-butoxycarbonyl-methyl-amino)-propionic acid methyl ester (0.6 g, 1.86 mmol) was dissolved in dichloromethane and then added slowly into a mixture of hydrochloric acid in isopropyl alcohol ([5M], 3 mL). The reaction mixture was stirred for 2 hours at room temperature. The solvent was then evaporated and the residue was kept on high vacuum atmosphere overnight to yield a crude product as an oil. The crude product was stored in the freezer as an oil.

EXAMPLE 14

3-(S)-Benzyloxy-2-[(4-tert-butoxycarbonylamino-5-methyl-(S)-hexanoyl)-methyl-amino]-propionic acid methyl ester

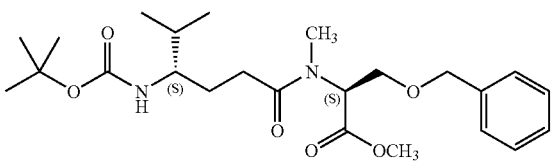

A mixture of 3-benzyloxy-2-methylamino-propionic acid methyl ester hydrochloride salt (0.6 g, 2.3 mmol), 4-tert-butoxycarbonylamino-5-methyl-hexanoic acid (0.6 g, 2.35 mmol), HBTU (1.31 g, 3.5 mmol), DIPEA (0.9 mL, 5.17 mmol) and DMF (50 mL) was stirred at room temperature for 16 hours. To the reaction mixture was added aqueous sodium bicarbonate solution (200 mL) and the crude product was extracted into ethyl acetate (200 mL×2). The combined organic layers were washed with water, dried over MgSO$_4$ and concentrated to yield an oil. The oil (crude product) was purified by column chromatography (50% EtOAc/Heptane) to yield the title compound as an oil.

EXAMPLE 15

1-{2-[(2-(S)-Benzyloxy-1-methoxycarbonyl-ethyl)-methyl-carbamoyl]-ethyl}-2-methyl-propyl-amine hydrochloride salt

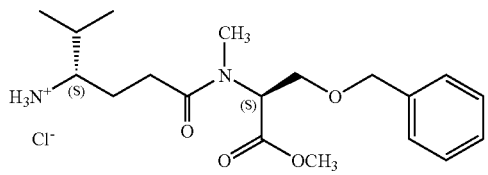

3-Benzyloxy-2-[(4-tert-butoxycarbonylamino-5-methyl-hexanoyl)-methyl-amino]-propionic acid methyl ester (0.76 g, 1.69 mmol) was added slowly into hydrochloric acid in isopropyl alcohol ([5M], 12 mL) and toluene (0.1 mL). The reaction mixture was then stirred for 3 hours at room temperature. The reaction solvent was evaporated under high vacuum atmosphere overnight to yield the title compound as an oil.

EXAMPLE 16

3-(S)-Benzyloxy-2-(methyl-{5-methyl-4-[(5-nitro-2-phenoxy-pyridin-4-ylmethyl)-amino]-(S)-hexanoyl}-amino)-propionic acid methyl ester

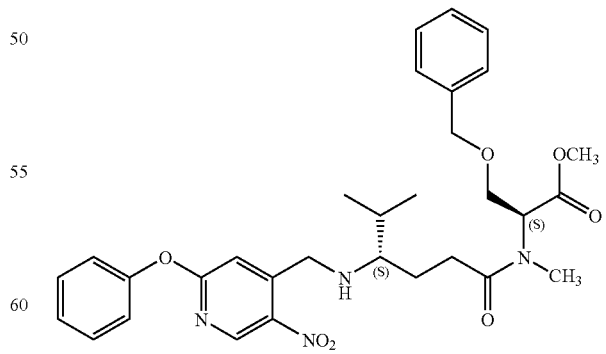

A mixture of 1-{2-[(2-benzyloxy-1-methoxycarbonyl-ethyl)-methyl-carbamoyl]-ethyl}-2-methyl-propyl-amine hydrochloride salt (0.65 g, 1.83 mmol), 5-nitro-2-phenoxy-pyridine-4-carbaldehyde (0.45 g, 1.83 mmol), dichloroethane (120 mL), and triethylamine (0.25 mL, 1.83 mmol) was stirred for 30 min. To the reaction mixture was then added sodium triacetoxyborohydride (0.85 g, 4 mmol) and the reaction mixture stirred overnight for 16 hrs. Sodium hydroxide solution ([0.1N], 100 mL) was then added, and the organic layer was separated, treated with MgSO$_4$, filtered and the solvent evaporated to provide a residue. $^1$H NMR showed imine intermediate present so the crude product was resubjected to sodium triacetoxyborohydride (1.3 g, 6.1 mmol) as above and stirred overnight. Sodium hydroxide solution ([0.1N], 100 mL) was added; the organic layer was separated, treated with MgSO$_4$, then filtered and the solvent evaporated to yield the title compound as a crude oil which was taken directly to the next step without further purification.

EXAMPLE 17

2-({4-[(5-Amino-2-phenoxy-pyridin-4-ylmethyl)-amino]-5-methyl-(S)-hexanoyl}-methyl-amino)-3-(S)-benzyloxy-propionic acid methyl ester

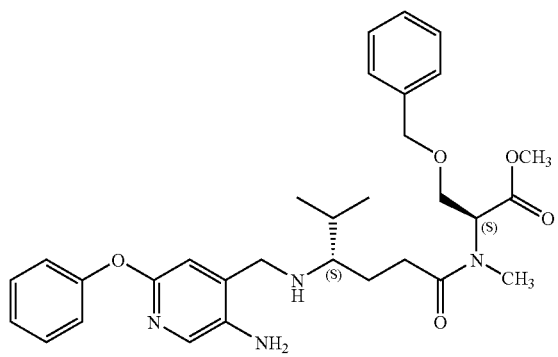

A solution of 3-(S)-benzyloxy-2-(methyl-{5-methyl-4-[(5-nitro-2-phenoxy-pyridin-4-ylmethyl)-amino]-(S)-hexanoyl}-amino)-propionic acid methyl ester (1.2 g, 1.83 mmol), zinc (0.9 g), ammonium chloride (0.2 g, 3.74 mmol) and methanol (4 mL) were reacted in the microwave (95° C., 900 sec). The reaction mixture was filtered through Celite which was then washed with MeOH (200 mL). Low boiling materials were removed under low pressure to yield the title compound as an oil.

EXAMPLE 18

2-{[4-(2-Amino-6-phenoxy-4H-pyrido[3,4-d]pyrimidin-3-yl)-5-methyl-(S)-hexanoyl]-methyl-amino}-3-(S)-benzyloxy-propionic acid methyl ester trifluoroacetate salt (Compound #51)

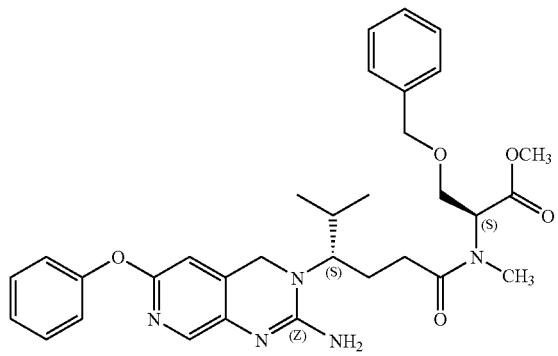

To a solution of 2-({4-[(5-amino-2-phenoxy-pyridin-4-ylmethyl)-amino]-5-methyl-(S)-hexanoyl}-methyl-amino)-3-(S)-benzyloxy-propionic acid methyl ester (0.69 g, 1.25 mmol) in ethanol was added cyanogen bromide in dichloromethane (0.5 mL, [3M]) and the reaction mixture stirred at room temperature for two hours. The solvent was evaporated to yield the title compound as a brown solid which was purified by reverse phase chromatography to yield an oil.

EXAMPLE 19

2-{[4-(2-Amino-6-phenoxy-4H-pyrido[3,4-d]pyrimidin-3-yl)-5-methyl-(S)-hexanoyl]-methyl-amino}-3-(S)-benzyloxy-propionic acid trifluoroacetate salt (Compound #52)

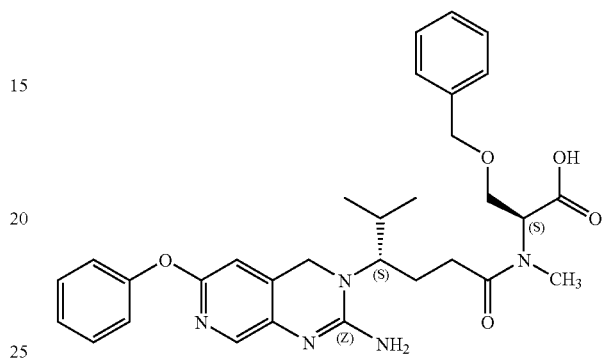

2-{[4-(2-Amino-6-phenoxy-4H-pyrido[3,4-d]pyrimidin-3-yl)-5-methyl-(S)-hexanoyl]-methyl-amino}-3-(S)-benzyloxy-propionic acid methyl ester trifluoroacetate salt (55 mg, 0.08 mmol) was dissolved in THF. Aqueous LiOH (2.5N 0.2 mL) in water was then added and the reaction mixture was stirred 2 hours. The solvent was evaporated under high vacuum, and then 1N HCl (1 mL) was added and the reaction mixture was evaporated under high vacuum overnight to yield a solid. The residue was purified by reverse phase chromatography to yield the title compound, 2-{[4-(2-Amino-6-phenoxy-4H-pyrido[3,4-d]pyrimidin-3-yl)-5-methyl-(S)-hexanoyl]-methyl-amino}-3-(S)-benzyloxy-propionic acid trifluoroacetate salt, as a solid.

$^1$H NMR (400 MHz, CD$_3$OD): δ 0.8 (d, 3H), 1.1 (d, 3H), 1.8-2.0 (m, 2H), 2.1 (m, 1H), 2.3 (m, 1H), 2.5 (m, 1H), 3.0 (s, 3H), 3.3 (m, 2H), 3.7 (m, 1H), 3.9 (m, 2H), 4.4 (m, 1H), 4.5 (m, 4H), 5.1 (m, 1H), 6.8 (d, 1H), 7.1 (d, 2H), 7.15-7.5 (m, 8H), 7.8 (s, 1H)

LC-MS (ES) MH+=560.8, 559.8, 469.9.

EXAMPLE 20

4-(2-Amino-6-phenoxy-4H-quinazolin-3-yl)-N-(1-(S)-tert-butoxymethyl-2-hydroxy-ethyl)-4-(S)-cyclohexyl-butyramide (Compound 107)

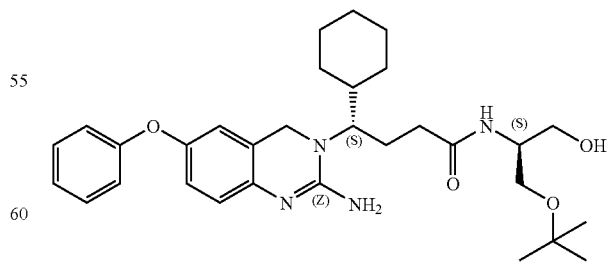

To a solution of 2-[4-(2-amino-6-phenoxy-4H-quinazolin-3-yl)-4-cyclohexyl-butyrylamino]-3-tert-butoxy-propionic acid methyl ester (TFA salt, 50 mg) in methanol (5 mL), NaBH$_4$ (0.04 g) was added slowly over a 30 minute period.

The resulting solution was then stirred at room temperature overnight. LC/MS indicated very little product formed and most of the starting material remained. Additional NaBH₄ (0.04 g) was added at room temperature, and the solution was stirred for an additional 8 hrs. Additional NaBH₄ (0.08 g) was added over a 4 day period. LC/MS then indicated that most of the starting material was converted. The crude reaction mixture was purified by Gilson HPLC to yield the title compound as a white solid.

MH⁺ 538.0

¹H NMR (300 MHz, CDCl₃): δ0.89-1.25 (m, 7H), 1.18 (s, 9H), 1.41-2.3 (m, 9H), 3.53 (m, 1H), 3.75-4.14 (m, 5H), 4.21 (m, 1H), 6.62 (s, 1H), 7.1 (d, J=7.7 Hz, 2H), 7.18 (t, J=7.43 Hz, 1H), 7.39 (t, J=7.72 Hz, 2H,), 8.06 (s, 1H).

EXAMPLE 21

Benzyl cis-4-aminocyclohexanecarboxylate

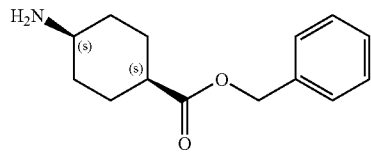

A solution of cis-(4-aminocyclohexane)carboxylic acid (10.00 g, 0.0698 mole) in 1N HCl solution (70 mL) was concentrated in vacuo. To the residue was added toluene (50 mL), and the resulting mixture was concentrated in vacuo. This step was then repeated. The resulting residue was dissolved in toluene (220 mL) in a 3-neck round bottom flask fitted with a reflux condenser and Dean-Stark trap, and then benzyl alcohol (14.46 g, 13.9 mL, 0.134 mol) and p-toluenesulfonic acid monohydrate (6.23 g) were added. The reaction mixture was refluxed 25 h and then was cooled to ambient temperature. A heavy precipitate came out of solution on cooling. The reaction mixture was filtered under vacuum, and the resulting solid was washed with diethyl ether (500-600 mL). The resulting sticky white solid was taken up in chloroform (250 mL). To the mixture was then added saturated cold sodium carbonate solution (250 mL), at which point the chloroform solution became clear. The layers were separated, and the aqueous solution was extracted twice with chloroform, dried (Na₂SO₄), filtered, and concentrated to yield benzyl cis-4-aminocyclohexanecarboxylate as a colorless oil.

The above procedure was a modification of the synthesis as disclosed in U.S. Pat. No. 5,030,654 and PCT Publication WO03/068235.

EXAMPLE 22

4-[[4-(2-Amino-6-phenoxy-4H-pyrido[3,4-d]pyrimidin-3-yl)-4-(S)-(tetrahydro-pyran-4-yl)-butyryl]-(2-hydroxy-ethyl)-amino]-cyclohexanecarboxylic acid (Compound #38)

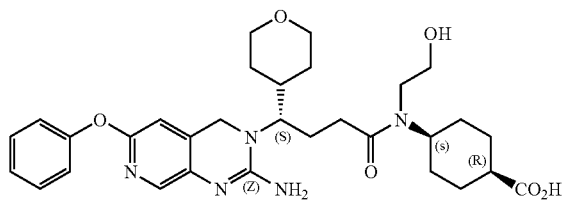

and 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cyclohexanecarboxylic acid (Compound #39)

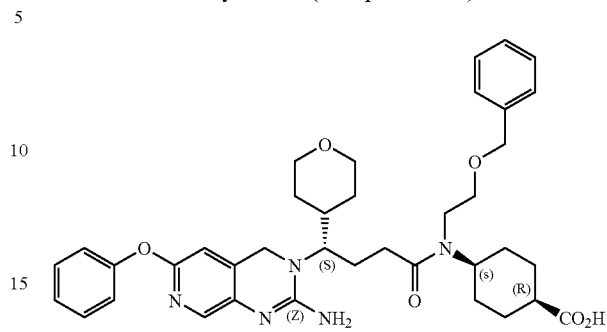

Step A: cis-4-(2-Benzyloxy-ethylamino)-cyclohexanecarboxylic acid benzyl ester

A solution of cis-4-amino-cyclohexanecarboxylic acid benzyl ester (8 g, 34 mmol) and benzyloxyacetaldehyde (4.8 mL, 34 mmol) in 1,2-dichloroethane (2 L), was stirred at room temperature overnight. Then NaBH(OAc)₃ (11 g, 51 mmol) was added and the reaction mixture was stirred at room temperature for 2 hours. Most of the solvent was then removed by vacuum. EtOAc (1 L) was added, and the resulting solution as washed with brine. The organic layer was dried over MgSO₄, filtered, and evaporated to yield a residue. The residue was purified by column chromatography with flash silica gel (1:1 heptane/EtOAc) to yield cis-4-(2-benzyloxy-ethylamino)-cyclohexanecarboxylic acid benzyl ester as an oil.

MH⁺ 368.2

Step B: 4-{(2-Benzyloxy-ethyl)-[4-tert-butoxycarbonylamino-4-(S)-(tetrahydro-pyran-4-yl)-butyryl]-amino}-cis-cyclohexanecarboxylic acid benzyl ester To an ice cooled solution of cis-4-(2-benzyloxy-ethylamino)-cyclohexanecarboxylic acid benzyl ester (3 g, 8.2 mmol), 4-tert-butoxycarbonylamino-4-(S)-tetrahydro-pyran-4-yl-butyric acid (2.4 g, 8.4 mmol) (prepared as in Example 35) and HOBT (2.4 g, 10.5 mmol) in CH₂Cl₂ (100 mL) was added TEA (2.3 mL), followed by addition of 1,3-dimethylamino propyl-3-ethylcarbodiimide (EDC, 2.0 g, 10 mmol). The reaction mixture was allowed to warm to room temperature and then was stirred overnight. EtOAc (200 mL) was added and the resulting mixture washed with citric acid solution, NaHCO₃ solution, and aq. NaCl solution. The organic layer was dried with MgSO₄. The EtOAc was evaporated to yield a colorless oil. The colorless oil (crude product) was purified by column chromatography (1:1 EtOAc/Hexane) to yield 4-{(2-benzyloxy-ethyl)-[4-tert-butoxycarbonylamino-4-(S)-(tetrahydro-pyran-4-yl)-butyryl]-amino}-cis-cyclohexanecarboxylic acid benzyl ester as a residue.

MH⁺ 637.3

Step C: 4-[[4-Amino-4-(S)-(tetrahydro-pyran-4-yl)-butyryl]-(2-benzyloxy-ethyl)-amino]-cis-cyclohexanecarboxylic acid benzyl ester A solution of 4-{(2-benzyloxy-ethyl)-[4-tert-butoxycarbonylamino-4-(S)-(tetrahydro-pyran-4-yl)-butyryl]-amino}-cis-cyclohexanecarboxylic acid benzyl ester (4.8 g, 7.5 mmol) in TFA (5% in CH₂Cl₂, 100 mL) was stirred at room temperature overnight. The solvent and most of the TFA was evaporated, and EtOAc (300 mL) was added to the residue. The solution was washed with aq. NaHCO₃ and aq. NaCl. The organic layer was dried with MgSO₄ and evaporated to yield 4-[[4-amino-4-(S)-(tetrahydro-pyran-4-yl)-butyryl]-(2-benzyloxy-ethyl)-amino]-cis-cyclohexanecarboxylic acid benzyl ester as a light brown oil.

MH⁺ 537.2

Step D: 4-{(2-Benzyloxy-ethyl)-[4-[(5-nitro-2-phenoxy-pyridin-4-ylmethyl)-amino]-4-(S)-(tetrahydro-pyran-4-yl)-butyryl]-amino}-cyclohexanecarboxylic acid benzyl ester A solution of 4-[[4-amino-4-(S)-(tetrahydro-pyran-4-yl)-butyryl]-(2-benzyloxy-ethyl)-amino]-cis-cyclohexanecarboxylic acid benzyl ester (1.9 g, 3.5 mmol) and 5-nitro-2-phenoxy-pyridine-4-carboxaldehyde (0.86 g, 3.53 mmol) in 1,2 dichloroethane (100 mL) was stirred at room temperature for 4 hours, and then NaBH(OAc)₃ (1.4 g, 6.6 mmol) was added. The resulting mixture was stirred at room temperature overnight. Then 1N NaOH was added, and the reaction mixture was then poured into EtOAc (200 mL). The organic layer washed with aq. NaCl, dried with MgSO₄, filtered, and evaporated to yield a residue. The residue was purified by column chromatography (1:1 heptane/EtOAc) to yield 4-{(2-benzyloxy-ethyl)-[4-[(5-nitro-2-phenoxy-pyridin-4-ylmethyl)-amino]-4-(S)-(tetrahydro-pyran-4-yl)-butyryl]-amino}-cis-cyclohexanecarboxylic acid benzyl ester as an oil.

MH⁺ 765.2

Step E: 4-[[4-[(5-Amino-2-phenoxy-pyridin-4-ylmethyl)-amino]-4-(S)-(tetrahydro-pyran-4-yl)-butyryl]-(2-benzyloxy-ethyl)-amino]-cis-cyclohexanecarboxylic acid benzyl ester Zinc dust (21.4 g, 330 mmol) was carefully added into a solution of 4-{(2-benzyloxy-ethyl)-[4-[(5-nitro-2-phenoxy-pyridin-4-ylmethyl)-amino]-4-(S)-(tetrahydro-pyran-4-yl)-butyryl]-amino}-cis-cyclohexanecarboxylic acid benzyl ester (1.85 g, 2.4 mmol) and NH₄Cl (2.6 g, 48 mmol) in MeOH (300 mL). The resulting mixture was refluxed 4 hours. The MeOH was removed before EtOAc (300 mL) was added. The resulting solution washed with aq. NaHCO₃ and aq. NaCl. The organic layer was dried with MgSO₄, filtered, and evaporated to yield 4-[[4-[(5-amino-2-phenoxy-pyridin-4-ylmethyl)-amino]-4-(S)-(tetrahydro-pyran-4-yl)-butyryl]-(2-benzyloxy-ethyl)-amino]-cis-cyclohexanecarboxylic acid benzyl ester as a light brown oil.

MH⁺ 735.3

Step F: 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cis-cyclohexanecarboxylic acid benzyl ester A solution of 4-[[4-[(5-amino-2-phenoxy-pyridin-4-ylmethyl)-amino]-4-(S)-(tetrahydro-pyran-4-yl)-butyryl]-(2-benzyloxy-ethyl)-amino]-cis-cyclohexanecarboxylic acid benzyl ester (0.5 g, 0.7 mmol) and BrCN (3M in CH₂Cl₂, 0.25 mL) in EtOH (20 mL) was stirred at room temperature overnight. The EtOH was evaporated. The resulting oil was stirred in diethyl ether (50 mL) for 30 min. 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cis-cyclohexanecarboxylic acid benzyl ester was collected as a solid as its corresponding HBr salt.

MH⁺ 760.3

Step G: 4-[[4-(2-Amino-6-phenoxy-4H-pyrido[3,4-d]pyrimidin-3-yl)-4-(S)-(tetrahydro-pyran-4-yl)-butyryl]-(2-hydroxy-ethyl)-amino]-cis-cyclohexanecarboxylic acid and 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cis-cyclohexanecarboxylic acid A solution of 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cyclohexanecarboxylic acid benzyl ester (0.4 g, 0.42 mmol) and Pd (10% on carbon, 0.2 g) in EtOH (50 mL) was subjected to hydrogenation under 10 psi for 48 h. HPLC purification yielded 4-[[4-(2-Amino-6-phenoxy-4H-pyrido[3,4-d]pyrimidin-3-yl)-4-(S-(tetrahydro-pyran-4-yl)-butyryl]-(2-hydroxy-ethyl)-amino]-cyclohexanecarboxylic acid as a white solid and 4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cis-cyclohexanecarboxylic acid as a white solid.

4-[[4-(2-Amino-6-phenoxy-4H-pyrido[3,4-d]pyrimidin-3-yl)-4-(S)-(tetrahydro-pyran-4-yl)-butyryl]-(2-hydroxy-ethyl)-amino]-cis-cyclohexanecarboxylic acid

MH⁺ 580.2

¹H NMR (300 MHz, CDCl₃): δ1.25-2.18 (m, 20H), 2.58-2.69 (m, 4H), 3.30-3.45 (m, 4H), 3.62-3.67 (m, 1H), 3.86-4.14 (m, 3H), 4.17-4.24 (t, J=13 Hz, 1H), 4.34-4.42 (t, J=14.6 Hz, 1H), 6.66 (d, J=7.10 Hz, 1H), 7.10 (d, J=7.85 Hz, 2H), 7.19 (s, 1H), 7.38 (t, J=7.70 MHz, 2H), 7.98 (s, 1H).

4-[[4-(2-Amino-6-phenoxy-4H-pyrido[3,4-d]pyrimidin-3-yl)-4-(S)-(tetrahydro-pyran-4-yl)-butyryl]-(2-benzyloxy-ethyl)-amino]-cis-cyclohexanecarboxylic acid:

MH⁺ 670.4

¹H NMR (300 MHz, CDCl₃): δ1.22-1.67 (m, 11H), 2.09-2.37 (m, 3H), 2.68 (s, 2H), 2.96 (s, 1H), 3.53 (m, 10H), 3.97 (m, 4H), 4.46 (d, J=7.45 Hz, 1), 6.57 (s, 1H), 7.10 (d, J=8.24 Hz, 2H), 7.19-7.42 (m, 8H), 8.07 (s, 1H).

EXAMPLE 23

2-[4-(2-Amino-6-phenoxy-4H-pyrido[3,4-d]pyrimidin-3-yl)-4-(S)-cyclohexyl-butyryl-(R)-amino]-3-tert-butoxy-propionic acid methyl ester (Compound #63)

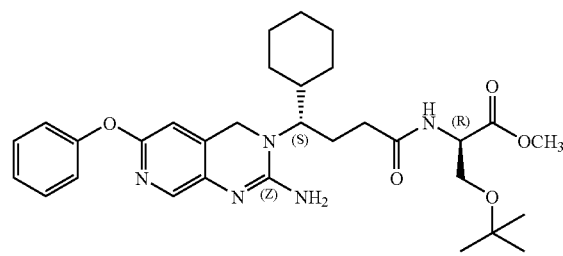

Step A: 3-tert-Butoxy-2-(4-tert-butoxycarbonylamino-4-(S)-cyclohexyl-butyryl-(R)-amino)-propionic acid methyl ester To an ice cooled solution of 2-(R)-amino-3-tert-butoxy-propionic acid methyl ester (0.4 g, 1.9 mmol), 4-tert-butoxycarbonylamino-4-(S)-cyclohexyl-butyric acid (0.5 g, 1.8 mmol) and HOBT (0.32 g, 2.4 mmol) in $CH_2Cl_2$ (50 mL) was added TEA (0.7 mL), followed by addition of 1,3-dimethylamino propyl-3-ethylcarbodiimide (EDC, 0.45 g, 2.4 mmol). The reaction mixture was allowed to warm to room temperature and was then stirred overnight. EtOAc (200 mL) was added, and the resulting mixture washed with dilute (about 0.1 N)HCl solution (50 mL), aqueous $NaHCO_3$ solution and aqueous NaCl solution. The organic layer was dried with $MgSO_4$, filtered, and evaporated to yield 3-tert-butoxy-2-(4-tert-butoxycarbonylamino-4-(S)-cyclohexyl-butyryl-(R)-amino)-propionic acid methyl ester crude product as an oil.
$MH^+$ 443.3

Step B: 2-(4-Amino-4-(S)-cyclohexyl-butyryl-(R)-amino)-3-tert-butoxy-propionic acid methyl ester A solution of 3-tert-butoxy-2-(4-tert-butoxycarbonylamino-4-(S)-cyclohexyl-butyryl-(R)-amino)-propionic acid methyl ester (0.98 g, 2 mmol) in TFA (5% in $CH_2Cl_2$, 50 mL) was stirred for 4 hours at room temperature. The solvent and most of the TFA was evaporated, and EtOAc (100 mL) was added. The mixture washed with aqueous $NaHCO_3$ solution and aqueous NaCl solution. The organic layer was dried with $MgSO_4$, filtered, and evaporated yield 2-(4-amino-4-(S)-cyclohexyl-butyryl-(R)-amino)-3-tert-butoxy-propionic acid methyl ester as an oil.
$MH^+$ 343.0

Step C: 3-tert-Butoxy-2-{4-(S)-cyclohexyl-4-[(5-nitro-2-phenoxy-pyridin-4-ylmethyl)-amino]-butyryl-(R)-amino}-propionic acid methyl ester A solution of 2-(4-Amino-4-(S)-cyclohexyl-butyryl-(R)-amino)-3-tert-butoxy-propionic acid methyl ester (0.34 g, 1 mmol) and 5-nitro-2-phenoxypyridine-4-carboxaldehyde (0.24 g, 1 mmol) in methylene chloride (20 mL) was stirred at room temperature for 5 hours, and then $NaBH(OAc)_3$ (0.4 g, 1.9 mmol) was added. The reaction mixture was stirred at room temperature for 3 hours. The solution was then poured into EtOAc (100 mL). The layers were separated, and the organic layer washed with aqueous NaCl solution, dried with $MgSO_4$, filtered, and evaporated to yield a residue, which was purified by column chromatography (1:1 heptane:EtOAc) to yield 3-tert-butoxy-2-{4-(S)-cyclohexyl-4-[(5-nitro-2-phenoxy-pyridin-4-ylmethyl)-amino]-butyryl-(R)-amino}-propionic acid methyl ester as an oil.
$MH^+$ 570.9

Step D: 2-{-4-[(5-Amino-2-phenoxy-pyridin-4-ylmethyl)-amino]-4S-cyclohexyl-butyryl-(R)-amino}-3-tert-butoxy-propionic acid methyl ester To a solution of 3-tert-butoxy-2-{4-(S)-cyclohexyl-4-[(5-nitro-2-phenoxy-pyridin-4-ylmethyl)-amino]-butyryl-(R)-amino}-propionic acid methyl ester (0.26 g, 0.46 mmol) in MeOH (10 mL) was added 10% Pd on activated carbon (0.05 g) under $N_2$. The mixture was subjected to hydrogenation under 5 psi for 2 hours. The catalyst was filtered out, and the MeOH was evaporated to yield 2-{4-[(5-amino-2-phenoxy-pyridin-4-ylmethyl)-amino]-4-(S)-cyclohexyl-butyryl-(R)-amino}-3-tert-butoxy-propionic acid methyl ester as an oil.
$MH^+$ 540.9

Step E: 2-[4-(2-Amino-6-phenoxy-4H-pyrido[3,4-d]pyrimidin-3-yl)-4-(S)-cyclohexyl-butyryl-(R)-amino]-3-tert-butoxy-propionic acid methyl ester A solution of 2-{4-[(5-amino-2-phenoxy-pyridin-4-ylmethyl)-amino]-4-(S)-cyclohexyl-butyryl-(R)-amino}-3-tert-butoxy-propionic acid methyl ester (0.24 g, 0.44 mmol) and BrCN (3M in $CH_2Cl_2$, 0.15 mL) in EtOH (50 mL) was stirred at room temperature overnight. The EtOH was evaporated, and the resulting oil was stirred in diethyl ether (50 mL) for 30 min. A precipitate formed, and the product, 2-[4-(2-amino-6-phenoxy-4H-pyrido[3,4-d]pyrimidin-3-yl)-4-(S)-cyclohexyl-butyryl-(R)-amino]-3-tert-butoxy-propionic acid methyl ester, was collected as its corresponding HBr salt, as a solid.
$MH^+$ 566.4
$^1H$ NMR (300 MHz, $CDCl_3$): δ1.13 (s, 9H), 0.92-1.79 (m, 13H), 2.22-2.39 (m, 2H), 2.39 (m, 1H), 3.55 (dd, J=9.33 Hz, 2.96 Hz, 1H), 3.77 (s, 3H), 3.80-3.90 (m, 1H), 4.22 (m, 2H), 4.60 (m, 1H), 6.6 (s, 1H), 6.87 (d, J=7.69 Hz, 1H), 7.09 (d, J=7.64 Hz, 2H), 7.20 (t, J=7.4 Hz, 1H), 7.39 (t, J=7.68 Hz, 2H), 8.05 (s, 1H).

EXAMPLE 24

2-[4-(2-Amino-6-phenoxy-4H-pyrido[3,4-d]pyrimidin-3-yl)-4-(S)-cyclohexyl-butyryl-(R)-amino]-3-tert-butoxy-propionic acid (Compound #64)

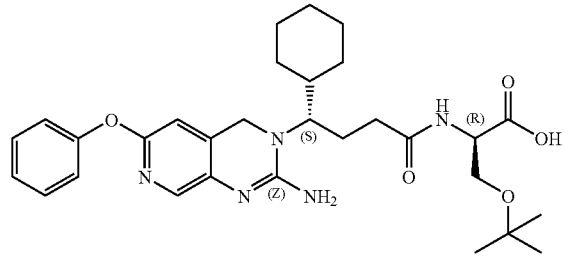

To a solution of 2-[4-(2-Amino-6-phenoxy-4H-pyrido[3,4-d]pyrimidin-3-yl)-4-(S)-cyclohexyl-butyryl-(R)-amino]-3-tert-butoxy-propionic acid methyl ester (0.11 g, 0.2 mmol) in MeOH (5 mL) and water (1 mL) was added LiOH (0.01 g, 0.4 mmol). The reaction mixture was stirred at room temperature for 2 days, before acidification with a dilute HCl solution (pH2). The MeOH was evaporated under vacuum to yield a crude oil. The crude oil was purified by Gilson HPLC to yield 2-[4-(2-amino-6-phenoxy-4H-pyrido[3,4-d]pyrimidin-3-yl)-4-(S)-cyclohexyl-butyryl-(R)-amino]-3-tert-butoxy-propionic acid as its corresponding TFA salt, as a solid.
$MH^+$ 552.3
$^1H$ NMR (300 MHz, $CDCl_3$): δ1.14 (s, 9H), 0.92-1.78 (m, 13H), 2.0-2.18 (m, 2H), 2.39 (m, 1H), 3.60 (m, 1H), 3.70 (m, 1H), 4.2 (m, 2H), 4.60 (m, 1H), 6.6 (s, 1H), 6.87 (d, J=7.69 Hz, 1H,), 7.09 (d, J=7.64 Hz, 2H), 7.20 (t, J=7.4 Hz, 1H,), 7.39 (t, J=7.68 Hz, 2H,), 8.05 (s, 1H).

EXAMPLE 25

4-(2-Amino-6-phenoxy-4H-pyrido[3,4-d]pyrimidin-3-yl)-4-(S)—N-dicyclohexyl-N-(1H-tetrazol-5-ylmethyl)-butyramide (Compound #77)

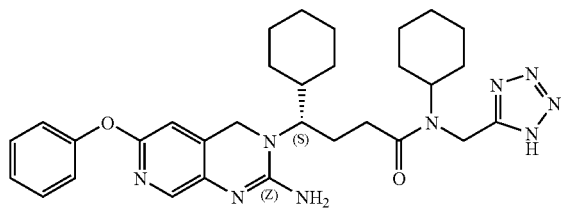

Step A: N-Benzyl-2-(1,3-dioxo-1,3-dihydro-isoindol-2-yl)-acetamide

To a stirred solution of N-phthaloylglycine (11.92 g, 58 mmol) in dichloromethane (200 mL) at room temperature, oxalyl chloride (7.5 mL, 87 mmol) was added. To the reaction mixture was then added DMF (two drops). The reaction mixture was concentrated after stirring four hours at room temperature. Dichloromethane (100 mL, dry) was added; then benzylamine (9.5 mL, 87 mmol) was added slowly into the solution, followed by addition of triethylamine (12 mL, 87 mmol), slowly into the solution. Dichloromethane (200 mL) and methanol (50 mL) were then added, 30 min. after the completed addition of triethylamine. The reaction mixture was extracted with 2N HCl solution twice, 1N NaOH solution one time, and 1N HCl one time, then dried over MgSO$_4$. The solution was filtered and concentrated to yield N-benzyl-2-(1,3-dioxo-1,3-dihydro-isoindol-2-yl)-acetamide as a white solid.

MH$^+$=294.9.

Step B: 2-(1-Benzyl-1H-tetrazol-5-ylmethyl)-isoindole-1,3-dione

Dissolution of N-benzyl-2-(1,3-dioxo-1,3-dihydro-isoindol-2-yl)-acetamide (8.02 g, 27.2 mmol) in acetonitrile (100 mL) was achieved by heating to reflux. After the reaction mixture was cooled to 0° C., NaN$_3$ (2.30 g, 35.4 mmol) and trifluoromethanesulfonic anhydride (10 g, 35.4 mmol) were added. The reaction mixture was then stirred at room temperature overnight. Dichloromethane (200 mL) was added. The reaction mixture was extracted with saturated sodium bicarbonate solution three times and brine one time and then was dried over MgSO$_4$. The solution was filtered and concentrated to yield 2-(1-benzyl-1H-tetrazol-5-ylmethyl)-isoindole-1,3-dione as a white solid.

MH$^+$=320.0.

Step C: (1-Benzyl-1H-tetrazol-5-yl)-methylamine hydrochloride salt

To a stirred solution of 2-(1-benzyl-1H-tetrazol-5-ylmethyl)-isoindole-1,3-dione (7.88 g, 24.7 mmol) in ethanol (300 mL) was added hydrazine (1.58 g, 49.3 mmol). The reaction mixture was refluxed four hours and then was cooled. After cooling down to room temperature, the white solid from the solution was removed by filtration. The filtrate was concentrated and acetonitrile (50 mL) was added to the residue. The precipitate from the solution was removed by filtration. The filtrate was concentrated to yield a colorless oil which was treated with 1N HCl in diethyl ether to yield (1-benzyl-1H-tetrazol-5-yl)-methylamine, as a white solid, as its corresponding HCl salt.

MH$^+$=190.1.

Step D: (1-Benzyl-1H-tetrazol-5-ylmethyl)-cyclohexyl-amine

To a stirred solution of (1-benzyl-1H-tetrazol-5-yl)-methylamine hydrochloride salt (3.27 g, 14.5 mmol) in methanol (100 mL) were added sodium acetate (1.43 g, 17.4 mmol) and cyclohexanone (1.65 mL, 15.9 mmol). The reaction mixture was concentrated, and then THF (50 mL) and dichloromethane (50 mL) were added. The reaction mixture was cooled to 0° C., and sodium triacetoxyborohydride (6.14 g, 29 mmol) was added. The reaction mixture was stirred at this temperature for six hours and then at room temperature for six hours. The reaction mixture was concentrated to yield a residue. The residue was dissolved in 1N hydrochloric acid solution (50 mL). The solution was extracted with diethyl ether once. Sodium bicarbonate was then added slowly into the aqueous solution until no more bubbling from the solution was observed. The solution was extracted with ethyl acetate three times. The combined ethyl acetate extracts were dried over MgSO$_4$. The solution was concentrated to yield (1-benzyl-1H-tetrazol-5-ylmethyl)-cyclohexyl-amine as a colorless oil.

MH$^+$=272.1.

Step E: {3-[(1-Benzyl-1H-tetrazol-5-ylmethyl)-cyclohexyl-carbamoyl]-1-(S)-cyclohexyl-propyl}-carbamic acid To a stirred solution of 4-tert-butoxycarbonylamino-4-(S)-cyclohexyl-butyric acid (2.63 g, 9.2 mmole) were added (1-benzyl-1H-tetrazol-5-ylmethyl)-cyclohexyl-amine (2.50 g, 9.2 mmole) and N,N-diisopropylethylamine (3.2 mL, 18.4 mmole) in DMF (50 mL) and HBTU (4.19 g, 11.0 mmole). After stirring at room temperature overnight, the reaction mixture was diluted with diethyl ether (200 mL). The reaction mixture was extracted with water three times and dried over magnesium sulfate. The solution was concentrated to yield {3-[(1-benzyl-1H-tetrazol-5-ylmethyl)-cyclohexyl-carbamoyl]-(S)-cyclohexyl-propyl}-carbamic acid as a colorless oil.

MH$^+$=539.2.

Step F: 4-Amino-4-(S),N-dicyclohexyl-N-(1H-tetrazol-5-ylmethyl)-butyramide

To a stirred solution of {3-[(1-benzyl-1H-tetrazol-5-ylmethyl)-cyclohexyl-carbamoyl]-1-(S)-cyclohexyl-propyl}-carbamic acid (4.77 g, 8.8 mmole) in dichloromethane (30 mL), trifluoroacetic acid (30 mL) was added. The reaction mixture was stirred at room temperature for 1 hour. The reaction mixture was then concentrated, and hydrochloric acid solution (10 mL) was added. The reaction mixture was extracted with diethyl ether one time. Sodium bicarbonate then was added until there was no bubbling from the aqueous solution. The solution was extracted with ethyl acetate three times. The combined ethyl acetate extracts were dried over magnesium sulfate. The solution was filtered and concentrated to yield a residue. The residue was hydrogenated with Pd(OH)$_2$ (3.5 g) in ethanol (100 mL) at 50 psi at room temperature overnight to yield 4-amino-4-(S), N-dicyclohexyl-N-(1H-tetrazol-5-ylmethyl)-butyramide as a colorless oil.

MH$^+$=349.2.

Step G: 4-(S),N-Dicyclohexyl-4-[(5-nitro-2-phenoxy-pyridin-4-ylmethyl)-amino]-N-(1H-tetrazol-5-ylmethyl)-butyramide To a stirred solution of crude 4-amino-4-(5, N-dicyclohexyl-N-(1H-tetrazol-5-ylmethyl)-butyramide (0.65 g, 1.9 mmole) and 2-nitro-5-phenoxy-benzaldehyde (0.65 g, 1.9 mmole) in THF (30 mL) was added acetic acid (0.1 mL). After stirring at room temperature for 1 h, the reaction mixture was cooled to 0° C., then sodium triacetoxyborohydride (0.79 g, 3.7 mmol) was added slowly. The reaction mixture was stirred at 0° C. for 8 h and then stirred at room temperature overnight. Diethyl ether (200 mL) was added to the reaction mixture. The solution was extracted with saturated sodium bicarbonate solution three times and dried over magnesium sulfate. The solution was filtered and concentrated to yield crude 4-(S),N-dicyclohexy-4-[(5-nitro-2-phenoxy-pyridin-4-ylmethyl)-amino]-N-(1H-tetrazol-5-ylmethyl)-butyramide as a slightly colored oil.

$MH^+ = 577.2$.

Step H: 4-{[4-(2-Amino-6-phenoxy-4H-pyrido[3,4-d]pyrimidin-3-yl)-4-(S),N-dicyclohexyl-N-(1H-tetrazol-5-ylmethyl)-butyramide To a solution of 4-(S),N-dicyclohexy-4-[(5-nitro-2-phenoxy-pyridin-4-ylmethyl)-amino]-N-(1H-tetrazol-5-ylmethyl)-butyramide (0.75 g, 1.3 mmole) in ethanol (30 mL) and THF (20 mL) was added palladium on carbon (10%, 0.48 g). The reaction mixture was hydrogenated for 1 hour at 20 psi. The reaction mixture was then filtered. Cyanogen bromide (3 M in dichloromethane, 0.65 ml, 1.9 mmole) was added, and the reaction mixture was stirred at room temperature overnight. The reaction mixture was concentrated and the resulting residue was purified by reverse phase HPLC to yield 4-{[4-(2-amino-6-phenoxy-4H-pyrido[3,4-d]pyrimidin-3-yl)-4-(S),N-dicyclohexyl-N-(1H-tetrazol-5-ylmethyl)-butyramide as a white solid, as its corresponding TFA salt.

$MH^+ = 572.3$ $^1$HNMR (300 MHz, DMSO-$d_6$): δ8.02 (s, 1H), 6.98-7.89 (m, 6H), 4.62 (s, 2H), 4.42-4.58 (m, 2H), 3.84 (m, 1H), 3.51 (m, 1H), 2.00-2.38 (m, 4H), 1.00-2.00 (m, 24H).

EXAMPLE 26

4-(2-Amino-6-phenoxy-4H-pyrido[3,4-d]pyrimidin-3-yl)-4-(S),N-dicyclohexyl-N-(1H-imidazol-2-ylmethyl)-butyramide (Compound #78)

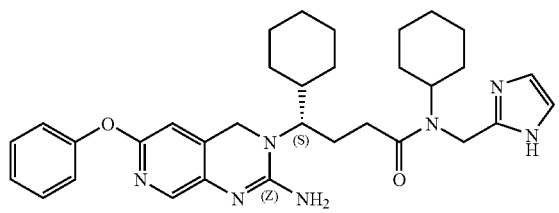

Step A: Cyclohexyl-(1H-imidazol-2-ylmethyl)-amine

To a stirred solution of cyclohexylamine (2.4 mL, 26.8 mmole) in methanol (30 mL) was added 1H-imidazole-2-carboxaldehyde (2.00 g, 26.8 mmole). After stirring at room temperature for one hour, the solution was cooled to 0° C. Sodium borohydride (1.57 g, 41.5 mmol) was then added slowly into the reaction mixture and the reaction mixture was stirred at 0° C. for one hour. Aqueous hydrochloric acid (1 N, 30 mL) was then added. The reaction mixture washed with diethyl ether twice, and then basified by addition of solid sodium carbonate. The aqueous phase was extracted with ethyl acetate twice. The combined ethyl acetate extracts were washed with saturated sodium bicarbonate solution twice and saturated aqueous sodium chloride solution once, and then dried over magnesium sulfate. The solvent was removed to yield cyclohexyl-(1H-imidazol-2-ylmethyl)-amine as a colorless oil.

$MH^+ = 180.1$

Step B: {1-(S)-Cyclohexyl-3-[cyclohexyl-(1H-imidazol-2-ylmethyl)-carbamoyl]-propyl}-carbamic acid tert-butyl ester Following the procedure as in Example 25, Step E, substituting the cyclohexyl-(1H-imidazol-2-ylmethyl)-amine for (1-benzyl-1H-tetrazol-5-ylmethyl)-cyclohexylamine, {1-(S)-cyclohexyl-3-[cyclohexyl-(1H-imidazol-2-ylmethyl)-carbamoyl]-propyl}-carbamic acid tert-butyl ester was obtained as a white solid.

$MH^+ = 447.3$.

Step C: 4-Amino-4-(S),N-dicyclohexyl-N-(1H-imidazol-2-ylmethyl)-butyramide

To a stirred solution of the white solid (2.60 g, 5.8 mmole) isolated in Step B above, in dichloromethane (45 mL) was added trifluoroacetic acid (45 mL). The resulting solution was stirred at room temperature for 2 hours. The solution was then concentrated. Hydrochloric acid solution (1N, 10 mL) was added and the resulting solution washed with diethyl ether one time. Sodium bicarbonate was added until there was no bubbling observed from the aqueous solution. The solution was extracted with ethyl acetate three times. The combined ethyl acetate extracts were dried over magnesium sulfate. The resulting solution was filtered and concentrated to yield 4-amino-4-(S),N-dicyclohexyl-N-(1H-imidazol-2-ylmethyl)-butyramide as a white solid.

$MH^+ = 347.2$

Step D: 4-(S),N-Dicyclohexyl-N-(1H-imidazol-2-ylmethyl)-4-[(5-nitro-2-phenoxy-pyridin-4-ylmethyl)-amino]-butyramide Following the procedure as in Example 25, Step G, substituting 4-amino-4-(S),N-dicyclohexyl-N-(1H-imidazol-2-ylmethyl)-butyramide for 4-amino-4,N-dicyclohexyl-N-(1H-tetrazol-5-ylmethyl)-butyramide, 4-(S),N-dicyclohexyl-N-(1H-imidazol-2-ylmethyl)-4-[(5-nitro-2-phenoxy-pyridin-4-ylmethyl)-amino]-butyramide was obtained as a white solid.

$MH^+ = 574.3$.

Step E: 4-(2-Amino-6-phenoxy-4H-pyrido[3,4-d]pyrimidin-3-yl)-4-(S),N-dicyclohexyl-N-(1H-imidazol-2-ylmethyl)-butyramide Following the procedure as in Example 25, Step H, substituting 4-(S),N-dicyclohexyl-N-(1H-imidazol-2-ylmethyl)-4-[(5-nitro-2-phenoxy-pyridin-4-ylmethyl)-amino]-butyramide for 4-(S),N-dicyclohexy-4-[(5-nitro-2-phenoxy-pyridin-4-ylmethyl)-amino]-N-(1H-tetrazol-5-ylmethyl)-butyramide, the title compound was obtained as a white solid.

$MH^+ = 570.3$ $^1$H NMR (300 MHz, DMSO): δ14.17 (s, 1H), 8.20 (s, 1H), 6.98-7.89 (m, 8H), 4.49-4.76 (m, 4H), 3.85 (m, 1H), 3.51 (m, 1H), 2.00-2.45 (m, 5H), 1.00-2.00 (m, 22H).

EXAMPLE 27

4-(2-Amino-6-phenoxy-4H-pyrido[3,4-d]pyrimidin-3-yl)-5-methyl-(S)-hexanoic acid [2-(R)-tert-butoxy-1-(1H-tetrazol-5-yl)-ethyl]-amide (Compound #97)

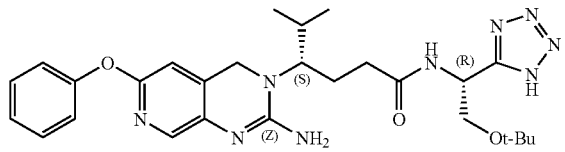

Step A: (2-(R)-tert-Butoxy-1-carbamoyl-ethyl)-carbamic acid 9H-fluoren-9-ylmethyl ester A solution of Fmoc-D-Ser(tBu)-OH (3 g, 7.8 mmol) and TEA (1.1 mL, 7.8 mmol) in THF (20 mL) was cooled to −10° C. Ice cooled ClCO$_2$CH$_2$CH$_3$ was then dripped into the reaction mixture. The resulting solution was stirred at −10° C. for 20 min. Ammonia gas was then bubbled into the reaction mixture for 10 min while the temperature was maintained below −5° C. The reaction mixture was stirred at room temperature overnight, then water (100 mL) was added. The resulting mixture was extracted with EtOAc (2×200 mL). The combined organic layers were washed with NaCl (aq.), dried over MgSO$_4$, filtered, and evaporated to yield crude product. The crude product was purified by column chromatography (1:1 heptane:EtOAc) to yield (2-(R)-tert-butoxy-1-carbamoyl-ethyl)-carbamic acid 9H-fluoren-9-ylmethyl ester as an off-white solid.
MH$^+$ 383.3

Step B: (2-(R)-tert-Butoxy-1-cyano-ethyl)-carbamic acid 9H-fluoren-9-ylmethyl ester A solution of (2-(R)-tert-butoxy-1-carbamoyl-ethyl)-carbamic acid 9H-fluoren-9-ylmethyl ester (1.7 g, 4.4 mmol) and TEA (1.24 mL, 8.8 mol) in THF (50 mL) was cooled to 0° C. Trifluoroacetic anhydride (0.7 mL, 5 mmol) was added, and the resulting solution was stirred at room temperature for one hour, and then water was added (100 mL). The mixture was extracted with EtOAc (200 mL). The combined organic layers were washed with NaCl (aq.), dried with MgSO$_4$, filtered, and evaporated to yield (2-(R)-tert-butoxy-1-cyano-ethyl)-carbamic acid 9H-fluoren-9-ylmethyl ester as a yellow solid.
$^1$H NMR (300 MHz, CDCl$_3$): δ1.21 (s, 9H), 3.53 (m, 1H), 3.65 (m, 1H), 4.23 (m, 1H), 4.47 (d, J=7.1 Hz, 2H), 4.72 (m, 1H), 5.47 (m, 1H), 6.6 (s, 1H), 7.32 (m, 2H), 7.40 (m, 2H), 7.59 (d, J=7.54 Hz, 2H), 7.78 (d, J=7.41 Hz, 2H).

Step C: [2-(R)-tert-Butoxy-1-(1H-tetrazol-5-yl)-ethyl]-carbamic acid 9H-fluoren-9-ylmethyl ester A solution of (2-(R)-tert-butoxy-1-cyano-ethyl)-carbamic acid 9H-fluoren-9-ylmethyl ester (4 g, 11 mmol), NaN$_3$ (1.43 g, 22), and zinc bromide (1.3 g, 5 mmol) in isopropyl alcohol (100 mL), and water (30 mL) was refluxed overnight. The alcohol was removed by vacuum, and the resulting mixture was extracted with EtOAc (200 mL). The organic layer was washed with dilute aqueous HCl, aqueous NaHCO$_3$, and brine, and then dried with MgSO$_4$. The EtOAc was evaporated, and the crude product was purified by column chromatography (1:1 heptane/EtOAc) to yield [2-(R)-tert-butoxy-1-(1H-tetrazol-5-yl)-ethyl]-carbamic acid 9H-fluoren-9-ylmethyl ester as a yellow solid.
MH$^+$ 408.3

Step D: [1-(1-Benzyl-1H-tetrazol-5-yl)-2-(R)-tert-butoxy-ethyl]-carbamic acid 9H-fluoren-9-ylmethyl ester A solution of [2-(R)-tert-butoxy-1-(1H-tetrazol-5-yl)-ethyl]-carbamic acid 9H-fluoren-9-ylmethyl ester (4 g, 10 mmol), benzyl bromide (1.3 mL, 11 mmol) and K$_2$CO$_3$ (1.6 g, 12 mmol) in DMF (50 mL) was stirred at room temperature overnight. EtOAc (300 mL) was then added to the reaction mixture. The organic layer washed by NaCl (aq.) (3×100 mL), dried over MgSO$_4$, filtered, and evaporated to yield [1-(1-benzyl-1H-tetrazol-5-yl)-2-(R)-tert-butoxy-ethyl]-carbamic acid 9H-fluoren-9-ylmethyl ester as an oil.
MH$^+$ 498.3

Step E: 1-(1-Benzyl-1H-tetrazol-5-yl)-2-(R)-tert-butoxy-ethylamine

A solution of [1-(1-benzyl-1H-tetrazol-5-yl)-2-(R)-tert-butoxy-ethyl]-carbamic acid 9H-fluoren-9-ylmethyl ester (1 g, 2 mmol) in piperidine (1 mL) and DMF (7 mL) was stirred at room temperature for 30 min. EtOAc (200 mL) was then added to the reaction mixture. The organic layer washed with NaCl (aq.) (3×50 mL), dried over MgSO$_4$, filtered, and evaporated to yield a light sticky solid which was purified by column chromatography (0-10% MeOH:CH$_2$Cl$_2$) to yield 1-(1-benzyl-1H-tetrazol-5-yl)-2S-tert-butoxy-ethylamine as a colorless oil.
MH$^+$ 276.1

Step F: (1-{2-[1-(1-Benzyl-1H-tetrazol-5-yl)-2-(R)-tert-butoxy-ethylcarbamoyl]-ethyl}-2-(S)-methyl-propyl)-carbamic acid tert-butyl ester To an ice cooled solution of 1-(1-benzyl-1H-tetrazol-5-yl)-2-(R)-tert-butoxy-ethylamine (0.9 g, 3 mmol), 4-tert-butoxycarbonylamino-5-methyl-(S)-hexanoic acid (0.8 g, 3 mmol) and HOBT (0.6 g, 4.4 mmol) in CH$_2$Cl$_2$ (50 mL) was added TEA (0.9 mL) followed by addition of 1,3-dimethylamino propyl-3-ethylcarbodiimide (EDC, 0.8 g, 4.4 mmol). The reaction mixture was then allowed to warm to room temperature and stirred overnight. Then, EtOAc (200 mL) was added, and the resulting solution washed with dilute HCl solution (about 0.1 N, 50 mL), NaHCO$_3$ (aq.), and NaCl (aq.) solution. The organic layer was dried with MgSO$_4$, filtered, and evaporated to yield (1-{2-[1-(1-benzyl-1H-tetrazol-5-yl)-2-(R)-tert-butoxy-ethylcarbamoyl]-ethyl}-2-(S)-methyl-propyl)-carbamic acid tert-butyl ester as an oil.
MH$^+$ 503.4

Step G: 4-Amino-5-methyl-(I)-hexanoic acid [1-(1-benzyl-1H-tetrazol-5-yl)-2-(R)-1-butoxy-ethyl]-amide A solution of (1-{2-[1-(1-benzyl-1H-tetrazol-5-yl)-2-(R)-tert-butoxy-ethylcarbamoyl]-ethyl}-2-(S)-methyl-propyl)-carbamic acid tert-butyl ester (1.5 g, 3 mmol) in 10% TFA in CH$_2$Cl$_2$ (30 mL) was stirred at room temperature for 3 hours. The solvent and most of the TFA was evaporated, and EtOAc (100 mL) was added. The reaction mixture was then washed with NaHCO$_3$ (aq.) and NaCl (aq.). The organic layer was dried (MgSO$_4$) and evaporated to yield 4-amino-5-methyl-(S)-hexanoic acid [1-(1-benzyl-1H-tetrazol-5-yl)-2-(R)-tert-butoxy-ethyl]-amide as an oil.
MH$^+$ 403.4

Step H: 5-Methyl-4-[(5-nitro-2-phenoxy-pyridin-4-ylmethyl)-amino]-(S)-hexanoic acid[1-(1-benzyl-1H-tetrazol-5-yl)-2-(R)-tert-butoxy-ethyl]-amide A solution of 4-amino-5-methyl-(S)-hexanoic acid [1-(1-benzyl-1H-tetrazol-5-yl)-2-(R)-tert-butoxy-ethyl]-amide (0.8 g, 2 mmol) and 5-nitro-2-phenoxy-pyridine-4-carboxaldehyde (0.4 g, 2 mmol) in methylene chloride (25 mL) was stirred at room temperature overnight before NaBH(OAc)$_3$ (0.6 g, 3 mmol) was added. The reaction mixture was then stirred at room temperature for 3 hours. The solution was poured into EtOAc (100 mL). The organic layer washed with NaCl (aq.), dried over MgSO$_4$, filtered, and evaporated to yield a residue which was purified by column chromatography (1:1 heptane:EtOAc) to yield 5-methyl-4-[(5-nitro-2-phenoxy-pyridin-4-ylmethyl)-amino]-(I)-hexanoic acid [1-(1-benzyl-1H-tetrazol-5-yl)-2-(R)-tert-butoxy-ethyl]-amide as an oil.
MH$^+$ 630.9

Step I: 4-[(5-Amino-2-phenoxy-pyridin-4-ylmethyl)-amino]-5-methyl-(S)-hexanoic acid[1-(1-benzyl-1H-tetrazol-5-yl)-2-(R)-tert-butoxy-ethyl]-amide To a solution of 5-methyl-4-[(5-nitro-2-phenoxy-pyridin-4-ylmethyl)-amino]-(S)-hexanoic acid [1-(1-benzyl-1H-tetrazol-5-yl)-2-(R)-tert-butoxy-ethyl]-amide (0.69 g, 1.1 mmol) in MeOH (20 mL) was added 10% Pd—C on activated carbon (0.06 g) under N$_2$. The reaction mixture was subjected to hydrogenation at 5 psi for 2 hour. The catalyst was removed by filtration, and the MeOH was evaporated to yield 4-[(5-amino-2-phenoxy-pyridin-4-ylmethyl)-amino]-5-methyl-(S)-hexanoic acid [1-(1-benzyl-1H-tetrazol-5-yl)-2-(R)-tert-butoxy-ethyl]-amide as an oil.
MH$^+$ 601.2

Step J: 4-(2-Amino-6-phenoxy-4H-pyrido[3,4-d]pyrimidin-3-yl)-5-methyl-(S)-hexanoic acid[1-(1-benzyl-1H-tetrazol-5-yl)-2-(R)-tert-butoxy-ethyl]-amide A solution of 4-[(5-amino-2-phenoxy-pyridin-4-ylmethyl)-amino]-5-methyl-(S)-hexanoic acid [1-(1-benzyl-1H-tetrazol-5-yl)-2-(R)-tert-butoxy-ethyl]-amide (0.6 g, 1 mmol) and BrCN (3M in CH$_2$Cl$_2$, 0.45 mL) in EtOH (10 mL) was stirred at room temperature overnight. The EtOH was evaporated to yield 4-(2-amino-6-phenoxy-4H-pyrido[3,4-d]pyrimidin-3-yl)-5-methyl-(S)-hexanoic acid [1-(1-benzyl-1H-tetrazol-5-yl)-2-(R)-tert-butoxy-ethyl]-amide as a crude solid, as its corresponding HBr salt.
MH$^+$ 626.4

Step K: 4-(2-Amino-6-phenoxy-4H-pyrido[3,4-d]pyrimidin-3-yl)-5-methyl-(S)-hexanoic acid[2-(R)-tert-butoxy-1-(1H-tetrazol-5-yl)-ethyl]-amide To a solution of 4-(2-amino-6-phenoxy-4H-pyrido[3,4-d]pyrimidin-3-yl)-5-methyl-(S)-hexanoic acid [1-(1-benzyl-1H-tetrazol-5-yl)-2-(R)-tert-butoxy-ethyl]-amide as its corresponding HBr salt (0.5 g, 0.8 mmol) in MeOH (20 mL) was added 10% Pd—C on activated carbon (0.9 g) under N$_2$. The reaction mixture was subjected to hydrogenation under 20 psi overnight. The catalyst was filtered out, and the MeOH was evaporated to yield a crude oil. The crude oil was separated by Gilson HPLC to yield 4-(2-amino-6-phenoxy-4H-pyrido[3,4-d]pyrimidin-3-yl)-5-methyl-(S)-hexanoic acid [2-(R)-tert-butoxy-1-(1H-tetrazol-5-yl)-ethyl]-amide as a solid.
MH$^+$ 536.4
$^1$H NMR (300 MHz, CDCl$_3$): δ0.73 (d, J=6.24 Hz, 3H), 0.94 (d, J=6.24 Hz, 3H), 0.98 (s, 9H), 1.66 (m, 2H), 3.60 (m, 1H), 2.1 (m, 2H), 2.38 (m, 1H), 3.68-4.4 (m, 6H), 6.6 (s, 1H), 7.02 (d, J=7.26 Hz, 2H), 7.14 (t, J=7.4 Hz, 1H), 7.37 (t, J=7.66 Hz, 2H), 7.89 (s, 1H).

EXAMPLE 28

4-(2-Amino-6-phenoxy-4H-pyrido[3,4-d]pyrimidin-3-yl)-N-(1-(R)-tert-butoxymethyl-2-morpholin-4-yl-2-oxo-ethyl)-4-(S)-cyclohexyl-butyramide (Compound #103)

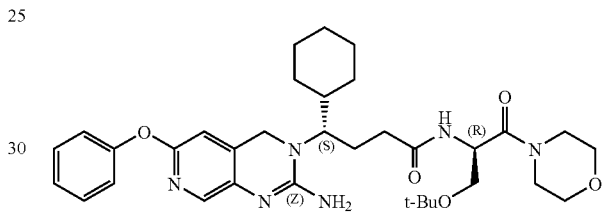

Step A: (1-tert-Butoxymethyl-2-morpholin-4-yl-2-oxo-ethyl)-(R)-carbamic acid tert-butyl ester To an ice cooled solution of morpholine (0.6 mL, 6.9 mmol), Boc-D-Ser(tBu)-OH (3 g, 6.8 mmol) and HOBT (1.2 g, 9 mmol) in CH$_2$Cl$_2$ (50 mL), TEA (1.9 mL) was added followed by addition of 1,3-dimethylamino propyl-3-ethyl-carbodiimide (EDC, 1.7 g, 8.6 mmol). The reaction mixture was allowed to warm to room temperature and was then stirred overnight. EtOAc (200 mL) was added to the reaction mixture. This resulting solution was washed with dilute HCl solution, NaHCO$_3$ (aq.) solution, and NaCl (aq.) solution. The organic layer was dried over MgSO$_4$, filtered, and evaporated to yield (1-tert-butoxymethyl-2-morpholin-4-yl-2-oxo-ethyl)-(R)-carbamic acid tert-butyl ester as a crude oil.
MH$^+$ 331.2

Step B: 2-(R)-Amino-3-tert-butoxy-1-morpholin-4-yl-propan-1-one

A solution of (1-tert-butoxymethyl-2-morpholin-4-yl-2-oxo-ethyl)-(R)-carbamic acid tert-butyl ester (0.5 g, 1.5 mmol) in 5% TFA in CH$_2$Cl$_2$ (50 mL) was stirred at room temperature 5 hours. The solvent and most of the TFA was evaporated. EtOAc (100 mL) was then added to the residue. The resulting solution washed with NaHCO$_3$ (aq.) and NaCl (aq.). The organic layer was dried with MgSO$_4$, filtered and evaporated to yield 2-(R)-amino-3-tert-butoxy-1-morpholin-4-yl-propan-1-one as an oil.
MH$^+$ 231.1

Step C: [3-(R)-(1-tert-Butoxymethyl-2-morpholin-4-yl-2-oxo-ethylcarbamoyl)-1-(S-)cyclohexyl-propyl]-carbamic acid tert-butyl ester To an ice cooled solution of 2-(R)-amino-3-tert-butoxy-1-morpholin-4-yl-propan-1-one (0.3 g, 1.3 mmol), 4-tert-butoxycarbonylamino-4-(S)-cyclohexyl-butyric acid (0.37 g, 1.3 mmol), and HOBT (0.23 g, 1.5 mmol) in CH$_2$Cl$_2$ (50 mL) was added TEA (0.36 mL) followed by the addition of 1,3-dimethylamino propyl-3-ethylcarbodiimide (EDC, 0.33 g, 1.5 mmol). The reaction mixture was then allowed to warm to room temperature and stirred overnight. EtOAc (100 mL) was added. The resulting solution washed with dilute HCl solution, NaHCO$_3$ (aq.) solution, and NaCl (aq.) solution. The organic layer was dried over MgSO$_4$, filtered, and evaporated to yield [3-(R)-(1-tert-butoxymethyl-2-morpholin-4-yl-2-oxo-ethylcarbamoyl)-1-(S)-cyclohexyl-propyl]-carbamic acid tert-butyl ester as a crude oil.

MH$^+$ 498.3

Step D: 4-Amino-N-(1-tert-butoxymethyl-2-morpholin-4-yl-2-oxo-ethyl)-4-(S)-cyclohexyl-butyramide A solution of [3-(R)-(1-tert-butoxymethyl-2-morpholin-4-yl-2-oxo-ethylcarbamoyl)-1-(S)-cyclohexyl-propyl]-carbamic acid tert-butyl ester (0.65 g, 1.3 mmol) in TFA (10% in CH$_2$Cl$_2$, 50 mL) was stirred at room temperature for 3 hours. The solvent and most of the TFA was evaporated, and EtOAc (100 mL) was added to the residue. The solution washed with NaHCO$_3$ (aq.) solution and NaCl (aq.) solution. The organic layer was dried with MgSO$_4$ and evaporated to yield 4-amino-N—((R)-1-tert-butoxymethyl-2-morpholin-4-yl-2-oxo-ethyl)-4-(S)-cyclohexyl-butyramide as an oil.

MH$^+$ 398.3

Step E: N-(1-(R)-tert-Butoxymethyl-2-morpholin-4-yl-2-oxo-ethyl)-4-(S)-cyclohexyl-4-[(5-nitro-2-phenoxy-pyridin-4-ylmethyl)-amino]-butyramide A solution of 4-(R)-amino-N-(1-tert-butoxymethyl-2-morpholin-4-yl-2-oxo-ethyl)-4-(S)-cyclohexyl-butyramide (0.4 g, 1.2 mmol) and 5-nitro-2-phenoxy-pyridine-4-carboxaldehyde (0.3 g, 1.2 mmol) in methylene chloride (50 mL) was stirred at room temperature overnight, then NaBH(OAc)$_3$ (0.5 g, 2.3 mmol) was added. The reaction mixture was stirred at room temperature for 3 hours. The reaction mixture was then poured into CH$_2$Cl$_2$ (100 mL). The organic layer washed with NaCl (aq.) solution, dried with MgSO$_4$, filtered, and evaporated to yield a residue which was purified by column chromatography (EtOAc) to yield N-(1-(R)-tert-butoxymethyl-2-morpholin-4-yl-2-oxo-ethyl)-4-(S)-cyclohexyl-4-[(5-nitro-2-phenoxy-pyridin-4-ylmethyl)-amino]-butyramide as an oil.

MH$^+$ 626.4

Step F: 4-[(5-Amino-2-phenoxy-pyridin-4-ylmethyl)-amino]-N-(1-(R)-tert-butoxymethyl-2-morpholin-4-yl-2-oxo-ethyl)-4-(S)-cyclohexyl-butyramide To a solution of N-(1-(R)-tert-butoxymethyl-2-morpholin-4-yl-2-oxo-ethyl)-4-(S)-cyclohexyl-4-[(5-nitro-2-phenoxy-pyridin-4-ylmethyl)-amino]-butyramide (0.4 g, 0.6 mmol) in MeOH (10 mL) was added 10% Pd on activated carbon (0.1 g) under N$_2$. The reaction mixture was subjected to hydrogenation under 5 psi for 2 h. The catalyst was filtered out, and the MeOH was evaporated to yield 4-[(5-amino-2-phenoxy-pyridin-4-ylmethyl)-amino]-N-(1-(R)-tert-butoxymethyl-2-morpholin-4-yl-2-oxo-ethyl)-4-(S)-cyclohexyl-butyramide as an oil.

MH$^+$ 596.4

Step G: 4-(2-Amino-6-phenoxy-4H-pyrido[3,4-d]pyrimidin-3-yl)-N-(1-(R)-tert-butoxymethyl-2-morpholin-4-yl-2-oxo-ethyl)-4-(S)-cyclohexyl-butyramide A solution of 4-[(5-amino-2-phenoxy-pyridin-4-ylmethyl)-amino]-N-(1-(R)-tert-butoxymethyl-2-morpholin-4-yl-2-oxo-ethyl)-4-(S)-cyclohexyl-butyramide (0.37 g, 0.6 mmol) and BrCN (3M in CH$_2$Cl$_2$, 0.25 mL) in EtOH (20 mL) was stirred at room temperature overnight. The EtOH was evaporated to yield an oil, which was purified by Gilson HPLC to yield 4-(2-amino-6-phenoxy-4H-pyrido[3,4-d]pyrimidin-3-yl)-N-(1-(R)-tert-butoxymethyl-2-morpholin-4-yl-2-oxo-ethyl)-4-(S)-cyclohexyl-butyramide as a white solid, as its corresponding TFA salt.

MH$^+$ 621.5

$^1$H NMR (300 MHz, CDCl$_3$): δ1.08 (s, 9H), 0.92-1.71 (m, 12H), 2.1 (d, J=10.8 Hz, 2H), 2.39 (m, 1H), 2.26 (m, 1H), 3.34-3.69 (m, 10H), 3.96 (m, 1H), 4.15 (m, 2H), 4.8 (m, 1H), 6.54 (s, 1H), 6.95 (d, J=6.6 Hz, 1H), 7.07 (d, J=8.66 Hz, 2H), 7.12 (t, J=7.42 Hz, 1H), 7.28 (t, J=8.0 Hz, 2H), 8.0 (s, 1H).

EXAMPLE 29

4-(2-Amino-6-phenoxy-4H-pyrido[3,4-d]pyrimidin-3-yl)-N-(2-(R)-tert-butoxy-1-morpholin-4-ylmethyl-ethyl)-4-(S)-cyclohexyl-butyramide (Compound #102)

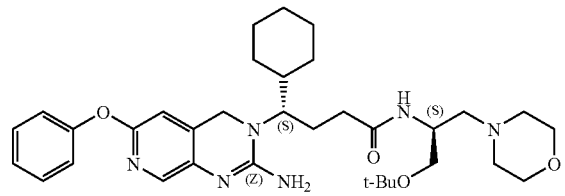

Step A: (2-(R)-tert-Butoxy-1-morpholin-4-ylmethyl-ethyl)-carbamic acid tert-butyl ester To a solution of (1-(R)-tert-butoxymethyl-2-morpholin-4-yl-2-oxo-ethyl)-carbamic acid tert-butyl ester (0.6 g, 1.8 mmol) in THF (10 mL) was added BH$_3$-THF complex (1M in THF, 6.6 mL, 6.6 mmol). The resulting solution was stirred at room temperature overnight before ethylenediamine (0.5 mL, 7.2 mmol) was added. The reaction mixture was then stirred for another 3 hours, and then CH$_2$Cl$_2$ (100 mL) was added. The reaction mixture washed with brine. The layers were separated, and the aqueous layer was extracted with CH$_2$Cl$_2$ again (100 mL). The combined organic layers were dried with MgSO$_4$, filtered, and evaporated to yield (2-(R)-tert-butoxy-1-morpholin-4-ylmethyl-ethyl)-carbamic acid tert-butyl ester as an oil.

MH$^+$ 317.3

Step B: 2-(R)-tert-Butoxy-1-morpholin-4-ylmethyl-ethylamine

A solution of (2-(R)-tert-butoxy-1-morpholin-4-ylmethyl-ethyl)-carbamic acid tert-butyl ester (0.6 g, 1.9 mmol) in 10% TFA in CH$_2$Cl$_2$ (50 mL) was stirred at room temperature for 3 hours. The solvent and most of the TFA was evaporated to yield a residue. NaHCO$_3$ (aq.) solution was then added to the residue and the resulting solution was extracted with 3% MeOH in CH$_2$Cl$_2$ (3×100 mL). The combined organic layers were dried with MgSO$_4$ and evaporated to yield 2-(S)-tert-butoxy-1-morpholin-4-ylmethyl-ethylamine as an oil.
MH$^+$ 217.2

Step C: [3-(2-(S)-tert-Butoxy-1-morpholin-4-ylmethyl-ethylcarbamoyl)-1-(S)-cyclohexyl-propyl]-carbamic acid tert-butyl ester To an ice cooled solution of 2-(S)-tert-butoxy-1-morpholin-4-ylmethyl-ethylamine (0.4 g, 1.9 mmol), 4-tert-butoxy-carbonylamino-5-methyl-(S)-hexanoic acid (0.5 g, 1.8 mmol), and HOBT (0.33 g, 2.5 mmol) in CH$_2$Cl$_2$ (50 mL) was added TEA (0.55 mL) followed by the addition of 1,3-dimethylamino propyl-3-ethylcarbodiimide (EDC, 0.5 g, 2.4 mmol). The reaction mixture was allowed to warm to room temperature and then was stirred overnight. CH$_2$Cl$_2$ (100 mL) was added. The reaction mixture was then washed with dilute HCl solution, NaHCO$_3$ (aq.) solution, and NaCl (aq.) solution. The organic layer was dried over MgSO$_4$, filtered, and evaporated to yield [3-((S)—S-tert-butoxy-1-morpholin-4-ylmethyl-ethylcarbamoyl)-1-(S)-cyclohexyl-propyl]-carbamic acid tert-butyl ester as a crude oil.
MH$^+$ 484.4

Step D: 4-Amino-N-(2-(S)-tert-butoxy-1-morpholin-4-ylmethyl-ethyl)-4-(S)-cyclohexyl-butyramide A solution of [3-(2-(S)-tert-butoxy-1-morpholin-4-ylmethyl-ethylcarbamoyl)-1-(S)-cyclohexyl-propyl]-carbamic acid tert-butyl ester (0.69 g, 1.4 mmol) in 10% TFA in CH$_2$Cl$_2$ (50 mL) was stirred at room temperature for 3 h. The solvent and most of the TFA was evaporated. CH$_2$Cl$_2$ (100 mL) was added to the residue. The resulting solution washed with NaHCO$_3$ (aq.) solution and NaCl (aq.) solution. The organic layer was dried with MgSO$_4$, filtered, and evaporated to yield 4-amino-N-(2-(S)-tert-butoxy-1-morpholin-4-ylmethyl-ethyl)-4-(S)-cyclohexyl-butyramide as an oil.
MH$^+$ 384.3

Step E: N-(2-(S)-tert-Butoxy-1-morpholin-4-ylmethyl-ethyl)-4-(S)-cyclohexyl-4-[(5-nitro-2-phenoxy-pyridin-4-ylmethyl)-amino]-butyramide A solution of 4-amino-N-(2-(S)-tert-butoxy-1-morpholin-4-ylmethyl-ethyl)-4-(S)-cyclohexyl-butyramide (0.56 g, 1.4 mmol) and 5-nitro-2-phenoxypyridine-4-carboxaldehyde (0.38 g, 1.5 mmol) in methylene chloride (50 mL) was stirred at room temperature over the weekend. NaBH(OAc)$_3$ (0.6 g, 2.8 mmol) was then added. The reaction mixture was stirred at room temperature for 3 hours and then was poured into CH$_2$Cl$_2$ (100 mL). The organic layer washed with NaCl (aq.) solution, dried with MgSO$_4$, filtered, and evaporated to yield a residue which was purified by column chromatography (EtOAc) to yield N-(2-(S)-tert-butoxy-1-morpholin-4-ylmethyl-ethyl)-4-(S)-cyclohexyl-4-[(5-nitro-2-phenoxy-pyridin-4-ylmethyl)-amino]-butyramide as an oil.
MH$^+$ 612.5

Step F: 4-[(5-Amino-2-phenoxy-pyridin-4-ylmethyl)-amino]-N-(2-(S)-tert-butoxy-1-morpholin-4-ylmethyl-ethyl)-4-(S)-cyclohexyl-butyramide To a solution of N-(2-(S)-tert-butoxy-1-morpholin-4-ylmethyl-ethyl)-4-(S)-cyclohexyl-4-[(5-nitro-2-phenoxy-pyridin-4-ylmethyl)-amino]-butyramide (0.45 g, 0.7 mmol) in MeOH (10 mL) was added 10% Pd—C on activated carbon (0.06 g) under N$_2$. The reaction mixture was subjected to hydrogenation under 5 psi for 1 hour. The catalyst was filtered out, and the MeOH was evaporated to yield 4-[(5-amino-2-phenoxy-pyridin-4-ylmethyl)-amino]-N-(2-(S)-tert-butoxy-1-morpholin-4-ylmethyl-ethyl)-4-(S)-cyclohexyl-butyramide as an oil.
MH$^+$ 582.5

Step G: 4-(2-Amino-6-phenoxy-4H-pyrido[3,4-d]pyrimidin-3-yl)-N-(2-(S)-tert-butoxy-1-morpholin-4-ylmethyl-ethyl)-4S-cyclohexyl-butyramide A solution of 4-[(5-amino-2-phenoxy-pyridin-4-ylmethyl)-amino]-N-(2-(S)-tert-butoxy-1-morpholin-4-ylmethyl-ethyl)-4-(S)-cyclohexyl-butyramide (0.40 g, 0.7 mmol) and BrCN (3M in CH$_2$Cl$_2$, 0.2 mL) in EtOH (5 mL) was stirred at room temperature overnight. The EtOH was evaporated, and the resulting crude oil was purified by Gilson HPLC to yield 4-(2-amino-6-phenoxy-4H-pyrido[3,4-d]pyrimidin-3-yl)-N-(2-(S)-tert-butoxy-1-morpholin-4-ylmethyl-ethyl)-4-(S)-cyclohexyl-butyramide as an off-white solid, as its corresponding TFA salt.
MH$^+$ 607.3
$^1$H NMR (300 MHz, CDCl$_3$): δ1.1 (s, 9H), 0.9-1.8 (m, 12H), 2.1-2.4 (m, 4H), 2.8-3.1 (m, 4H), 3.2-3.5 (m, 4H), 3.8-4.2 (m, 6H), 4.4 (m, 1H), 6.56 (s, 1H), 7.02 (d, J=7.6 Hz, 2H), 7.13 (t, J=7.41 Hz, 1H), 7.3 (t, J=8.12 Hz, 2H), 8.0 (s, 1H).

EXAMPLE 30

4-(2-Amino-6-phenoxy-4H-pyrido[3,4-d]pyrimidin-3-yl)-4-(S),N-dicyclohexyl-N-(4H-[1,2,4]triazol-3-ylmethyl)-butyramide (Compound 80)

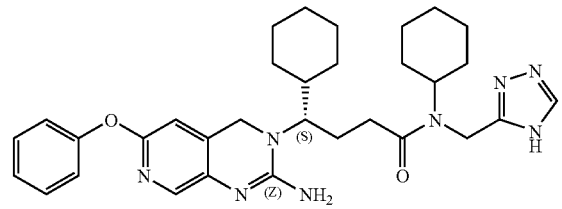

Step A: 1-Benzyl-1H-[1,2,4]triazole-3-carboxylic acid methyl ester

A solution of methyl 1,2,4-triazole-2-carboxylate (6.89 g, 54.2 mmole), benzyl bromide (7.7 mL, 65.0 mmol) and potassium carbonate (11.24 g, 81.3 mmol) in acetonitrile (100 mL) was refluxed overnight. The solution was then filtered and concentrated to a residue. The residue was dissolved in diethyl ether. The solution washed with 1N sodium hydroxide one time and water one time, and then dried over MgSO$_4$. The solution was filtered and concentrated to yield 1-benzyl-1H-

[1,2,4]triazole-3-carboxylic acid methyl ester as a brown oil, which was used in next step without further purification.

Step B: 1-Benzyl-1H-[1,2,4]triazole-3-carboxylic acid

To a stirred solution of 1-benzyl-1H-[1,2,4]triazole-3-carboxylic acid methyl ester (4.11 g) in THF (30 mL) in methanol (30 mL), was added sodium hydroxide solution (1.0 N, 28 mL, 28 mmol). The solution was stirred at room temperature for 3 hours. The organic solvents were removed by evaporation. The aqueous phase washed with diethyl ether one time. The aqueous solution was acidified by adding 2 N HCl and then filtered to yield 1-benzyl-1H-[1,2,4]triazole-3-carboxylic acid as a white solid.

MH$^+$ =204.1.

Step C: 1-Benzyl-1H-[1,2,4]triazole-3-carboxylic acid cyclohexylamide

To a stirred solution of 1-benzyl-1H-[1,2,4]triazole-3-carboxylic acid (1.54 g, 7.6 mmol), cyclohexylamine (0.87 mL, 7.6 mmol) and N,N-diisopropylethylamine (2.65 mL, 15.1 mmol) in DMF (30 mL) was added HBTU (3.45 g, 9.1 mmol). The solution was then stirred at room temperature overnight. Aqueous hydrochloric acid was added and the solution was filtered to yield 1-benzyl-1H-[1,2,4]triazole-3-carboxylic acid cyclohexylamide as a white solid.

MH$^+$ =285.1

Step D: (1-Benzyl-1H-[1,2,4]triazol-3-ylmethyl)-cyclohexyl-amine

A solution of 1-benzyl-1H-[1,2,4]triazole-3-carboxylic acid cyclohexylamide (3.63 g, 12.8 mmol) in phosphorus oxychloride (10 mL) was heated at 70° C. for 4 hours. The solution was then concentrated. Toluene was added and then evaporated. The residue was dissolved in THF (100 mL). The solution was cooled to 0° C., and LiAlH$_4$ (1.0 M in THF, 25.6 mL, 25.6 mmol) was added slowly into the solution. The solution was allowed to return to room temperature and then stirred for 1 hour. Potassium sodium tartrate tetrahydrate (5 g) was added. Water was added slowly to terminate the reaction. The solution was filtered and ethyl acetate was used to wash the filter cake. The filtrate was concentrated. HCl (1.0 M) in diethyl ether was added. The resulting precipitate was collected and recrystallized from acetone/methanol to yield (1-benzyl-1H-[1,2,4]triazol-3-ylmethyl)-cyclohexyl-amine as its corresponding hydrochloric acid salt, as a white solid.

MH$^+$ =271.1

Step E: {3-[(1-Benzyl-1H-[1,2,4]triazol-3-ylmethyl)-cyclohexyl-carbamoyl]-1-(S)-cyclohexyl-propyl}-carbamic acid tert-butyl ester Following the procedure as described in Example 25, STEP E, (1-benzyl-1H-[1,2,4]triazol-3-ylmethyl)-cyclohexyl-amine was reacted to yield {3-[(1-Benzyl-1H-[1,2,4]triazol-3-ylmethyl)-cyclohexyl-carbamoyl]-1-(S)-cyclohexyl-propyl}-carbamic acid tert-butyl ester as a white solid.

MH$^+$ =538.3.

Step F: 4-Amino-(1-benzyl-1H-[1,2,4]triazol-3-ylmethyl)-4-(S),N-dicyclohexyl-butyramide Following the procedure as described in Example 26, STEP C, {3-[(1-benzyl-1H-[1,2,4]triazol-3-ylmethyl)-cyclohexyl-carbamoyl]-1-(S)-cyclohexyl-propyl}-carbamic acid 1-butyl ester was reacted to yield 4-amino-(1-benzyl-1H-[1,2,4]triazol-3-ylmethyl)-4-(S),N-dicyclohexyl-butyramide as a slightly colored oil.

MH$^+$ =438.3

Step G: 4-Amino-4-(S),N-dicyclohexyl-N-(1H-[1,2,4]triazol-3-ylmethyl)-butyramide To the solution of 4-amino-(1-benzyl-1H-[1,2,4]triazol-3-ylmethyl)-4(S),N-dicyclohexyl-butyramide (1.44 g, 3.3 mmol) in ethanol (80 mL), palladium on carbon (10%) (1.30 g) and acetic acid (1.0 mL) were added. The solution was hydrogenated at 50 psi and 50° C. for 20 hours to yield 4-amino-4(S)-,N-dicyclohexyl-N-(1H-[1,2,4]triazol-3-ylmethyl)-butyramide as a colorless oil.

MH$^+$ =348.1

Step H: 4-(S),N-Dicyclohexyl-4-[(5-nitro-2-phenoxy-pyridin-4-ylmethyl)-amino]-N-(4H-[1,2,4]triazol-3-ylmethyl)-butyramide Following the procedure as described in Example 25, STEP G, 4-amino-4-(S)—,N-dicyclohexyl-N-(1H-[1,2,4]triazol-3-ylmethyl)-butyramide was reacted to yield 4-(S),N-dicyclohexyl-4-[(5-nitro-2-phenoxy-pyridin-4-ylmethyl)-amino]-N-(4H-[1,2,4]triazol-3-ylmethyl)-butyramide as a white solid.

MH$^+$ =575.2.

Step I: 4-(2-Amino-6-phenoxy-4H-pyrido[3,4-d]pyrimidin-3-yl)-4-(S),N-dicyclohexyl-N-(4H-[1,2,4]triazol-3-ylmethyl)-butyramide Following the procedure as described in Example 25, STEP H, 4-(S),N-dicyclohexyl-4-[(5-nitro-2-phenoxy-pyridin-4-ylmethyl)-amino]-N-(4H-[1,2,4]triazol-3-ylmethyl)-butyramide was reacted to yield 4-(2-amino-6-phenoxy-4H-pyrido[3,4-d]pyrimidin-3-yl)-4-(S)—,N-dicyclohexyl-N-(4H-[1,2,4]triazol-3-ylmethyl)-butyramide as a white solid.

MH$^+$ =571.3

$^1$H NMR (300 MHz, DMSO): δ7.86-8.00 (m, 3H), 7.72 (s, 1H), 6.93-7.43 (m, 5H), 4.40-4.53 (m, 4H), 3.83 (m, 1H), 3.23 (m, 1H), 1.94-2.24 (m, 4H), 1.00-1.94 (m, 23H).

EXAMPLE 31

{[4-(2-Amino-6-phenoxy-4H-pyrido[3,4-d]pyrimidin-3-yl)-4-(S)-cyclohexyl-butyryl]cyclohexyl-amino}-acetic acid (Compound 84)

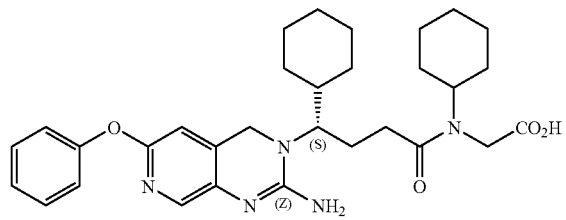

Step A: Cyclohexylamino-acetic acid benzyl ester hydrochloride

Following the procedure as described in Example 26, STEP A, glycine benzylester hydrochloride was reacted with cyclohexanone to yield cyclohexylamino-acetic acid benzyl ester hydrochloride as a white solid.

MH$^+$ =248.1.

Step B: [(4-tert-Butoxycarbonylamino-4-(S)-cyclo-
hexyl-butyryl)-cyclohexyl-amino]-acetic acid benzyl
ester Following the procedure as described in Example 25,
STEP E, cyclohexylamino-acetic acid benzyl ester hydro-
chloride was reacted to yield [(4-tert-butoxycarbonylamino-
4-(S)-cyclohexyl-butyryl)-cyclohexyl-amino]-acetic acid
benzyl ester as a slightly colored oil.
MH$^+$=515.3.

Step C: [(4-Amino-4-(S)-cyclohexyl-butyryl)-cyclo-
hexyl-amino]-acetic acid benzyl ester Following the procedure as described in Example 26,
STEP C, [(4-tert-butoxycarbonylamino-4-(S)-cyclohexyl-
butyryl)-cyclohexyl-amino]-acetic acid benzyl ester was
reacted to yield [(4-amino-4-(S)-cyclohexyl-butyryl)-cyclo-
hexyl-amino]-acetic acid benzyl ester as a lightly colored oil.
MH$^+$=415.2

Step D: (Cyclohexyl-{4-cyclohexy-4-[(5-nitro-2-
phenoxy-pyridin-4-ylmethyl)-amino]-butyryl}-
amino-acetic acid benzyl ester Following the procedure as described in Example 25,
STEP G, [(4-amino-4-(S)-cyclohexyl-butyryl)-cyclohexyl-
amino]-acetic acid benzyl ester was reacted to yield (cyclo-
hexyl-{4-(S)-cyclohexyl-4-[(5-nitro-2-phenoxy-pyridin-4-
ylmethyl)-amino]-butyryl}-amino-acetic acid benzyl ester as
a colorless oil.
MH$^+$=643.3.

Step E: {[4-(2-Amino-6-phenoxy-4H-pyrido[3,4-d]
pyrimidin-3-yl)-4-(S)-cyclohexyl-butyryl]cyclo-
hexyl-amino}-acetic acid Following the procedure as described in Example 25,
STEP H, (cyclohexyl-{4-(S)-cyclohexy-4-[(5-nitro-2-phe-
noxy-pyridin-4-ylmethyl)-amino]-butyryl}-amino-acetic
acid benzyl ester was reacted to yield {[4-(2-amino-6-phe-
noxy-4H-pyrido[3,4-d]pyrimidin-3-yl)-4-(S)-cyclohexyl-
butyryl]cyclohexyl-amino}-acetic acid as a white solid was
prepared.
MH$^+$=548.2
$^1$H NMR (300 MHz, DMSO): δ10.99 (s, 1H), 8.03 (s, 1H),
6.95-7.44 (m, 6H), 4.43-4.58 (m, 2H), 3.71-3.84 (m, 3H),
3.51 (m, 1H), 2.00-2.45 (m, 4H), 1.00-2.00 (m, 21H).

EXAMPLE 32

4-(S)-(2-Amino-6-phenoxy-4H-pyrido[3,4-d]pyrimi-
din-3-yl)-5-methyl-hexanoic acid methyl-[4-(1H-
tetrazol-5-yl)-cyclohexyl]-amide (Compound 13)

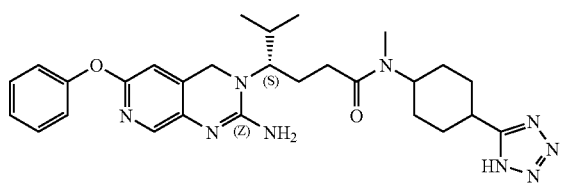

Step A: 4-Oxo-cyclohexanecarbonitrile

A solution of 1,4-dioxaspiro[4,5]decane-8-carbonitrile
(15.86 g, 94.8 mmol) (prepared according to the procedure in
Lucija Peterlin-Masic, Andreja Jurca, Petra Marrinko, Anita
Jancar and Danijel Kikelj, *Tetrahedron* 2002, 58, 1557-1563),
in a mixture of aqueous hydrochloric acid (2 N, 60 mL) and
acetone (100 mL) was refluxed overnight. The acetone was
removed by evaporation. The aqueous phase was extracted
with ethyl acetate three times. The combined organic extracts
were washed with water one time and then dried over mag-
nesium sulfate. The solution was filtered and concentrated to
yield 4-oxo-cyclohexanecarbonitrile as a colorless oil, which
was used in the next reaction without purification.

Step B: 4-Methlyamino-cyclohexanecarbonitrile

Following the procedure as described in Example 25,
STEP D, methyl amine and 4-oxo-cyclohexanecarbonitrile
were reacted to yield 4-methyamino-cyclohexanecarbonitrile
as a white solid, as its corresponding hydrochloride salt.
MH$^+$=139.2.

Step C: (1-{2-[(4-Cyano-cyclohexyl)-methyl-car-
bamoyl]-ethyl}-2-methyl-(S)-propyl)-carbamic tert-
butyl ester Following the procedure as described in Example 25,
STEP E, 4-methyamino-cyclohexanecarbonitrile and 4-(S)-
tert-butoxycarbonylamino-5-methyl-hexanoic acid were
reacted to yield (1-{2-[(4-cyano-cyclohexyl)-methyl-car-
bamoyl]-ethyl}-2-methyl-(S)-propyl)-carbamic tert-butyl
ester as a lightly colored oil was prepared.
MH$^+$=366.3

Step D: 4-(S)-Amino-5-methyl-hexanoic acid (4-cy-
ano-cyclohexyl)-methyl-amide

Following the procedure as described in Example 25,
STEP F, (1-{2-[(4-cyano-cyclohexyl)-methyl-carbamoyl]-
ethyl}-2-methyl-(S)-propyl)-carbamic tert-butyl ester was
reacted to yield 4-(S)-amino-5-methyl-hexanoic acid (4-cy-
ano-cyclohexyl)-methyl-amide as a lightly colored oil.
MH$^+$=266.2

Step E: 5-(S)-{Methyl-4-[5-nitro-2-phenoxyl-pyri-
din-4-ylmethyl)-amino]}-hexanoic acid (4-cyano-
cyclohexyl)-methyl-amide Following the procedure as described in Example 25,
STEP G, 4-amino-5-methyl-hexanoic acid (4-cyano-cyclo-
hexyl)-methyl-amide was reacted to yield 5-methyl-4-(S)-[5-
nitro-2-phenoxyl-pyridin-4-ylmethyl)-amino]-hexanoic acid
(4-cyano-cyclohexyl)-methyl-amide as a colorless oil.
MH$^+$=494.0

Step F: 4-(S)-(2-Amino-6-phenoxy-4H-pyrido[3,4-d]
pyrimidin-3-yl)-5-methyl-hexanoic acid (4-cyano-
cyclohexyl)-methyl-amide Following the procedure as described in Example 25,
STEP H, 5-methyl-4-(S)-[5-nitro-2-phenoxy-pyridin-4-yl-
methyl)-amino]-hexanoic acid (4-cyano-cyclohexyl)-me-
thyl-amide was reacted to yield 4-(S)-(2-amino-6-phenoxy-
4H-pyrido[3,4-d]pyrimidin-3-yl)-5-methyl-hexanoic acid
(4-cyano-cyclohexyl)-methyl-amide as a white solid.
MH$^+$=489.2

Step G: 4-(S)-(2-Amino-6-phenoxy-4H-pyrido[3,4-d]pyrimidin-3-yl)-5-methyl-hexanoic acid methyl-[4-(1H-tetrazol-5-yl)-cyclohexyl]-amide To a solution of 4-(S)-(2-amino-6-phenoxy-4H-pyrido[3,4-d]pyrimidin-3-yl)-5-methyl-hexanoic acid (4-cyano-cyclohexyl)-methyl-amide (0.26 g, 0.43 mmol) and trimethylsilylazide (0.17 mL, 1.29 mmol) in DME (1.5 mL) was added dibutyltin oxide (0.10 g, 0.40 mmol). The mixture was then heated in a microwave at 150° C. for 20 min. The solution was purified by HPLC to yield 4-(S)-(2-amino-6-phenoxy-4H-pyrido[3,4-d]pyrimidin-3-yl)-5-methyl-hexanoic acid methyl-[4-(1H-tetrazol-5-yl)-cyclohexyl]-amide as a white solid, as its corresponding trifluoroacetate salt.

$MH^+$ =532.5

$^1$H NMR (300 MHz, DMSO): δ8.10 (m, 1H), 7.88 (m, 1H), 6.96-7.43 (m, 6H), 4.41-4.59 (m, 2H), 3.73-3.82 (m, 3H), 3.51 (m, 1H), 2.68 (s, 3H), 2.00-2.45 (m, 5H), 1.29-2.00 (m, 11H), 0.90-1.00 (m, 6H)

EXAMPLE 33

4-(2-Amino-6-phenoxy-4H-pyrido[3,4-d]pyrimidin-3-yl)-4-(S)-cyclohexyl-butyric acid

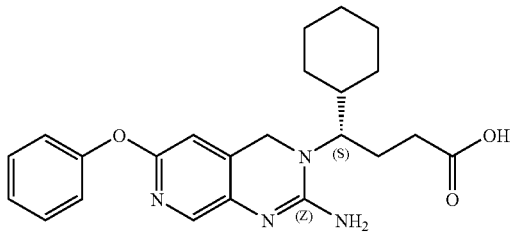

Step A: 4-Amino-4-(S)-cyclohexyl-butyric acid tert-butyl ester

A solution of 4-tert-butoxycarbonylamino-4-(S)-cyclohexylbutyric acid (6 gm, 21 mmol) in 20% TFA:DCM (80 mL) was stirred at room temperature overnight. The solvent and excess TFA were removed by vacuum to yield an oil. The oil was added to DCM (25 mL) to yield a solution.

A 250 mL pressure reaction bottle was flushed with $N_2$ and cooled to −78° C. Isobutylene gas from a cylinder was then introduced by a needle and condensed in the flask (about 80 mL). The solution prepared above was transferred into the flask followed by addition of concentrated $H_2SO_4$ (3 mL). The resulting mixture was warmed and stirred at room temperature overnight.

$NaHCO_3$ (4 g) was added to the reaction mixture, and the mixture was stirred for another 10 min. The solid was filtered, and the filtrate was concentrated under vacuum to yield an oil. The oil was purified by column (5% MeOH:DCM) to yield 4-amino-4-(S)-cyclohexylbutyric acid tert-butyl ester as a brown oil.

$MH^+$ 242.3

Step B: 4-(S)-Cyclohexyl-4-[(5-nitro-2-phenoxy-pyridin-4-ylmethyl)-amino]-butyric acid tert-butyl ester A solution of 4-amino-4-(S)-cyclohexyl-butyric acid tert-butyl ester (5 g, 20 mmol) and 4-formyl-5-nitro-2-phenoxy-pyridine (6 g, 24 mmol) in methylene chloride (100 mL) was stirred at room temperature overnight. NaBH(OAc)$_3$ (0.8 gm, 4 mmol) was added, and the solution was stirred at room temperature for 5 hours. Additional NaBH(OAc)$_3$ (7 g, 33 mmol) was added and the solution was stirred at room temperature for another one hour. The solution was then poured into EtOAc (100 mL). The organic layer washed with aqueous NaCl, dried over MgSO$_4$ and evaporated to yield a residue which was purified by column chromatography (10% EtOAc/Heptane) to yield 4-(S)-cyclohexyl-4-[(5-nitro-2-phenoxy-pyridin-4-ylmethyl)-amino]-butyric acid tert-butyl ester as a brown oil.

$MH^+$ 470.2

Step C: 4-[(5-Amino-2-phenoxy-pyridin-4-ylmethyl)-amino]-4-(S)-cyclohexyl-butyric acid tert-butyl ester To a solution of 4-(S)-cyclohexyl-4-[(5-nitro-2-phenoxy-pyridin-4-ylmethyl)-amino]-butyric acid tert-butyl ester (4.8 g, 10.2 mmol) in MeOH (50 mL) was added 10% Pd on activated carbon (0.8 g) under $N_2$. The resulting mixture was subjected to hydrogenation at 5 psi for 2 hours. The catalyst was removed by filtration, and the MeOH was evaporated in vacuo to yield 4-[(5-amino-2-phenoxy-pyridin-4-ylmethyl)-amino]-4-(S)-cyclohexyl-butyric acid tert-butyl ester as an oil.

$MH^+$ 440.2

Step D: 4-(2-Amino-6-phenoxy-4H-pyrido[3,4-d]pyrimidin-3-yl)-4-(S)-cyclohexyl-butyric acid tert-butyl ester A solution of 4-[(5-amino-2-phenoxy-pyridin-4-ylmethyl)-amino]-4-(S)-cyclohexyl-butyric acid tert-butyl ester (4.3 g, 9.8 mmol) and BrCN (3M in $CH_2Cl_2$, 3.6 mL) in EtOH (100 mL) was stirred at room temperature overnight. The EtOH was evaporated to yield a residue which was purified by column chromatography using 5-10% MeOH:DCM as eluent to yield 4-(2-amino-6-phenoxy-4H-pyrido[3,4-d]pyrimidin-3-yl)-4-(d-cyclohexyl-butyric acid tert-butyl ester as a brown oil.

$MH^+$ 465.0

Step E: 4-(2-Amino-6-phenoxy-4H-pyrido[3,4-d]pyrimidin-3-yl)-4-(S)-cyclohexyl-butyric acid A solution of 4-(2-amino-6-phenoxy-4H-pyrido[3,4-d]pyrimidin-3-yl)-4-(S)-cyclohexyl-butyric acid tert-butyl ester (4.5 g, 9.8 mmol) in 30% TFA:DCM (100 mL) was stirred at room temperature for 3 hours. The solvent and excess TFA were removed by vacuum. To the resulting oil was added DCM (300 mL) and NaHCO$_3$ (0.7 g) in water (50 mL). The resulting solution was then adjusted to pH 6 by adding saturated NaHCO$_3$ aqueous solution. The organic layer was separated, dried with MgSO$_4$ and evaporated to yield an oil.

The oil was re-dissolved in DCM (100 mL), and the solution was cooled to 0° C. HCl (1 N) in diethyl ether solution (50 mL) was added. The resulting mixture was stirred at 0° C. for 15 min, and the solvent was then removed by vacuum at room temperature. The resulting solid was further dried under high vacuum for 24 hours to yield 4-(2-amino-6-phenoxy-4H-pyrido[3,4-d]pyrimidin-3-yl)-4S-cyclohexyl-butyric acid as its corresponding HCl salt.

$MH^+$ 409.2

$^1$H NMR (300 MHz, CD$_3$OD): □0.92-1.31 (m, 6H), 1.49-1.93 (m, 7H), 2.05-2.23 (m, 2H), 3.21-3.23 (m, 1H), 4.36-4.50 (m, 2H), 6.84 (s, 1H), 7.0 (d, J=8.15 Hz, 2H), 7.13 (t, J=7.47 Hz, 1H), 7.33 (m 2H), 7.77 (s, 1H).

EXAMPLE 34

4-(2-Amino-6-phenoxy-4H-pyrido[3,4-d]pyrimidin-3-yl)-4-(S)-cyclohexyl-N-methyl-N-phenethyl-butyramide (Compound #122)

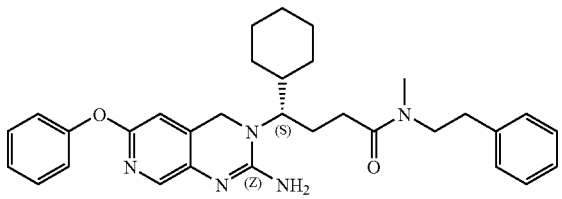

To a solution of 4-(2-amino-6-phenoxy-4H-pyrido[3,4-d]pyrimidin-3-yl)-4-(S)-cyclohexyl-butyric acid (0.1 g, 0.22 mmol) in DCM (10 mL) was added oxalyl chloride (2.0M in DCM, 1.4 mL, 2.2 mmol), and the resulting mixture was stirred at room temperature one hour. When an aliquot was quenched in MeOH and the resulting solution was analyzed by MS-HPLC, all the starting acid was gone with only the methyl ester detected. The solvent and excess oxalyl chloride were then removed by vacuum. DCM (10 mL) was added to the residue followed by addition of N-methylphenethylamine (0.18 mL, 1.1 mmol). The resulting solution was stirred at room temperature for one hour. The solvent was removed by vacuum, and the resulting crude oil was purified by Gilson HPLC to yield 4-(2-amino-6-phenoxy-4H-pyrido[3,4-d]pyrimidin-3-yl)-4-(S)-cyclohexyl-N-methyl-N-phenethyl-butyramide as its corresponding TFA salt.

The TFA salt was dissolved in DCM (50 mL) and basified with saturated aqueous $NaHCO_3$ solution (20 mL). The organic layer was separated, dried over $MgSO_4$ and evaporated by vacuum to yield 4-(2-amino-6-phenoxy-4H-pyrido[3,4-d]pyrimidin-3-yl)-4-(S)-cyclohexyl-N-methyl-N-phenethyl-butyramide as an oil.

The oil was redissolved in DCM (10 mL) and cooled to 0° C. 1N HCl in diethyl ether solution (1 mL) was added. The resulting mixture was stirred at 0° C. for 10 min, and the solvent was then removed under vacuum at room temperature. The resulting solid was further dried under high vacuum for 24 hours to yield 4-(2-amino-6-phenoxy-4H-pyrido[3,4-d]pyrimidin-3-yl)-4-(S)-cyclohexyl-N-methyl-N-phenethyl-butyramide as its corresponding HCl salt.

$MH^+$ 526.3

$^1H$ NMR (300 MHz, $CDCl_3$): □0.97-1.80 (m, 10H), 2.06-2.17 (m, 1H), 2.23-2.39 (m, 1H), 2.76-2.83 (m, 2H), 2.93 (s, 3H), 3.42-3.64 (m, 3H), 4.10-4.38 (m, 2H), 6.60 (d, J=9 Hz, 1H), 7.06-7.4 (m, 12H), 8.02 (d, J=8.04 Hz, 1H).

EXAMPLE 35

4-tert-butoxycarbonylamino-4-(S)-tetrahydro-pyran-4-yl-butyric acid

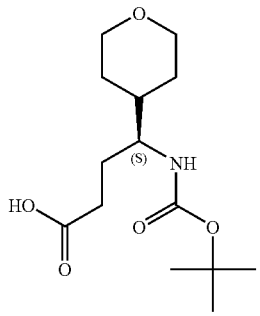

Step A

To a solution of N-benzyloxycarbonyl-□-phosphonoglycine trimethyl ester (6.6 g, 20 mmol) and 1,1,3,3-tetramethylguanidine (3.3 mL, 27 mmole) in THF (50 mL) was added dropwise a solution of tetrahydro-4H-pyran-4-one (2 g, 20 mmol) in THF (30 mL). The reaction mixture was stirred at room temperature overnight, and then 5% HCl (50 mL) was added. The reaction mixture was then extracted with EtOAc (200 mL and then 100 mL portions). The combined organic layers were washed with aqueous NaCl solution, dried with $MgSO_4$, and evaporated. The residue was recrystallized twice from EtOAc and hexane to yield a white solid.

$MH^+$ 306.0

Step B

A solution of the solid isolated in Step A (4 g, 13 mmol) and R, R-(+)-BPE (1,2-bis(phospholano)ethane)-Rh catalyst (0.08 g) in MeOH (60 mL) was placed into a Parr high pressure reactor and subjected to hydrogenation under 410 psi for three days. The MeOH was removed by evaporation, and the residue was purified on a column (1:1 hexane:EtOAc) to yield an oil which turned to solid on standing overnight.

$MH^+$ 308.1

Step C

To a solution of the solid isolated in Step B (4.5 g, 14.5 mmol) in MeOH (30 mL) was added 1N NaOH (14.5 mL, 14.5 mmol). The reaction mixture was stirred at room temperature overnight. The MeOH was evaporated, and resulting solution was extracted with EtOAc (200 mL). The organic layer washed with dilute aqueous HCl solution, $NaHCO_3$ solution, and NaCl solution, dried with $MgSO_4$, and evaporated to yield a colorless oil.

$MH^+$ 394.1, $MH^-$ 392.0

Step D

To an ice cooled solution of the oil isolated in Step C (3.8 g, 13 mmol), N,O-dimethylhydroxylamine HCl salt (1.4 g, 15 mmol), and HOBT (2 g, 16 mmol) in $CH_2Cl_2$ (100 mL) was added TEA (3.6 mL) followed by addition of EDC (3.0 g, 16 mmol). The reaction mixture was allowed to warm to room temperature and was stirred overnight. EtOAc (100 mL) was added, and the reaction mixture was then washed with citric acid solution, $NaHCO_3$ solution, and NaCl solution. The organic layer was separated, dried with $MgSO_4$, and evaporated to yield a colorless oil. The crude oil product was used without further purification.

$MH^+$ 337.1

Step E

To an ice cooled solution of the oil isolated in Step D (4.3 g, 13 mmol) in THF (200 mL) was slowly added LAH (1M solution in THF, 14 mL) while keeping the temperature below 5° C. The ice bath was removed, and the reaction mixture was stirred at room temperature for 20 min. A solution of $NaHSO_4$ (1.5 g) in water (5 mL) was slowly added to quench the reaction. The reaction mixture was then filtered through Celite®. Then, EtOAc (200 mL) was added, and the organic layer washed with NaCl solution, dried with $MgSO_4$ and evaporated to yield an oil. The crude oil product was used without further purification.

$MH^+$ 278.0

Step F

To an ice cooled solution of trimethyl phosphonoacetate (6.4 mL, 13 mmol) in THF (200 mL) was added 60% NaH in mineral oil (1.1 g, 26 mmol) in portions. The ice bath was removed, and the reaction mixture was stirred at room temperature for 30 min. The solution was cooled to 0° C. again before a solution of the oil isolated in Step E (3.8 g, 13 mmol) in THF (100 mL) was added. The cooling bath was removed, and the reaction mixture was stirred at room temperature for another 20 min. Water (50 mL) was added, and most of the THF was evaporated. The product was extracted into EtOAc (200 mL), and the organic layer was washed with NaCl solution, dried with MgSO$_4$, and evaporated to yield a residue. Purification by column chromatography (1:1 heptane: EtOAc) yielded an oil which turned to a white solid upon standing.

MH$^+$ 334.1

Step H

A solution of the solid isolated in Step G (2.7 g, 8 mmol), 10% Pd/C (2.7 g), Boc anhydride (1.83 g, 8 mmol), and 1,4-cyclohexadiene (7.5 mL, 80 mmol) in EtOH (50 mL) was stirred at room temperature for 3 hours. The catalyst was removed by filtration, and the EtOH was evaporated to yield an oil MH$^+$ 302.2, MH$^+$ 202.2 (M-Boc)

Step I

A solution of the oil isolated in Step H (2.5 g, 8 mmol) in MeOH (20 mL) and 1N NaOH (8.0 mL) was stirred at room temperature overnight. Then the pH was adjusted to about pH 2 by the addition of dilute HCl solution. The MeOH was removed in vacuo, and the product was extracted into EtOAc (100 mL). The organic layer washed with NaCl solution, dried with MgSO$_4$, and evaporated to yield the title compound as an oil.

MH$^−$ 286.1

EXAMPLE 36

(S)-4-tert-Butoxycarbonylamino-5-methyl-hexanoic acid (Smrcina, M., Majer, P., Majerová, E., Guerassina, T. A., Eissenstat, M. A., *Tetrahedron*, 1997, 53 (38), 12867)

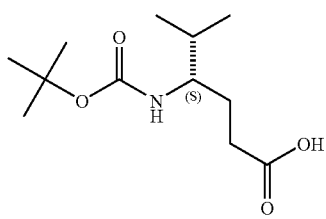

Step A: (R)-[1-(2,2-Dimethyl-4,6-dioxo-[1,3]dioxane-5-carbonyl)-2-methyl-propyl]-carbamic acid tert-butyl ester A 5 L four-necked flask (equipped with mechanical stirrer, nitrogen inlet, thermocouple, and glass stopper) was charged with Boc-D-Valine (143.6 g, 0.661 mol) and dichloromethane (2.8 L). The reaction was chilled to ~3° C. in an ice bath, and then 4-N,N-dimethylaminopyridine (124.6 g, 1.02 mol) and Meldrum's acid (104.8 g, 0.727 mol) were added to the reaction. To the reaction mixture was then added 1-[3-(dimethylaminopropyl)]-3-ethylcarbodiimide hydrochloride (EDCl, 139.4 g, 0.727 mol) over a five-minute period, and then the reaction mixture was allowed to warm to room temperature over 18 h (overnight). The reaction mixture washed with 5% (w/w) aqueous potassium bisulfate (4×600 mL), dried (MgSO$_4$), and the solution was used directly in the next step without concentration or purification. A small portion was concentrated and displayed the following analytical data.

MS: m/z=342 (M−1).

Step B: (S)-[1-(2,2-Dimethyl-4,6-dioxo-[1,3]dioxan-5-ylmethyl)-2-methyl-propyl]-carbamic acid tert-butyl ester In a 5 L one-neck flask four-necked flask (equipped with mechanical stirrer, nitrogen inlet, thermocouple, and glass stopper), was charged the solution of (R)-[1-(2,2-dimethyl-4,6-dioxo-[1,3]dioxane-5-carbonyl)-2-methyl-propyl]-carbamic acid, tert-butyl ester in dichloromethane prepared in Step A above, (~3.2 L). The reaction was chilled to ~3° C. in an ice bath, and acetic acid was added (437 g, 7.27 mol). The reaction mixture was then treated with sodium borohydride granules (62.5 g, 1.65 mol), which were added in portions over 1 h. During the addition the reaction temperature increased to ~9° C. and was stirred at that temperature 1.5 h and then was split into two portions. Each portion was poured into brine (1 L), stirred (magnetically) for 20 minutes, and partitioned. Each organic phase washed with brine (3×750 mL) and distilled water (2×500 mL). The combined organic phases were dried (MgSO$_4$) and concentrated to yield crude product. The crude product was dissolved in heptane-dichloromethane (~1:1) and loaded onto a Biotage 150M cartridge (2.5 kg silica gel) and then eluted with heptane (2 L), 15:85 (14 L), 3:7 (16 L), and 1:1 ethyl acetate-heptane (8 L) to give two main fractions. The first fraction yielded the desired material contaminated with minor impurities.

m.p.: 108-112° C.

The second fraction yielded additional product, which displayed the following analytical data.

m.p.: 115-117° C.

MS: m/z=328 (M−1)

Step C:
(S)-2-Isopropyl-5-oxo-pyrrolidine-1-carboxylic acid tert-butyl ester

In a 3 L, one-necked flask (equipped with a magnetic stir bar and a condenser with nitrogen inlet) was charged (S)-[1-(2,2-dimethyl-4,6-dioxo-[1,3]dioxan-5-ylmethyl)-2-methyl-propyl]-carbamic acid, tert-butyl ester prepared in Step B above (147 g, 0.446 mol) and toluene (1.4 L). The reaction mixture was heated to reflux for 4 h then cooled to room temperature and concentrated in vacuo to yield crude product as a residual oil. The crude product was dissolved in heptane (~200 mL) and loaded onto a Biotage 75 L (800 g silica gel) and eluted with heptanes (1 L), 1:9 (7 L), and 1:3 ethyl acetate-heptane (2 L) to yield the product as an oil.

Step D:
(S)-4-tert-Butoxycarbonylamino-5-methyl-hexanoic acid

A 2 L, one-necked flask (equipped with a magnetic stir bar and a nitrogen inlet) was charged with (S)-2-isopropyl-5-oxo-pyrrolidine-1-carboxylic acid, tert-butyl ester prepared in Step C above (77.4 g, 0.341 mol) and acetone (260 mL). To this solution was added 1M aqueous sodium hydroxide (408 mL, 0.408 mol), and the reaction mixture was stirred 30 minutes. The acetone was removed in vacuo and the resulting aqueous slurry was acidified, with vigorous stirring, by addition of solid sodium bisulfate (55 g, 0.45 mol) and diluted to 1 L with deionized water. The slurry was stirred for 2 h and the resulting white solid was collected by filtration, washed with deionized water, and dried in a vacuum oven to yield the product as a white solid.

m.p.: 107-109° C.
MS: m/z=267.9 (M+Na)

The opposite enantiomer was prepared in an identical fashion starting from Boc-L-Valine and gave the following analytical data.

m.p.: 91-95° C.
MS: m/z=268.0 (M+Na)

4-tert-Butoxycarbonylamino-4-cyclohexylbutyric acid may be similarly prepared according to the process outlined in Example 36 above, with appropriate selection and substitution of starting materials and reagents.

EXAMPLE 37

3-[2-(2-Amino-6-phenoxy-4H-pyrido[3,4-d]pyrimidin-3-yl)-2-(R)-cyclohexyl-ethyl]-1,3-diaza-spiro[4.5]decane-2,4-dione (Compound #229)

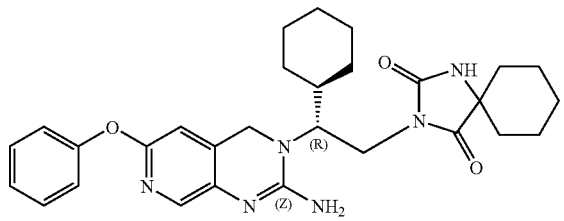

Step A:

To a solution of Boc-(R)-2-amino-2-cyclohexylethanol (5.42 g, 22.3 mmol), 1,3-diazaspiro[4.5]decane-2,4-dione (3.75 g, 22.3 mmol), triphenylphosphine (8.76 g, 33.4 mmol) in THF (50 mL) and dichloromethane (50 mL) at 0° C., di-tert-butyl acetylene dicarboxylate (7.69 g, 33.4 mmol) was added. The reaction mixture was stirred at room temperature overnight, and then the reaction mixture was concentrated to a residue. The residue was dissolved in ethyl acetate, and the resulting solution was extracted with saturated aqueous sodium bicarbonate three times, then once with brine and then dried over magnesium sulfate. The resulting solution was filtered and concentrated to yield a residue. The residue was purified on a silica gel column with 10:90 to 20:80 ethyl acetate:heptane) to yield a white solid which was used in the next step without further purification.

MH$^+$ =394.3

Step B:

To a solution of the solid isolated in Step A in dichloromethane (30 mL) was added trifluoroacetic acid (30 mL). The reaction mixture was stirred at room temperature for 1 hour and then concentrated to yield a residue. Water (50 mL) was added, followed by sodium bicarbonate, until there was no bubbling from the solution. The resulting solution was extracted with dichloromethane three times. The combined organic phases were dried over magnesium sulfate. The solution was filtered and concentrated to yield a white solid.

MH$^+$ =294.2

Step C:

To a stirring solution of the white solid isolated in Step B (1.00 g, 3.4 mmol) were added 5-nitro-2-phenoxy-pyridine-4-aldehyde (0.83 g, 3.4 mmole) in dichloromethane (50 mL) and 4 Å molecular sieves (3.0 g). After stirring at room temperature overnight, sodium triacetoxyborohydride (1.44 g, 6.80 mmol) was added slowly into the solution. The reaction mixture was stirred at room temperature 20 hours. The solution was filtered and concentrated to yield a yellow solid which was used in next step without further purification.

MH$^+$ =522.4

Step D:

To a solution of the yellow solid isolated in Step C in a solvent mixture of THF (20 mL) and ethanol (50 mL) was added palladium on carbon (10%, 1.03 g). The resulting solution was hydrogenated at 10 psi for 1 hour and then filtered. Cyanogen bromide (3 M, 2.1 mL, 6.3 mmole) in dichloromethane was added. The reaction mixture was stirred at room temperature overnight and then concentrated to yield a residue. The residue was purified by Gilson HPLC to yield the title compound as a white solid.

MH$^+$ =517.4

$^1$HNMR (300 MHz, DMSO): δ8.71 (s, 1H), 8.10 (s, 2H), 7.80 (s, 1H), 7.40 (m, 2H), 7.23 (m, 1H), 7.10 (m, 2H), 6.86 (s, 1H), 4.75 (d, J=16 Hz, 1H), 4.38 (d, J=16 Hz, 1H), 4.12 (m, 1H), 3.80 (m, 1H), 3.60 (m, 1H), 1.05-1.95 (m, 21H).

EXAMPLE 38

3-[2-(2-Amino-6-phenoxy-4H-pyrido[3,4-d]pyrimidin-3-yl)-2-(R)-cyclohexyl-ethyl]-1,3-diaza-spiro[4.5]decan-2-one (Compound #135)

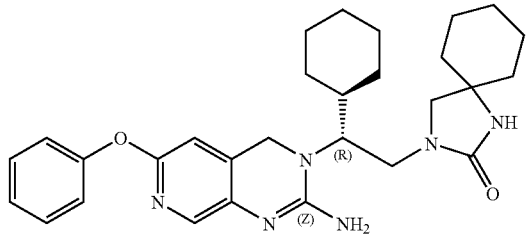

To a solution of the solid isolated in Example 1, Step D (0.60 g, 0.95 mmol) in THF (20 mL) was added borane (1.0 M, 5.7 mL, 5.7 mmol) in THF. The resulting mixture was refluxed for 5 hours and then cooled and concentrated to yield a residue. The residue was dissolved in methanol (5 mL). Hydrochloric acid (6 M, 3 mL) was added, and the resulting solution was stirred at room temperature for 10 min, then concentrated to a residue. The residue was purified by Gilson HPLC to yield a TFA salt which was dissolved in ethyl acetate. The solution was extracted with saturated aqueous sodium bicarbonate solution twice, once with brine and then dried over magnesium sulfate. The resulting solution was filtered and concentrated to yield a residue. The residue was treated with HCl in diethyl ether to yield the title compound as a white solid. as its corresponding HCl salt.

MH$^+$ =503.4.

$^1$H NMR (300 MHz, DMSO): δ7.86 (s, 1H), 6.91-7.86 (m, 6H), 4.84-4.89 (m, 2H), 4.51 (s, 1H), 3.40-3.80 (m, 5H), 1.00-2.00 (m, 21H).

EXAMPLE 39

4-(2-Amino-6-phenoxy-4H-pyrido[3,4-d]pyrimidin-3-yl)-4-(S)-cyclohexyl-N-(3,3-dimethyl-butyl)-N-(2-sulfamido-ethyl)-butyramide (Compound #147)

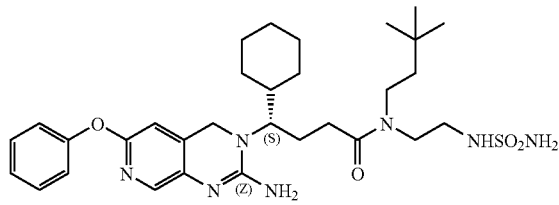

Step A:

To a solution of (2-amino-ethyl)-carbamic acid tert-butyl ester (0.99 g, 6.2 mmol) in methanol (15 mL) was added 3,3-dimethylbutyraldehyde (0.62 g, 6.2 mmol). After stirring at room temperature for one hour, the reaction mixture was cooled to 0° C. Sodium borohydride (0.23 g, 6.2 mmol) was added slowly to the solution, which was stirred at room temperature overnight, then concentrated to a residue. The residue was dissolved in ethyl acetate (100 mL). The resulting solution was extracted with saturated aqueous sodium bicarbonate solution twice and brine once and then dried over magnesium sulfate. The solution was filtered and concentrated to yield a colorless oil.

$MH^+$ =245.3.

Step B:

To a solution of 4-(2-amino-6-phenoxy-4H-pyrido[3,4-d]pyrimidin-3-yl)-4-(S)-cyclohexyl-butyric acid (0.467 g, 0.97 mmol) in dichloromethane (100 mL), oxalyl chloride (0.83 mL, 9.7 mmol) was added. The reaction mixture was stirred at room temperature for one hour and then concentrated. The resulting residue was dissolved in dichloromethane (50 mL). After the resulting solution was cooled to 0° C., the oil isolated in Step A (1.42 g, 5.83 mmol) was added. The resulting mixture was stirred at 0° C. for three hours and then concentrated to yield a residue. The residue was purified by Gilson HPLC to yield a white solid, as a TFA salt.

$MH^+$ =635.5.

Step C:

To a solution of the white solid TFA salt isolated in Step B (0.46 g, 0.61 mmol) in dichloromethane (12 mL), trifluoroacetic acid (12 mL) was added. The resulting mixture was stirred at room temperature for 2 hours and then concentrated to a residue. The residue was dissolved in chloroform (60 mL). The resulting solution washed with sodium hydroxide solution (1 M) three times and once with brine, then dried over magnesium sulfate. The resulting solution was filtered and concentrated to yield a white solid.

$MH^+$ =535.5

Step D:

The white solid isolated in Step C (0.226 g, 0.42 mmol) and sulfamide (0.085 g, 0.88 mmol) were heated under reflux in dioxane (4.0 mL) overnight. The reaction mixture was then concentrated, and the resulting residue was purified by Gilson HPLC. To the purified HPLC solution was added 2 M HCl solution (5 mL). Lyophilization yielded the title compound as a white solid as its corresponding HCl salt.

$MH^+$ =614.4

$^1$HNMR (300 MHz, DMSO): δ8.10 (s, 2H), 7.86 (s, 1H), 6.96-7.45 (m, 6H), 4.46-4.58 (m, 2H), 3.70-4.10 (br m, 3H), 2.90-3.40 (m, 7H), 1.00-2.40 (m, 17H), 0.79 (s, 9H).

EXAMPLE 40

3-[2-(4-tert-Butyl-[1,2,3]triazol-1-yl)-1-(R)-cyclohexyl-ethyl]-6-phenoxy-3,4-dihydro-pyrido[3,4-d]pyrimidin-2-ylamine (Compound #152)

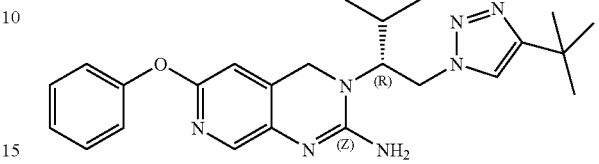

Step A:

To a solution of Boc-(R)-2-amino-2-cyclohexylethanol (5.31 g, 21.8 mmol) and triethylamine (6.0 mL, 43.6 mmol) in dichloromethane (60 mL) at 0° C., methanesulfonyl chloride (2.0 mL, 25.7 mmol) was added. After stirring at 0° C. for 1 hour, the reaction mixture washed with 1 M hydrochloric acid solution three times and brine once, then dried over sodium sulfate. The resulting solution was filtered and concentrated to yield a white solid.

$MH^+$ =322.2

Step B:

The white solid (6.80 g, 21.1 mmol) isolated in Step A and sodium azide (6.88 g, 105.8 mmol) were heated at 50° C. in DMF for 5 hours. After cooling to room temperature, water (50 mL) was added to the reaction mixture. The resulting solution was extracted with diethyl ether three times. The combined organic phases were washed with water twice and brine once, then dried over magnesium sulfate. The resulting solution was filtered and concentrated to yield a white solid.

$MH^+$ =269.2

Step C:

Following the procedure as described in Example 37, Step B, substituting the solid isolated in Step B above for the solid isolated in Example 37, Step A, resulted in the preparation of a colorless oil.

$MH^+$ =169.2

Step D:

Following the procedure as described in Example 37, Step C, substituting the solid isolated in Step C above for the solid isolated in Example 37, Step B, resulted in the preparation of a colorless oil.

$MH^+$ =397.2

Step E:

To a solution of the colorless oil isolated in STEP D above (0.235 g, 0.59 mmol) and 3,3-dimethyl-1-butyne (0.060 g, 0.73 mmol) in ethanol (8 mL) and water (1.5 mL), sodium ascorbate (0.024 g, 0.12 mmol) was added. Copper sulfate (0.005 g, 0.03 mmol) was then added. The resulting mixture was stirred in the dark at room temperature overnight. Ethyl acetate (30 mL) was then added. The resulting solution washed with saturated sodium bicarbonate twice, water once, and brine once, then dried over magnesium sulfate. The resulting solution was filtered and concentrated to yield a white solid.

$MH^+$ =479.0

Step F:
Following the procedure described in Example 37, Step D, substituting the white solid isolated in Step E above for Example 37, Step C, the title compound was prepared as a lightly colored solid.
MH+ =474.3
¹HNMR (300 MHz, DMSO): δ8.10 (s, 2H), 7.72 (s, 1H), 7.61 (s, 1H), 6.92-7.46 (m, 6H), 4.41-4.80 (m, 5H), 1.10-2.00 (m, 11H), 1.06 (s, 9H).

EXAMPLE 41

4-(S)-(2-Amino-6-phenoxy-4H-pyrido[3,4-d]pyrimidin-3-yl)-5-(R)-hydroxy-hexanoic acid (2,2-dimethyl-propyl)-amide (Compound #186)

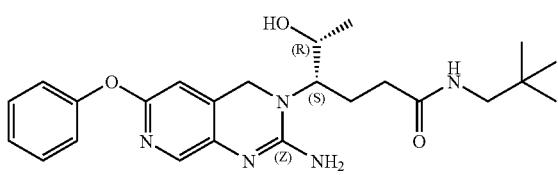

Step A:
To a solution of N-(tert-butyloxycarbonyl)-O-benzyl-D-threonine (15.55 g, 50.2 mmol), DMAP (11.07 g, 75.39 mmol), and Meldrum's acid (7.97 g, 55.3 mmol) in dichloromethane (250 mL) at 0° C., EDCl (10.60 g, 55.3 mmol) was added slowly. The resulting mixture was stirred at room temperature overnight. The solution was then extracted with hydrochloric acid solution (1 M) twice, water once, and brine once, then dried over magnesium sulfate. The resulting solution was filtered and used in next step without further purification or isolation.
MH+ =434.2

Step B:
To the solution prepared in Step A, cooled to 0° C., acetic acid (33.2 g) was added. Then, sodium borohydride (2.75 g, 125.6 mmol) was added slowly over 30 min. The resulting mixture was stirred at 0° C. for 4 h. The solution was then washed with water once and brine twice, then dried over magnesium sulfate. The resulting solution was filtered and concentrated to yield a residue. The residue was dissolved in toluene (250 mL). The resulting solution was heated under reflux for 24 hrs. The solution was then concentrated to a residue. The residue was purified over silica gel column eluted with ethyl acetate and heptane (20:80) to yield (49% from N-(tert-butyloxycarbonyl)-O-benzyl-D-threonine) as a colorless oil.
¹H NMR (300 MHz, CDCl₃): δ7.20-7.40 (m, 5H), 4.35-4.69 (m, 3H), 3.90 (m, 1H), 2.30 (m, 2H), 2.05 (m, 2H), 1.49 (s, 9H), 1.18 (d, 3H).

Step C:
To a solution of the colorless oil isolated in Step B (7.94 g, 24.9 mmol) in acetone (100 mL), sodium hydroxide solution (1 M, 37.3 mL, 37.3 mmol) was added. The resulting mixture was stirred at room temperature for 4 hours. The acetone was then removed by evaporation. The aqueous solution was extracted with diethyl ether twice, then acidified with hydrochloric acid (1 M). The resulting solution was extracted with chloroform twice. The combined chloroform extracts were washed with brine and then dried over magnesium sulfate. The resulting solution was filtered and concentrated to a residue. The residue was purified on a silica gel column eluted with methanol and dichloromethane from 0:100 to 3:97 to yield a colorless oil.

¹H NMR (300 MHz, CDCl₃): δ7.20-7.40 (m, 5H), 4.83 (m, 1H), 4.60 (d, 1H), 4.40 (d, 1H), 3.60 (m, 1H), 2.38 (2H), 1.85 (m, 2H), 1.44 (s, 9H), 1.20 (d, 3H).

Step D:
To a solution of the colorless oil isolated in Step C (1.29 g, 3.82 mmol), neopentylamine (0.67 g, 7.69 mmol), and diethylisopropylamine (2.00 mL, 11.4 mmol) in DMF (30 mL), HBTU (1.74 g, 4.59 mmol) was added. The resulting solution was stirred at room temperature overnight. Diethyl ether (150 mL) was added. The resulting solution washed with hydrochloric acid (1 M) three times, and brine once, then dried over magnesium sulfate. The resulting solution was filtered and concentrated to yield a colorless oil.
MH+ =407.0

Step E:
To a solution of the colorless oil isolated in Step D (1.35 g, 3.32 mmol) in dichloromethane (20 mL), trifluoroacetic acid (20 mL) was added. The resulting mixture was stirred at room temperature for 1 hour and then concentrated. Water (50 mL) was added followed by sodium bicarbonate until there was no bubbling from the solution. The solution was extracted with dichloromethane three times. The combined organic phases were dried over magnesium sulfate. The resulting solution was filtered and concentrated to yield a residue which was dissolved in ethanol (40 mL). Palladium on carbon (0.67 g, 10%) was then added. The resulting mixture was hydrogenated (50 psi) at 50° C. overnight. After cooling to room temperature, the resulting solution was filtered and concentrated to yield a colorless oil.
MH+ =217.2

Step F:
Following the procedure as described Example 37, Step C, substituting the colorless oil isolated in Step E above for the product of Example 37, Step B, crude product as a residue was obtained. The crude product was purified on a silica gel column eluted with methanol and dichloromethane from 0:100 to 10:90 to yield a white solid.
MH+ =444.9

Step G:
Following the procedure as described in Example 37, Step D, substituting the solid obtained in Step F above for the product of Example 37, Step C, resulted in the preparation of the title compound as lightly colored solid.
MH+ =440.2
¹HNMR (300 MHz, DMSO): δ8.10 (s, 1H), 7.85 (s, 1H), 7.05-7.45 (m, 5H), 6.91 (s, 1H), 4.53 (s, 2H), 3.56 (m, 1H), 3.10 (m, 1H), 2.80 (s, 2H), 2.18 (m, 2H), 1.80 (m, 2H), 1.12 (d, 3H), 0.80 (s, 9H).

EXAMPLE 42

4-(S)-(2-Amino-6-phenoxy-4H-pyrido[3,4-d]pyrimidin-3-yl)-5-(R)-benzyloxy-hexanoic acid (3,3-dimethyl-butyl)-pyridin-4-ylmethyl-amide (Compound #185)

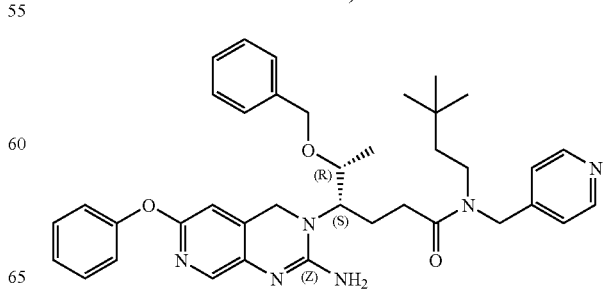

Step A:

Following the procedure as described in Example 39, Step A, substituting 4-pyridine carboxaldehyde for t-butylacetaldehyde and 3,3-dimethylbutylamine for (2-amino-ethyl)-carbamic acid tert-butyl ester, resulted in the preparation of a colorless oil.

MH$^+$ =193.2

Step B:

Following the procedure as described in Example 41, Step D, substituting the oil isolated in Step A above for neopentylamine, a colorless oil was prepared.

MH$^+$ =512.2

Step C:

Following the procedure as described in Example 37, Step B, substituting the product of Step B above for the product of Example 37, Step A, a colorless oil was prepared.

MH$^+$ =412.0

Step D:

Following the procedure as described in Example 37, Step C, substituting the product of Step C above, for the product of Example 37, Step B, a colorless oil was prepared.

MH$^+$ =639.9

Step E:

Following the procedure as described in Example 37, Step D, substituting the product of Step D above for the product of Example 37, Step C, the title compound was prepared as a light colored solid.

MH$^+$ =635.0

$^1$H NMR (300 MHz, DMSO): δ8.90 (m, 2H), 8.36 (s, 2H), 7.8 (m, 3H), 6.90-7.45 (m, 13H), 4.34-4.70 (m, 6H), 3.70 (m, 2H), 3.10-3.30 (m, 2H), 1.95 (m, 2H), 1.20-1.40 (m, 7H), 0.79 (s, 9H).

EXAMPLE 43

3-[—(S)-cyclohexyl-3-(4-cyclohexyl-[1,2,3]triazol-1-yl)-propyl]-6-phenoxy-3,4-dihydro-pyrido[3,4-d]pyrimidin-2-ylamine (Compound #198)

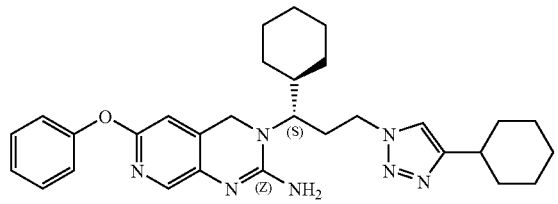

Step A:

To a solution of Boc-D-cyclohexylglycine (4.25 g, 16.5 mmol) and triethylamine (2.7 mL, 19.8 mmol) in THF (100 mL) at 0° C., ethyl chloroformate was added. The resulting mixture was stirred at this temperature for 1 h. Diazomethane in diethyl ether freshly prepared from N-methyl-N-nitrosourea (6.0 g, 58.2 mmol) was added slowly into the solution. The resulting mixture was stirred at 0° C. for two hours and then at room temperature overnight. Ethyl acetate (100 mL) was then added. The resulting solution washed with aqueous hydrochloric acid (1 N) once and saturated sodium bicarbonate solution once, then dried over magnesium sulfate. The resulting solution was filtered and concentrated to yield a white solid.

$^1$HNMR (300 MHz, CDCl$_3$): δ5.40 (br s, 1H), 5.12 (br m, 1H), 4.04 (br m, 1H), 0.98-1.76 (m, 11H), 1.43 (s, 9H).

Step B:

To a solution of the solid isolated in Step A (4.99 g, 17.6 mmol) in a solvent mixture of THF (100 mL) and water (10 mL) at 0° C., silver trifluoroacetate (0.78 g, 3.5 mmol) in triethylamine (7.3 mL, 52.7 mmol) was added. The resulting solution was stirred at room temperature in the dark for four hours. Diethyl ether (100 mL) was then added. The resulting solution was extracted with aqueous sodium hydroxide (1 N) three times. The combined aqueous phases were acidified with 2 N HCl solution. The resulting solution was extracted with ethyl acetate three times. The combined ethyl acetate solutions were dried over magnesium sulfate. The solution was then filtered and concentrated to yield a lightly colored solid.

$^1$H NMR (300 MHz, CDCl$_3$): δ5.63 (br s, 1H), 3.74 (br m, 1H), 2.57 (br m, 2H), 0.98-1.76 (m, 11H), 1.44 (s, 9H).

Step C:

To a solution of the solid isolated in Step B (4.54 g, 16.7 mmol) and N-methyl morpholine (2.5 mL, 18.3 mmol) in THF (80 mL) at 0° C., ethyl chloroformate (1.7 mL, 18.5 mmol) was added. The resulting solution was stirred at 0° C. for 1 h. Sodium borohydride (1.90 g, 50.2 mmol) was then added followed by slow addition of methanol (20 mL). The reaction mixture was stirred at 0° C. for another hour, and then ethyl acetate (100 mL) was added. The resulting solution washed with hydrochloric acid (1 M) three times and brine once, then dried over magnesium sulfate. The resulting solution was filtered and concentrated to yield a colorless oil which was used d in next step without further purification.

MH$^+$ =258.6

Step D:

To a stirring solution of the oil isolated in Step C and triethylamine (4.6 mL, 33.2 mmol) in dichloromethane (100 mL) at 0° C., methanesulfonyl chloride (1.56 mL, 20.1 mmol) was added. The resulting solution was stirred at 0° C. for 1 h. The solution was then washed with hydrochloric acid (1 M) three times and brine once, then dried over sodium sulfate. The resulting solution was filtered, and concentrated to yield a colorless oil. The colorless oil was dissolved in DMF (40 mL), and sodium azide (5.34 g, 79.5 mmol) was added. The resulting solution was stirred at 50° C. overnight. The reaction mixture was cooled, and diethyl ether (300 mL) was added. The resulting solution washed with water three times and then dried over magnesium sulfate. The solution was filtered and concentrated to yield a residue that was purified on a silica gel column eluted with ethyl acetate and heptane from 0:100 to 10:90 to yield a white solid.

$^1$H NMR (300 MHz, CDCl$_3$): δ3.50 (br m, 1H), 3.35 (m, 1H), 1.10-1.85 (m, 15H), 1.41 (s, 9H).

Step E:

Following the procedure as described in Example 37, Step B, substituting the white solid isolated in Step D above for the product of Example 37, Step A, a colorless oil was isolated, which was used in the next step without further purification.

MH$^+$ =183.5

Step F:

Following the procedure as described in Example 37, Step C, substituting the oil isolated in Step E above, for the product of Example 37, Step B, a colorless oil was isolated.

MH$^+$ =411.2

Step G:

Following the procedure as described in Example 40, Step E, substituting the product of Step F for above the product of Example 40, Step D and cyclohexylacetylene for 3,3-dimethyl-1-butyne, 0.53 g (98%), a lightly colored oil was prepared.

MH$^+$ =519.3

Step H:

Following the procedure as described in Example 37, Step D, substituting the product of Step G above for the product of Example 37, Step C, the title compound was prepared as a lightly colored solid.

MH$^+$ =514.3.

$^1$HNMR (300 MHz, DMSO): δ8.14 (s, 2H), 7.87 (m, 1H), 6.91-7.44 (m, 7H), 4.60 (s, 2H), 4.40 (m, 2H), 4.05 (m, 1H), 2.40 (m, 1H), 0.90-2.00 (m, 23H).

EXAMPLE 44

{3-[2-(4-tert-Butyl-[1,2,3]triazol-1-yl)-1-(R)-cyclohexyl-ethyl]-6-phenoxy-3,4-dihydro-pyrido[3,4-d]pyrimidin-2-yl}-hydrazine (Compound #245)

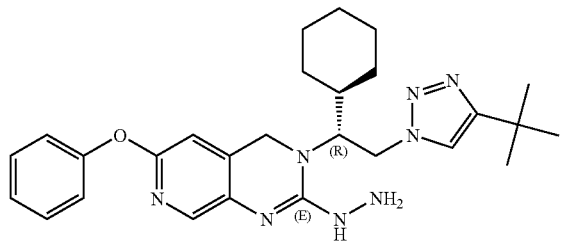

Step A:

Following the procedure as described in Example 4, Step E, substituting the product of Example 4, Step B above for the product of Example 40, Step E, a lightly colored oil was prepared.

MH$^+$ =351.3

Step B:

Following the procedure as described in Example 37, Step B, substituting the product of Step A above for the product of Example 37, Step A, a colorless oil was isolated and used in the next step without further purification.

Step C:

Following the procedure as described in Example 37, Step C, substituting the product of Step B above for the product of Example 37, Step B, a colorless oil was prepared.

MH$^+$ =479.3

Step D:

To a solution of the oil isolated in Step C (4.97 g, 10.4 mmol) in a solvent mixture of THF (40 mL) and ethanol (40 mL), palladium on carbon (10%, 2.0 g) was added. The resulting solution was hydrogenated for 1 hour at 10 psi and then filtered and concentrated to a residue. The residue was dissolved in acetonitrile (50 mL), and 1,1-thiocarbonyldiimidazole (2.41 g, 13.5 mmol) was added. The resulting solution was stirred at room temperature for 3 days. Ethyl acetate (100 mL) was then added. The resulting solution was extracted with water three times and brine once, then dried over magnesium sulfate. The resulting solution was filtered and concentrated to yield a yellow solid.

MH$^+$ =491.3

Step E:

To a solution of the solid isolated in Step D (4.58 g, 9.3 mmol) in ethanol (50 mL), sodium hydride (0.56 g, 60%, 14 mmol) was added. The resulting solution was stirred at room temperature for 30 min, and then iodomethane (0.87 mL, 14.0 mmol) was added. The resulting solution was stirred at room temperature for another two hours and then concentrated to a residue. The residue was dissolved in ethyl acetate (100 mL). The resulting solution was extracted with water three times and brine once, then dried over magnesium sulfate. The solution resulting was filtered and concentrated to yield a yellow solid.

MH$^+$ =505.3

Step F:

To a solution of the solid isolated in Step E (1.04 g, 2.1 mmol) and silver perchlorate (1.64 g, 7.9 mmol) in ethanol (10 mL), hydrazine (0.50 g, 15.6 mmol) was added. The resulting mixture was refluxed overnight and then was cooled, filtered, and concentrated to yield a residue. The residue was purified by Gilson HPLC to yield the title compound as its corresponding TFA salt.

The salt was dissolved in ethyl acetate. The resulting solution washed with saturated sodium bicarbonate twice and brine once, then dried over magnesium sulfate. The resulting solution was filtered and concentrated to a residue. The residue was treated with HCl in diethyl ether to yield the title compound as a lightly colored solid as its corresponding HCl salt.

MH$^+$ =489.3

$^1$H NMR (300 MHz, DMSO): δ8.30 (s, 1H), 8.09 (s, 1H), 7.60 (s, 1H), 6.96-7.45 (m, 6H), 4.75 (m, 2H), 4.35-4.60 (m, 3H), 1.10-1.90 (m, 11H), 1.06 (s, 9H).

EXAMPLE 45

N-{3-[2-(4-tert-Butyl-[1,2,3]triazol-1-yl)-1-(R)-cyclohexyl-ethyl]-6-phenoxy-3,4-dihydro-pyrido[3,4-d]pyrimidin-2-yl}-hydroxylamine (Compound #245)

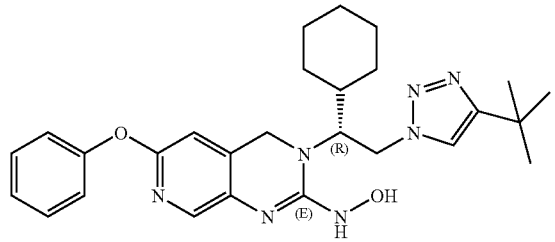

Step A:

To a solution of the product isolated in Example 44, Step E (0.396 g, 0.78 mmol), potassium carbonate (1.08 g, 7.8 mmol), and hydroxylamine hydrochloride (0.545 g, 7.8 mmol) in ethanol (10 mL), mCPBA (0.406 g, 3.9 mmol) were added. The resulting mixture was refluxed for 16 h, and then cooled, filtered, and concentrated to yield a residue. The residue was purified by Gilson HPLC to yield the title compound as its corresponding TFA salt.

The TFA salt was dissolved in ethyl acetate. The resulting solution washed with saturated sodium bicarbonate twice and once with brine, then dried over magnesium sulfate. The resulting solution was filtered and concentrated to yield a residue. The residue was treated with HCl in diethyl ether to yield the title compound as a yellow solid as its corresponding HCl salt.

MH$^+$ =490.3

$^1$H NMR (300 MHz, DMSO): δ8.03 (s, 1H), 7.69 (s, 1H), 7.03-7.50 (m, 6H), 6.95 (s, 1H), 4.70-4.90 (m, 3H), 4.37-4.52 (m, 2H), 1.10-1.90 (m, 11H), 1.10 (s, 9H).

EXAMPLE 46

N-{3-[1-(R)—Cyclohexyl-4-(2,2-dimethyl-propylamino)-butyl]-6-phenoxy-3,4-dihydro-pyrido[3,4-d]pyrimidin-2-yl}-hydroxylamine (Compound #250)

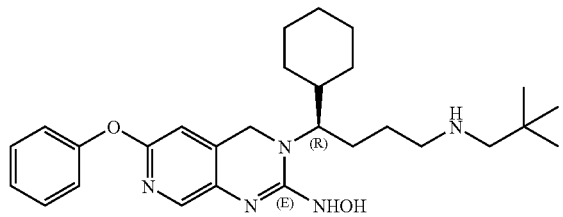

Step A:

Following the procedure as described in Example 41, Step D, substituting 4-tert-butoxycarbonylamino-4-(S)-cyclohexyl-butyric acid for the product of Example 41, Step C, a white solid was isolated which was used in the next step without further purification.

MH$^+$ =355.0

Step B:

Following the procedure as described in Example 37, Step B, substituting the product Step A above for the product of Example 37, Step A, a colorless oil was isolated which was used in next step without further purification.

MH$^+$ =255.0

Step C:

Following the procedure as described in Example 37, Step C, substituting the product of Step B above for the product of Example 37, Step B, and applying purification on a silica gel column eluted with ethyl acetate and heptane from 20:80 to 70:30 yielded a lightly colored oil.

MH$^+$ =483.0

Step D:

Following the procedure as described in Example 44, Step D, substituting the oil from Step C above for the product of Example 44, Step C, a lightly colored oil was prepared.

MH$^+$ =495.3.

Step E:

To a solution of the oil isolated in Step D (1.99 g, 4.0 mmol) in THF (80 mL), lithium aluminum hydride (2.0 M, 8.0 mL, 16.0 mmol) in THF was added. The resulting solution was refluxed for 4 h. Potassium sodium tartrate tetrahydrate (5 g) was then added when the solution was hot. After cooling to room temperature, the solution was filtered and concentrated to yield a residue. The residue was dissolved in ethyl acetate (200 mL). The resulting solution was washed with water once and brine once, then dried over magnesium sulfate. The resulting solution was filtered and concentrated to yield a lightly colored solid.

MH$^+$ =481.3.

Step F:

To a solution of the solid isolated in Step E (1.65 g, 3.4 mmol) in dichloromethane (20 mL), di-t-butydicarbonate (0.90 g, 4.1 mmol) was added. The resulting mixture was stirred at room temperature for 4 h and then concentrated to a residue. The residue was purified on a silica gel column eluted with ethyl acetate and heptane from 0:100 to 50:50 to yield a white solid.

MH$^+$ =581.3

Step G:

Following the procedure as described in Example 44, Step E, substituting the product of Step F above for the product of Example 44, Step D, a colorless oil was prepared.

MH$^+$ =595.4

Step H:

To a solution of the oil isolated in Step G (0.67 g, 1.1 mmol), potassium carbonate (1.08 g, 11.3 mmol), and hydroxylamine hydrochloride (0.78 g, 11.2 mmol) in ethanol (20 mL), mCPBA (0.35 g, 3.4 mmol) was added. The resulting solution was refluxed for 20 h and then was cooled, filtered, and concentrated to yield a residue. The residue was dissolved in dichloromethane (10 mL), and then TFA (10 mL) was added. The resulting solution was stirred at room temperature for 1 h and then concentrated to a residue. The residue was purified by Gilson HPLC to yield the title compound as its corresponding TFA salt.

The TFA salt was dissolved in ethyl acetate. The resulting solution was extracted with saturated sodium bicarbonate twice and brine once, then dried over magnesium sulfate. The resulting solution was filtered and concentrated to yield a residue. The residue was treated with HCl in diethyl ether to yield the title compound as a white solid as its corresponding HCl salt.

MH$^+$ =480.4

$^1$H NMR (300 MHz, DMSO): δ8.20 (s, 1H), 7.65 (s, 1H), 7.05-7.45 (m, 5H), 6.96 (s, 1H), 4.41-4.59 (m, 2H), 3.73-3.82 (m, 1H), 2.70-3.00 (m, 2H), 2.65 (s, 2H), 1.10-1.85 (m, 15H), 0.97 (s, 9H).

EXAMPLE 47

2-[4-(2-Amino-6-phenoxy-4H-pyrido[3,4-d]pyrimidin-3-yl)-4-cyclohexyl-butyrylamino]-3-tert-butoxy-propionic acid isopropyl ester (Compound #140)

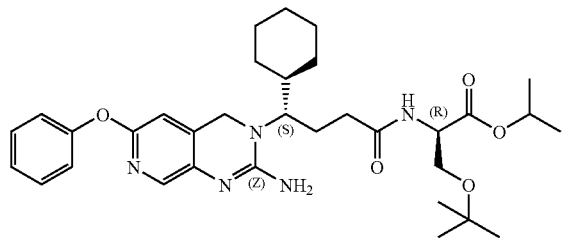

Step A:

To a solution of N-(benzyloxycarbonyl)-O-tert-butyl-D-serine (4.0 g, 13.5 mmol) in THF (20 mL) was added DCC (1.0 M in DCM, 15 mL), DMAP (0.17 g, 1.3 mmol) and isopropyl alcohol. The resulting solution was stirred at room temperature overnight. A solid formed which was removed by filtration. The filtrate was concentrated under vacuum to yield a residue that was purified by column chromatography (20% EtOAc:heptane) to yield an oil.

MH$^+$ 338.0

Step B:

To a solution of the oil isolated in Step A (4.5 g, 13.3 mmol) in ethanol (50 mL), 10% Pd—C (4 g) was added under $N_2$ followed by 1,4-cyclohexadiene (12 mL). The resulting solution was stirred at room temperature for 3 h. The catalyst was filtered out, and the solvent was concentrated under vacuum to yield an oil.

MH+ 204.0

Step C:

To a solution of 4-(2-amino-6-phenoxy-4H-pyrido[3,4-d]pyrimidin-3-yl)-4-(S)-cyclohexyl-butyric acid (0.21 g, 0.5 mmol) in DCM (15 mL) was added oxalyl chloride (2.0M in DCM, 2.6 mL, 5 mmol). The resulting mixture was stirred at room temperature one hour. An aliquot from the reaction mixture was quenched in methanol and analyzed by MS-HPLC which indicated that all of the acid was converted to the corresponding acid chloride. The solvent and excess oxalyl chloride was removed by vacuum. DCM (10 mL) was added followed by the oil isolated in Step B (0.5 g, 2.5 mmol). The resulting solution was stirred at room temperature for one hour. The solvent was removed by vacuum, and the resulting crude oil was purified by Gilson HPLC. The purified TFA salt was dissolved in DCM (50 mL) and basified with saturated aqueous $NaHCO_3$ solution (20 mL). The organic layer was collected, dried with $MgSO_4$ and evaporated under vacuum to yield an oil. The resulting oil was dissolved in DCM (10 mL) and cooled to 0° C. 1N HCl in diethyl ether solution (1 mL) was added. The resulting mixture was stirred under 0° C. for 10 min, and then the solvent was removed under vacuum at room temperature. The resulting solid was further dried under high vacuum for 24 hours to yield the title compound as its corresponding HCl salt.

MH+ 594.5

$^1$H NMR (300 MHz, $CD_3OD$): δ0.8-1.0 (m, 3H), 1.0-1.2 (m, 2H), 1.07 (s, 9H), 1.16 (t, 6H, J=6.05 Hz), 1.4 (m, 1H), 1.5-1.7 (m, 6H), 2.0-2.2 (m, 3H), 3.4 (dd, 1H), 3.6 (dd, 1H), 3.75 (m, 1H), 4.3 (m, 1H), 4.40 (m, 2H), 4.9 (m, 1H), 6.82 (s, 1H), 6.99 (d, 2H, J=8.57 Hz), 7.15 (t, 1H), 7.31 (t, 2H), 7.75 (s, 1H),

EXAMPLE 48

3-[3-Cyclohexyl-4-(2,2-dimethyl-propylamino)-butyl]-6-phenoxy-3,4-dihydro-pyrido[3,4-d]pyrimidin-2-ylamine (Compound #161)

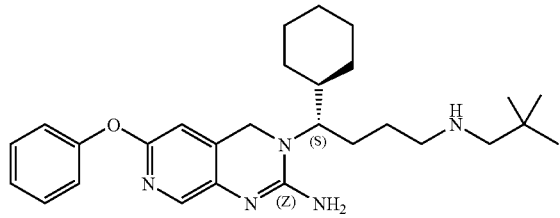

Step A:

To a solution of (4-(2-amino-6-phenoxy-4H-pyrido[3,4-d]pyrimidin-3-yl)-4-(S)-cyclohexyl-butyric acid (0.1 g, 0.2 mmol) in DCM (20 mL) was added oxalyl chloride (2.0M in DCM, 0.8 mL, 1.6 mmol). The resulting mixture was stirred at room temperature one hour. An aliquot from the reaction mixture was quenched in MeOH and analyzed by MS-HPLC which indicated that all of the acid was converted to the corresponding acid chloride. The solvent and excess oxalyl chloride was removed by vacuum. DCM (10 mL) was added followed by 2,2-dimethyl propylamine (0.08 mL, 0.6 mmol). The resulting solution was stirred at room temperature for one hour. The solvent was removed by vacuum, and the resulting crude oil was purified by Gilson HPLC to yield a TFA salt. The purified TFA salt was dissolved in DCM (50 mL1) and basified with saturated aqueous $NaHCO_3$ solution (20 mL). The organic layer was collected, dried with $MgSO_4$ and evaporated under vacuum to yield a residue.

MH+ 478.4

Step B:

To a solution of the product isolated in Step A (0.2 g, 0.4 mmol) in THF (1.0 mL) in a 8 mL microwave tube, LAH (1M in THF, 1.6 ml) was added very slowly at room temperature. The tube was irradiated in the microwave at 130° C. for 600 seconds. The reaction was quenched with MeOH. Purification by Gilson HPLC yielded the desired product as a solid. The above procedure was repeated nine times. The crude products, as their corresponding TFA salts, were combined and dissolved in EtOAc (100 mL). The resulting solution was basified by washing with saturated aqueous $NaHCO_3$ solution. The organic layer was separated, dried with $MgSO_4$, and evaporated under vacuum. A solution of HCl (1 N in diethyl ether, 2.0 eq) was added, and the solvent was removed under vacuum at room temperature. The solid was further dried in a lyophilizer for 12 h to yield the title compound as a solid, as its corresponding HCl salt.

MH+ 464.20

$^1$H NMR (300 MHz, $CD_3OD$): δ0.95 (s, 9H), 1.1-1.9 (m, 17H), 2.73 (s, 2H), 2.95 (m, 2H), 3.8 (m, 1H), 4.78 (m, 2H), 6.87 (s, 1H), 6.99 (d, 2H, J=8.0 Hz), 7.12 (t, 1H), 7.30 (t, 2H, J=7.65 Hz), 7.78 (s, 1H).

EXAMPLE 49

$N^2$-[4-(2-Amino-6-phenoxy-4H-pyrido[3,4-d]pyrimidin-3-yl)-4-cyclohexyl-butyl]-3-tert-butoxy-propane-1, 2-diamine (Compound #167)

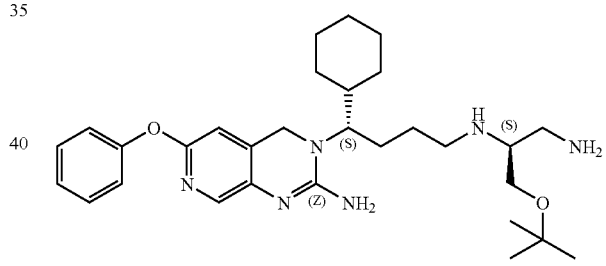

and N-(2-Amino-1-tert-butoxymethyl-ethyl)-4-(2-amino-6-phenoxy-4H-pyrido[3,4-d]pyrimidin-3-yl)-4-cyclohexyl-butyramide (Compound #111)

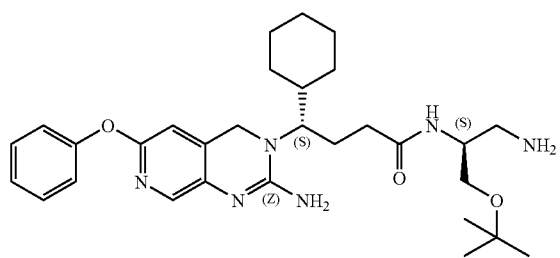

Step A:

To a solution of (4-(2-amino-6-phenoxy-4H-pyrido[3,4-d]pyrimidin-3-yl)-4-(S)-cyclohexyl-butyric acid (0.2 g, 0.45 mmol) in DCM (20 mL) was added oxalyl chloride (2.0M in DCM, 2.0 mL, 4 mmol). The resulting mixture was stirred at room temperature one hour. An aliquot from the reaction mixture was quenched in MeOH and analyzed by MS-HPLC which indicated that all of the acid was converted to the corresponding acid chloride. The solvent and excess oxalyl chloride was removed by vacuum. DCM (10 mL) was added followed by addition of 2-amino-3-tert-butoxy-propionamide (0.45 g, 2.8 mmol). The resulting solution was stirred at room temperature for one hour. The solvent was removed by vacuum, and the resulting crude oil was purified by Gilson HPLC to yield a TFA salt. The purified TFA salt was dissolved in DCM (50 mL) and basified with saturated aqueous NaHCO$_3$ solution (20 mL). The organic layer was collected, dried with MgSO$_4$ and evaporated by vacuum to yield a residue.

MH$^+$ 551.2

Step B:

To a solution of the material isolated in Step A (0.080 g, 0.14 mmol) in THF (20 ml) was added borane-THF complex (1.0 M in THF, 0.5 mL). The resulting mixture was stirred at room temperature overnight. The reaction was quenched with dilute HCl and the crude product was purified by Gilson HPLC to yield N2-[4-(2-Amino-6-phenoxy-4H-pyrido[3,4-d]pyrimidin-3-yl)-4-cyclohexyl-butyl]-3-tert-butoxy-propane-1,2-diamine

MH$^+$ 523.3

$^1$H NMR (300 MHz, CD$_3$OD): δ1.11 (s, 9H), 0.89 (m, 4H), 1.1-1.8 (m, 13H), 3.0 (m, 2H), 3.67 (m, 2H), 3.89 (m, 1H), 4.42 (s, 2H), 6.87 (s, 1H), 6.98 (d, 2H, J=7.59 Hz), 7.12 (t, 1H), 7.31 (t, 2H, J=7.58 Hz), 7.78 (s, 1H)

and N-(2-Amino-1-tert-butoxymethyl-ethyl)-4-(2-amino-6-phenoxy-4H-pyrido[3,4-d]pyrimidin-3-yl)-4-cyclohexyl-butyramide

MH$^+$ 537.3

$^1$H NMR (300 MHz, CD$_3$OD): δ1.11 (s, 9H), 0.9-1.9 (m, 17H), 2.9 (m, 2H), 3.67 (m, 2H), 3.2 (m, 2H), 3.5-3.7 (m, 3H), 4.4 (s, 2H), 6.81 (s, 1H), 6.97 (d, 2H, J=7.62 Hz), 7.12 (t, 1H), 7.31 (t, 2H, J=7.61 Hz), 7.89 (s, 1H).

EXAMPLE 50

4-(2-Amino-6-phenoxy-4H-pyrido[3,4-d]pyrimidin-3-yl)-5-methyl-hexanoic acid benzyl ester (Compound #231)

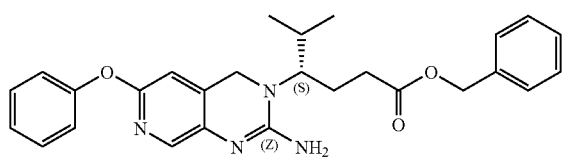

Step A:

To a solution of (4-(2-amino-6-phenoxy-4H-pyrido[3,4-d]pyrimidin-3-yl)-4-(S)-cyclohexyl-butyric acid (0.1 g, 0.25 mmol) in DCM (10 mL) was added oxalyl chloride (2.0M in DCM, 0.8 mL, 2 mmol). The resulting mixture was stirred at room temperature one hour. An aliquot from the reaction mixture was quenched in MeOH and analyzed by MS-HPLC which indicated that all of the acid was converted to the corresponding acid chloride. The solvent and excess oxalyl chloride was removed by vacuum. DCM (10 mL) was added followed by benzyl alcohol (0.089 mL, 0.8 mmol). The resulting solution was stirred at room temperature for one hour. The solvent was removed under vacuum to yield an oil which was purified by Gilson HPLC to yield the title compound as a solid, as its corresponding TFA salt.

MH$^+$ 459.3

$^1$H NMR (300 MHz, CD$_3$OD): δ0.85 (d, 3H, J=6.65 Hz), 0.97 (d, 3H, J=6.57 Hz), 1.83-2.15 (m, 3H), 2.27 (t, 2H, J=6.80 Hz), 3.6 (m, 1H), 4.4 (m, 2H), 4.9 (d, 2H, J=3.5 Hz), 6.78 (s, 1H), 6.98 (m, 2H), 7.12 (m, 1H), 7.19-7.32 (m, 7H), 7.71 (s, 1H).

EXAMPLE 51

4-(2-Amino-6-phenoxy-4H-pyrido[3,4-d]pyrimidin-3-yl)-N-cyclohexyl-N-methyl-butyramide (Compound #196)

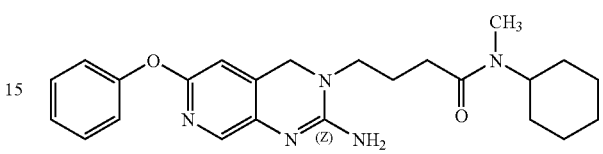

Step A:

To an ice cooled solution of 4-benzyloxycarbonylamino-butyric acid (2.8 g, 3 mmol), N-methyl, N-cyclohexyl amine (2.1 mL, 14 mmol), and HOBT (2.4 g, 18 mmol) in CH$_2$Cl$_2$ (50 mL), TEA (3.3 mL) was added, followed by addition of 1,3-dimethylaminopropyl-3-ethylcarbodiimide (EDC, 3.5 g, 18 mmol). The resulting mixture was allowed to warm to room temperature and stirred overnight. The resulting solution was acidified by adding citric acid solution and then extracted with EtOAc (2×100 mL). The organic layers were combined, dried with MgSO$_4$, and evaporated. The resulting crude product was purified by column chromatography (10-50% EtOAc:heptane) to yield a white solid.

MH$^+$ 333.0

Step B:

To a solution of the solid isolated in step A (3.6 g, 11 mmol) in MeOH (30 mL) was added 1.5 g of 10% palladium on activated carbon under N$_2$. The resulting mixture was subjected to hydrogenation at 40 psi for 3 hours. The catalyst was filtered out, and MeOH was evaporated under vacuum to yield an oil.

MH$^+$ 199.1

Step C:

A solution of the oil isolated in Step B (0.6 g, 3 mmol), 2-nitro-5-phenoxy-benzaldehyde (0.65 g, 2.6 mmol) in methylene chloride (50 mL) was stirred at room temperature overnight. NaBH(OAc)$_3$ (0.85 g, 4 mmol) was added, and the resulting mixture was stirred at room temperature for two hours and then poured into EtOAc (100 mL). The organic layer washed with aqueous NaCl solution, dried with MgSO$_4$ and evaporated to yield a residue. The residue was purified by column chromatography (50-100% EtOAc:heptane) to yield a residue.

MH$^+$ 427.09

Step D:

To a solution of the product of Step C (1.1 g, 2.5 mmol) in methanol (20 mL), was added 10% palladium on activated carbon (0.2 g) under N$_2$. The resulting mixture was subjected to hydrogenation at 5 psi for 1.5 hours. The catalyst was filtered out, and methanol was evaporated under vacuum to yield an oil.

MH$^+$ 397.13

Step E:

To a solution of the oil isolated in Step D (1.0 g, 2.5 mmol), BrCN (3M in CH$_2$Cl$_2$, 0.9 mL) in EtOH (30 mL) was added. The resulting mixture was stirred at room temperature overnight. The ethanol was then evaporated under vacuum. The resulting crude oil was purified by Gilson HPLC to yield the corresponding TFA salt. The purified TFA salt was dissolved in EtOAc (100 mL), and the solution was basified with saturated aqueous NaHCO$_3$ solution (20 mL). The organic layer was collected, dried with MgSO$_4$, and evaporated under vacuum. The resulting residue base was dissolved in EtOAc (5 mL), then HCl (1 N in diethyl ether solution, 1.5 mL) was added. The solvent was removed under vacuum at room temperature. The resulting solid was further dried in a lyophilizer for 12 hours to yield the title compound as a solid, as its corresponding HCl salt.

MH$^+$ 422.0

$^1$H NMR (300 MHz, CD$_3$OD): δ1.1-2.0 (m, 12H), 2.3-2.5 (m, 2H), 2.7 (d, 3H, J=22 Hz), 3.4 (m, 2H), 3.56 (m, 0.4×1H), 4.2 (m, 0.6×1H), 4.63 (s, 2H), 6.77 (s, 1H), 7.0 (d, 2H, J=7.69 Hz), 7.13 (t, 1H, J=7.43 Hz), 7.32 (t, 2H, J=8.05 Hz), 7.77 (s, 1H).

EXAMPLE 52

3-(2-Amino-6-phenoxy-4H-pyrido[3,4-d]pyrimidin-3-yl)-3(S)-cyclohexyl-N-(3,3-dimethyl-butyl)-propionamide hydrochloride salt (Compound #202)

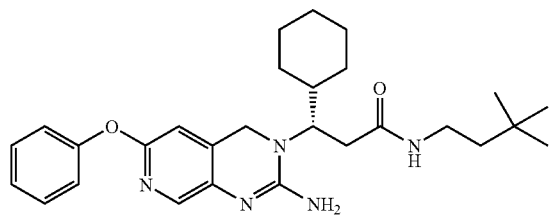

Step A: 3-Cyclohexyl-acrylic acid tert-butyl ester t-Butyl-P,P-dimethylphosphonate (8.8 mL, 44.6 mmol) was added to a suspension of NaH (60% in oil, 1.8 g, 45 mmol) in toluene (200 mL) at 0° C. The resulting mixture was stirred at 0° C. for one additional hour, then warmed to 40° C. Cyclohexylcarboxaldehyde (5.4 mL, 45 mmol) was added to the solution and the resulting mixture was stirred 2 hours at 40° C. The reaction was quenched with NH$_4$Cl(s) and extracted with EtOAc. The organic layers were combined, dried with MgSO$_4$, filtered and the solvent evaporated under reduced pressure to yield an oil. The oil was purified by column chromatography (20% EtOAc/heptane) to yield a residue.

Step B: 3-[Benzyl-(1-phenyl-ethyl)-amino]-3-cyclohexyl-propionic acid tert-butyl ester A solution of N-benzyl-(+)-methyl-benzylamine (8.5 mL, 40.4 mmol) in THF (100 mL) was cooled to 0° C., then n-butyl lithium (16 mL, [2.5 M], 40.4 mmol) was added and the resulting mixture stirred for 1 hour. The reaction mixture was cooled to –78° C., then a solution of 3-cyclohexyl-acrylic acid tert-butyl ester (7.71 g, 36.7 mmol) in THF (20 mL) was added dropwise for 30 min and the resulting mixture was stirred an additional 1 hour at –78° C. The reaction was quenched with NH$_4$CT (s), and extracted with EtOAc, the organic layer was dried with MgSO$_4$, filtered and evaporated under reduced pressure to yield a residue. The residue was purified by column chromatography (10%-70% EtOAc/heptane) to yield a residue.

Step C: 3-[Benzyl-(1-phenyl-ethyl)-amino]-3-cyclohexyl-propionic acid

To a solution of 3-[benzyl-(1-phenyl-ethyl)-amino]-3-cyclohexyl-propionic acid tert-butyl ester (13.7 g, 32.5 mmol) in dichloromethane (65 mL) at 0° C., trifluoroacetic acid (65 mL) was slowly added (over 30 min). The reaction mixture was then stirred for 2 hours at room temperature. The solvent was evaporated and the residue azeotroped (3×50 ml, toluene) to yield a residue.

Step D: 3-[Benzyl-(1-phenyl-ethyl)-amino]-3-cyclohexyl-N-(3,3-dimethyl-butyl)-propionamide A mixture of 3,3-dimethyl butylamine (0.6 mL, 4.2 mmol), 3-[benzyl-(1-phenyl-ethyl)-amino]-3-cyclohexyl-propionic acid (1.83 g, 3.8 mmol), HBTU (2.2 g, 5.7 mmol), DIPEA (1.5 mL, 8.6 mmol) and DMF (25 mL) was stirred at room temperature for 14 hours. To the reaction mixture was then added sodium bicarbonate(s) (100 mL) and the desired product was extracted with ethyl acetate (100 mL×2). The combined organic layers were washed with water, dried over MgSO$_4$ and concentrated to yield a solid. The solid was purified by column chromatography (10% EtOAc/heptane) to yield a residue.

Step E: 3-Amino-3-cyclohexyl-N-(3,3-dimethyl-butyl)-propionamide

In a Parr bottle 10% Pd/C (0.8 g) was cooled to –78° C., followed by addition of a solution of 3-[benzyl-(1-phenyl-ethyl)-amino]-3-cyclohexyl-N-(3,3-dimethyl-butyl)-propionamide (0.8 g, 1.78 mmol) in ethyl acetate (10 mL), ethanol (100 mL), and methanol (20 mL). The resulting mixture was subjected to hydrogen atmosphere and shaken for 3 h. The hydrogen was purged with nitrogen, the reaction mixture was filtered (glass fiber filter paper) and the solvent was evaporated under reduced pressure to yield a residue.

Step F: 3-Cyclohexyl-N-(3,3-dimethyl-butyl)-3-[(5-nitro-2-phenoxy-pyridin-4-ylmethyl)-amino]-propionamide A mixture 3-amino-3-cyclohexyl-N-(3,3-dimethyl-butyl)-propionamide (0.57 g, 2.24 mmol), 5-nitro-2-phenoxy-pyridine-4-carbaldehyde (0.57 g, 2.35 mmol), and dichloroethane (100 mL) was stirred for 12 hrs. Sodium triacetoxyborohydride (1.09 g, 5.15 mmol) was added and the resulting mixture was stirred 4 hours at room temperature. Sodium hydroxide solution ([0.1N], 100 mL) was added, the organic layer was separated, treated with MgSO$_4$, filtered and the solvent evaporated under reduced pressure to yield an oil. The oil was purified by column chromatography (10%-40% ethyl acetate/heptane) to yield a residue.

Step G: 3-[(5-Amino-2-phenoxy-pyridin-4-ylmethyl)-amino]-3-cyclohexyl-N-(3,3-dimethyl-butyl)-propionamide In a Parr bottle 10% Pd/C (0.42 g) was added and cooled to –78° C., then a solution of 3-cyclohexyl-N-(3,3-dimethyl-butyl)-3-[(5-nitro-2-phenoxy-pyridin-4-ylmethyl)-amino]-propionamide (0.42 g, 0.87 mmol) in ethyl acetate (5 mL) and ethanol (20 mL) was added. The resulting mixture was subjected to hydrogen atmosphere and shaken for 3.5 h. The hydrogen was purged with nitrogen, then the reaction mixture was filtered (glass fiber filter paper) and the solvent was evaporated under reduced pressure to yield the title compound as a residue.

Step H: 3-(2-Amino-6-phenoxy-4H-pyrido[3,4-d]pyrimidin-3-yl)-3(S)-cyclohexyl-N-(3,3-dimethyl-butyl)-propionamide hydrochloride salt To a solution of 3-[(5-amino-2-phenoxy-pyridin-4-ylmethyl)-amino]-3-cyclohexyl-N-(3,3-dimethyl-butyl)-propionamide (0.38 g, 0.84 mmol) and isopropyl alcohol (1 mL), cyanogen bromide (0.5 mL, [3M] in dichloromethane) was added and the resulting mixture was stirred at room temperature for 16 hours, then at 70° C. for 3 hours. The solvent was evaporated under reduced pressure to yield a brown solid. The brown solid was purified by column chromatography (amine column) and the desired solute was treated with 1N HCl to yield the title compound as an off-white solid, as its corresponding hydrochloride salt.

LCMS 478.2 [M+H$^+$]

$^1$H NMR: (400 MHz, CD$_3$OD) δ=8.09 (s, 1H), 7.5 (m, 2H), 7.35 (m, 1H), 7.25 (d, 2H), 7.17 (s, 1H), 4.7-4.55 (m, 2H), 4.2 (m, 1H), 3.05 (m, 2H), 2.8-2.6 (m, 2H), 1.85-1.65 (m, 6H), 1.32-1.05 (m, 7H), 0.88 (s, 9H)

EXAMPLE 53

3-[1(S)-Cyclohexyl-3-(3,3-dimethyl-butylamino)-propyl]-6-phenoxy-3,4-dihydro-pyrido[3,4-d]pyrimidin-2-ylamine hydrochloride salt (Compound #215)

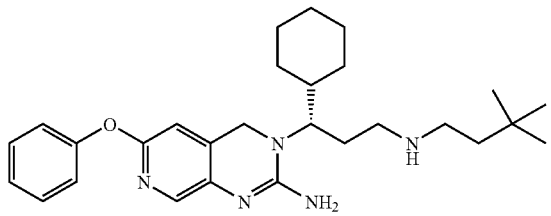

3-(2-Amino-6-phenoxy-4H-pyrido[3,4-d]pyrimidin-3-yl)-3-cyclohexyl-N-(3,3-dimethyl-butyl)-propionamide (0.75 g, 1.57 mmol) was placed with DBALH ([1M in THF], 12 mL) in a microwave tube and microwaved for 1200 sec (300 watt, 130° C.). To the reaction mixture was then added Rochelle's solution and diethyl ether. The organic layer was separate and dried with MgSO$_4$, then filtered and the solvent evaporated under reduced pressure to yield a solid. The solid was purified by reverse phase chromatography. 1N HCl (2 mL) was then added to the eluent as the solvent was evaporated to yield the title compound as an amber glass, as its corresponding hydrochloride salt.

LCMS 464.2 [M+H$^+$]

$^1$H NMR: (400 MHz, CD$_3$OD) δ=7.9 (s, 1H), 7.4 (m, 2H), 7.25 (m, 1H), 7.15 (d, 2H), 6.99 (s, 1H), 4.7-4.5 (m, 2H), 4.0 (m, 1H), 3.12-3.0 (m, 8H), 2.3-2.0 (m, 4H), 1.80-1.5 (m, 12H), 1.4-1.2 (m, 6H), 0.95 (s, 9H)

EXAMPLE 54

2-(2-Amino-6-phenoxy-4H-pyrido[3,4-d]pyrimidin-3-yl)-3,N-dimethyl-N-phenethyl-butyramide hydrochloride salt (R enantiomer) (Compound #221)

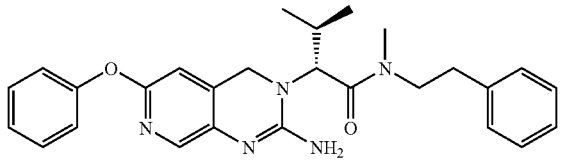

Step A: [2-Methyl-1-(methyl-phenethyl-carbamoyl)-propyl]-carbamic acid tert-butyl ester A mixture of N-methyl-phenethyl-amine (2.2 mL, 15.3 mmol), 2-tert-butoxycarbonylamino-3-methyl-butyric acid (3.33 g, 15.3 mmol), HBTU (8.7 g, 22.95 mmol), DIPEA (6.1 mL, 33.7 mmol) and DMF (75 mL) was stirred at room temperature for 14 hours. To the resulting mixture was added sodium bicarbonate (400 mL) and the desired product was extracted with ethyl acetate (400 mL×2). The combined organic layers were washed with water, dried over MgSO$_4$ and concentrated under reduced pressure to yield an oil. The oil was purified by column chromatography (50% EtOAc/heptane) to yield a residue.

Step B:
2-Amino-3,N-dimethyl-N-phenethyl-butyramide

[2-Methyl-1-(methyl-phenethyl-carbamoyl)-propyl]-carbamic acid tert-butyl ester (3.79 g, 11.3 mmol) was added slowly in hydrochloric acid in isopropyl alcohol ([5M], 25 mL). The resulting mixture was stirred for 5 hours at room temperature, then the solvent was evaporated under reduced pressure to yield an oil. The oil was dissolved in ethyl acetate and treated with sodium bicarbonate solution. The organic layer was dried with MgSO$_4$, filtered and the solvent evaporated under reduced pressure to yield an oil, which was purified by column chromatgraphy (10-50% EtOAc/heptane) to yield a residue.

Step C: 3,N-Dimethyl-2-[(5-nitro-2-phenoxy-pyridin-4-ylmethyl)-amino]-N-phenethyl-butyramide A mixture of 2-amino-3,N-dimethyl-N-phenethyl-butyramide (1.5 g, 6.48 mmol), 5-nitro-2-phenoxy-pyridine-4-carbaldehyde (1.5 g, 6.1 mmol), dichloromethane (75 mL), and THF (75 mL) was stirred for 5 hrs. Sodium triacetoxyborohydride (3.0 g, 14.25 mmol) was then added and the resulting mixture was stirred 16 hrs. Sodium hydroxide solution ([0.1 N], 100 mL) was added, the organic layer was separated, treated with MgSO$_4$, filtered and the solvent evaporated to yield an oil. The oil was purified by column chromatography (10%-40% ethyl acetate/heptane) to yield a residue.

Step D: 2-[(5-Amino-2-phenoxy-pyridin-4-ylmethyl)-amino]-3,N-dimethyl-N-phenethyl-butyramide A solution of 3,N-dimethyl-2-[(5-nitro-2-phenoxy-pyridin-4-ylmethyl)-amino]-N-phenethyl-butyramide (2.1 g, 1.38 mmol), 10% Pd on carbon (2 g), ethanol (75 mL) and ethyl acetate (75 mL) were shaken under a hydrogen atmosphere (50 psi). After 2 hours, the hydrogen was evacuated and the bottle was purged with nitrogen. The resulting mixture was filtered through glass fiber filter paper and the solvent evaporated under low pressure to yield a solid.

Step E: 2-(2-Amino-6-phenoxy-4H-pyrido[3,4-d]pyrimidin-3-yl)-3,N-dimethyl-N-phenethyl-butyramide hydrochloride salt A solution of 2-[(5-amino-2-phenoxy-pyridin-4-ylmethyl)-amino]-3,N-dimethyl-N-phenethyl-butyramide (1.69 g, 3.9 mmol) and isopropyl alcohol (10 mL) was added cyanogen bromide in dichloromethane (1.3 mL, [3M]) and the resulting mixture was stirred at room temperature for 16 hours. The solvent was evaporated to yield a brown solid. The brown solid was purified by reverse phase chromatography. The solvent was evaporated from the desired fractions, and the solute was treated with 1N HCl to yield the title compound as a solid, as its corresponding hydrochloride salt.

LCMS 458.3 [M+H$^+$]

$^1$H NMR: (400 MHz, CD$_3$OD) δ=8.09 (s, 1H), 7.5 (m, 2H), 7.35 (m, 1H), 7.2 (m, 7H), 6.9 (s, 1H), 4.9 (m, 1H), 4.5 (m, 2H), 3.5 (m, 1H), 3.6 (m, 1H), 3.1 (s, 3H), 2.95-2.8 (m, 4H), 2.5 (m, 1H), 1.05-0.8 (m, 6H)

EXAMPLE 55

4-(2-Amino-6-phenoxy-4H-pyrido[3,4-d]pyrimidin-3-yl)-4-(S),N-dicyclohexyl-N-(2-{2-[2-(2-hydroxy-ethoxy)-ethoxy]-ethoxy}-ethyl)-butyramide (Compound #176)

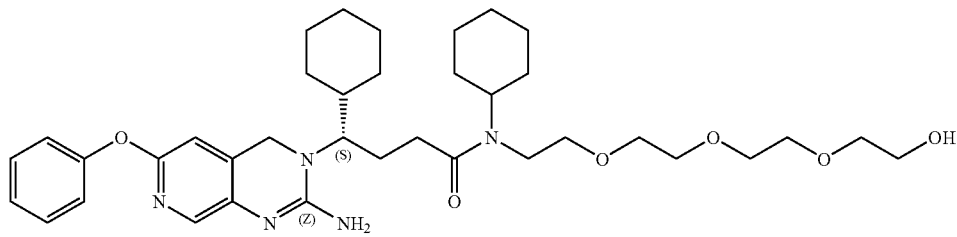

Step A:

A solution of 2,4-dinitro-benzenesulfonyl chloride (2.66 g, 10 mmol), cyclohexyl amine (1.14 mL, 10 mmol), and DIPEA (3.5 mL, 20 mmol) were taken into THF (25 mL) and stirred at room temperature overnight. The reaction was quenched with water, and the resulting mixture was extracted with ethyl acetate. The organic layer washed with saturated aqueous sodium bicarbonate and brine, and then was dried over sodium sulfate. After the solvent was removed in vacuo, the resulting crude product was purified by normal phase chromatography (heptanes:EtOAc) to yield a residue.

$^1$H NMR (300 MHz, CDCl$_3$): δ61.1-1.4 (m, 4H), 1.5-1.9 (m, 6H), 3.3-3.5 (m, 1H), 5.3 (d, 1H), 8.4 (d, 1H), 8.6 (d, 1H), 8.7 (s, 1H).

Step B:

The product from Step A (1.88 g, 5.7 mmol), 2{2-[2-(2-hydroxy-ethoxy)-ethoxy]-ethoxy}-ethanol (1.48 mL, 8.6 mmol), triphenylphosphine (2.25 g, 8.6 mmol), and DIAD (1.69 mL, 8.6 mmol) were taken up in THF (25 mL) at 0° C. under N$_2$. The reaction mixture was stirred at room temperature overnight. The reaction mixture was then taken up into EtOAc and washed with saturated aqueous sodium bicarbonate and brine. After removal of the solvent in vacuo, the resulting crude product was purified by normal phase chromatography (heptanes:EtOAc) to yield a residue.

$^1$H NMR (300 MHz, CDCl$_3$): δ1.0-1.2 (m, 1H), 1.3-1.9 (m, 9H), 2.15 (s, 1H), 3.5-3.8 (m, 17H), 8.35 (d, 1H), 8.48 (s, 1H) 8.54 (d, 1H).

Step C:

The product from Step B (0.70 g, 1.4 mmol), mercaptoacetic acid (0.125 mL, 1.82 mmol), and triethylamine (0.39 mL, 2.8 mmol) were taken up in DCM (10 mL) and stirred at room temperature for two hours. The reaction was quenched with 1N HCl, and the resulting mixture washed with DCM. The aqueous layer was made basic with 3N NaOH and then extracted with DCM. The organic layer washed with brine, dried over sodium sulfate and removed in vacuo to yield a residue.

MH$^+$ 276.0

Step D:

The material from Step C (0.50 g, 1.81 mmol), 4-tert-butoxycarbonylamino-4-(S)-cyclohexyl-butyric acid (0.52 g, 1.81 mmol), HOBt (293 mg, 2.2 mmol), EDCl (422 mg, 2.2 mmol), and DIEA (472 µL, 2.7 mmol) were taken up in DMF (10 mL) and stirred at room temperature overnight. The reaction was quenched with water and extracted with ethyl acetate. The organic layer washed with saturated aqueous sodium bicarbonate and brine, and then dried over sodium sulfate. The solvent was removed in vacuo and the resulting crude material was taken up into DCM (10 mL). To the resulting mixture was then added TFA (5 mL). The resulting mixture was stirred at room temperature for 1 hour. The reaction was quenched with saturated aqueous sodium bicarbonate, and the resulting mixture was extracted with ethyl acetate. The organic layer washed with saturated aqueous sodium bicarbonate and brine and then was dried over sodium sulfate. The solvent was removed in vacuo to yield a residue.

MH$^+$ 443.0

Step E:

To a solution of the material from Step D (0.40 g, 0.90 mmol) in DCM (15 mL) was added 5-nitro-2-phenoxy-pyridine-4-carbaldehyde (0.22 g, 0.90 mmol). After stirring overnight at room temperature, sodium triacetoxyborohydride (0.29 g, 1.35 mmol) was added, and the reaction mixture was stirred at room temperature for two hours. The reaction was quenched with water, and the mixture was extracted with ethyl acetate. The organic layer was washed with saturated aqueous sodium bicarbonate and brine, and then was dried over sodium sulfate. The solvent was removed in vacuo, and the resulting crude material was purified using normal phase column chromatography (heptane:EtOAc) to yield a residue.

MH$^+$ 671.4

Step F:

The material from Step E (0.155 g, 0.23 mmol) was taken into ethanol (5 mL) and 10% Pd/C (50 mg) was added. The reaction was hydrogenated at atmospheric pressure for three hours. The reaction mixture was filtered, and the collected catalyst washed with ethanol. The solvent was removed in vacuo, and ethanol (5 mL) was added to the residue. Cyanogen bromide in DCM (3M, 0.115 mL, 0.32 mmol) was added, and the reaction mixture was stirred at 80° C. for two hours. The reaction was quenched with water, and the resulting mixture was extracted with ethyl acetate. The organic layer washed with saturated aqueous sodium bicarbonate and brine, and then dried over sodium sulfate. The solvent was removed in vacuo and purified on the Gilson reversed phase HPLC to yield the title compound as a red solid.

MH$^+$ 666.0-$^1$H NMR (300 MHz, CDCl$_3$): δ0.8-1.9 (m, 21H), 2.0-2.4 (m, 4H), 2.6-2.8 (m, 2H), 3.3-3.8 (m, 15H), 4.0-4.4 (m, 3H), 4.5 (m, 1H), 6.7 (s, 1H), 7.15 (d, 2H), 7.2 (t, 1H), 7.3-7.5 (m, 2H), 8.1 (d, 1H), 8.5 (d, 2H).

EXAMPLE 56

3-[1-(2-cyclohexyl-ethoxymethyl)-(R)-(2-methyl-propyl)]-6-phenoxy-3,4-dihydro-pyrido[3,4-d]pyrimidin-2-ylamine (Compound #232)

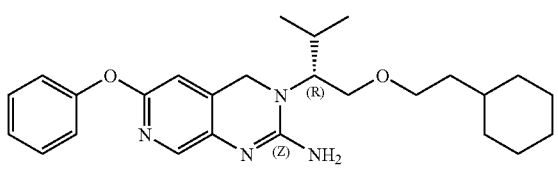

Step A:

N-(tert-butoxycarbonyl)-D-valinol (1.0 g, 4.9 mmol) and (2-bromo-ethyl)-cyclohexane (1.53 mL, 9.8 mmol) were taken into DMF (10 mL). Crushed potassium hydroxide (0.55 g, 9.8 mmol) was added, and the reaction mixture was stirred at room temperature overnight. The reaction was quenched with water, and the resulting mixture was extracted with ethyl acetate. The organic layer washed with saturated aqueous sodium bicarbonate and brine, and then dried over sodium sulfate. The solvent was removed in vacuo to crude material which was used in the next step without further purification.
MH+ 314.0

Step B:

The product from Step A (1.8 g, 5.8 mmol) was taken into DCM (10 mL), and then TFA (4 mL) was added. The reaction mixture was stirred at room temperature for 2 hours. Ethyl acetate was added, and the resulting mixture washed with saturated aqueous NaHCO$_3$ and brine. The organic layer was dried over sodium sulfate, and then the solvent was removed in vacuo to yield an oil which was used in the next step without further purification.
MH+ 214.0

Step C:

To a solution of the oil from Step B (1.2 g, 5.6 mmol) in DCM (15 mL) was added 5-nitro-2-phenoxy-pyridine-4-carbaldehyde (1.1 g, 4.5 mmol). After stirring overnight at room temperature, sodium triacetoxyborohydride (2.4 g, 11.2 mmol) was added, and the reaction mixture was stirred at room temperature for two hours. The reaction was quenched with water, and the resulting mixture was extracted with ethyl acetate. The organic washed with saturated aqueous sodium bicarbonate and brine, and then dried over sodium sulfate. The solvent was removed in vacuo, and the resulting crude material was purified using normal phase column chromatography (heptanes:EtOAc) to yield a residue.
MH+ 442.2

Step D:

The material from Step C (0.45 g, 1.1 mmol) was taken into ethanol (8 mL), and then 10% Pd/C (100 mg) was added. The reaction mixture was hydrogenated at atmospheric pressure for three hours. The reaction mixture was filtered, and the catalyst washed with ethanol. The solvent was removed in vacuo, and ethanol (5 mL) was added to the residue. Cyanogen bromide in DCM (3M, 0.50 mL, 1.65 mmol) was added, and the reaction mixture was stirred at 80° C. for two hours. The reaction was quenched with water and extracted with ethyl acetate. The organic layer washed with saturated aqueous sodium bicarbonate and brine, and then dried over sodium sulfate. The solvent was removed in vacuo, and the residue was purified on the Gilson reverse phase HPLC. The residue was then made basic with saturated aqueous NaHCO$_3$ solution before adding HCl to yield the title compound, as a white powder, as its corresponding HCl salt.
MH+ 437.0

$^1$H NMR (300 MHz, CDCl$_3$): δ0.7-0.9 (d, 6H), 1.0-1.7 (m, 13H), 2.1-2.3 (m, 1H), 3.3-3.5 (m, 2H), 3.6 (s, 2H), 3.9-4.0 (m, 1H), 4.3-4.4 (d, 2H), 6.5 (s, 1H), 6.9-7.0 (d, 2H), 7.1-7.15 (m, 1H), 7.25-7.3 (m, 2H), 7.9 (s, 1H), 8.2 (s, 2H), 11.2 (s, 1H).

EXAMPLE 57

3-[2-Methyl-1-(3-methyl-but-2-enyloxymethyl)-propyl]-6-phenoxy-3,4-dihydro-pyrido[3,4-d]pyrimidin-2-ylamine (Compound #233)

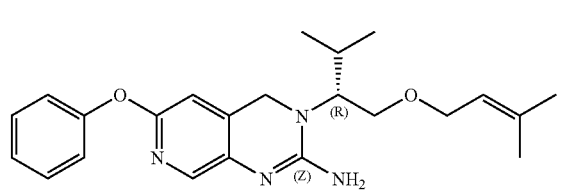

Step A:

N-(tert-butoxycarbonyl)-D-valinol (1.1 g, 5.4 mmol) and 1-bromo-3-methyl-but-2-ene (1.26 mL, 10.8 mmol) were taken into DMF (10 mL). Crushed potassium hydroxide (0.61 g, 10.8 mmol) was added, and the reaction mixture was stirred at room temperature overnight. The reaction was quenched with water, and the resulting mixture was extracted with ethyl acetate. The organic layer washed with saturated aqueous sodium bicarbonate and brine, and then dried over sodium sulfate. The solvent was removed in vacuo to yield a residue which was taken to the next step without further purification.
MNa+ 294.1

Step B:

The product from Step A (1.05 g, 3.9 mmol) was taken into formic acid (7 mL), and the reaction mixture was stirred at room temperature overnight. The reaction mixture was diluted with DCM and quenched with saturated aqueous sodium bicarbonate. The organic layer was washed with brine and then dried over sodium sulfate. The solvent was removed in vacuo to yield a residue which was taken to the next step without further purification.
MH+ 172.2

Step C:

To a solution of the oil from Step B (0.45 g, 2.6 mmol) in DCM (15 mL) was added 5-nitro-2-phenoxy-pyridine-4-carbaldehyde (0.64 g, 2.6 mmol). After stirring overnight at room temperature, sodium triacetoxyborohydride (1.1 g, 5.2 mmol) was added, and the reaction mixture was stirred at room temperature for two hours. The reaction was quenched with water, and the resulting mixture was extracted with ethyl acetate. The organic layer washed with saturated aqueous sodium bicarbonate and brine, and then dried over sodium sulfate. The solvent was removed in vacuo, and the resulting crude material was purified using normal phase column chromatography (heptane:EtOAc) to yield a residue.
MH+ 400.2

Step D:
The material from Step C (0.30 g, 0.75 mmol) was taken into methanol (8 mL) and then Zn (196 mg, 3.0 mmol) was added. Ammonium chloride (241 mg, 4.5 mmol) was added, and the reaction mixture was stirred at 75° C. for four hours. The reaction mixture was filtered and the collected precipitate washed with methanol. The methanol was removed in vacuo. The resulting crude material was taken into ethyl acetate, and the solution washed with saturated aqueous sodium bicarbonate and brine, and then dried over sodium sulfate. The solvent was removed in vacuo, and the resulting material was taken into ethanol (5 mL). Cyanogen bromide in DCM (3M, 0.40 mL, 1.13 mmol) was added and the reaction mixture was stirred at 80° C. for two hours. The solvent was removed in vacuo, and the resulting residue was purified on the Gilson reverse phase HPLC to yield the title compound as a powder, as its corresponding TFA salt.
MH+ 395.2
$^1$H NMR (300 MHz, CDCl$_3$): δ0.75 (d, 3H), 0.95 (d, 3H), 1.6 (s, 3H), 1.7 (s, 3H), 2.0-2.1 (m, 1H), 3.4-3.7 (m, 3H), 3.8-3.95 (m, 3H), 4.3 (s, 2H), 5.1-5.25 (t, 1H), 6.5 (s, 1H), 7.0 (d, 2H), 7.1-7.2 (t, 1H), 7.3-7.4 (m, 2H), 7.95 (s, 1H), 12.8 (s, 1H).

EXAMPLE 58

3-[1-(3-tert-Butyl-4,5-dihydro-isoxazol-5-yl-methoxymethyl)-2-methyl-propyl]-6-phenoxy-3,4-dihydro-pyrido[3,4-d]pyrimidin-2-ylamine

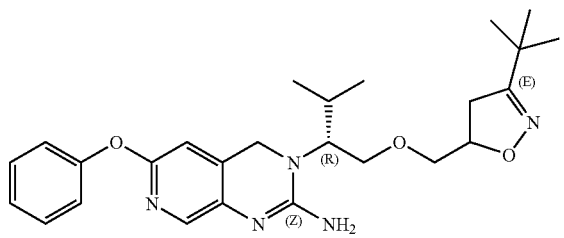

Step A:
2,2-Dimethyl-propionaldehyde (2.17 mL, 20 mmol) was taken into water (20 mL) and cooled to 0° C. To the resulting mixture were added NH$_2$OH.HCl (2.1 g, 30 mmol) and sodium carbonate (3.2 g, 30 mmol), and the reaction mixture was stirred at 0° C. for one hour. Ethyl acetate was added, and the organic solution washed with brine, and then dried over sodium sulfate. The solvent was removed in vacuo to yield a residue.
$^1$H NMR (300 MHz, CDCl$_3$): δ1-1 (s, 9H), 7.48 (s, 1H).

Step B:
The product from Step A (1.8 g, 17.8 mmol) was taken into DMF (10 mL), and NCS (2.6 g, 19.6 mmol) was added. An exotherm was observed. The reaction mixture was stirred at room temperature for two hours. The reaction was quenched with water, and the resulting mixture was extracted three times with diethyl ether. The combined organic layers were washed with brine, then dried over sodium sulfate, and concentrated in vacuo to yield a residue.
$^1$H NMR (300 MHz, CDCl$_3$): δ1.2 (s, 9H), 8.25 (s, 1H).

Step C:
N-(tert-butoxycarbonyl)-D-valinol (2.38 g, 11.7 mmol) and 3-bromo-propene (2.02 mL, 23.4 mmol) were taken into DMF (10 mL). Crushed potassium hydroxide (1.3 g, 23.4 mmol) was added, and the reaction mixture was stirred at room temperature overnight. The reaction was quenched with water, and the resulting mixture was extracted with ethyl acetate. The organic layer washed with saturated aqueous sodium bicarbonate and brine, and then dried over sodium sulfate. The solvent was removed in vacuo to yield a residue which was used in the next step without further purification.
MH+ 244.2

Step D:
The material from Step C (0.81 g, 3.34 mmol) and the material from Step B (0.54 g, 4.0 mmol) were taken up into EtOAc (40 mL). Triethylamine (0.56 mL, 4.0 mmol) in EtOAc (20 mL) was added over 45 minutes. The reaction was then stirred overnight at room temperature. Ethyl acetate was added, and the resulting solution washed with water and brine. The organic layer was dried over sodium sulfate and then concentrated in vacuo to yield a residue.
MNa+365.0

Step E:
The product from Step D (0.90 g, 2.6 mmol) was taken into DCM (5 mL), and then TFA (2 mL) was added. The reaction mixture was stirred at room temperature for 2 hours. To the mixture was then added ethyl acetate and the resulting solution washed with saturated aqueous NaHCO$_3$ and brine. The resulting solution was dried over sodium sulfate, and the solvent was removed in vacuo to an oil which used in the next step without further purification.
MH+ 243.0

Step F:
To a solution of the material from Step E (0.55 g, 2.3 mmol) in DCM (10 mL) was added 5-nitro-2-phenoxy-pyridine-4-carbaldehyde (0.55 g, 2.3 mmol). After stirring overnight at room temperature, sodium triacetoxyborohydride (0.72 g, 3.45 mmol) was added, and the reaction mixture was stirred at room temperature for two hours. The reaction was quenched with water and extracted with ethyl acetate. The organic washed with saturated aqueous sodium bicarbonate and brine, and then dried over sodium sulfate. The solvent was removed in vacuo to yield crude material which was purified using normal phase column chromatography (heptanes:EtOAc) to yield a residue.
MH+ 471.2

Step G:
The material from Step F (0.60 g, 1.28 mmol) was taken into methanol (8 mL), and then Zn (0.33 mg, 5.12 mmol) was added. Ammonium chloride (0.41 mg, 7.68 mmol) was then added and the reaction mixture was stirred at 75° C. for four hours. The reaction mixture was filtered, and the collected solids were washed with methanol. The methanol was removed in vacuo to yield a crude material which was taken into ethyl acetate and washed with saturated aqueous sodium bicarbonate and brine, then dried over sodium sulfate. The solvent was removed in vacuo, and ethanol (5 mL) was added. Cyanogen bromide in DCM (3M, 0.64 mL, 1.92 mmol) was added, and the reaction mixture was stirred at 80° C. for two hours. The reaction was quenched with water, and the resulting mixture was extracted with ethyl acetate. The organic layer washed with saturated aqueous sodium bicarbonate and brine, and then dried over sodium sulfate. The solvent was removed in vacuo, and the resulting residue was purified on the Gilson reverse phase HPLC. The resulting material was then made basic with saturated aqueous NaHCO$_3$ before add ing HCl to yield the title compound as a white powder, as its corresponding HCl salt.

MH+ 466.14

$^1$H NMR (300 MHz, DMSO): δ0.85 (d, 3H), 0.98 (d, 3H), 1.1 (s, 9H), 1.95-2.05 (m, 1H), 2.6-2.7 (m, 1H), 2.85-3.0 (m, 1H), 3.3-3.5 (m, 3H), 3.7-3.8 (m, 2H), 4.0-4.1 (m, 1H), 4.5 (s, 2H), 6.95 (d, 1H), 7.1 (d, 2H), 7.2 (t, 1H), 7.4 (t, 2H), 7.85 (s, 1H), 8.25 (s, 1H).

EXAMPLE 59

N-{3-[2-(4-tert-Butyl-[1,2,3]triazol-1-yl)-1-(S)-cyclohexyl-ethyl]-6-phenoxy-3,4-dihydro-pyrido[3,4-d]pyrimidin-2-yl}-2-methoxy-acetamide (Compound #247)

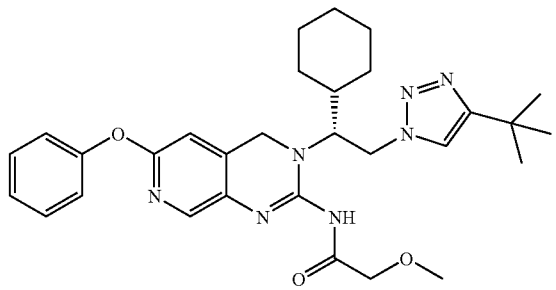

Step A:

Compound #152 (0.115 g, 0.24 mmol), prepared, for example, as described in Example 44 above, was taken up into DCM (5 mL) and then triethylamine (34 µL, 0.24 mmol) was added. Methoxy-acetyl chloride (22 µL, 0.24 mmol) was added, and the reaction mixture was stirred at room temperature overnight. The reaction mixture was purified using normal phase chromatography (heptanes:EtOAc) to yield the title compound as a white powder.

MH+ 546.5

$^1$H NMR (300 MHz, CDCl$_3$): δ1.2 (s, 9H), 1.3-2.0 (m, 11H), 3.4 (s, 3H), 3.7-4.1 (m, 4H), 4.2-4.7 (m, 3H), 6.55 (s, 1H), 6.9-7.2 (m, 3H), 7.25-7.4 (m, 3H), 7.6 (s, 1H), 12.3 (s, 1H).

Additional compounds of the present invention were similarly prepared according to the procedures and schemes described herein, selecting and substituting suitably substituted reagents and starting materials.

EXAMPLE 60

BACE FS1 Assay (% Inhibition and K$_i$)

The following reagents were used in this assay: sodium acetate, PEG8000 (Sigma), DMSO, HEPES, FS1 substrate [R(AedensE)EEVNLDAEFK-(DabcylK)R], β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 µg/mL. The β-secretase (BACE) working solution was prepared by diluting a 0.83 mg/mL BACE stock solution with enzyme assay buffer to a final concentration of 4 µg/mL.

Test compounds were dissolved in DMSO to 10 mM. Compounds were further diluted in vehicle to various concentrations in the range of 405 µM to 4.05 µM (13.5× final compound concentration in screening plate).

The screening procedure for this assay was as follows: 15 µL of BACE working solution was pipetted into each well of a 96-well plate. To each well was then pipetted 2 µL of test compound at the selected concentration. Test compound and BACE were then mixed with a pipettor and incubated for 20 min at room temperature. To each well was then added 10 µL of the FS1 substrate working solution. The plates were then incubated for 1 hour at room temperature. The fluorescence for each well was then measured on an LJL analyst (Ex 360 nm/Em 530 nm).

The procedure for the blank was as follows. 15 µL of assay buffer was pipetted into each well to be used as a blank control. To each well was then added 2 µL of vehicle and 10 mL of FS1-substrate working solution. The plates were then incubated for 1 hour at room temperature. The fluorescence was measured on an LJL analyst (Ex 360 nm/Em 530 nm).

The procedure for the positive control was as follows: 15 µL of BACE working solution was pipetted into each well to be used as a positive control. To each well was then pipetted 2 µL of vehicle. Vehicle and BACE were then mixed with a pipettor and incubated for 20 min at room temperature. To each well was then added 10 µL of the FS1 substrate working solution. The plates were then incubated for 1 hour at room temperature. The fluorescence (F1) was then measured on an LJL analyst (Ex 360 nm/Em 530 nm).

For test compounds, % inhibition was determined at each concentration as follows:

$$\% \text{ Inhibition} = \frac{[F1(\text{compound}) - F1(\text{negative control})]}{[F1(\text{positive control}) - F1(\text{negative control})]}$$

% Inhibition values of less than 30% were indistinguishable from control are listed as ≦30% in Table 18, below.

For test compounds, measured at multiple concentrations, the measured T$_0$ and T$_{60}$ values were used to calculate an IC$_{50}$ value using Graphpad Software (or PIR). K$_i$ inhibition was determined as follows: For each compound concentration and positive control, rate of cleavage of substrate (V$_i$, where i=compound concentration in µM) was determined as ∆ Fluorescence/∆ time (min). Cleavage rates (V$_i$) were plotted as a function of inhibitor concentration in µM [I]. The K$_i$ was then determined by fitting the following equation to the graph of [I] vs V$_i$ $$Y = aV_{max}/(50 + 24*(1 + X/K_i)),$$

where 50=substrate concentration (µM) and 24=K$_m$ of substrate (µM).

Representative compounds of the present invention were tested according to procedure described in Example 60 above with results as listed in Table 19, below.

TABLE 19

| | % Inhibition (FS) | | | |
|---|---|---|---|---|
| | | % Inhibition | | |
| ID No | @ 3 µM | @ 1 µM | @ 0.3 µM | $K_i$ (µM) |
| 1 | 110 | 102 | 75 | 0.166 |
| 2 | 124 | 102 | 70 | 0.091 |
| 3 | 139 | 132 | 130 | 0.018 |
| 4 | 132 | 127 | 113 | 0.035 |
| 5 | 138 | 131 | 125 | 0.025 |
| 6 | 138 | 139 | 122 | 0.021 |
| 7 | 134 | 136 | 136 | 0.010 |
| 8 | 138, 130 | 129, 115 | 106, 121 | 0.027, 0.016 |
| 10 | 114 | 80 | 55 | 0.207 |
| 11 | 120 | 78 | 47 | 0.124 |
| 12 | 95 | 63 | 30 | 0.503 |
| 13 | 87 | 63 | 30 | 0.517 |
| 14 | 108 | 66 | 11 | 0.241 |
| 15 | 110 | 94 | 68 | 0.129 |
| 16 | 80 | 51 | 12 | 1.09 |
| 17 | 86 | 61 | 4 | 0.222 |
| 18 | 128 | 121 | 119 | 0.017 |
| 19 | 104 | 103 | 88 | 0.055 |
| 20 | 104 | 102 | 97 | 0.013 |
| 21 | 97 | 83 | 51 | 0.074 |
| 22 | 93 | 61 | 0 | 0.173 |
| 23 | 103 | 86 | 32 | 0.151 |
| 24 | 103 | 71 | 40 | 0.234 |
| 25 | 55 | 17 | −22 | |
| 26 | 124 | 124 | 110 | 0.022 |
| 27 | 110 | 96 | 16 | 0.193 |
| 28 | 128 | 124 | 116 | 0.017 |
| 29 | 119 | 115 | 93 | 0.031 |
| 30 | 117 | 106 | 91 | 0.097 |
| 31 | 125 | 125 | 129 | 0.008 |
| 32 | 109 | 101 | 79 | 0.020 |
| 33 | 113 | 112 | 114 | 0.005 |
| 34 | 115 | 106 | 96 | 0.032 |
| 35 | 80 | 24 | 17 | |
| 36 | 114 | 112 | 114 | 0.021 |
| 37 | 114 | 111 | 112 | 0.012 |
| 38 | 115 | 110 | 112 | 0.009 |
| 39 | 115 | 110 | 112 | 0.013 |
| 40 | 67 | 38 | 22 | |
| 41 | 66 | 39 | 10 | |
| 42 | 105 | 82 | 75 | |
| 43 | 115 | 107 | 110 | 0.016 |
| 44 | 105 | 88 | 61 | 0.148 |
| 45 | 110 | 91 | 82 | 0.127 |
| 46 | 52 | 31 | 7 | |
| 47 | 115 | 109 | 109 | 0.072 |
| 48 | 116 | 107 | 73 | 0.036 |
| 49 | 102 | 60 | 10 | |
| 50 | 112 | 100 | 68 | 0.058 |
| 51 | 118 | 118 | 114 | 0.014 |
| 52 | 118 | 118 | 107 | 0.009 |

EXAMPLE 61

CEREP BACE Inhibition Assay

This assay was run by CEREP (Catalog Ref. 761-B, Referred to SOP No. 1C131; ERMOLIEFF, J., LOY, J. A., KOELSCH, G. and TANG, J., Proteolytic activation of recombinant pro-memapsin 2 (pro-β-secretase) studied with new fluorogenic substrates, Biochemistry, (2000) Vol. 39, p. 12450).

More specifically the assay, run at 50 µL in a 96 well plate, evaluated the effect of test compound on the activity of the human BACE-1 quantified by measuring the formation of Mca-S-E-V-N-L—NH$_2$ from Mca-S-E-V-N-L-D-A-E-F-R-K(Dnp)-R-R-NH$_2$, using a recombinant enzyme.

The test compound, reference compound or water (control) were added to a buffer containing 0.09 M sodium acetate (pH 4.5) and 0.25 µg BACE-1. Compound interference with the fluorimetric detection method due to autofluorescence was then checked by measurements at the wavelengths defined to evaluate the enzyme activity. Thereafter, the reaction was initiated by adding 7.5 µM of the substrate Mca-S-E-V-N-L-D-A-E-F-R-K(Dnp)-R-R—NH$_2$ and the mixture was incubated for 60 min at 37° C. For control basal measurement, the substrate was omitted from the reaction mixture. Immediately after the incubation, the fluorescence intensity emitted by the reaction product Mca-S-E-V-N-L-NH$_2$ was measured at λex=320 nm and λem=405 nm using a microplate reader (Ultra, Tecan). The standard inhibitory reference compound was OM99-2, which was tested in each experiment at several concentrations to obtain an inhibition curve from which its IC$_{50}$ value was calculated.

Representative compounds of the present invention were tested according to procedure described in Example 61 above with results, presented as a percent inhibition of the control activity, as listed in Table 20, below. If a compound was tested more than once, each result is listed in the Table below, separated by commas.

TABLE 20

| ID No | % Inhibition @ 0.3 µM | % Inhibition @ 1.0 µM | % Inhibition @ 10.0 µM | IC$_{50}$ (µM) |
|---|---|---|---|---|
| 7 | 91, 95, 100 | | | 0.14, 0.15 |
| 53 | 95 | | | 0.14 |
| 54 | 97 | | | 0.17 |
| 56 | 93 | | | 0.075 |
| 58 | 57 | | | 0.27 |
| 60 | 91 | | | 0.10 |
| 61 | 81 | | | 0.24 |
| 62 | 65 | | | 0.25 |
| 63 | 94 | | | 0.19 |
| 65 | 91 | | | 0.11 |
| 66 | 96 | | | 0.26 |
| 69 | 57 | | | 0.34 |
| 70 | 66 | | | 0.26 |
| 75 | | 90 @ 1 µM | | 0.24 |
| 77 | 78 | | | 0.33 |
| 78 | 91 | | | 0.19 |
| 79 | 88 | | | 0.15 |
| 80 | 97 | | | 0.17 |
| 83 | | 99 @ 1 µM | | 0.09 |
| 84 | 100 | | | 0.10 |
| 86 | 99 | | | 0.12 |
| 87 | 84 | | | 0.096 |
| 88 | 98 | | | 0.10 |
| 89 | 41 | | | |
| 90 | 99 | | | 0.14 |
| 91 | 70 | | | 0.34 |
| 92 | 100 | | | 0.16 |
| 93 | 94 | | | 0.11 |
| 94 | 97, 70 | | | 0.20 |
| 95 | 86 | | | 0.21 |
| 96 | 88 | | | 0.24 |
| 97 | 96 | | | 0.11 |
| 98 | 72 | | | 0.15 |
| 99 | 59 | | | |
| 100 | 93 | | | 0.11 |
| 101 | 43 | | | 0.32 |
| 102 | 55 | | | 0.46 |
| 103 | 96 | | | 0.082 |
| 104 | 100 | | | |
| 105 | 99 | | | |
| 106 | 6 | | | |
| 107 | 87 | | | |
| 108 | 94 | | | 0.14 |
| 109 | 95 | | | 0.12 |
| 110 | | 90 | | 0.062 |
| 111 | | 100 | | 0.11 |
| 112 | | 100 | | |

TABLE 20-continued

| ID No | % Inhibition @ 0.3 µM | % Inhibition @ 1.0 µM | % Inhibition @ 10.0 µM | IC$_{50}$ (µM) |
|---|---|---|---|---|
| 114 | | 100 | | |
| 115 | | 80 | | 0.23 |
| 116 | | 54 | | 0.63 |
| 117 | | 98 | | |
| 118 | | 97 | | |
| 119 | | 63 | | |
| 120 | | 23, 27 | | |
| 121 | | 50 | | |
| 122 | | 97 | | |
| 135 | | 52 | | 0.20 |
| 136 | | 98 | | 0.19 |
| 137 | | 101 | | 0.17 |
| 138 | | 8 | | 0.31 |
| 139 | | 94 | | 0.20 |
| 140 | | 98 | | 0.15 |
| 141 | | 98 | | 0.12 |
| 142 | | 90 | | 0.20 |
| 143 | | 65 | | 1.20 |
| 144 | | 81 | | 0.82 |
| 145 | | 99 | | 0.057 |
| 146 | | 100 | | 0.072 |
| 147 | | 100 | | 0.18 |
| 148 | | 32 | | |
| 149 | | 66 | | 0.74 |
| 150 | | 95 | | 0.17 |
| 151 | | 98 | | 0.15 |
| 152 | | 99 | | 0.088 |
| 153 | | 45 | | |
| 154 | | 102 | | 0.11 |
| 155 | | 100 | | 0.084 |
| 156 | | 102 | | 0.10 |
| 157 | | 101 | | |
| 158 | | 102 | | 0.13 |
| 159 | | 102 | | 0.11 |
| 160 | | 101 | | 0.066 |
| 161 | | 94 | | 0.20 |
| 162 | | 99 | | 0.09 |
| 163 | | 40 | | |
| 164 | | 82 | | 0.22 |
| 165 | | 34 | | |
| 166 | | 85 | | 0.20 |
| 167 | | 82 | | 0.52 |
| 168 | | 101 | | |
| 169 | | 17 | | |
| 170 | | 48 | | 0.83 |
| 171 | | 77 | | 0.27 |
| 172 | | 99 | | 0.17 |
| 173 | | 92 | | 0.13 |
| 174 | | 100 | | 0.086 |
| 175 | | 93 | | 0.097 |
| 176 | | 101 | | 0.14 |
| 177 | | 80 | | 0.32 |
| 178 | | 10 | | |
| 179 | | 100 | | 0.081 |
| 180 | | 99 | | 0.091 |
| 181 | | 96 | | 0.085 |
| 182 | | 100 | | 0.089 |
| 183 | | 70 | | 0.58 |
| 184 | | 45 | | 2.30 |
| 185 | | 85 | | 0.27 |
| 186 | | 81 | | 0.19 |
| 187 | | 99 | | 0.044 |
| 188 | | 89 | | |
| 189 | | 99 | | 0.14 |
| 190 | | 86 | | 0.19 |
| 191 | | 24 | | |
| 192 | | 101 | | 0.073 |
| 193 | | 60 | | 0.054 |
| 194 | | 94 | | |
| 195 | | 96 | | |
| 196 | | 34 | | |
| 197 | | 37 | | |
| 198 | | 95 | | 0.14 |
| 199 | | 100 | | 0.086 |
| 200 | | 50, 53 | | 0.78, 0.76 |
| 202 | | 88, 73 | | 0.22, 0.22 |
| 204 | | 100 | | 0.077 |
| 205 | | 81 | | 0.29 |
| 206 | | 91, 90 | | 0.18, 0.12 |
| 208 | | 98 | | 0.13 |
| 209 | | 93 | | 0.12 |
| 210 | | 98 | | 0.12 |
| 211 | | 88 | | 0.16 |
| 212 | | 99 | | 0.076 |
| 213 | | 88 | | 0.24 |
| 214 | | 57, 53 | | 0.93, 1.00 |
| 216 | | 96, 95 | | 0.087, 0.12 |
| 218 | | 1 | | |
| 219 | | 64 | | 0.64 |
| 220 | | 12 | | |
| 221 | | 52 | | 0.98 |
| 222 | | 24 | | |
| 223 | | 13 | | |
| 224 | | 100 | | 0.082 |
| 225 | | 96 | | 0.11 |
| 227 | | | 99 | |
| 228 | | | 99 | |
| 229 | | 78 | | 0.39 |
| 231 | | 97 | | 0.13 |
| 232 | | 99 | | 0.11 |
| 233 | | 52 | | 0.88 |
| 234 | | 94 | | 0.18 |
| 235 | | 59 | | 0.61 |
| 236 | | 92 | | 0.18 |
| 237 | | 87 | | 0.27 |
| 238 | | 72 | | 0.54 |
| 239 | | 34 | | |
| 240 | | 25 | | |
| 241 | | 20 | | |
| 245 | | | 29 | |
| 246 | | | 94 | |
| 247 | | 3 | | |
| 248 | | 20 | | |
| 249 | | 1 | | |
| 250 | | | | |

EXAMPLE 62

In Vivo Testing

Compounds of the present invention may be further tested for their effectiveness in for the treatment of disorders mediated by the BACE enzyme, for example Alzheimer's disease, by testing the compounds in vivo assay, for example, as disclosed in Sirinathsinghji, D. J. S. (Merck Sharp and Dohme Research Laboratories, Neuroscience Research Centre, Essex, UK.), *Transgenic mouse models of Alzheimer's disease* Biochemical Society Transactions (1998), 26(3), pp 504-508;

Van Leuven, F. (Experimental Genetics Group, Center for Human Genetics, Flemish Institute for Biotechnology (VIB), K. U. Leuven, Louvain, Belg.), *Single and multiple transgenic mice as models for Alzheimer's disease*, Progress in Neurobiology (Oxford) (2000), 61(3), pp 305-312;

Hsiao, K.; Chapman, P.; Nilsen, S.; Eckman, C.; Harigaya, Y.; Younkin, S.; Yang, F.; Cole, G. (Dep. Neurology, Univ. Minnesota, Minneapolis, Minn., USA), *Correlative memory deficits, Aβ elevation and amyloid plaques in transgenic mice*, Science (Washington, D.C.) (1996), 274(5284), pp 99-102 (Tg2576 mice);

Oddo, S.; Caccamo, A.; Shepherd, J. D.; Murphy, M. P.; Golde, T. E.; Kayed, R.; Metherate, R.; Mattson, M. P.; Akbari, Y.; LaFerla, F. M. (Department of Neurobiology and Behavior, University of California, Irvine, Irvine, Calif., USA), *Triple-transgenic model of Alzheimer's disease with plagues and tangles: Intracellular Aβ and synaptic dysfunction*, Neuron (2003), 39(3), pp 409-421 (APP Triple Transgenic Mice);

Ruberti, F.; Capsoni, S.; Comparini, A.; Di Daniel, E.; Franzot, J.; Gonfloni, S.; Rossi, G.; Berardi, N.; Cattaneo, A. (Neuroscience Program, International School for Advanced Studies (SISSA), Trieste, Italy), *Phenotypic knockout of nerve growth factor in adult transgenic mice reveals severe deficits in basal forebrain cholinergic neurons, cell death in the spleen, and skeletal muscle dystrophy*, Journal of Neuroscience (2000), 20(7), pp 2589-2601 (AD11 mice);

Games, D.; Adams, D.; Alessandrini, R.; Barbour, R.; Berthelette, P.; Blackwell, C.; Carr, T.; Clemens, J.; Donaldson, T.; et al. (Athena Neurosciences, Inc., South San Francisco, Calif., USA), *Alzheimer-type neuropathology in transgenic mice overexpressing V717F β-amyloid precursor protein*, Nature (London) (1995), 373(6514), pp 523-7 (V717F mice);

Neve, R. L.; Boyce, F. M.; McPhie, D. L.; Greenan, J.; Oster-Granite, M. L. (Dep. Genetics, Harvard Medical School and McLean Hospital, Belmont, Mass., USA), *Transgenic mice expressing APP-C100 in the brain*, Neurobiology of Aging (1996), 17(2), pp 191-203 (APP-C100 mice);

and/or as disclosed in U.S. Pat. No. 5,811,633; U.S. Pat. No. 5,877,399; U.S. Pat. No. 5,672,805; U.S. Pat. No. 5,720,936; U.S. Pat. No. 5,612,486; U.S. Pat. No. 5,580,003; U.S. Pat. No. 5,850,003; U.S. Pat. No. 5,387,742; U.S. Pat. No. 5,877,015; U.S. Pat. No. 5,811,633; U.S. Pat. No. 6,037,521; U.S. Pat. No. 6,184,435; U.S. Pat. No. 6,187,922; U.S. Pat. No. 6,211,428; and U.S. Pat. No. 6,340,783.

EXAMPLE 63

Human Testing

Compounds of the present invention may be further tested for their effectiveness in the treatment of disorders mediated by the BACE enzyme, for example Alzheimer's disease, by testing the compounds in human subjects, for example, as disclosed in Lins, H.; Wichart, I.; Bancher, C.; Wallesch, C.-W.; Jellinger, K. A.; Roesler, N. (Department of Neurology, Otto-von-Guericke-University, Magdeburg, Germany), *Immunoreactivities of amyloid β peptide(1-42) and total τ protein in lumbar cerebrospinal fluid of patients with normal pressure hydrocephalus*, Journal of Neural Transmission (2004), 111(3), pp 273-280;

Lewczuk, P.; Esselmann, H.; Otto, M.; Maler, J. M.; Henkel, A. W.; Henkel, M. K.; Eikenberg, O.; Antz, C.; Krause, W.-R.; Reulbach, U.; Kornhuber, J.; Wiltfang, J. (Department of Psychiatry and Psychotherapy, Molecular Neurobiology Lab, University of Erlangen-Nuremberg, Erlangen, Germany), *Neurochemical diagnosis of Alzheimer's dementia by CSF Aβ42, Aβ42/Aβ40 ratio and total tau*, Neurobiology of Aging (2004), 25(3), pp 273-281;

Olsson, A.; Hoglund, K.; Sjogren, M.; Andreasen, N.; Minthon, L.; Lannfelt, L.; Buerger, K.; Moller, H.-J.; Hampel, H.; Davidsson, P.; Blennow, K. (Sahlgrenska University Hospital, Experimental Neuroscience Section, Institute of Clinical Neuroscience, Goteborg University, Moelndal, Sweden), *Measurement of α- and β-secretase cleaved amyloid precursor protein in cerebrospinal fluid from Alzheimer patients*, Experimental Neurology (2003), 183(1), pp 74-80;

Wahlund, L.-O.; Blennow, K. (Karolinska Institute, Section of Geriatric Medicine, Department of Clinical Neuroscience and Family Medicine, Huddinge University Hospital, Stockholm, Sweden), *Cerebrospinal fluid biomarkers for disease stage and intensity in cognitively impaired patients*, Neuroscience Letters (2003), 339(2), pp 99-102;

El Mouedden, M.; Vandermeeren, M.; Meert, T.; Mercken, M. (Johnson & Johnson Pharmaceutical Research and Development, Division of Janssen Pharmaceutica N.V., Turnhoutseweg 30, Beerse, Belg.), *Development of a specific ELISA for the quantitative study of amino-terminally truncated beta-amyloid peptides*, Journal of Neuroscience Methods (2005), 145(1-2), pp 97-105;

Vanderstichele, H., Van Kerschaver, E., Hesse, C., Davidsson, P., Buyse, M.-A., Andreasen, N., Minthon, L., Wallin, A., Blennow, K., Vanmechelen, E., (Innogenetics NV, Ghent, Belg.), *Standardization of measurement of β-amyloid (1-42) in cerebrospinal fluid and plasma*, Amyloid (2000), 7(4), pp 245-258;

and/or Schoonenboom, N. S., Mulder, C., Van Kamp, G. J., Mehta, S. P., Scheltens, P., Blankenstein, M. A., Mehta, P. D., *Amyloid β38, 40, and 42 species in cerebrospinal fluid: More of the same?*, Annals of Neurology (2005), 58(1), pp 139-142.

EXAMPLE 64

As a specific embodiment of an oral composition, 100 mg of the Compound #103, prepared as in Example 28 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

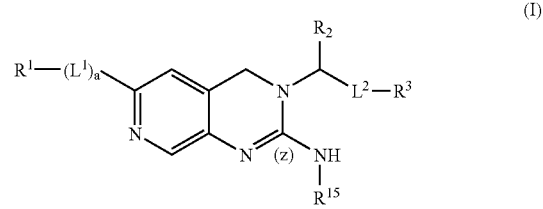

wherein a in an integer from 0 to 1;

$L^1$ is selected from the group consisting of —O—, —S—, —SO—, —SO$_2$— and —NR$^0$—; wherein R$^0$ is selected from the group consisting of hydrogen and C$_{1-4}$alkyl;

$R^1$ is selected from the group consisting of cycloalkyl, aryl, heteroaryl of heterocycloalkyl;

wherein the cycloalkyl, aryl, heteroaryl or heterocycloalkyl of $R^1$ is optionally substituted with one or more substituents independently selected from the group consisting of halogen, hydroxy, oxo, carboxy, C$_{1-4}$alkyl, hydroxy substituted C$_{1-4}$alkyl, halogen substituted C$_{1-4}$alkyl, cyano substituted C$_{1-4}$alkyl, C$_{1-4}$alkoxy, halogen substituted C$_{1-4}$alkoxy, nitro and cyano;

$R^2$ is selected from the group consisting of hydrogen, C$_{1-8}$alkyl, C$_{1-8}$alkoxy, hydroxy substituted C$_{1-6}$alkyl, amino substituted C$_{1-6}$alkyl, —C$_{1-4}$alkyl-O—C$_{1-4}$alkyl, —C$_{1-4}$alkyl-O-aralkyl, cycloalkyl, —C$_{1-4}$alkyl-cycloalkyl, aryl, aralkyl, biphenyl, heteroaryl, —$C_{1-4}$alkyl-heteroaryl, heterocycloalkyl and —$C_{1-4}$alkyl-heterocycloalkyl;

wherein the cycloalkyl, aryl, heteroaryl or heterocycloalkyl group, of $R^2$ whether alone or as part of a substituent group, is optionally substituted with one or more substituents independently selected from the group consisting of halogen, hydroxy, oxo, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one);

$L^2$ is selected from the group consisting of —$(CH_2)_b$—;

b is an integer from 0 to 4;

$R^3$ is selected from the group consisting of

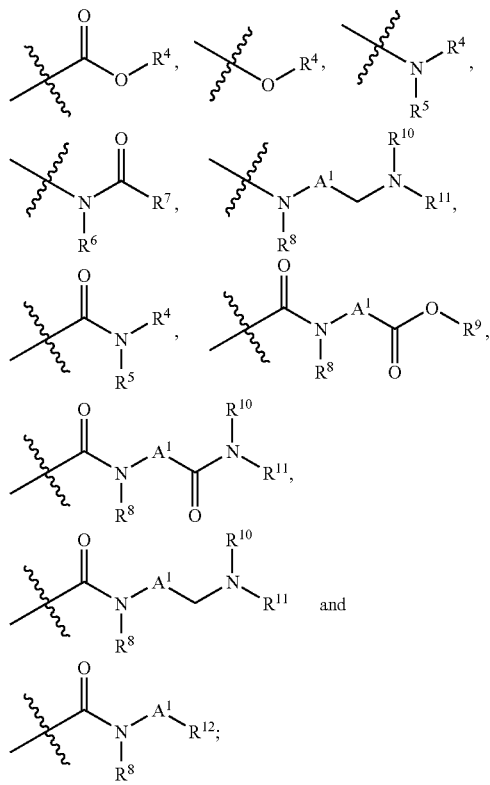

$R^4$ and $R^5$ are each independently selected from the group consisting of hydrogen, $C_{1-8}$alkyl, —$C_{2-8}$alkenyl, —$C_{2-4}$alkyl-O—$C_{1-4}$alkyl, —$C_{2-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$CH_2CH_2$—O—$CH_2CH_2$—O—$CH_2CH_2$—O—$CH_2CH_2$—OH;

wherein the alkyl, whether alone or as part of a substituent group, is optionally substituted with one or more substituents independently selected from the group consisting of hydroxy, carboxy, $C_{1-4}$alkoxy, —C(O)O—$C_{1-4}$alkyl, $NR^AR^B$, —$NR^L$—C(O)O—$C_{1-4}$alkyl and $NR^L$—$SO_2$—$NR^AR^B$;

wherein the cycloalkyl, aryl, heteroaryl or heterocycloalkyl, of $R^4$ and $R^5$ whether alone or as part of a substituent group, is optionally substituted with one or more substituents independently selected from the group consisting of oxo, fluoro, chloro, hydroxy, carboxy, —C(O)O—$C_{1-4}$alkyl, $C_{1-8}$alkyl, $C_{1-4}$alkoxy, trifluoromethyl, cyano, nitro, amino, $C_{1-4}$alkylamino, di($C_{1-4}$alkylamino), cycloalkyl, —$C_{1-4}$alkyl-cycloalkyl, 5-(1,2,3,4-tetrazolyl) and 1-(1,4-dihydro-tetrazol-5-one);

wherein $R^L$, $R^A$ and $R^B$, at each occurrence, are each independently selected from the group consisting of hydrogen, $C_{1-4}$alkyl, t-butoxycarbonyl and aralkyl;

provided that the chloro is not bound to a cycloalkyl or heterocycloalkyl;

alternatively $R^4$ and $R^5$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is saturated, partially unsaturated or aromatic;

wherein the heterocyclyl ring is optionally substituted with one or more substituents independently selected from the group consisting of halogen, hydroxy, carboxy, —C(O)O—$C_{1-4}$alkyl, $C_{1-6}$alkyl, —$C_{1-4}$alkyl-OH, —$C_{1-4}$alkyl-$CO_2H$, $C_{1-4}$alkoxy, trifluoromethyl, cyano, nitro, amino, $C_{1-4}$alkylamino, di($C_{1-4}$alkylamino), $C_{4-8}$cycloalkyl, phenyl, 5 to 6 membered heteroaryl 5-(1,2,3,4-tetrazolyl) and 1-(1,4-dihydro-tetrazol-5-one);

wherein the phenyl or 5 to 6 membered heteroaryl substituent is further optionally substituted with one or more substituents independently selected from the group consisting of halogen, $C_{1-4}$alkyl and halogenated $C_{1-4}$alkyl;

$R^6$ is selected from the group consisting of hydrogen and $C_{1-4}$alkyl;

$R^7$ is selected from the group consisting of hydrogen, $C_{1-10}$alkyl, $C_{1-8}$alkoxy, cycloalkyl, aryl, biphenyl, partially unsaturated carbocyclyl, heteroaryl, heterocycloalkyl, —$C_{1-4}$alkyl-cycloalkyl, $C_{1-4}$aralkyl, —$C_{1-4}$alkyl-partially unsaturated carbocyclyl, —$C_{1-4}$alkyl-heteroaryl, —$C_{1-4}$alkyl-heterocycloalkyl and spiro-heterocyclyl;

wherein the alkyl, cycloalkyl, aryl, heteroaryl, heterocycloalkyl or spiro-heterocyclyl, whether of $R^7$ alone or as part of a substituent group is optionally substituted with one or more substituents independently selected from the group consisting of halogen, hydroxy, oxo, carboxy, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^CR^D$)$_2$, —$C_{1-4}$alkyl-C(O)—N($R^CR^D$)$_2$, —$NR^C$—C(O)—$C_{1-4}$alkyl, —$SO_2$—N($R^CR^D$), —$C_{1-4}$alkyl-$SO_2$—N($R^CR^D$)$_2$, phenyl, 5-(1,2,3,4-tetrazolyl) and 1-(1,4-dihydro-tetrazol-5-one);

provided that the halogen is not bound to an alkyl, cycloalkyl or heterocycloalkyl; wherein $R^C$ and $R^D$ at each occurrence are independently selected from the group consisting of hydrogen and $C_{1-4}$alkyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

alternatively, $R^6$ and $R^7$ are taken together with the atoms to which they are bound to form a 5 to 10 membered, saturated heterocycloakyl; wherein the 5 to 10 membered, saturated heterocycloalkyl is optionally substituted with one to two oxo groups;

$R^8$ is selected from the group consisting of hydrogen, $C_{1-4}$alkyl and cycloalkyl;

$A^1$ is —$C_{1-6}$alkylene-; wherein the —$C_{1-6}$alkylene- is optionally substituted with one or more substituents independently selected from the group consisting of $C_{2-8}$alkyl, hydroxy substituted $C_{1-6}$alkyl, $C_{1-4}$alkoxy substituted $C_{1-4}$alkyl, aralkyloxy substituted $C_{1-4}$alkyl, $C_{3-6}$alkenyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, —$C_{1-4}$alkyl-$NR^E R^F$, —S—$C_{1-4}$alkyl, —$C_{1-3}$alkyl-O—$C_{1-3}$alkyl, —$C_{1-3}$alkyl-S—$C_{1-3}$alkyl, —$C_{1-3}$alkyl-O-aralkyl, —$C_{1-4}$alkyl-guanidino, —$C_{1-4}$alkyl-$CO_2R^E$ and —$C_{1-4}$alkyl-C(O)O—$C_{1-4}$alkyl;

wherein $R^E$ and $R^F$, at each occurrence, are independently selected from the group consisting of hydrogen and $C_{1-4}$alkyl;

wherein the cycloalkyl, aryl, heteroaryl or heterocycloalkyl, of $A^1$ whether alone or as part of a substituent group, is optionally substituted with one or more substituents independently selected from the group consisting of fluoro, chloro, hydroxy, oxo, carboxy, $C_{1-4}$alkyl, $C_{1-4}$alkoxy, hydroxy substituted $C_{1-4}$alkyl, halogen substituted $C_{1-4}$alkyl, halogen substituted $C_{1-4}$alkyl, —C(O)O—$C_{1-4}$alkyl, 5-(1,2,3,4-tetrazolyl) and 1-(1,4-dihydro-tetrazol-5-one);

provided that the chloro is not bound to a cyloalkyl or heterocycloalkyl;

$R^9$ is selected from the group consisting of hydrogen, $C_{1-12}$alkyl, hydroxy substituted $C_{1-6}$alkyl, amino substituted $C_{1-6}$alkyl, allyl, $C_{1-8}$alkoxy, cycloalkyl, —$C_{1-4}$alkyl-cycloalkyl, aryl, aralkyl, biphenyl, heteroaryl, —$C_{1-4}$alkyl-heteroaryl, heterocycloalkyl, —$C_{1-4}$alkyl-heterocycloalkyl, —$C_{1-4}$alkyl-O—$C_{1-8}$alkyl, —$C_{1-4}$alkyl-O-aryl, —$C_{1-4}$alkyl-O-aralkyl, $C_{1-4}$alkyl-O—C(O)—$C_{1-6}$alkyl, —$C_{1-4}$alkyl-O—C(O)—O—$C_{1-6}$alkyl, —$C_{1-4}$alkyl-O—C(O)—O—$C_{1-8}$cycloalkyl, —$C_{1-4}$alkyl-O—C(O)—C(NHCO($C_{1-6}$alkyl))=CH—$C_{1-6}$alkyl, 5-methyl-2-oxo-[1,3]dioxol-4-ylmethyl-, —$CH_2$—N($C_{1-4}$alkyl)-C(O)-aryl, —$CH_2$—C(O)—$NR^G R^H$, $CH_2$-O—$CH_2$-O—C(O)-2-(N-alkyl-1,4-dihydropyridyl),α-cyclodextrinyl, β-cyclodextrinyl and γ-cyclodextrinyl;

wherein $R^G$ and $R^H$ are each independently selected from the group consisting of hydrogen and $C_{1-4}$alkyl;

wherein the cycloalkyl, aryl, heteroaryl or heterocycloalkyl, of $R^9$ whether alone or as part of a substituent group, is optionally substituted with one or more substituents independently selected from the group consisting of fluoro, hydroxy, carboxy,—C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{10}$ and $R^{11}$ are each independently selected from the group consisting of hydrogen, $C_{1-8}$alkyl, hydroxy substituted $C_{1-4}$alkyl, —$C_{2-4}$alkyl-O—$C_{1-4}$alkyl, aralkyloxy substituted $C_{1-4}$alkyl, —$C_{1-4}$alkyl-$NR^J R^K$, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, $C_{2-6}$dialkanoic acid and —$C_{1-4}$alkyl-C(O)O—$R^J$;

wherein $R^J$ and $R^K$, at each occurrence, are each independently selected from the group consisting of hydrogen and $C_{1-4}$alkyl;

wherein the cycloalkyl, aryl, heteroaryl or heterocycloalkyl, of $R^{10}$ and $R^{11}$ whether alone or as part of a substituent group is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^{10}$ and $R^{11}$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$, alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{12}$ is selected from the group consisting of $C_{1-4}$, alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, aryl, heteroaryl or heterocycloalkyl group is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), aralkyl, 5-(1,2,3,4-tetrazolyl) and 1-(1,4-dihydro-tetrazol-5-one);

$R^{15}$ is selected from the group consisting of hydrogen, hydroxy, amino, —C(O)—$C_{1-6}$alkyl and —C(O)—$C_{1-4}$alkyl-O—$C_{1-4}$alkyl;

or a pharmaceutically acceptable salt thereof.

2. A compound as in claim 1 wherein a in an integer from 0 to 1;

$L^1$ is selected from the group consisting of —O—, —S—, —SO— and —$SO_2$—;

$R^1$ is selected from the group consisting of aryl and heteroaryl; wherein the aryl or heteroaryl is optionally substituted with one to two substituents independently selected from the group consisting of halogen, hydroxy, carboxy, $C_{1-4}$alkyl, hydroxy substituted $C_{1-4}$alkyl, halogen substituted $C_{1-4}$alkyl, $C_{1-4}$alkoxy and halogen substituted $C_{1-4}$alkoxy;

$R^2$ is selected from the group consisting of hydrogen, $C_{1-6}$alkyl, hydroxy substituted $C_{1-4}$alkyl, —$C_{1-4}$alkyl-O—$C_{1-4}$alkyl, —$C_{1-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl;

wherein the cycloalkyl, aryl, heteroaryl or heterocyloalkyl group, of $R^2$ whether alone or as part of a substituent group, is optionally substituted with one to two substituents independently selected from the group consisting of hydroxy, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one);

$L^2$ is selected from the group consisting of —$(CH_2)_b$—;

b is an integer from 0 to 3;

$R^3$ is selected from the group consisting of

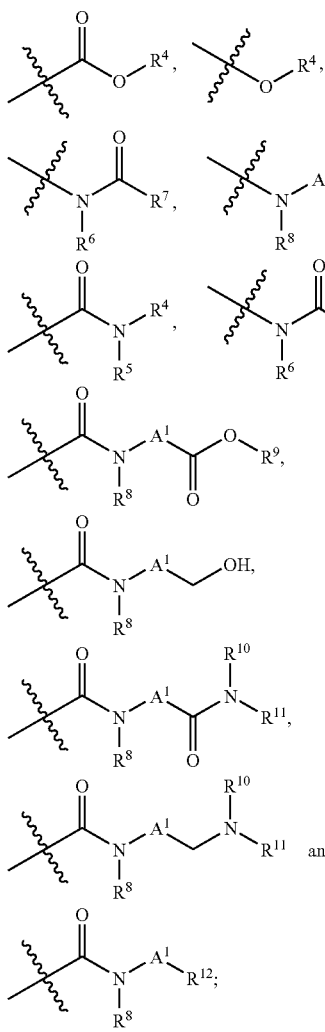

R⁴ and R⁵ are each independently selected from the group consisting of hydrogen, $C_{1-8}$alkyl, $C_{2-8}$alkenyl, —$C_{2-4}$alkyl-O—$C_{1-4}$alkyl, —$C_{2-4}$alkyl-O-aralkyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$CH_2CH_2$—O—$CH_2CH_2$—O—$CH_2CH_2$—O—$CH_2CH_2$—OH;

wherein the alkyl, whether alone or as part of a substituent group, is optionally substituted with one to two substituents independently selected from the group consisting of hydroxy, carboxy, $C_{1-4}$alkoxy, —C(O)O—$C_{1-4}$alkyl, $NR^AR^B$, —$NR^L$—C(O)O—$C_{1-4}$alkyl and —$NR^L$—$SO_2$—$NR^AR^B$;

wherein the cycloalkyl, aryl, heteroaryl or heterocycloalkyl, of R⁴ and R⁵ whether alone or as part of a substituent group, is optionally substituted with one or more substituents independently selected from the group consisting of fluoro, chloro, hydroxy, carboxy, oxo, —C(O)O—$C_{1-4}$alkyl, $C_{1-6}$alkyl, $C_{1-4}$alkoxy, cycloalkyl, —$C_{1-4}$alkyl-cycloalkyl, cyano, 5-(1,2,3,4-tetrazolyl) and 1-(1,4-dihydro-tetrazol-5-one);

wherein $R^L$, $R^A$ and $R^B$, at each occurrence, are each independently selected from the group consisting of hydrogen, $C_{1-2}$alkyl and t-butoxy-carbonyl-;

provided that the chloro is not bound to a cycloalkyl or heterocycloalkyl;

alternatively R⁴ and R⁵ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—$C_{1-4}$alkyl, $C_{1-6}$alkyl, —$C_{1-4}$alkyl-OH, $C_{1-4}$alkyl-$CO_2$H, $C_{1-4}$alkoxy, cyano, $C_{4-8}$cycloalkyl, phenyl, trifluoromethylphenyl, a 5 to 6 membered heteroaryl group and 1-(1,4-dihydro-tetrazol-5-one);

R⁶ is selected from the group consisting of hydrogen and $C_{1-2}$alkyl;

R⁷ is selected from the group consisting of hydrogen, $C_{1-6}$alkyl, $C_{1-6}$alkoxy, cycloalkyl, aryl, heteroaryl, heterocycloalkyl, —$C_{1-4}$alkyl-cycloalkyl, $C_{1-4}$aralkyl, —$C_{1-4}$alkyl-heteroaryl and —$C_{1-4}$alkyl-heterocycloalkyl-;

wherein the alkyl, cycloalkyl, aryl, heteroaryl or heterocycloalkyl, of R⁷ whether alone or as part of a substituent group is optionally substituted with one to two substituents independently selected from the group consisting of hydroxy, carboxy, $C_{1-6}$alkyl, hydroxy substituted $C_{1-4}$alkyl, carboxy substituted $C_{1-4}$alkyl, $C_{1-4}$alkoxy, cyano, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, phenyl, 5-(1,2,3,4-tetrazolyl) and 1-(1,4-dihydro-tetrazol-5-one);

wherein the phenyl is optionally substituted with one to two substituent independently selected from the group consisting of hydroxy, carboxy, —C(O)O—$C_{1-4}$alkyl, —C(O)—$C_{1-4}$alkyl, $C_{1-4}$alkyl and $C_{1-4}$alkoxy;

alternatively, R⁶ and R⁷ are taken together with the atoms to which they are bound to form a 5 to 10 membered, saturated nitrogen containing heterocyclyl; wherein the 5 to 10 membered, saturated nitrogen containing heterocyclyl is optionally substituted with one to two oxo groups;

R⁸ is selected from the group consisting of hydrogen, $C_{1-4}$alkyl and $C_{3-8}$cycloalkyl;

$A^1$ is —$C_{1-4}$alkylene- wherein the —$C_{1-4}$alkylene- is optionally substituted with one to two substituents independently selected from the group consisting of $C_{2-8}$alkyl, hydroxy substituted $C_{1-4}$alkyl, $C_{1-4}$alkoxy substituted $C_{1-4}$alkyl, aralkyloxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl;

wherein the cycloalkyl, aryl, heteroaryl or heterocycloalkyl, $A^1$ whether alone or as part of a substituent group, is optionally substituted with one to two substituents independently selected from the group consisting of hydroxy, carboxy, $C_{1-4}$alkyl, $C_{1-4}$alkoxy, hydroxy substituted $C_{1-4}$alkyl, —C(O)O—$C_{1-4}$alkyl, 5-(1,2,3,4-tetrazolyl) and 1-(1,4-dihydro-tetrazol-5-one);

R⁹ is selected from the group consisting of hydrogen, $C_{1-6}$alkyl, hydroxy substituted $C_{1-6}$alkyl, $C_{1-6}$alkoxy, $C_{3-8}$cycloalkyl, —$C_{1-4}$alkyl-$C_{3-8}$cycloalkyl, aryl, aralkyl, heteroaryl, —$C_{1-4}$alkyl-heteroaryl, heterocycloalkyl and —$C_{1-4}$alkyl-heterocycloalkyl;

wherein the $C_{3-8}$cycloalkyl, aryl, heteroaryl or heterocycloalkyl, of R⁹ whether alone or as part of a substituent group, is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one);

R$^{10}$ and R$^{11}$ are each independently selected from the group consisting of hydrogen, C$_{1-6}$alkyl, hydroxy substituted C$_{1-4}$alkyl, —C$_{2-4}$alkyl-O—C$_{1-4}$alkyl, benzyloxy substituted C$_{1-4}$alkyl, cycloalkyl, —C$_{1-4}$alkyl-cycloalkyl, aryl, aralkyl, heteroaryl, —C$_{1-4}$alkyl-heteroaryl, heterocycloalkyl, —C$_{1-4}$alkyl-heterocycloalkyl and C$_{2-6}$dialkanoic acid;

wherein the cycloalkyl, aryl, heteroaryl or heterocycloalkyl, of R$^{10}$ and R$^{11}$ whether alone or as part of a substituent group is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one);

alternatively R$^{10}$ and R$^{11}$ are taken together with the nitrogen atom to which they are bound to form a heterocyclyl ring containing at least one nitrogen atom and further optionally containing 0 to 1 heteroatoms independently selected from O, S or N; wherein the heterocyclyl ring is optionally substituted with one to two substituents independently selected from the group consisting of hydroxy, carboxy, —C(O)O—C$_{1-4}$alkyl, C$_{1-4}$alkyl, C$_{1-4}$alkoxy, cyano, 5-(1,2,3,4-tetrazolyl) and 1-(1,4-dihydro-tetrazol-5-one);

R$^{12}$ is selected from the group consisting of C$_{1-4}$alkyl, hydroxy substituted C$_{1-4}$alkyl, cycloalkyl, —C$_{1-4}$alkyl-cycloalkyl, aryl, aralkyl, heteroaryl, —C$_{1-4}$alkyl-heteroaryl, heterocycloalkyl and —C$_{1-4}$alkyl-heterocycloalkyl; wherein the cycloalkyl, aryl, heteroaryl or heterocycloalkyl group is optionally substituted with one to two substituents independently selected from the group consisting of hydroxy, carboxy, —C(O)O—C$_{1-4}$ alkyl, C$_{1-4}$alkyl, C$_{1-4}$alkoxy, cyano, benzyl, 5-(1,2,3,4-tetrazolyl) and 1-(1,4-dihydro-tetrazol-5-one);

R$^{15}$ is selected from the group consisting of hydrogen, hydroxy, amino, —C(O)—C$_{1-4}$alkyl, and —C(O)—C$_{1-4}$alkyl-O—C$_{1-4}$alkyl;

or a pharmaceutically acceptable salt thereof.

3. A compound as in claim 2 wherein a is an integer from 0 to 1;

L$^1$ is —O—;

R$^1$ is selected from the group consisting of aryl; wherein the aryl is optionally substituted with a substituent selected from the group consisting of halogen and C$_{1-4}$alkoxy;

R$^2$ is selected from the group consisting of hydrogen, C$_{1-4}$alkyl, hydroxy substituted C$_{1-4}$alkyl, —C$_{1-4}$alkyl-O—C$_{1-4}$alkyl, —C$_{1-4}$alkyl-O-aralkyl, cycloalkyl, heterocycloalkyl and —C$_{1-4}$alkyl-heterocycloalkyl;

L$^2$ is selected from the group consisting of —(CH$_2$)$_b$—;

b is an integer selected from 0 to 3;

R$^3$ is selected from the group consisting of

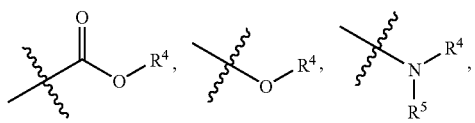

-continued

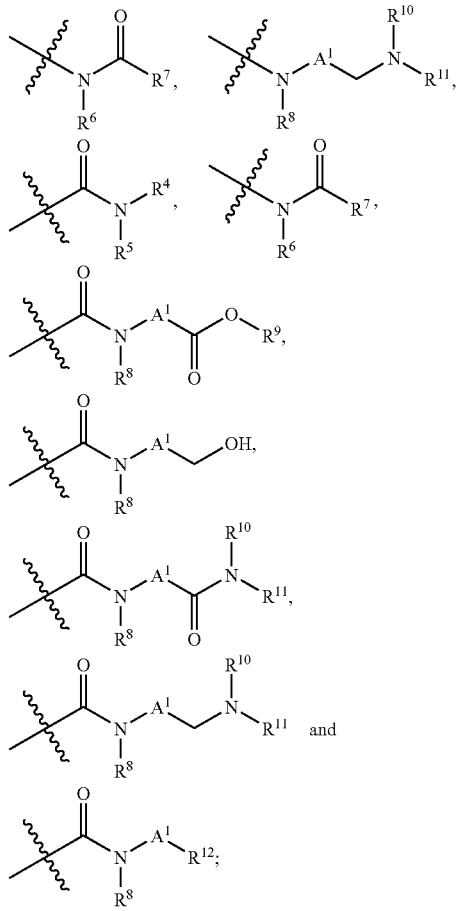

R$^4$ is selected from the group consisting of hydrogen, C$_{1-6}$alkyl, C$_{2-8}$alkenyl, hydroxy substituted C$_{1-4}$alkyl, —C$_{2-4}$alkyl-O—C$_{1-4}$alkyl, —C$_{2-4}$alkyl-O-aralkyl, cycloalkyl, —C$_{1-4}$alkyl-cycloalkyl, aralkyl, —C$_{1-4}$ alkyl-heteroaryl and —C$_{1-4}$alkyl-heterocycloalkyl;

wherein the —C$_{1-4}$alkyl-heteroaryl or —C$_{1-4}$alkyl-heterocycloalkyl is optionally substituted on the heteroaryl or heterocycloalkyl portion with a substituent selected from the group consisting of C$_{1-6}$alkyl, C$_{3-8}$cycloalkyl and —C$_{1-4}$alkyl-C$_{3-8}$cycloalkyl;

R$^5$ is selected from the group consisting of C$_{1-6}$alkyl, —C$_{2-4}$alkyl-O—C$_{1-4}$alkyl, cycloalkyl, —C$_{1-4}$alkyl-cycloalkyl, aralkyl, heteroaryl, —C$_{1-4}$alkyl-heteroaryl, —C$_{1-4}$alkyl-heterocycloalkyl and —CH$_2$CH$_2$—O—CH$_2$CH$_2$—O—CH$_2$CH$_2$—O—CH$_2$CH$_2$—OH;

wherein the alkyl, whether alone or as part of a substituent group, is optionally substituted with one to two substituents independently selected from the group consisting of hydroxy, carboxy, C$_{1-4}$alkoxy, —C(O)O—C$_{1-4}$alkyl, NR$^A$R$^B$, —NR$^L$—C(O)—O—C$_{1-4}$alkyl, and —NR$^L$—SO$_2$—NR$^A$R$^B$;

wherein the cycloalkyl, aryl, heteroaryl or heterocycloalkyl, whether alone or as part of a substituent group, is optionally substituted with one to three substituents independently selected from the group consisting of fluoro, chloro, hydroxy, carboxy, oxo, cyano, C$_{1-4}$alkyl, C$_{1-4}$alkoxy, —C(O)O—C$_{1-4}$alkyl and 5-(1,2,3,4-tetrazolyl); wherein R$^L$, R$^A$ and R$^B$, at each occurrence, are each independently selected from the group consisting of hydrogen, $C_{1-2}$alkyl and t-butoxy-carbonyl-;

provided that the chloro is not bound to a cycloalkyl or heterocycloalkyl;

alternatively, $R^4$ and $R^5$ are taken together with the nitrogen atom to which they are bound to form a heterocyclyl ring containing at least one nitrogen atom; wherein the heterocyclyl ring is optionally substituted with a substituent selected from the group consisting of hydroxy, carboxy, $C_{1-6}$alkyl, —$C_{1-4}$alkyl-OH, —$C_{1-4}$alkyl-$CO_2H$, $C_{4-8}$cycloalkyl, phenyl, trifluoromethylphenyl and a 5 to 6 membered heteroaryl group;

$R^6$ is hydrogen;

$R^7$ is selected from the group consisting of $C_{1-4}$alkoxy and cycloalkyl;

alternatively, $R^6$ and $R^7$ are taken together with the atoms to which they are bound to form a 5 to 10 membered, saturated nitrogen containing heterocyclyl; wherein the 5 to 10 membered, saturated nitrogen containing heterocyclyl is substituted with one to two oxo groups;

$R^8$ is selected from the group consisting of hydrogen, $C_{1-4}$alkyl and $C_{5-6}$cycloalkyl;

$A^1$ is —$C_{1-2}$alkyl-; wherein the —$C_{1-2}$alkylene- is optionally substituted with a substituent selected from the group consisting of hydroxy-$C_{1-2}$alkyl, $C_{1-4}$alkoxy substituted $C_{1-2}$alkyl, benzyloxy substituted $C_{1-2}$alkyl and aralkyl;

$R^9$ is selected from the group consisting of hydrogen, $C_{1-4}$alkyl and aralkyl;

$R^{10}$ is hydrogen;

$R^{11}$ is selected from the group consisting of hydrogen, hydroxy substituted $C_{1-4}$alkyl and $C_{2-6}$dialkanoic acid;

alternatively, $R^{10}$ and $R^{11}$ are taken together with the nitrogen atom to which they are bound to form a 5 to 6 membered heterocyclyl ring containing at least one nitrogen atom;

$R^{12}$ is selected from the group consisting of hydroxy substituted $C_{1-4}$alkyl, 5-(1,2,3,4-tetrazolyl), 4-(1,2,3,5-tetrazolyl), benzyl substituted 5-(1,2,3,4-tetrazolyl), benzyl substituted 4-(1,2,3,5-tetrazolyl) and —$C_{1-4}$alkyl-(5 to 6 membered heterocyclyoalkyl);

$R^{15}$ is selected from the group consisting of hydrogen, hydroxy, amino, —C(O)—$C_{1-4}$alkyl, and —C(O)—$C_{1-4}$alkyl-O—$C_{1-4}$alkyl;

or a pharmaceutically acceptable salt thereof.

4. A compound as in claim 3 wherein a is an integer from 0 to 1;

$L^1$ is —O—;

$R^1$ is selected from the group consisting of phenyl, 2-fluorophenyl and 2-methoxyphenyl;

$R^2$ is selected from the group consisting of hydrogen, cyclohexyl, (S)-cyclohexyl, (R)-cyclohexyl, isopropyl, (S)-isopropyl, (R)-isopropyl, (S)-isobutyl, 1-(2-hydroxy-ethyl), 1-(S)-(1-(R)-hydroxy-ethyl), 1-(2-methoxy-ethyl), 1-(2-isopropyloxy-ethyl), 1-(S)-(1-(R)-benzyloxy-ethyl), (S)-(2-benzyloxy-ethyl), 4-tetrahydropyranyl, (S)-4-tetrahydropyranyl and (S)-4-tetrahydropyranyl-methyl;

$L^2$ is selected from the group consisting of —$(CH_2)_b$—; wherein b is an integer from 0 to 3;

$R^3$ is selected from the group consisting of

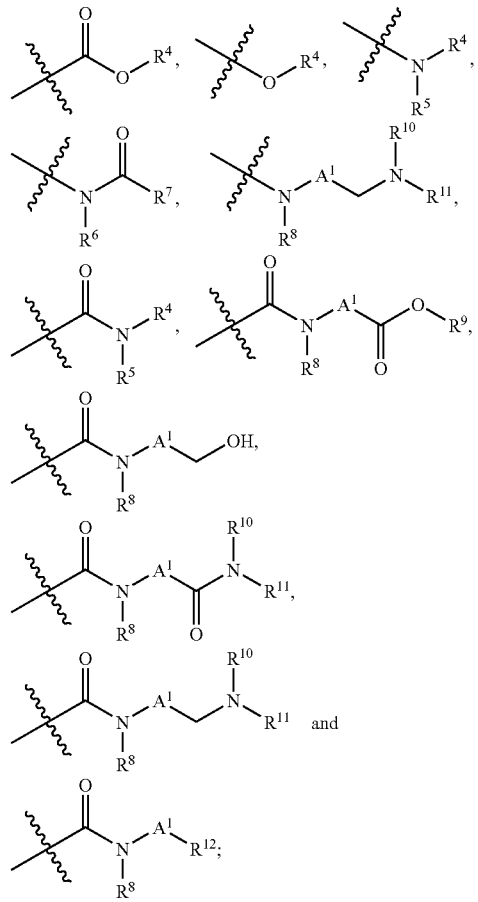

$R^4$ is selected from the group consisting of hydrogen, methyl, n-propyl, isobutyl, t-butyl, 1-(2-hydroxy-ethyl), 1-(2-benzyloxy-ethyl), 1-(3-hydroxy-n-propyl), 1-(2-methoxy-ethyl), 1-(2-t-butoxy-ethyl), 1-(3,3-dimethyl-n-butyl), 1-(3-methyl-buten-2-yl), 1-(2-propen-2-yl), cyclohexyl, cyclohexyl-methyl, cyclohexyl-ethyl, benzyl, 5-(3-t-butyl-isoxazolyl)-methyl, 5-(3-cyclohexyl-4,5-dihydro-isoxazolyl)-methyl, 5-(3-t-butyl-4,5-dihydro-isoxazolyl)-methyl, 5-(3-(2,2-dimethyl-n-propyl)-4,5-dihydro-isoxazolyl)-methyl and 4-(1-cyclohexylmethyl-1,2,3-triazolyl)-methyl;

$R^5$ is selected from the group consisting of 1-(2-ethoxycarbonyl-ethyl), 1-(2-methoxy-ethyl), 1-(2-carboxy-ethyl), 1-(2-hydroxy-ethyl), 1-(2-t-butoxycarbonylamino-ethyl), 1-(1,1-dimethyl-2-hydroxy-ethyl), 1-(2-t-butoxy-ethyl), 1-(2-amino-ethyl), 1-(2-dimethylamino-ethyl), 1-(2-aminosulfonylamino-ethyl), 1-(1-(R)-methyl-2-hydroxy-ethyl), 1-(1-(S)-methyl-2-hydroxy-ethyl), 1-(1-(R)-isopropyl-2-hydroxy-ethyl), isopropyl, 1-(3-ethoxy-n-propyl), 2-(1,3-dihydroxy-n-propyl), 1-(2,2-dimethyl-n-propyl), 1-(2,2-dimethyl-3-hydroxy-n-propyl), isobutyl, 1-(4-carboxy-n-butyl), 3-n-pentyl, isobutyl, t-butyl, 1-(3,3-dimethyl-n-butyl), cyclohexyl, 4-carboxy-cyclohexyl, 4-cyano-cyclohexyl, 4-(5-(1,2,3,4-tetrazolyl))-cyclohexyl, 4-ethoxy-carbonyl-cyclohexyl, cis-(4-methoxy-carbonyl-cyclohexyl), cis-(4-carboxy-cyclohexyl), trans-(4-methoxy-carbonyl-cyclohexyl), trans-(4-carboxy-cyclohexyl), 4-fluorobenzyl, phenyl-ethyl, 1-(3- phenyl-n-propyl), cyclopropyl-methyl, cyclopentyl-methyl, 2-adamantyl, 5-(1,2,3,4-tetrazolyl)-methyl, 2-imidazolyl-methyl, 2-(1-methyl-4,5-dichloro-imidazolyl)-methyl, 2-pyridyl-methyl, 3-pyridyl-methyl, 4-pyridyl-methyl, 4-pyridyl-ethyl, 3-(1,2,4-triazolyl)-methyl, 1-(2-(1-pyrrolidinyl)-ethyl), 4-imidazolyl-methyl, 2-(1-methyl-imidazolyl), 2-(1-methyl-imidazolyl)-methyl, 2-furyl-methyl, 2-(R)-tetrahydrofuryl-methyl, 2-thienyl-methyl, 3-thienyl-methyl, 3-(1,1-dioxo-tetrahydro-thienyl), 2-thiazolyl-methyl, 5-thiazolyl-methyl, 1-(2-(4-morpholinyl)-ethyl), 1'-(3-(4-morpholinyl)-n-propyl), 4-(1-t-butoxycarbonyl-piperidinyl), 5-(2,2-dimethyl-1,3-dioxanyl), —CH((R)-isopropyl)-CH$_2$OH, 2-(S)-(1-hydroxy-3-t-butoxy-n-propyl), 1-(R)-(1-(3-(5-methyl-1,2,4-oxadiazolyl))-2-t-butoxy)-ethyl, 1-(1-(5-(R)-1,2,3,4-tetrazolyl)-2-t-butoxy)-ethyl and —CH$_2$CH$_2$—O—CH$_2$CH$_2$—O—CH$_2$CH$_2$—O—CH$_2$CH$_2$—OH;

alternatively, $R^4$ and $R^5$ are taken together with the nitrogen atom to which they are bound to form a heterocyclyl ring selected form the group consisting of 4-morpholinyl, 1-(2-(S)-hydroxymethyl-pyrrolidinyl), 1-(2-(R)-hydroxymethyl-pyrrolidinyl), 1-(2-(S)-carboxy-pyrrolidinyl), 1-(2-(S)-carboxy-octahydroindolyl), 1-(4-t-butyl-1,2,3-triazolyl), 1-(4-(3,3-dimethyl-n-propyl)-1,2,3-triazolyl), 1-(4-cyclohexyl-1,2,3-triazolyl), 1-(4-hydroxymethyl-1,2,3-triazolyl), 1-(4-(2-pyridyl)-1,2,3-triazolyl), 1-(4-methyl-piperazinyl), 1-(4-phenyl-piperidinyl), 1-(4-hydroxyethyl-piperidinyl), 1-(4-hydroxy-4-(3-trifluoromethylphenyl)-piperidinyl), 1-(2-(S)-carboxymethyl-piperidinyl) and 1-(2-(S)-carboxy-piperidinyl);

$R^6$ is hydrogen;

$R^7$ is selected from the group consisting of cyclohexyl and t-butoxy;

alternatively, $R^6$ and $R^7$ are taken together with the atoms to which they are bound to form a 5 to 10 membered, saturated heterocycloalkyl selected from the group consisting of 3-(1,3-diaza-spiro[4.5]decan-2-one) and 1-(1,3-diaza-spiro[4.5]decane-2,4-dione);

$R^8$ is selected from the group consisting of hydrogen, methyl and cyclohexyl;

$A^1$ is selected from the group consisting of —CH$_2$—, —CH(CH$_2$—OH)—, —CH—((R)—CH$_2$—OH)—, —CH—((S)—CH$_2$—OH)—, —CH(CH$_2$—O-t-butyl)-, —CH((R)—CH$_2$—O-t-butyl)-, —CH((S)—CH$_2$—)-t-butyl)-, —CH(CH$_2$—O-benzyl)-, —CH((S)—CH$_2$—O-benzyl)-, —CH((R)—CH$_2$—O-benzyl)-, —CH(benzyl)-, —CH((R)-benzyl)- and —CH((S)-benzyl)-;

$R^9$ is selected from the group consisting of hydrogen, methyl, ethyl, isopropyl and benzyl;

$R^{10}$ is hydrogen;

$R^{11}$ is selected from the group consisting of hydrogen, —CH—(CH$_3$)—CH$_2$OH, —CH—((R)—CH$_3$)—CH$_2$OH, —CH—((S)—CH$_3$)—CH$_2$OH, 2-(S)-pentadoic acid and 2-(R)-pentadoic acid;

alternatively, $R^{10}$ and $R^{11}$ are taken together with the nitrogen atom to which they are bound to form a heterocyclyl ring selected from the group consisting of 1-piperidinyl and 4-morpholinyl;

$R^{12}$ is selected from the group consisting of hydroxy-methyl, 5-(1-benzyl-1,2,3,4-tetrazolyl), 4-(1-benzyl-1,2,3,5-(1,2,3,4-tetrazolyl)) 5-(1,2,3,4-tetrazolyl), 1-piperidinyl-methyl and 4-morpholinyl-methyl;

$R^{15}$ is selected from the group consisting of hydrogen, hydroxy, amino, isopropyl-carbonyl-, n-butyl-carbonyl- and methoxy-methyl-carbonyl-;

or a pharmaceutically acceptable salt thereof.

5. A compound as in claim 4 wherein a is an integer from 0 to 1;

$L^1$ is —O—;

$R^1$ is selected from the group consisting of phenyl, 2-fluorophenyl and 2-methoxyphenyl;

$R^2$ is selected from the group consisting of hydrogen, (S)-cyclohexyl, isopropyl, (S)-isopropyl, and (S)-4-tetrahydropyranyl;

$L^2$ is selected from the group consisting of —CH$_2$— and —CH$_2$—CH$_2$—;

$R^3$ is selected from the group consisting of

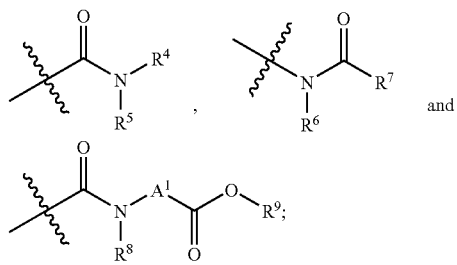

$R^4$ is selected from the group consisting of hydrogen, methyl, 1-(2-hydroxy-ethyl), 1-(2-benzyloxy-ethyl) and 1-(3-hydroxy-n-propyl);

$R^5$ is selected from the group consisting of cyclohexyl, isopropyl, 3-n-pentyl, 4-carboxy-cyclohexyl, cis-(4-methoxy-carbonyl-cyclohexyl), cis-(4-carboxy-cyclohexyl), trans-(4-methoxy-carbonyl-cyclohexyl), 2-adamantyl and —CH((R)-isopropyl)-CH$_2$—OH;

$R^6$ is hydrogen;

$R^7$ is t-butoxy;

$R^8$ is selected from the group consisting of hydrogen and methyl;

$A^1$ is selected from the group consisting of —CH—((R)—CH$_2$—OH)—, —CH—((S)—CH$_2$—OH)—, —CH((S)—CH$_2$—O-benzyl)- and —CH((R)—CH$_2$—O-benzyl)-;

$R^9$ is selected from the group consisting of hydrogen and methyl;

$R^{15}$ is hydrogen;

or a pharmaceutically acceptable salt thereof.

6. A compound as in claim 5 wherein a is an integer from 0 to 1;

$L^1$ is —O—;

$R^1$ is selected from the group consisting of phenyl, 2-fluorophenyl and 2-methoxyphenyl;

$R^2$ is selected from the group consisting of (S)-cyclohexyl, (S)-isopropyl, and (S)-4-tetrahydropyranyl;

$L^2$ is —CH$_2$—CH$_2$—;

$R^3$ is selected from the group consisting of

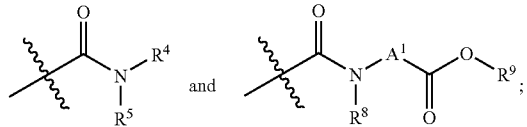

R⁴ is selected from the group consisting of hydrogen, methyl, 1-(2-hydroxy-ethyl) and 1-(2-benzyloxy-ethyl);

R⁵ is selected from the group consisting of cyclohexyl, 3-n-pentyl, 4-carboxy-cyclohexyl, cis-(4-methoxy-carbonyl-cyclohexyl), cis-(4-carboxy-cyclohexyl), trans-(4-methoxy-carbonyl-cyclohexyl), 2-adamantyl and —CH((R)-isopropyl)-CH₂—OH;

R⁸ is selected from the group consisting of hydrogen and methyl;

A¹ is selected from the group consisting of —CH—((R)—CH₂—OH)—, —CH((S)—CH₂—O-benzyl)- and —CH((R)—CH₂—O-benzyl)-;

R⁹ is selected from the group consisting of hydrogen and methyl;

R¹⁵ is hydrogen;

or a pharmaceutically acceptable salt thereof.

7. A compound as in claim 6 wherein
a is an integer from 0 to 1;
L¹ is —O—;
R¹ is selected from the group consisting of phenyl, 2-fluorophenyl and 2-methoxyphenyl;
R² is selected from the group consisting of (S)-cyclohexyl, (S)-isopropyl and (S)-4-tetrahydropyranyl;
L² is —CH₂—CH₂—;
R³ is selected from the group consisting of

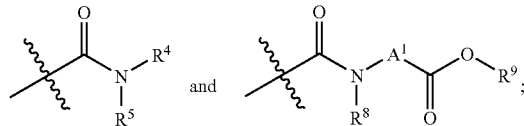

R⁴ is selected from the group consisting of methyl, 1-(2-hydroxy-ethyl) and 1-(2-benzyloxy-ethyl);

R⁵ is selected from the group consisting of cyclohexyl, 4-carboxy-cyclohexyl, cis-(4-methoxy-carbonyl-cyclohexyl) and cis-(4-carboxy-cyclohexyl);

R⁸ is selected from the group consisting of hydrogen and methyl;

A¹ is selected from the group consisting of —CH—((R)—CH₂—OH)— and —CH((S)—CH₂—O-benzyl)-;

R⁹ is selected from the group consisting of hydrogen and methyl;

R¹⁵ is hydrogen;

or a pharmaceutically acceptable salt thereof.

8. A compound as in claim 4 wherein
a is 1;
L¹ is —O—;
R¹ is phenyl;
R² is selected from the group consisting of (S)-cyclohexyl, (R)-cyclohexyl, (S)-isopropyl, (R)-isopropyl, 1-(S)-(1-(R)-hydroxy-ethyl), 1-(S)-(1-(R)-benzyloxy-ethyl) and (S)-4-tetrahydropyranyl;
L² is selected from the group consisting of —CH₂—, —CH₂—CH₂— and —CH₂CH₂CH₂—;
R³ is selected from the group consisting of

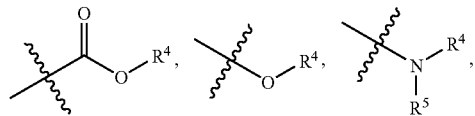

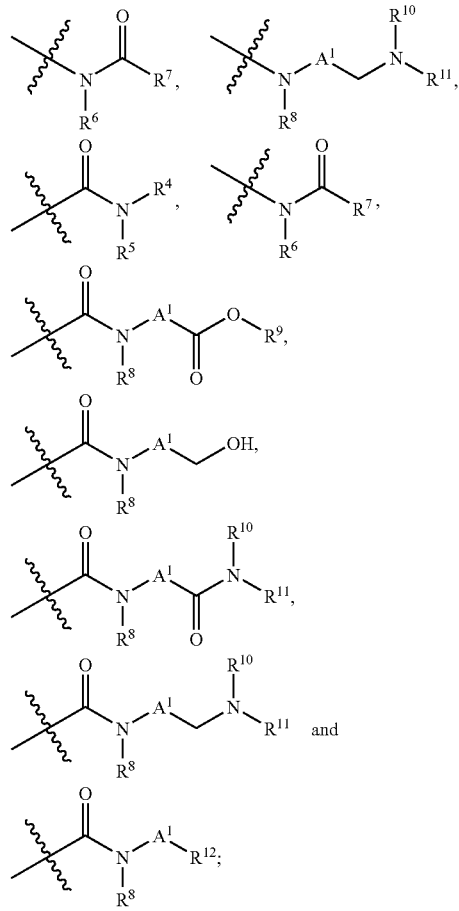

R⁴ is selected from the group consisting of hydrogen, methyl, isobutyl, 1-(2-hydroxy-ethyl), 1-(3,3-dimethyl-n-butyl), 1-(2-methoxy-ethyl), 1-(2-t-butoxy-ethyl), cyclohexyl, cyclohexyl-methyl, cyclohexyl-ethyl, benzyl, 5-(3-t-butyl-isoxazolyl)-methyl and 5-(3-t-butyl-4,5-dihydro-isoxazolyl)-methyl;

R⁵ is selected from the group consisting of cyclohexyl, isobutyl, t-butyl, 1-(2-methoxy-ethyl), 1-(2-hydroxy-ethyl), 1-(2-t-butoxy-ethyl), 1-(3-ethoxy-n-propyl), 1-(2,2-dimethyl-3-hydroxy-n-propyl), 1-(1,1-dimethyl-2-hydroxy-ethyl), 1-(2,2-dimethyl-n-propyl), 1-(3,3-dimethyl-n-butyl), 4-fluorobenzyl, cyclopropyl-methyl, 5-(1,2,3,4-tetrazolyl)-methyl, 2-imidazolyl-methyl, 5-thiazolyl-methyl, 2-pyridyl-methyl, 4-pyridyl-methyl, 2-thienyl-methyl, 3-thienyl-methyl, 3-(1,2,4-triazolyl)-methyl, 2-(1-methyl-imidazolyl)-methyl, 2-(1-methyl-4,5-dichloro-imidazolyl)-methyl, 1-(2-(4-morpholinyl)-ethyl), 2-(R)-tetrahydrofuryl-methyl, 1-(R)-(1-(3-(5-methyl-1,2,4-oxadiazolyl))-2-t-butoxy)-ethyl, 1-(1-(R)-methyl-2-hydroxy-ethyl), 1-(1-(S)-methyl-2-hydroxy-ethyl), 1-(2-t-butoxycarbonyl-amino-ethyl), 1-(2-aminosulfonylamino-ethyl), 1-(4-t-butoxycarbonyl-piperidinyl) and —CH₂CH₂—O—CH₂CH₂—O—CH₂CH₂—O—CH₂CH₂—OH;

alternatively, R⁴ and R⁵ are taken together with the nitrogen atom to which they are bound to form a heterocyclyl ring selected form the group consisting of 1-(2-(S)-carboxy-octahydroindolyl), 1-(2-(S)-carboxy-piperidinyl), 1-(2- hydroxyethyl-piperidinyl), 4-morpholinyl, 1-(4-t-butyl-1,2,3-triazolyl) and 1-(4-cyclohexyl-1,2,3-triazolyl);

$R^6$ and $R^7$ are taken together with the atoms to which they are bound to form a ring structure selected from the group consisting of 3-(1,3-diaza-spiro[4.5]decan-2-one) and 3-(1,3-diaza-spiro[4.5]decane-2,4-dione);

$R^8$ is selected from the group consisting of hydrogen, methyl and cyclohexyl;

$A^1$ is selected from the group consisting of —CH$_2$—, —CH((R)—CH$_2$—O-t-butyl)-, —CH((S)—CH$_2$—O-t-butyl)-, —CH((S)—CH$_2$—O-benzyl)- and —CH((R)—CH$_2$—O-benzyl)-;

$R^9$ is selected from the group consisting of hydrogen, methyl and isopropyl;

$R^{10}$ is hydrogen;

$R^{11}$ is selected from the group consisting of hydrogen, —CH—((R)—CH$_3$)—CH$_2$OH, —CH—((S)—CH$_3$)—CH$_2$OH, 2-(S)-pentadioic acid and 2-(R)-pentadioic acid;

alternatively, $R^{10}$ and $R^{11}$ are taken together with the nitrogen atom to which they are bound to form a heterocyclyl ring selected from the group consisting of 1-piperidinyl and 4-morpholinyl;

$R^{12}$ is selected from the group consisting of hydroxy-methyl, 5-(1-benzyl-1,2,3,4-tetrazolyl), 4-(1-benzyl-1,2,35-(1,2,3,4-tetrazolyl)), 5-(1,2,3,4-tetrazolyl), 1-piperidinyl-methyl and 4-morpholinyl-methyl;

$R^{15}$ is hydrogen;

or a pharmaceutically acceptable salt thereof.

9. A compound as in claim 8 wherein
a is 1;
$L^1$ is —O—;
$R^1$ is phenyl;
$R^2$ is selected from the group consisting of (S)-cyclohexyl, (R)-cyclohexyl, (S)-isopropyl, (R)-isopropyl, (S)-4-tetrahydropyranyl and 1-(S)-(1-(R)-hydroxy-ethyl);
$L^2$ is selected from the group consisting of —CH$_2$—, —CH$_2$—CH$_2$— and —CH$_2$CH$_2$CH$_2$—;
$R^3$ is selected from the group consisting of

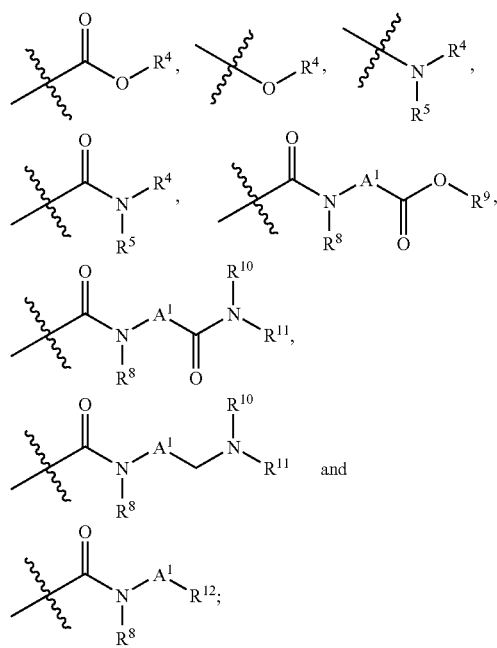

$R^4$ is selected from the group consisting of hydrogen, methyl, isobutyl, 1-(2-hydroxy-ethyl), 1-(3,3-dimethyl-n-butyl), 1-(2-t-butoxy-ethyl), cyclohexyl, cyclohexyl-methyl, cyclohexyl-ethyl, benzyl and 5-(3-t-butyl-4,5-dihydro-isoxazolyl)-methyl;

$R^5$ is selected from the group consisting of isobutyl, 1-(2,2-dimethyl-n-propyl), 1-(3,3-dimethyl-n-butyl), 1-(3-ethoxy-n-propyl), 1-(2-t-butoxy-ethyl), 1-(2,2-dimethyl-3-hydroxy-n-propyl), 1-(1,1-dimethyl-2-hydroxy-ethyl), 1-(1-(R)-methyl-2-hydroxy-ethyl), cyclohexyl, cyclopropyl-methyl, 4-fluorobenzyl, 1-(2-(4-morpholinyl)-ethyl), 2-imidazolyl-methyl, 2-pyridyl-methyl, 4-pyridyl-methyl, 2-thienyl-methyl, 3-thienyl-methyl, 3-(1,2,4-triazolyl)-methyl, 5-thiazolyl-methyl, 2-(1-methyl-imidazolyl)-methyl, 2-(1-methyl-4,5-dichloro-imidazolyl)-methyl, 1-(R)-(1-(3-(5-methyl-1,2,4-oxadiazolyl))-2-t-butoxy)-ethyl, 4-(1-t-butoxycarbonyl-piperidinyl), 2-(R)-tetrahydrofuryl-methyl, 1-(2-t-butoxycarbonylamino-ethyl) and 1-(2-aminosulfonylamino-ethyl) and —CH$_2$CH$_2$—O—CH$_2$CH$_2$—O—CH$_2$CH$_2$—O—CH$_2$CH$_2$—OH;

alternatively, $R^4$ and $R^5$ are taken together with the nitrogen atom to which they are bound to form a heterocyclyl ring selected from the group consisting of 1-(2-(S)-carboxy-octahydroindolyl), 1-(2-(S)-carboxy-piperidinyl), 1-(4-t-butyl-1,2,3-triazolyl) and 1-(4-cylohexyl-1,2,3-triazolyl);

$R^8$ is selected from the group consisting of hydrogen, methyl and cyclohexyl;

$A^1$ is selected from the group consisting of —CH$_2$—, —CH((R)—CH$_2$—O-t-butyl)-, —CH((S)—CH$_2$—O-t-butyl)-, —CH((S)—CH$_2$—O-benzyl)- and —CH((R)—CH$_2$—O-benzyl)-;

$R^9$ is selected from the group consisting of hydrogen, methyl and isopropyl;

$R^{10}$ is hydrogen;

$R^{11}$ is selected from the group consisting of hydrogen, —CH—((R)—CH$_3$)—CH$_2$OH, —CH—((S)—CH$_3$)—CH$_2$OH, 2-(S)-pentadioic acid and 2-(R)-pentadioic acid;

alternatively, $R^{10}$ and $R^{11}$ are taken together with the nitrogen atom to which they are bound to form a heterocyclyl ring selected from the group consisting of 1-piperidinyl and 4-morpholinyl;

$R^{12}$ is selected from the group consisting of 5-(1,2,3,4-tetrazolyl) and 4-(1-benzyl-1,2,3,5-(1,2,3,4-tetrazolyl));

$R^{15}$ is hydrogen;

or a pharmaceutically acceptable salt thereof.

10. A compound as in claim 9 wherein
a is 1;
$L^1$ is —O—;
$R^1$ is phenyl;
$R^2$ is selected from the group consisting of (S)-cyclohexyl, (R)-cyclohexyl, (S)-isopropyl and (S)-4-tetrahydropyranyl;
$L^2$ is selected from the group consisting of —CH$_2$—, —CH$_2$—CH$_2$— and —CH$_2$—CH$_2$CH$_2$—;
$R^3$ is selected from the group consisting of

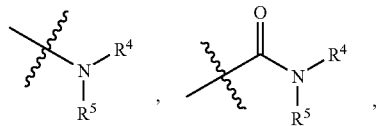

-continued

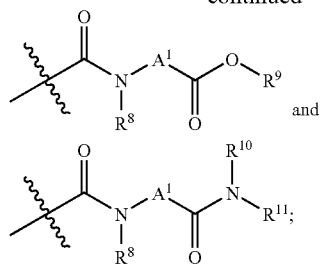

R⁴ is selected from the group consisting of hydrogen, methyl, isobutyl, 1-(2-hydroxy-ethyl), 1-(2-t-butoxy-ethyl), 1-(3,3-dimethyl-n-butyl) and cyclohexyl;

R⁵ is selected from the group consisting of 1-(1-(R)-methyl-2-hydroxy-ethyl), 1-(1,1-dimethyl-2-hydroxy-ethyl), 1-(2-t-butoxy-ethyl), 1-(2-t-butoxycarbonylamino-ethyl), 1-(2-aminosulfonylamino-ethyl), 1-(2,2-dimethyl-n-propyl), 1-(2,2-dimethyl-3-hydroxy-n-propyl), 1-(3,3-dimethyl-n-butyl), cyclopropyl-methyl, 2-(1-methyl-imidazolyl)-methyl, 2-pyridyl-methyl and 1-(2-(4-morpholinyl)-ethyl);

alternatively, R⁴ and R⁵ are taken together with the nitrogen atom to which they are bound to form 1-(4-t-butyl-1,2,3-triazolyl);

R⁸ is hydrogen;

A¹ is selected from the group consisting of —CH((R)—CH₂—O-t-butyl)- and —CH((S)—CH₂—O-benzyl)-;

R⁹ is methyl;

R¹⁰ is hydrogen;

R¹¹ is 2-(S)-pentadioic acid;

alternatively, R¹⁰ and R¹¹ are taken together with the nitrogen atom to which they are bound to form 4-morpholinyl;

R¹⁵ is hydrogen;

or a pharmaceutically acceptable salt thereof.

11. A compound of formula (I-O)

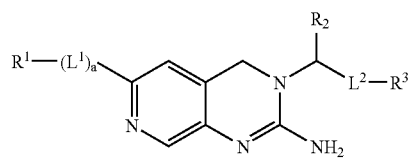

(I-O)

wherein a in an integer from 0 to 1;

L¹ is selected from the group consisting of —O—, —S—, —SO—, —SO₂— and —NR⁰—; wherein R⁰ is selected from the group consisting of hydrogen and $C_{1-4}$alkyl;

R¹ is selected from the group consisting of cycloalkyl, aryl, heteroaryl and heterocycloalkyl;

wherein the cycloalkyl, aryl, heteroaryl or heterocycloalkyl is optionally substituted with one or more substituents independently selected from the group consisting of halogen, hydroxy, oxo, carboxy, $C_{1-4}$alkyl, hydroxy substituted $C_{1-4}$alkyl, halogen substituted $C_{1-4}$alkyl, cyano substituted $C_{1-4}$alkyl, $C_{1-4}$alkoxy, halogen substituted $C_{1-4}$alkoxy, nitro and cyano;

R² is selected from the group consisting of hydrogen, $C_{1-8}$alkyl, $C_{1-8}$alkoxy, hydroxy substituted $C_{1-6}$alkyl, amino substituted $C_{1-6}$alkyl, —$C_{1-4}$alkyl-O—$C_{1-4}$alkyl, —$C_{1-4}$alkyl-O-aralkyl, cycloalkyl, —$C_{1-4}$alkyl-cycloalkyl, aryl, aralkyl, biphenyl, heteroaryl, —$C_{1-4}$alkyl-heteroaryl, heterocycloalkyl and —$C_{1-4}$alkyl-heterocycloalkyl;

wherein the cycloalkyl, aryl, heteroaryl or heterocycloalkyl group, whether alone or as part of a substituent group, is optionally substituted with one or more substituent independently selected from the group consisting of halogen, hydroxy, oxo, carboxy, $C_{1-4}$alkyl, $C_{1-4}$alkoxy, —C(O)—($C_{1-4}$alkoxy), hydroxy substituted $C_{1-4}$alkyl, fluoro substituted $C_{1-4}$alkyl, fluoro substituted $C_{1-4}$alkoxy, 5-(1,2,3,4-tetrazolyl) and 1-(1,4-dihydro-tetrazol-5-one);

L² is selected from the group consisting of —(CH₂)$_b$—;

b is an integer from 0 to 4;

R³ is selected from the group consisting of

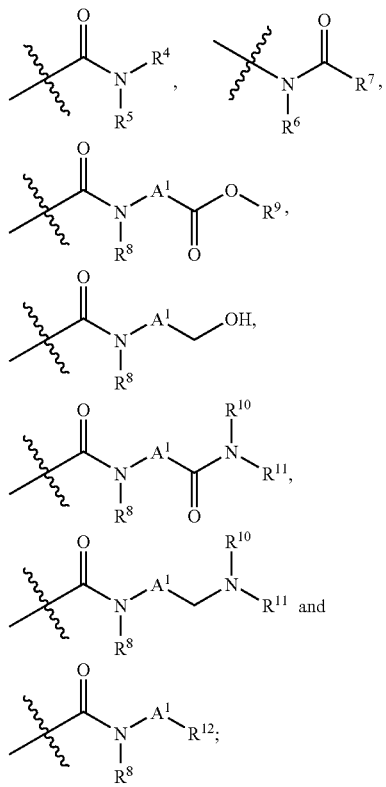

R⁴ and R⁵ are each independently selected from the group consisting of hydrogen, $C_{1-8}$alkyl, hydroxy substituted $C_{1-4}$alkyl, —$C_{2-4}$alkyl-O—$C_{1-4}$alkyl, —$C_{2-4}$alkyl-O-aralkyl, —$C_{1-4}$alkyl-NR$^A$R$^B$, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl;

wherein R$^A$ and R$^B$, at each occurrence, are each independently selected from the group consisting of hydrogen, $C_{1-4}$alkyl and aralkyl;

wherein the $C_{1-8}$alkyl is optionally substituted with one or more substituents independently selected from the group consisting of hydroxy and carboxy;

wherein the cycloalkyl, aryl, heteroaryl or heterocycloalkyl, of R⁴ and R⁵ whether alone or as part of a substituent group, is optionally substituted with one or more substituents independently selected from the group consisting of fluoro, hydroxy, carboxy, —C(O)

O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^4$ and $R^5$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^6$ is selected from the group consisting of hydrogen and $C_{1-4}$alkyl;

$R^7$ is selected from the group consisting of hydrogen, $C_{1-10}$alkyl, cycloalkyl, aryl, biphenyl, partially unsaturated carbocyclyl, heteroaryl, heterocycloalkyl, —$C_{1-4}$alkyl-cycloalkyl, $C_{1-4}$aralkyl, —$C_{1-4}$alkyl-partially unsaturated carbocyclyl, —$C_{1-4}$alkyl-heteroaryl, —$C_{1-4}$alkyl-heterocycloalkyl and spiro-heterocyclyl;

wherein the $C_{1-10}$alkyl, cycloalkyl, aryl, heteroaryl, heterocycloalkyl or spiro-heterocyclyl, of $R^7$ whether alone or as part of a substituent group is optionally substituted with one or more substituents independently selected from the group consisting of halogen, hydroxy, oxo, carboxy, $C_{1-6}$alkyl, fluoro substituted $C_{1-4}$alkyl, hydroxy substituted $C_{1-4}$alkyl, carboxy substituted $C_{1-4}$alkyl, $C_{1-4}$alkoxy, nitro, cyano, amino, $C_{1-4}$alkylamino, di($C_{1-4}$alkyl)amino, —C(O)—$C_{1-4}$alkyl, —C(O)—$C_{1-4}$aralkyl, —C(O)O—$C_{1-4}$alkyl, —C(O)O—$C_{1-4}$aralkyl, —$C_{1-4}$alkyl-C(O)O—$C_{1-4}$alkyl, —$C_{1-4}$alkyl-S—$C_{1-4}$alkyl, —C(O)—N($R^C R^D$)$_2$, —$C_{1-4}$alkyl-C(O)—N($R^C R^D$)$_2$, —$NR^C$—C(O)—$C_{1-4}$alkyl, —SO$_2$—N($R^C R^D$), —$C_{1-4}$alkyl-SO$_2$—N($R^C R^D$)$_2$, phenyl, 5-(1,2,3,4-tetrazolyl) and 1-(1,4-dihydro-tetrazol-5-one);

provided that the halogen is not bound to a $C_{1-10}$alkyl, cycloalkyl or heterocycloalkyl;

wherein $R^C$ and $R^D$ at each occurrence are independently selected from the group consisting of hydrogen and $C_{1-4}$alkyl;

wherein the phenyl is optionally substituted with one or more substituent independently selected from the group consisting of halogen, hydroxy, oxo, carboxy, —C(O)O—$C_{1-4}$alkyl, —C(O)—$C_{1-4}$alkyl, $C_{1-4}$alkyl, fluoro substituted $C_{1-4}$alkyl, $C_{1-4}$alkoxy, nitro, cyano, amino, $C_{1-4}$alkylamino and di($C_{1-4}$alkyl)amino;

$R^8$ is selected from the group consisting of hydrogen, $C_{1-4}$alkyl and cycloalkyl;

$A^1$ is —$C_{1-6}$alkyl-; wherein the alkyl is optionally substituted with one or more substituents independently selected from the group consisting of $C_{2-8}$alkyl, hydroxy substituted $C_{1-6}$alkyl, $C_{1-4}$alkoxy substituted $C_{1-4}$alkyl, aralkyloxy substituted $C_{1-4}$alkyl, $C_{3-6}$alkenyl, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl, —$C_{1-4}$alkyl-NR$^E$R$^F$, —S—$C_{1-4}$alkyl, —$C_{1-3}$alkyl-O—$C_{1-3}$alkyl, —$C_{1-3}$alkyl-S—$C_{1-3}$alkyl, —$C_{1-3}$alkyl-O-aralkyl, —$C_{1-4}$alkyl-guanidino, —$C_{1-4}$alkyl-CO$_2$R$^E$ and —$C_{1-4}$alkyl-C(O)O—$C_{1-4}$alkyl;

wherein $R^E$ and $R^F$, at each occurrence, are independently selected from the group consisting of hydrogen and $C_{1-4}$alkyl;

wherein the cycloalkyl, aryl, heteroaryl or heterocycloalkyl, of $A^1$ whether alone or as part of a substituent group, is optionally substituted with one or more substituents independently selected from the group consisting of fluoro, chloro, hydroxy, oxo, carboxy, $C_{1-4}$alkyl, $C_{1-4}$alkoxy, hydroxy substituted $C_{1-4}$alkyl, halogen substituted $C_{1-4}$alkyl, halogen substituted $C_{1-3}$alkyl, —C(O)O—$C_{1-4}$alkyl, 5-(1,2,3,4-tetrazolyl) and 1-(1,4-dihydro-tetrazol-5-one);

provided that the chloro is not bound to a cycloalkyl or heterocycloalkyl;

$R^9$ is selected from the group consisting of hydrogen, $C_{1-12}$alkyl, hydroxy substituted $C_{1-6}$alkyl, amino substituted $C_{1-6}$alkyl, allyl, $C_{1-8}$alkoxy, cycloalkyl, —$C_{1-4}$alkyl-cycloalkyl, aryl, aralkyl, biphenyl, heteroaryl, —$C_{1-4}$alkyl-heteroaryl, heterocycloalkyl, —$C_{1-4}$alkyl-heterocycloalkyl, —$C_{1-4}$alkyl-O—$C_{1-8}$alkyl, —$C_{1-4}$alkyl-O-aryl, —$C_{1-4}$alkyl-O-aralkyl, $C_{1-4}$alkyl-O—C(O)—$C_{1-6}$alkyl, —$C_{1-4}$alkyl-O—C(O)—O—$C_{1-6}$alkyl, —$C_{1-4}$alkyl-O—C(O)—O—$C_{1-8}$cycloalkyl, —$C_{1-4}$alkyl-O—C(O)—C(NHCO($C_{1-6}$alkyl))=CH—$C_{1-6}$alkyl, 5-methyl-2-oxo-[1,3]dioxol-4-ylmethyl-, —CH$_2$—N($C_{1-4}$alkyl)-C(O)-aryl, —CH$_2$—C(O)—NR$^G$R$^H$, CH$_2$—O—CH$_2$—O—C(O)-2-(N-alkyl-1,4-dihydropyridyl), α-cyclodextrinyl, β-cyclodextrinyl and γ-cyclodextrinyl;

wherein $R^G$ and $R^H$ are each independently selected from the group consisting of hydrogen and $C_{1-4}$alkyl;

wherein the cycloalkyl, aryl, heteroaryl or heterocycloalkyl, of $R^9$ whether alone or as part of a substituent group, is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{10}$ and $R^{11}$ are each independently selected from the group consisting of hydrogen, $C_{1-8}$alkyl, hydroxy substituted $C_{1-4}$alkyl, —$C_{2-4}$alkyl-O—$C_{1-4}$alkyl, benzyloxy substituted $C_{1-4}$alkyl, —$C_{1-4}$alkyl-NR$^J$R$^K$, cycloalkyl, —$C_{1-4}$alkyl-cycloalkyl, aryl, aralkyl, heteroaryl, —$C_{1-4}$alkyl-heteroaryl, heterocycloalkyl, —$C_{1-4}$alkyl-heterocycloalkyl and —$C_{1-4}$alkyl-C(O)O—R$^J$;

wherein $R^J$ and $R^K$, at each occurrence, are each independently selected from the group consisting of hydrogen and $C_{1-4}$alkyl;

wherein the cycloalkyl, aryl, heteroaryl or heterocycloalkyl, of $R^{10}$ and $R^{11}$ whether alone or as part of a substituent group is optionally substituted with one or more substituents independently selected from the group consisting of fluoro, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

alternatively $R^{10}$ and $R^{11}$ are taken together with the nitrogen atom to which they are bound to form a heterocyclyl ring containing at least one nitrogen atom and further optionally containing 0 to 2 heteroatoms independently selected from O, S or N; wherein the heterocyclyl ring is optionally substituted with one or more substituents independently selected from the group consisting of halogen, hydroxy, carboxy, —C(O)O—$C_{1-4}$alkyl, $C_{1-4}$alkyl, $C_{1-4}$alkoxy, trifluoromethyl, cyano, nitro, amino, $C_{1-4}$alkylamino, di($C_{1-4}$alkylamino), 5-(1,2,3,4-tetrazolyl) and 1-(1,4-dihydro-tetrazol-5-one);

$R^{12}$ is selected from the group consisting of $C_{1-4}$alkyl, hydroxy substituted $C_{1-4}$alkyl, cycloalkyl, —$C_{1-4}$alkyl-cycloalkyl, aryl, aralkyl, heteroaryl, —$C_{1-4}$alkyl-heteroaryl, heterocycloalkyl and —C$_{1-4}$alkyl-heterocycloalkyl; wherein the cycloalkyl, aryl, heteroaryl or heterocycloalkyl group is optionally substituted with one or more substituents independently selected from the group consisting of halogen, hydroxy, carboxy, —C(O)O—C$_{1-4}$alkyl, C$_{1-4}$alkyl, C$_{1-4}$alkoxy, trifluoromethyl, cyano, nitro, amino, C$_{1-4}$alkylamino, di(C$_{1-4}$alkylamino), aralkyl, 5-(1,2,3,4-tetrazolyl) and 1-(1,4-dihydro-tetrazol-5-one);

or a pharmaceutically acceptable salt thereof.

12. A pharmaceutical composition comprising a pharmaceutically acceptable carrier and a compound of claim 1.

13. A pharmaceutical composition made by mixing a compound of claim 1 and a pharmaceutically acceptable carrier.

14. A process for making a pharmaceutical composition comprising mixing a compound of claim 1 and a pharmaceutically acceptable carrier.

* * * * *